US012162945B2

(12) United States Patent
Scholz et al.

(10) Patent No.: US 12,162,945 B2
(45) Date of Patent: Dec. 10, 2024

(54) EPHA2 ANTIBODIES

(71) Applicant: Immunome, Inc., Bothell, WA (US)

(72) Inventors: Alexander Scholz, San Carlos, CA (US); Nikhil Vad, San Carlos, CA (US); Michael Samuel Weiss, San Carlos, CA (US); Anne Ye, San Carlos, CA (US); Danhui Zhang, San Carlos, CA (US); Iraz T. Aydin, San Carlos, CA (US); Maryam M. Bhatti, San Carlos, CA (US); Sean Carroll, San Carlos, CA (US); Jessica Finn, San Carlos, CA (US); Shuning Gai, San Carlos, CA (US); Shaun M. Lippow, San Carlos, CA (US); Amy Manning-Bog, San Carlos, CA (US); Philippe Marguet, San Carlos, CA (US); Ngan Nguyen Atkins, San Carlos, CA (US)

(73) Assignee: Immunome, Inc., Bothell, WA (US)

( * ) Notice: Subject to any disclaimer, the term of this patent is extended or adjusted under 35 U.S.C. 154(b) by 0 days.

(21) Appl. No.: 17/687,558

(22) Filed: Mar. 4, 2022

(65) Prior Publication Data

US 2022/0306752 A1 Sep. 29, 2022

Related U.S. Application Data

(60) Provisional application No. 63/298,093, filed on Jan. 10, 2022, provisional application No. 63/157,320, filed on Mar. 5, 2021.

(51) Int. Cl.
*C07K 16/28* (2006.01)
*A61K 39/00* (2006.01)
*A61K 39/395* (2006.01)
*A61K 45/06* (2006.01)
*A61K 47/68* (2017.01)
*A61P 35/00* (2006.01)

(52) U.S. Cl.
CPC .......... *C07K 16/2866* (2013.01); *A61K 39/001122* (2018.08); *A61K 39/39558* (2013.01); *A61K 45/06* (2013.01); *A61K 47/6849* (2017.08); *A61K 47/6851* (2017.08); *A61P 35/00* (2018.01); *C07K 16/2809* (2013.01); *C07K 16/2818* (2013.01); *C07K 16/2878* (2013.01); *A61K 2039/505* (2013.01); *A61K 2039/54* (2013.01); *C07K 2317/31* (2013.01); *C07K 2317/34* (2013.01); *C07K 2317/72* (2013.01); *C07K 2317/732* (2013.01); *C07K 2317/76* (2013.01); *C07K 2317/92* (2013.01)

(58) Field of Classification Search
CPC ........ C07K 16/2866; A61K 39/001122; A61K 47/6849

See application file for complete search history.

(56) References Cited

U.S. PATENT DOCUMENTS

| 7,659,374 | B2 | 2/2010 | Wu |
| 7,803,915 | B2 | 9/2010 | Cairns |
| 8,449,882 | B2 | 5/2013 | Hasegawa |
| 8,992,912 | B2 | 3/2015 | Blanc |
| 9,150,657 | B2 | 10/2015 | Hasegawa |
| 9,220,772 | B2 | 12/2015 | Zhou |
| 11,241,485 | B2 | 2/2022 | Suri |
| 2007/0166314 | A1 | 7/2007 | Kinch |
| 2009/0304721 | A1 | 12/2009 | Kinch |
| 2010/0196398 | A1 | 8/2010 | Gazit-Bornstein et al. |
| 2015/0274824 | A1 | 10/2015 | Blanc |
| 2016/0031987 | A1 | 2/2016 | Hasegawa et al. |
| 2016/0367664 | A1 | 12/2016 | Wang et al. |
| 2017/0051068 | A1 | 2/2017 | Pillarisetti et al. |
| 2019/0070113 | A1 | 3/2019 | Merrimack et al. |
| 2019/0336615 | A1 | 11/2019 | Thompson |
| 2019/0359722 | A1* | 11/2019 | Kato .................... G01N 33/574 |

FOREIGN PATENT DOCUMENTS

| WO | 2003094859 | 11/2003 |
| WO | 2018231759 | 12/2018 |

OTHER PUBLICATIONS

Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Kussie et al. A single engineered amino acid substitution changes antibody fine specificity.J Immunol. Jan. 1, 1994;152(1):146-52. (Year: 1994).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding.PNAS Jan. 24, 2017 114(4) E486-E495;firstpublished Jan. 5, 2017. (Year: 2017).*
Annunziata, et al., "Phase 1, open-label study of MEDI-547 in patients with relapsed or refractory solid turmors", Invest New Drugs, 2013, vol. 31, pp. 77-84.
Ansuini, et al., "Anti-EphA2 Antibodies with Distinct In Vitro Properties Have Equal In Vivo Efficacy in Pancreatic Cancer", Journal of Oncology, vol. 2009, Article ID 951917, pp. 1-10.

(Continued)

*Primary Examiner* — Aurora M Fontainhas
*Assistant Examiner* — Jennifer A Benavides
(74) *Attorney, Agent, or Firm* — Goodwin Procter LLP

(57) ABSTRACT

Provided herein are EphA2 antibodies. These EphA2 antibodies bind preferentially to tumor tissue than normal tissue and bind to EphA2. Such antibodies are used in methods of inducing an immune response and methods of inhibiting tumor cell growth. Additionally provided are methods of producing such antibodies.

5 Claims, 64 Drawing Sheets

Specification includes a Sequence Listing.

(56) References Cited

OTHER PUBLICATIONS

Barquilla, et al., "Eph Receptors and Ephrins: Therapeutic Opportunities", Reviews in Advance, 2014, pp. 1-23.
Bennett, Gavin, "BT5528, an EphA2-targeting Bicycle Toxin Conjugate (BTC): Profound efficacy without bleeding and coagulation abnormalities in animal models", AACR Annual Meeting, 2019, Atlanta, Bicycle AACR, #4481, pp. 1-11.
Bennett, et al., "Bicycle Toxin Conjugates (BTCs) targeting EphA2 for the treatment of solid tumours: Discovery and election of BT5528", Bicycle Therapeutics, 2018, #5855.
Bennett, et al., "BT5528, an EphA2-targeting Bicycle Toxin Conjugate (BTC): profound efficacy withouth bleeding and coagulation abnormalities in animal models", Bicycle Therapeutics, 2019, #164.
Bennett, et al., "MMAR Delivery Using the Bicycle Toxin Conjugate", Mol Cancer Therapeutics, 2020, 19, pp. 1385-1394.
Boissier, et al., |EphA2 signalling following endocytosis: role of Tiam1, Traffic, 2013, 14 (12), pp. 1-30.
Shiuan, et al., "Tumor-specific EphA2 receptor tyrosine kinase inhibits anti-tumor immunity by recruiting suppressive myeloid populations in NSCLC", 2020, httpe://doi.org/10.1101/220.05.08.084830.
Singh, et al., "The EphA2 receptor is activated through induction of distinct, ligand-dependent oligomeric structures", Communications Biology, 2018.
Carles-Kinch, et al., "Antibody Targeting of the EphA2 Tyrosine Kinase INhibits Malignant Cell Behavior", Cancer Research 62, 2002, pp. 2840-2847.
Chavent, et al., "Interaction of the EphA2 Kinase Domain with PIPs in Membranes: Implications for Receptor Function", Structure, 26, pp. 1025-1034.
Chen et al., "Glycopeptides and Glycoproteins Indentified by Trypsin", Journal of Proteome Research, 2009.
Chen, et al. "EBV gH/gL and KSHV gH/gL bind to different sites on EphA2 to trigger fusion", JVI Accepted Manuscript, J. Virol, 2020.
Coffman, et al., "Differential EphA2 Epitope Display on Normal versus Malignant Cells", Cancer Research, 63, 2003, pp. 7907-7912.
Conejo-Garcia, et al., Breaking barriers for T cells by targeting the EPHA2/TGF-B/COX-s axis in pancreatic cancer:, The Journal of Clinical Investigation, 129 (9), 2019, pp. 3521-3523.
Damschroder, et al., "Framework shuffling of antibodies to reduce immunogenicity and manipulate functional and biophysical properties", Molecular Immunology, 44, 2007, pp. 3049-3060.
Eriksson, et al., "The Eph Tyrosine Kinase Receptors EphB2 and EphA2 are Novel Proteolytic Substrates of Tissue Factor/Coagulation Factor Vila", The Journal of Biological Chemistry, 280 (47), 2014, pp. 32379-32391.
Gambini, et al., "Structure-based design of novel EphA2 agonistic agents with nanomolar affinity in vitro and in cell", ACH Chemical Biology, 2018, pp. 1-41.
Giorgio, et al., "Ephrin or not? Six tough questions on Eph targeting", Expert Opinion on Therapeutic Targets, 2020.
Gomez-Soler, et al., "Engineering nanomolar peptide ligands that differetially modulate EphA2 receptor signaling", J. Biol. Chem., 294 (22), 2019, pp. 8791-8805.
Hammond et al., "Selective Targeting and Potent Control of Tumor Growth Using an EphA2/CD3-Bispecific Single-Chain Antibody Construct", Cancer Res, 2007, 67(8), pp. 3927-3935.
Himanen, et al., "Ligand Recognition by A-class Eph receptors: crystal structures of the EphA2 ligand-binding domain and the EphA2/ephrin-A1 complex", European Molecular Biology Organization, 10 (7), 2009, pp. 722-728.
Himanen, et al, Supporting Information, Proceedings of the National Academy of the United States of America, 2010. pnas. 1004148107, pp. 1-6.
Hsu, et al., "Chimeric Antigen Receptor-modified T cells targeting EphA2 for the immunotheraphy of paediatric bone tumours", Cancer Gene Therapy, 2020.
Huang, et al., "Formulation optimization of an eprin A2 targeted immunoliposome encapsulating reversibly modified taxane prodrugs", Journal of Controlled Release, 310, 2019, pp. 47-57.
Hughes, et al., "Harnessing the Power of Eph/ephrin Biosemiotics for Theranostic Applications", Pharmaceuticals, 13 (112), 2020, pp. 1-17.
Leguci, et al., "Roles of EphA1/A2 and ephrin-A1 in cancer", Cancer Science, 2019, 110, pp. 841-848.
Burvenich, et al., "Molecular Imaging and Quantitation of EphA2 Expression in Xenograft Models with 89Zr-DS-8895a", The Journal of Nuclear Medicine, vol. 57 (6), 2016, pp. 974-980.
Jackson et al., "A Human Antibody-Drug Conjugate Targeting EphA2 Inhibits Tumor Growth In vivo", Cancer Res, 2008, 68 (22), pp. 9367-9374.
Janes, et al., "Antibody Targeting of Eph Receptors in Cancer", Pharmaceuticals, 2020, 13 (88), pp. 1-14.
Kamoun, et al., "Targeting EphA2 in Bladder Cancer Using a Novel Antibody-Directed Nanotherapeutic", Pharmaceutics, 2020, 12, pp. 1-18.
Kiewlich, et al., "Anti-EphA2 Antibodies Decrease EphA2 Protein Levels in Murine CT26 Colorectal and Human MDAo-231 Breast Tumors But Do Not Inhibit Tumor Growth", Neoplasia, 8 (1), pp. 18-30.
Koshikawa, et al., "Proteolysis of EphA2 Converts It from a Tumor Suppressor to an Oncoprotein", American Associated for Cancer Research, 2015, 75 (06), pp. 3327-3329.
Kou, et al., "Differential Expression Patterns of Eph Receptors and Ephrin Ligands in Human Cancers", BioMed Research International, 2018, pp. 1-24.
Lee, et al., Interim Phase | Update on BT5528 and Preliminary Findings from BT8009 Program, Bicycle Therapeutics, 2021.
Li, et al., "Chimeric Antigen Receptor-Modified T Cells Redirected to EphA2 for the Immunotherapy of Non-Small Cell Lung Cancer", Translation Oncology, 11 , 2018, pp. 11-17.
Liang, et al., "Eph receptor signalling: from catalytic to non-catalytic functions", Oncogene, 2019, 38, pp. 6567-6584. pp.
Lodola, et al., "Targeting Eph/ephrin system in cancer therapy", European Journal of Medicinal Chemistry, 2017.
London, et al., "The EphA2 and cancer connection: potential for immune-based interventions", Molecular Biology Reports, 2020.
Markosyan, et al., "Tumor cell-intrinsic EPHA2 suppresses antitumor immunity by regulating PTGS2 (COX-2)", The Journal of Clinical Investigation, 129 (9), 2019, pp. 3594-3609.
Mudd, et al., "Identification and Optimization of EphA2-Selective Bicycles for the Delivery of Cytotoxic Payloads", The Journal of Medicinal Chemistry, 2020, pp. 4107-4116.
Oganesyan, et al., "Crystallization and preliminary X-ray diffraction analysis of the complext of a human anti-ephrin type-A receptor 2 antibody fragment and its cognate antigen", ACTA Cryst, 2010, F66, pp. 730-733.
Rezai, et al., "A new scfv-based recombinant immunotoxin against EPHA2-overexpressing breast cancer cells; High in vitro anti-cancer potency", European Journal of Pharmacology, 820, 2020, 172912.
Rezale, et al., Bioinformatics Predictions, Expression, Purification and Structural Analysis of the PE38KDEL-scfv Immunotoxin Against EPHA2 Receptor, International Journal of Peptide Research and Therapeutics, 2019.
Saha, et al., "Therapeutic potential of targeting the Eph/ephrin signalin", The International Journal of Biochemistry & Cell Biology, 2018.
Sahoo, et al., "Structural and Functional Insights into the Transmembrane Domain Association of Eph Receptors", International Journal of Molecular Sciences, 2021, 22, 8593.
Sakamoto, et al., "An Agonistic Antibody to EPHA2 Exhibits Antitumor Effects on Human Melanoma Cells", Anticancer Research, 38, 2018, pp. 3273-3282.
Seiradake, et al., "An extracellular steric seeding mechanism for Eph-ephrin signaling platform assembly", Nature Structural and Molecular Biology, 17 (4), 2010, pp. 399-403.
Chavent, et al., "Structures of the EphA2 Receptor at the Membrane: Role of Lipid Interactions", Structure, vol. 24, No. 2, Feb. 2, 2016, pp. 337-347.

(56) References Cited

OTHER PUBLICATIONS

PCT/US2022/019033, "International Search Report and Written Opinion", Aug. 12, 2022, 15 pages.
Geddie et al., MAbs. Jan. 2017; 9(1): 58-67.
Hasegawa J. et al., Cancer Biol Ther. Nov. 2016; 17(11):1158-1167. doi: 10.1080/15384047.2016.1235663. Epub Sep. 21, 2016.
Kamoun et al., Nat Biomed Eng. Apr. 2019;3(4):264-280, doi: 10.1038/s41551-019-0385-4. Epub Apr. 5, 2019.), Abstract.
Peng, L., et.al, (2011) J Mol Biol 413: 390-405.
Shitara K. et al., J Immunother Cancer, Aug. 14, 2019;7(1):219. doi: 10.1186/s40425-019-0679-9.
Ullman, et al., "High Affinity Binders to EphA2 Isolated from Abdurin Scaffold Libraries; Characterization, Binding and Tumor Targeting", PLOS One, 2015, pp. 1-25.
Takasugi, et al., "Small extracellular vesicles secreted from senescent cells promote cancer cell proliferation through EphA2", Nature Communications, 2017, pp. 1-11.
Upadhyaya, et al., "Anticancer immunity induced by a synthetic tumor-targeted CD137 agonist", Journal of Immuno Theraphy of Cancer.
Walker-Daniels, et al. "c-Cbl-Dependent EphA2 Protein Degradation Is Induced by Ligand Binding", Molecular Cancer Research, vol. 1, 2002, pp. 79-87.
Wesa, et al., "Ehancement in Specific CD8 T Cell Recognialion of EphA2 Tumors in Vitro and In Vivo after Treatment with Ligand Agonists", The Journal of Immunology, 2008, 181, pp. 7721-7727.
Xiao, et al., "Targeting EphA2 in cancel", Journal of Hermatology & Oncology, 2020, 13:114.
Zhou et al., "Internalizing cancer antibodies from phage libraries selected on tumor cells and yeast displayed tumor antigens", J Mol Biol, 2010, pp. 88-99.

\* cited by examiner

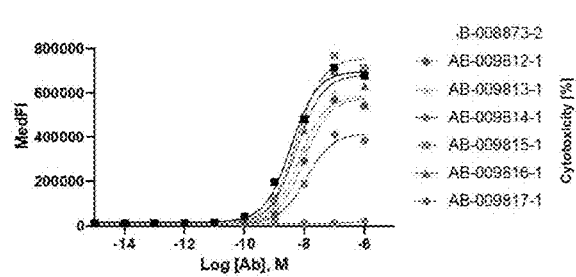
FIG. 21A
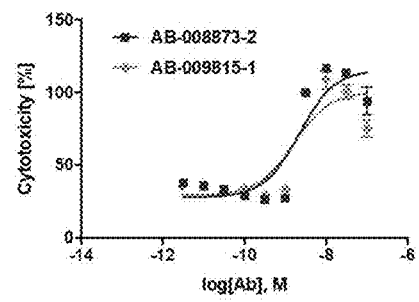
FIG. 21B
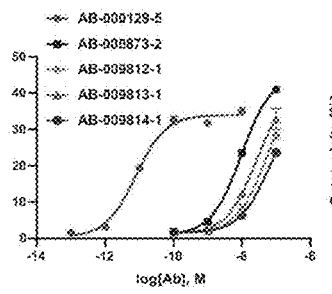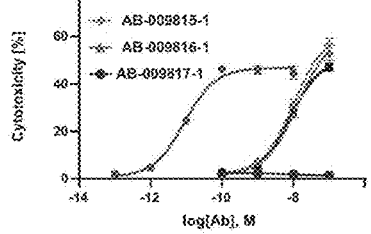
FIG. 21C

IHC score of 8873 and variants on 21 types of FF human tumor and TAT
- compared with clinical candidate EphA2 antibodies and commercial EphA2 Abs

FIG. 24A

Normal Stomach

VL CDRs

FIG. 39D

| A8-008873: Tm1 = 64.8 | | 10357 Average Tm1 (°C) | 10361 Average Tm1 (°C) | 10363 Average Tm1 (°C) |
|---|---|---|---|---|
| | Mutations | | | |
| | Parent | 64.8 | 64.7 | 66.0 |
| | H107TI_L23GR | 66.7 | 65.5 | 66.5 |
| | L23GR_L29SY | 64.7 | 65.5 | 66.4 |
| | L23GR_L30KM | 64.5 | 64.7 | 67.0 |
| | L23GR_L92SH | 64.4 | 64.1 | 65.8 |
| | H107TI_L29SY | 64.3 | 63.6 | 65.8 |
| | L29SY_L30KM | 64.5 | 63.9 | 65.7 |
| | L29SY_L92SH | 64.0 | 64.4 | 65.9 |
| | H107TI_L30KM | 64.5 | 64.4 | 66.8 |
| | L30KM_L92SH | 64.5 | 64.2 | 66.5 |
| | H107TI_L92SH | 65.0 | 64.4 | 66.3 |
| | H107TI_L29SY_L92SH | 64.9 | 64.2 | 66.4 |
| | L93SR | 64.7 | 65.2 | 66.8 |
| | L93SE | 65.3 | 64.9 | 67.3 |
| | L29SY_L93SE | 64.9 | 64.5 | 66.7 |

Epitope is conserved across tox species (mouse, rat, cyno)

| All FN2 Divergence | 446 | 455 | 460 | 461 | 479 | 485 | 488 | 496 | 500 | 529 | 533 | 534 |
|---|---|---|---|---|---|---|---|---|---|---|---|---|
| EphA2_FL(1-976) | G | S | P | P | S | R | E | D | D | P | G | N |
| cyEphA2_FL(1-976) | G | S | P | P | S | R | E | D | D | P | G | S |
| muEphA2_FL(1-977) | D | T | V | S | A | R | E | D | D | T | A | N |
| raEphA2_FL(1-977) | D | A | V | P | A | H | D | G | G | T | A | T |

| Epitope | 439 | 441 | 443 | 444 | 447 | 476 | 477 | 504 | 506 | 519 | 520 | 521 | 522 | 523 | 524 | 525 |
|---|---|---|---|---|---|---|---|---|---|---|---|---|---|---|---|---|
| EphA2_FL(1-976) | P | K | R | L | R | K | G | L | Q | S | K | V | H | E | F | Q |
| muEphA2_FL(1-977) | P | K | R | L | R | K | G | L | Q | S | K | V | H | E | F | Q |
| cyEphA2_FL(1-976) | P | K | R | L | R | K | G | L | Q | S | K | V | H | E | F | Q |
| raEphA2_FL(1-977) | P | K | R | L | R | K | G | L | Q | S | K | V | H | E | F | Q |

EphA2-IL15

In Vivo TGI/R with *Unoptimized* 8873 Fv

EphA2-41BB

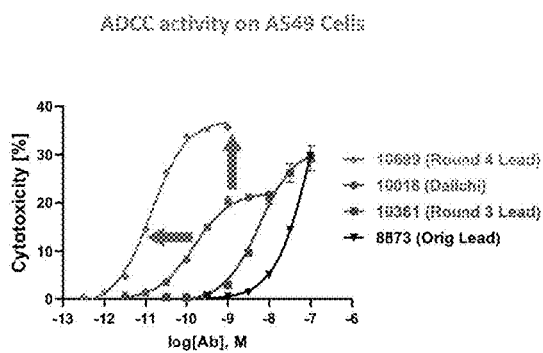 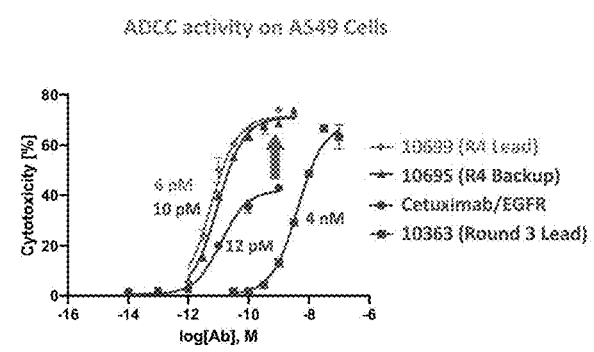
FIG. 50A                                FIG. 50B

EPHA2 ANTIBODIES

RELATED APPLICATIONS

This application claims priority to U.S. Provisional Application No. 63/157,320, filed on Mar. 5, 2021, and U.S. Provisional Application No. 63/298,093, filed on Jan. 10, 2022. The entire content of said provisional applications are incorporated herein by reference for all purposes.

SEQUENCE LISTING

The instant application contains a Sequence Listing which has been submitted electronically in ASCII format and is hereby incorporated by reference in its entirety. Said ASCII copy, created on Apr. 14, 2022, is named 097519-1305354_(2900US)_SL.txt and is 567,652 bytes in size.

FIELD OF CANCER THERAPEUTICS

This application relates to therapeutic antibodies for the treatment of various cancers.

BACKGROUND

EphA2 is a tyrosine kinase and belongs to the family of Ephrin receptors. Like other Ephrin receptors, it is a single-pass membrane protein with a large extracellular N-termini. EphA2 is typically involved in cell-cell repulsion or adhesion processes. EphA2 is also known to promote angiogenesis. EphA2 is overexpressed in tumor tissues as compared to normal adult tissues, indicating its potential application in cancer treatment. Although a number of EphA2 antibodies have been developed, some of which are being assessed in clinical trials, these antibodies have the shortcomings of high toxicity, insufficient efficacy, or both, and are unable to meet the needs of cancer patients.

BRIEF SUMMARY

Provided herein is an isolated antibody that binds to ephrin receptor A2 (EphA2).

In some embodiments, the antibody binds to an epitope of EphA2 located in the FN2 domain of EphA2, wherein the FN2 domain has the sequence of (SEQ ID NO: 95)
TEPPKVRLEGRSTTSLSVSWSIPPPQQSRVWKYEVTYRKKGDSNSYNVRR

TEGFSVTLDDLAPDTTYLVQVQALTQEGQGAGSKVHEFQTLSPEGSGN.

In some embodiments, the epitope comprises at least one, at least two, at least three, at least four, at least five, or at least six, at least seven, at least eight, or at least nine, or all ten of amino acid residues Leu444, Arg447, Lys476, Gln506, Ser519, Lys520, Val521, Glu523, Phe524, and Gln525 of SEQ ID NO: 94.

In some embodiments, the antibody has one or more properties of: a) activates the ephrin A1-EphA2 signaling axis at least 95%, 90%, 85%, or 80% less than ephrin-A1 activates the ephrin A1-EphA2 signaling axis, b) binds preferentially to a tumor tissue than normal tissue, c) has an EC50 for activation of the ephrinA1-EphA2 signaling axis that is at least 10-, 20-, 50-, 100-, 200-, 500-fold less potent than the ADCC EC50 of the antibody; and/or d) has ADCP activity, and e) has ADCC activity.

In some embodiments, the antibody binds to a polypeptide comprising a sequence of TEPPKVRLEGRSTTSLSVSWSIPPPQQSRVWKYEVTYRKKGDSNSYNVRRTEGFSVTLDDLAPDTTYLVQVQALTQEGQGAGSKVHEFQTLSPEGSGN (SEQ ID NO: 95) and wherein the antibody binds preferentially to a tumor tissue than normal tissue. In some embodiments, the polypeptide has a sequence of SEQ ID NO: 94.

In some embodiments, the antibody disclosed herein binds to a tumor tissue preferentially compared to a normal tissue.

In some embodiments, the antibody comprises a heavy chain variable region comprising: an HCDR1 of any one of SEQ ID NOS: 1-11 and 201-265 or a variant thereof in which 1, 2, 3, 4, or 5 amino acids are substituted relative to the sequence; an HCDR2 of any one of SEQ ID NOS: 12-22 and 266-330 or a variant thereof in which 1, 2, 3, 4, or 5 amino acid is substituted relative to the sequence; and an HCDR3 of any one of SEQ ID NOS: 23-33 and 331-395 or a variant thereof in which 1, 2, 3, 4, or 5 amino acids are substituted relative to the sequence; a light chain variable region comprising: an LCDR1 of any one of SEQ ID NOS: 34-44 and 396-460 or a variant thereof in which 1, 2, 3, 4, or 5 amino acid is substituted relative to the sequence; an LCDR2 of any one of SEQ ID NOS: 45-55 and 461-525 or a variant thereof in which 1, 2, or 3 amino acid is substituted relative to the sequence; and an LCDR3 of any one of SEQ ID NOS: 56-66 and 526-590 or a variant thereof in which 1, 2, 3, 4, or 5 amino acid is substituted relative to the sequence.

In some embodiments, the antibody comprises: a heavy chain variable region comprising: an HCDR1 comprising a sequence (SEQ ID NO:1), or a variant HCDR1 in which 1, 2, 3, 4, or 5 amino acids are substituted relative to the sequence; an HCDR2 comprising a sequence (SEQ ID NO:12), or a variant HCDR2 in which 1, 2, 3, 4, or 5 amino acid is substituted relative to the sequence; and an HCDR3 comprising a sequence (SEQ ID NO:23), or a variant HCDR3 in which 1, 2, 3, 4, or 5 amino acids are substituted relative to the sequence. The antibody further comprises a light chain variable region comprising: an LCDR1 comprising a sequence (SEQ ID NO:34), or a variant LCDR1 in which 1, 2, 3, 4, or 5 amino acid is substituted relative to the sequence; an LCDR2 comprising a sequence (SEQ ID NO:45), or variant LCDR2 in which 1, 2, or 3 amino acid is substituted relative to the sequence; and an LCDR3 comprising a sequence (SEQ ID NO:56), or a variant LCDR3 in which 1, 2, 3, 4, or 5 amino acid is substituted relative to the sequence.

In some embodiments, the antibody comprises: (a) an HCDR1 sequence of GGSX$_1$X$_2$X$_3$YX$_4$WS where X$_1$ is F or L, X$_2$ is S or N, and X$_3$ is D or G, and X$_4$ is Y or H (SEQ ID NO: 769); (b) an HCDR2 sequence of EX$_1$NHX$_2$GSX$_3$X$_4$YNNYNPSLKS, where X$_1$ is I or V, X$_2$ is A, Q, R or S, X$_3$ is I or T, and X$_4$ is N or S (SEQ ID NO: 770); (c) an HCDR3 sequence of AKPX$_1$RPHCX$_2$NGVCX$_3$SGDAFDI, where X$_1$ is L or F, X$_2$ is I or T; and X$_3$ is Y or S (SEQ ID NO: 771); (d) an LCDR1 sequence of X$_1$GNNIGX$_2$X$_3$X$_4$VH, where X; is G or R, X$_2$ is S, T, or Y, X$_3$ is K or M, and X$_4$ is N or S (SEQ ID NO: 772); (e) an LCDR2 sequence of DDSDRPS (SEQ ID NO: 45); and (f) an LCDR3 sequence of QVWDX1 X2SDHX3V, where X1 is H or S, X2 is E, R, or S, and X3 is L or V (SEQ ID NO: 773).

In some embodiments, the antibody comprises: (a) an HCDR1 sequence of GGSX$_1$X$_2$X$_3$YX$_4$WS where X$_1$ is F or L, $X_2$ is S or N, and $X_3$ is D or G, and $X_4$ is Y or H (SEQ ID NO: 769); (b) an HCDR2 sequence of $EX_1NHX_2GSX_3X_4YNPSLKS$, where $X_1$ is I or V, $X_2$ is A, Q, R or S, $X_3$ is I or T, and $X_4$ is N or S (SEQ ID NO: 774); (c) an HCDR3 sequence of $AKPX_1RPHCX_2NGVCX_3SGDAFDI$, where $X_1$ is L or F, $X_2$ is I or T; and $X_3$ is Y or S; (SEQ ID NO: 771) (d) an LCDR1 sequence of $X_1GNNIGX_2X_3X_4VH$, where $X_1$ is G or R, $X_2$ is S, T, or Y, $X_3$ is K or M, and $X_4$ is N or S (SEQ ID NO: 772); (e) an LCDR2 sequence of DDSDRPS (SEQ ID NO: 45); and (f) an LCDR3 sequence of QVWDX1 X2SDHX3V, where X1 is H or S, X2 is E, R, or S, and X3 is L or V (SEQ ID NO: 773).

In some embodiments, the antibody comprises: (a) an HCDR1 sequence of GGSX1X2DYX3WS where X1 is F or L, X2 is S or N, and X3 is Y or H (SEQ ID NO: 775); (b) an HCDR2 sequence of EX1NHX2 GS X3 X4YNPSLKS, where X1 is I or V, X2 is R or S, X3 is I or T, and X4 is N or S (SEQ ID NO: 776); or an HCDR2 sequence of EX1NHX2 GS X3 X4YNNYNPSLKS, where X1 is I or V, X2 is R or S, X3 is I or T, and X4 N or S (SEQ ID NO: 777); and (c) an HCDR3 sequence of AKP X1RPHCTNGVCX2SGDAFDI, where X1 is L or F and X2 is Y or S (SEQ ID NO: 778); (d) an LCDR1 sequence of GGNNIGX1KNVH, where X1 is S or T (SEQ ID NO: 779); (e) an LCDR2 sequence DDSDRPS (SEQ ID NO: 45); and (f) an LCDR3 sequence QVWDSSSDHLV (SEQ ID NO: 56).

In some embodiments, the antibody comprises a $V_H$ comprising an amino acid sequence having at least 95% identity to a $V_H$ in Table 8; and a $V_L$ comprising an amino sequence having at 95% identity to a $V_L$ in Table 8. In some embodiments, the $V_H$ comprises an amino acid sequence having at least 95% identity to (SEQ ID NO: 67); and the $V_L$ comprises an amino sequence having at 95% identity to (SEQ ID NO: 78). In some embodiments, the $V_H$ comprises an amino acid sequence having at least 95% identity to a $V_H$ of any one of SEQ ID NOS: 67-77 and 591-655; and the $V_L$ comprises an amino sequence having at 95% identity to a $V_L$ of any one of SEQ ID NOS: 78-88 and 656-720.

In some embodiments, the antibody comprises: a VH region comprising amino acid sequence SEQ ID NO:67 and a VL region comprising amino acid sequence SEQ ID NO:78; a VH region comprising amino acid sequence SEQ ID NO:68 and a VL region comprising amino acid sequence SEQ ID NO:79; a VH region comprising amino acid sequence SEQ ID NO:69 and a VL region comprising amino acid sequence SEQ ID NO:80; a VH region comprising amino acid sequence SEQ ID NO:70 and a VL region comprising amino acid sequence SEQ ID NO:81; a VH region comprising amino acid sequence SEQ ID NO:71 and a VL region comprising amino acid sequence SEQ ID NO:82; a VH region comprising amino acid sequence SEQ ID NO:72 and a VL region comprising amino acid sequence SEQ ID NO:83; a VH region comprising amino acid sequence SEQ ID NO:73 and a VL region comprising amino acid sequence SEQ ID NO:84; a VH region comprising amino acid sequence SEQ ID NO:74 and a VL region comprising amino acid sequence SEQ ID NO:85; a VH region comprising amino acid sequence SEQ ID NO:75 and a VL region comprising amino acid sequence SEQ ID NO:86; or a VH region comprising amino acid sequence SEQ ID NO:76 and a VL region comprising amino acid sequence SEQ ID NO:87; a VH region comprising amino acid sequence SEQ ID NO:77 and a VL region comprising amino acid sequence SEQ ID NO:88, a VH region comprising amino acid sequence SEQ ID NO:652 and a VL region comprising amino acid sequence SEQ ID NO:717, or a VH region comprising amino acid sequence SEQ ID NO:607 and a VL region comprising amino acid sequence SEQ ID NO: 672.

In some embodiments, antibody comprises: (1) a heavy chain variable (VH) region and a light chain variable (VL) region, wherein: (a) the VH region has at least 70% identity to SEQ ID NO: 67; and comprises a CDR1 of SEQ ID NO:1, or the CDR1 of SEQ ID NO: 1 in which 1, 2, 3, 4, or 5 amino acids are substituted; a CDR2 of SEQ ID NO: 12, or the CDR2 of SEQ ID NO: 12 in which 1, 2, 3, 4, or 5 amino acids are substituted; a CDR3 of SEQ ID NO:23 or the CDR3 of SEQ ID NO:23 in which 1, 2, 3, 4, or 5 are substituted; and (b) the VL region has at least 70% identity to SEQ ID NO: 78, and comprises a CDR1 of SEQ ID NO:34 or the CDR1 of SEQ ID NO:34 in which 1, 2, 3, 4, or 5 amino acids are substituted; a CDR2 of SEQ ID NO:45, or the CDR2 of SEQ ID NO:45 in which 1, 2, 3, 4, or 5 amino acids are substituted; a CDR3 of SEQ ID NO:56 or the CDR3 of SEQ ID NO:56 in which 1, 2, 3, 4, or 5 are substituted; (2) a heavy chain variable (VH) region and a light chain variable (VL) region, wherein:
  (a) the VH region has at least 70% identity to SEQ ID NO:652; and comprises a CDR1 of SEQ ID NO: 262, or the CDR1 of SEQ ID NO:262 in which 1, 2, 3, 4, or 5 amino acids are substituted; a CDR2 of SEQ ID NO:327, or the CDR2 of SEQ ID NO:327 in which 1, 2, 3, 4, or 5 amino acids are substituted; a CDR3 of SEQ ID NO:392 or the CDR3 of SEQ ID NO:392 in which 1, 2, 3, 4, or 5 are substituted; and (b) the VL region has at least 70% identity to SEQ ID NO: 717, and comprises a CDR1 of SEQ ID NO:457 or the CDR1 of SEQ ID NO:457 in which 1, 2, 3, 4, or 5 amino acids are substituted; a CDR2 of SEQ ID NO:522, or the CDR2 of SEQ ID NO: 522 in which 1, 2, 3, 4, or 5 amino acids are substituted; a CDR3 of SEQ ID NO:587 or the CDR3 of SEQ ID NO:587 in which 1, 2, 3, 4, or 5 are substituted; or
  (3) a heavy chain variable (VH) region and a light chain variable (VL) region, wherein: (a) the VH region has at least 70% identity to SEQ ID NO:607; and comprises a CDR1 of SEQ ID NO: 217, or the CDR1 of SEQ ID NO:217 in which 1, 2, 3, 4, or 5 amino acids are substituted; a CDR2 of SEQ ID NO:282, or the CDR2 of SEQ ID NO:282 in which 1, 2, 3, 4, or 5 amino acids are substituted; a CDR3 of SEQ ID NO:347 or the CDR3 of SEQ ID NO:347 in which 1, 2, 3, 4, or 5 are substituted; and (b) the VL region has at least 70% identity to SEQ ID NO: 672, and comprises a CDR1 of SEQ ID NO:412 or the CDR1 of SEQ ID NO:412 in which 1, 2, 3, 4, or 5 amino acids are substituted; a CDR2 of SEQ ID NO:477, or the CDR2 of SEQ ID NO:477 in which 1, 2, 3, 4, or 5 amino acids are substituted; a CDR3 of SEQ ID NO:542 or the CDR3 of SEQ ID NO:542 in which 1, 2, 3, 4, or 5 are substituted.

In some embodiments, the antibody comprises an HCDR1, HCDR2, HCDR3, LCDR1, LCDR2, and LCDR3 of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702, or a variant thereof in which at least one, two, three, four, five, or all six of the CDRs contain 1 or 2 amino acid substitutions compared to the corresponding CDR.

In some embodiments, the antibody comprises a heavy chain variable region and a light chain variable region of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702, or a variant thereof, wherein the variant comprises a heavy chain variable region having a sequence that is at least 95% identical to that of the corresponding heavy chain variable region and a light chain variable region having a sequence that is at least 95% identical to the corresponding light chain variable region.

In some embodiments, the at least 1 or 2 of the substitutions referenced above are conservative substitutions and at least 50% of the substitutions are conservative substitutions. In some embodiments, all of the substitutions are conservative substitutions.

In some embodiments, disclosed herein is an antibody that binds to the same epitope as the antibody of the EPHA2 antibody disclosed herein. In some embodiments, the antibody competes for binding with any one of the EPHA2 antibody disclosed herein.

In some embodiments, disclosed herein is an antibody comprising a VH region of any one of SEQ ID NO 67-77 and 591-655, and/or a VL region of any one of SEQ ID NO: 78-88 and 656-720, or an antibody comprising a VH region with at least 80% identity to any one of SEQ ID NO 67-77 and 591-655 and a VL region having at least 80% identity to any one of SEQ ID NO: 78-88 and 656-720, with variations to the corresponding VH or VL regions present only in Framework regions.

In some embodiments, disclosed herein an antibody comprising an HCDR1 of any one of SEQ ID NOS: 1-11, and 201-265, an HCDR2 of any one of SEQ ID NOS: 12-22 and 266-330, an HCDR3 of any one of SEQ ID NOS: 23-33 and 331-395, an LCDR1 of any one of SEQ ID NOS: 34-44 and 396-460, an LCDR2 of any one of SEQ ID NOS: 45-55 and 461-525, an LCDR3 of any one of SEQ ID NOS: 56-66 and 526-590, wherein the FW regions in the VH region are at least 80% identical to the FW regions present in the VH region of SEQ ID NO 67-77 and 591-655, and wherein the FW regions in the VL region are at least 80% identical to the FW regions present in the VL region of SEQ ID NO: 78-88 and 656-720.

In some embodiments, the antibody is a non-natural antibody.

In some embodiments, the antibody is a bispecific antibody comprising two antigen binding fragments, one binding to EphA2, and the other binds to a different antigen. In some embodiments, the different antigen is 4-1bb or CD3.

Also provided herein is an immunoconjugate comprising the antibody disclosed herein and a cytotoxic agent. Also provided herein is an immunoconjugate comprising the antibody disclosed herein and one or more of an IL-15 receptor agonist, a TGFβ trap, a TLR agonist, or a 4-1BB ligand (4-1BBL).

Also provided in this disclosure is an immunoconjugate comprising any one of the antibodies disclosed herein and a cytotoxic agent. In some embodiments, the immunoconjugate comprises any one of the antibodies disclosed herein and an IL-15 receptor agonist, a TGFβ trap, a TLR agonist, a 4-1BB ligand (4-1BBL), or an agonist anti-4-1BB antibody.

Also provided in this disclosure is an expression vector comprising a polynucleotide encoding the $V_H$ region and/or the $V_L$ region of any one of the antibodies disclosed herein. Also provided herein is a recombinant nucleic acid encoding an antibody disclosed herein.

Also provided in this disclosure is a polypeptide comprising (1) a VH sequence having at least 70% amino acid sequence identity to SEQ ID NO: 67 and/or (2) a VL sequence having at least 70% amino acid sequence identity to SEQ ID NO: 78.

Also provided in this disclosure is a polypeptide comprising (1) a VH sequence having at least 70% amino acid sequence identity to SEQ ID NO: 652 and/or (2) a VL sequence having at least 70% amino acid sequence identity to SEQ ID NO: 717

Also provided in this disclosure is a polypeptide comprising (1) a VH sequence having at least 70% amino acid sequence identity to SEQ ID NO: 607 and/or (2) a VL sequence having at least 70% amino acid sequence identity to SEQ ID NO: 672.

A polynucleotide encoding any of the polypeptide disclosed herein.

Also provided in this disclosure is a host cell that comprises an expression vector disclosed herein or a host cell comprising a polynucleotide that encodes the $V_H$ region and/or the $V_L$ region of any one of the antibodies disclosed herein.

Also provided in this disclosure is a pharmaceutical composition comprising any one of the antibodies disclosed herein and a pharmaceutically acceptable carrier.

Also provided in this disclosure is a method of inducing an immune response and/or treating cancer, the method comprising administering any one of the antibodies disclosed herein. In some embodiments, the immune response comprises an antibody-dependent cellular cytotoxicity (ADCC) and/or antibody dependent cellular phagocytosis (ADCP). In some embodiments, the antibody is administered intravenously.

Also provided in this disclosure is a method of treating a cancer patient having a tumor overexpressing EphA2, the method comprising administering any one of the antibodies disclosed herein to the patient. In some embodiments, the cancer is a gastric cancer, ovarian cancer, soft tissue sarcoma, lung cancer, head and neck cancer, uterine cancer, breast cancer, colorectal cancer, esophageal cancer, stomach cancer, kidney cancer, melanoma, liver cancer, bladder cancer, or testicular cancer. In some embodiments, the cancer is non-small cell lung cancer, triple negative breast cancer, colorectal cancer, ovarian cancer or melanoma. In some embodiments, the antibody is administered intravenously. In some embodiments, the method further comprises administering chemotherapy and/or radiation therapy. In some embodiments, the method comprises administering an agent that targets an immunological checkpoint antigen. In some embodiments, the agent is a monoclonal antibody. In some embodiments, the monoclonal antibody blocks PD-1 ligand binding to PD-1. In some embodiments, the monoclonal antibody is an anti-PD-1 antibody.

Also provided in this disclosure is a method of identifying a patient having a tumor overexpressing EphA2, wherein the method comprises contacting a tumor sample from the patient with any one of the antibodies disclosed herein and detecting binding of the antibody to the tumor sample, wherein detection of the binding indicates the patient having a tumor overexpressing EphA2. In some embodiments, the tumor is a lung cancer, a head and neck cancer, or a uterine cancer. In some embodiments, the method further comprises administering the antibody to treat the tumor. In some embodiments, the tumor is selected from a gastric cancer, ovarian cancer, soft tissue sarcoma, lung cancer, head and neck cancer, uterine cancer, breast cancer, colorectal cancer, esophageal cancer, stomach cancer, kidney cancer, melanoma, liver cancer, bladder cancer, or testicular cancer.

Also provided in this disclosure is a method of producing an antibody, the method comprising culturing a host cell as disclosed above under conditions in which the polynucleotide encoding the heavy chain and the polynucleotide encoding the light chain are expressed.

Also provided in this disclosure is a method of identifying an antibody having tumor-targeting activity, the method comprising mutagenizing a polynucleotide encoding a $V_H$ or a $V_L$ CDR3 of with any one of the antibodies disclosed herein, expressing an antibody comprising the mutagenized $V_H$ or $V_L$ CDR3; and selecting an antibody that inhibits tumor growth or decreases tumor size, tumor invasion, and/or metastasis in vivo.

Also provided in this disclosure is a use of any one of the antibodies disclosed herein for a method of inducing an immune response in vivo or for a method of treating cancer. In some embodiments, the cancer is a gastric cancer, ovarian cancer, soft tissue sarcoma, lung cancer, head and neck cancer, uterine cancer, breast cancer, colorectal cancer, esophageal cancer, stomach cancer, kidney cancer, melanoma, liver cancer, bladder cancer, or testicular cancer. In some embodiments, the cancer is non-small cell lung cancer, triple negative breast cancer, colorectal cancer, ovarian cancer or melanoma.

BRIEF DESCRIPTION OF THE DRAWINGS

FIG. 21A-C show the functional activity of engineered AB-008873 variants: flow binding, ADC activity and ADCC activity, respectively.

FIGS. 24A and 24B shows the reactivity of EphA2 antibodies across a panel of human cancer samples.

FIG. 39A-D show alignments and CDR designations for various EphA2 antibodies. FIG. 39A-D discloses SEQ ID NOS 67-88, 67, 75, 598, 603, 607, 609, 652, 78, 86, 663, 668, 672, 674, and 717, respectively, in order of appearance.

FIG. 45 discloses SEQ ID NOS 783-827 and 829-838, respectively, in order of appearance.

FIG. 46 shows the alignment of the epitope residues across multiple species: human, cynomolgus monkey ("cyno"), mouse, and rat. FIG. 46 discloses SEQ ID NOS 839-841 and 828, respectively, in order of appearance.

FIG. 50A compares the cytotoxicity of AB-008873, AB-010361, AB-010699, and AB-010018 on A549 cells.

FIG. 50B compares the cytotoxicity of AB-010699, AB-010695, AB-010363, AB-010699, and Cetuximab on A549 cells.

DETAILED DESCRIPTION

Figure 1:
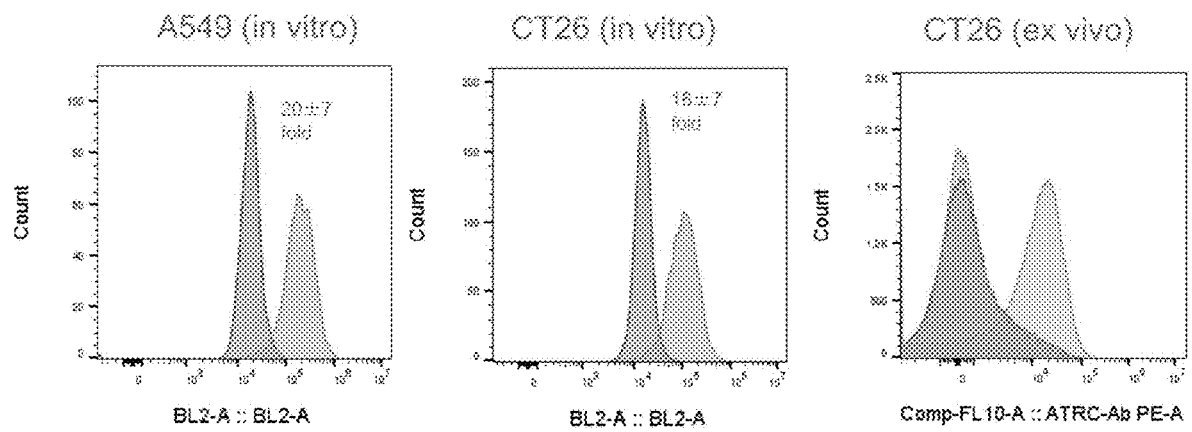
FIG. 1 shows surface binding profile of AB-008873 in A549 cells and CT26 cells (in vitro and ex vivo).

As used in herein, the singular forms "a", "an" and "the" include plural referents unless the content clearly dictates otherwise. Thus, for example, reference to "an antibody" optionally includes a combination of two or more such molecules, and the like.

The term "about" as used herein refers to the usual error range for the respective value readily known to the skilled person in this technical field, for example ±20%, ±10%, or ±5%, are within the intended meaning of the recited value.

As used herein, the term "antibody" means an isolated or recombinant binding agent that comprises the necessary variable region sequences to specifically bind an antigenic epitope. Therefore, an "antibody" as used herein is any form of antibody of any class or subclass or fragment thereof that exhibits the desired biological activity, e.g., binding a specific target antigen. Thus, it is used in the broadest sense and specifically covers a monoclonal antibody (including full-length monoclonal antibodies), human antibodies, chimeric antibodies, nanobodies, diabodies, multispecific antibodies (e.g., bispecific antibodies), and antibody fragments including but not limited to scFv, Fab, and the like so long as they exhibit the desired biological activity.

"Antibody fragments" comprise a portion of an intact antibody, for example, the antigen-binding or variable region of the intact antibody. Examples of antibody fragments include Fab, Fab', F(ab')₂, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')₂ fragment that has two antigen combining sites and is still capable of cross-linking antigen.

As used herein, the term "targets a tumor," or "tumor-targeting," with respect to an antibody, refers to an antibody that binds preferentially to a tumor tissue than normal tissue. In some embodiments, the normal tissue is the tissue that is adjacent to the tumor, referred to as tumor-adjacent tissue or TAT. In some embodiments, a tumor targeting antibody also decreases the rate of tumor growth, tumor size, invasion, and/or metastasis, via direct or indirect effects on tumor cells.

As used herein, "V-region" refers to an antibody variable region domain comprising the segments of Framework 1, CDR1, Framework 2, CDR2, and Framework 3, including CDR3 and Framework 4. The heavy chain V-region, $V_H$, is a consequence of rearrangement of a V-gene (HV), a D-gene (HD), and a J-gene (HJ), in what is termed V(D)J recombination during B-cell differentiation. The light chain V-region, $V_L$, is a consequence of rearrangement of a V-gene (LV) and a J-gene (LJ).

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3, numbered sequentially starting from the N-terminus, and are also identified by the chain in which the particular CDR is located. Thus, for example, a $V_H$ CDR3 (HCDR3) is located in the variable domain of the heavy chain of the antibody in which it is found, whereas a $V_L$ CDR3 (LCDR3) is the CDR3 from the variable domain of the light chain of the antibody in which it is found. The term "CDR" is used interchangeably with "HVR" in this application when referring to CDR sequences.

The amino acid sequences of the CDRs and framework regions can be determined using various well-known definitions in the art, e.g., Kabat, Chothia, international ImMunoGeneTics database (IMGT), and AbM (see, e.g., Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human $V_H$ segments J. Mol. Biol. 227, 799-817; Al-Lazikani et al., J. Mol. Biol. 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996). Reference to CDRs as determined by Kabat numbering are based, for example, on Kabat et al., Sequences of Proteins of Immunological Interest, 5$^{th}$ Ed. Public Health Service, National Institute of Health, Bethesda, MD (1991)). Chothia CDRs are determined as defined by Chothia (see, e.g., Chothia and Lesk J. Mol. Biol. 196:901-917 (1987)).

Figure 39A:
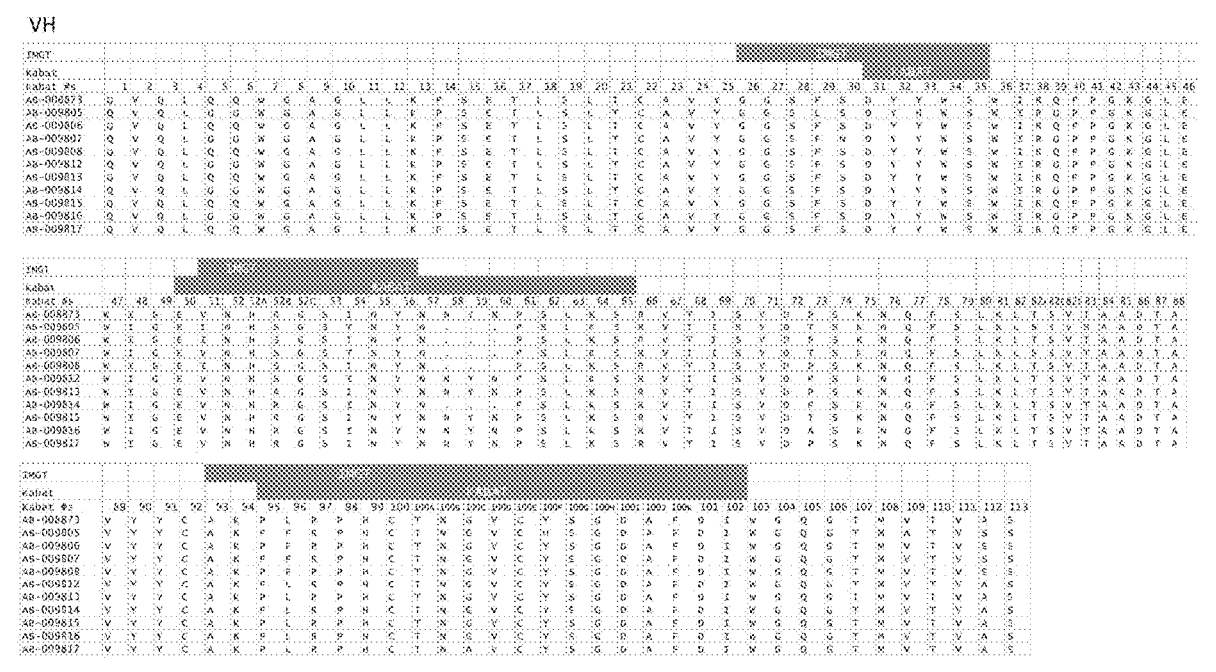
Figure 39B:
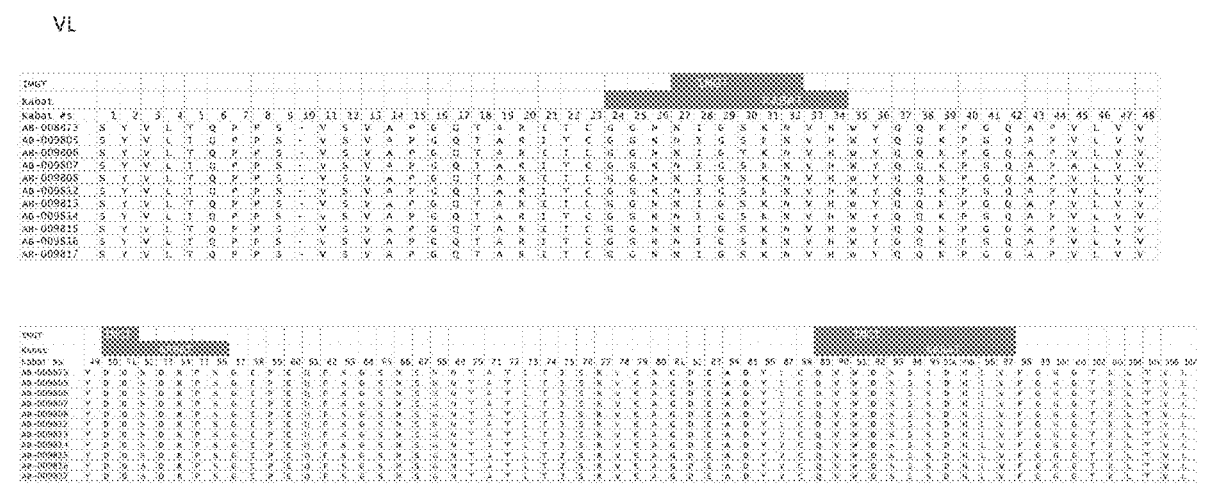
Figure 39C:
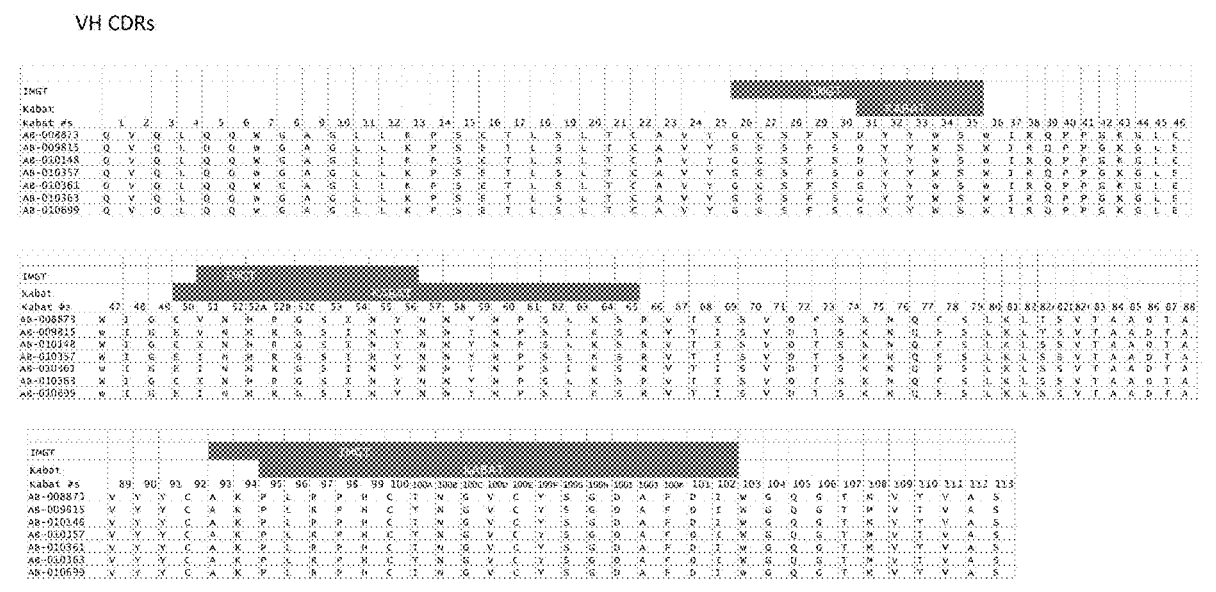
Figure 39D:
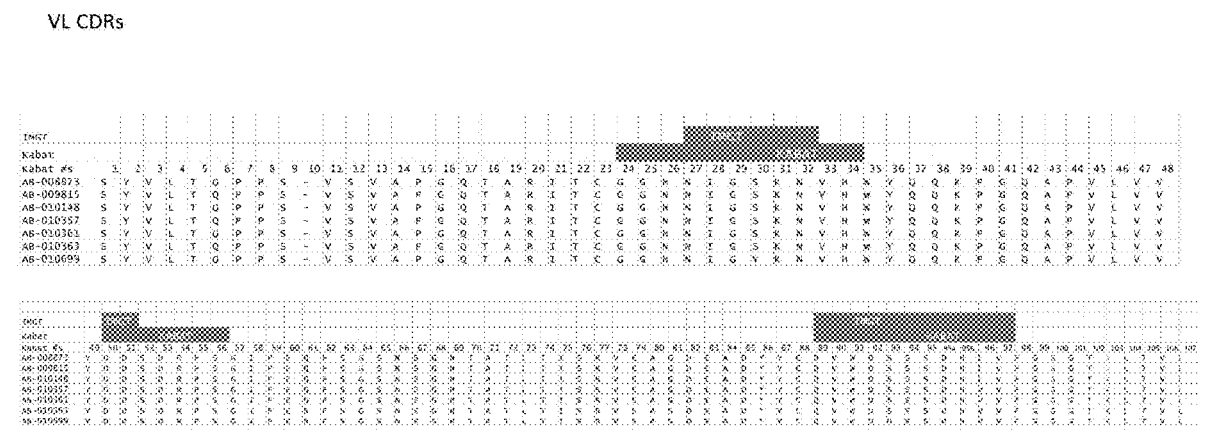

CDRs as shown in Tables 6 and 7 are defined by IMGT and Kabat. The $V_H$ CDRs as listed in Table 1, are defined as follows: HCDR1 is defined by combining Kabat and IMGT; HCDR2 is defined by Kabat; and the HCDR3 is defined by IMGT. The $V_L$ CDRs as listed in Table 7 are defined by Kabat. FIG. 39A-39B shows alignment of EphA2 antibody VH and VL sequences with CDRs designated by Kabat and IMGT. As known in the art, numbering and placement of the CDRs can differ depending on the numbering system employed. It is understood that disclosure of a variable heavy and/or variable light sequence includes the disclosure of the associated CDRs, regardless of the numbering system employed.

A "nonlinear epitope" or "conformational epitope" comprises noncontiguous polypeptides (or amino acids) within the antigenic protein to which an antibody specific to the epitope binds. A conformational epitope is typically formed by a three-dimensional interaction of amino acids in the epitope that may not necessarily be contained in a single stretch of amino acids.

An "Fc region" refers to the constant region of an antibody excluding the first constant region immunoglobulin domain. Thus, e.g., for human immunoglobulins, "Fc" refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region "includes naturally occurring allelic variants of the Fc region as well as modified Fc regions, e.g., that are modified to modulate effector function or other properties such as pharmacokinetics, stability or production properties of an antibody. Fc regions also include variants that do not exhibit alterations in biological function. For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, et al., *Science* 247:306-1310, 1990). For example, for IgG4 antibodies, a single amino acid substitution (S228P according to Kabat numbering; designated IgG4Pro) may be introduced to abolish the heterogeneity observed in recombinant IgG4 antibody (see, e.g., Angal, et al., *Mol Immunol* 30:105-108, 1993).

An "$EC_{50}$" as used herein in the context of a binding or functional assay, refers to the half maximal effective concentration, which is the concentration of an antibody that induces a response (readouts can include but are not limited to fluorescence or luminescence signals) halfway between the baseline and maximum after a specified exposure time. In some embodiments, the "fold over EC50" is determined by dividing the EC50 of a reference antibody by the $EC_{50}$ of the test antibody.

The term "equilibrium dissociation constant" abbreviated ($K_D$), refers to the dissociation rate constant ($k_d$, time$^{-1}$) divided by the association rate constant ($k_a$, time$^{-1}$ M$^{-1}$). Equilibrium dissociation constants can be measured using any method. Thus, in some embodiments antibodies of the present disclosure have a $K_D$ of less than about 50 nM, typically less than about 25 nM, or less than 10 nM, e.g., less than about 5 nM or than about 1 nM and often less than about 10 nM as determined by surface plasmon resonance analysis using a biosensor system such as a Biacore® system performed at 37° C. In some embodiments, an antibody of the present disclosure has a $K_D$ of less than 5×10$^{-5}$ M, less than 10$^{-5}$ M, less than 5×10$^{-6}$ M, less than 10$^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M, less than $10^{-14}$ M, less than $5 \times 10^{-15}$ M, or less than $10^{-15}$ M or lower as measured as a bivalent antibody. In the context of the present invention, an "improved" $K_D$ refers to a lower $K_D$. In some embodiments, an antibody of the present disclosure has a $K_D$ of less than $5 \times 10^{-5}$ M, less than $10^{-5}$ M, less than $5 \times 10^{-6}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M, less than $10^{-14}$ M, less than $5 \times 10^{-15}$ M, or less than $10^{-15}$ M or lower as measured as a monovalent antibody, such as a monovalent Fab. In some embodiments, an EphA2 antibody of the present disclosure has $K_D$ less than 100 pM, e.g., or less than 75 pM, e.g., in the range of 1 to 100 pM, when measured by surface plasmon resonance analysis using a biosensor system such as a Biacore® system performed at 37° C. In some embodiments, an EphA2 antibody of the present disclosure has $K_D$ of greater than 100 pM, e.g., in the range of 100-1000 pM or 500-1000 pM when measured by surface plasmon resonance analysis using a biosensor system such as a Biacore® system performed at 37° C. The term "EphA2 antibody" is used interchangeably with "anti-EphA2 antibody" in this application.

The term "monovalent molecule" as used herein refers to a molecule that has one antigen-binding site, e.g., a Fab or scFv.

The term "bivalent molecule" as used herein refers to a molecule that has two antigen-binding sites. In some embodiments, a bivalent molecule of the present invention is a bivalent antibody or a bivalent fragment thereof. In some embodiments, a bivalent molecule of the present invention is a bivalent antibody. In some embodiments, a bivalent molecule of the present invention is an IgG. In general, monoclonal antibodies have a bivalent basic structure. IgG and IgE have only one bivalent unit, while IgA and IgM consist of multiple bivalent units (2 and 5, respectively) and thus have higher valencies. This bivalency increases the avidity of antibodies for antigens.

The terms "monovalent binding" or "monovalently binds to" as used herein refer to the binding of one antigen-binding site to its antigen.

The terms "bivalent binding" or "bivalently binds to" as used herein refer to the binding of both antigen-binding sites of a bivalent molecule to its antigen. In some embodiments, both antigen-binding sites of a bivalent molecule share the same antigen specificity.

The term "valency" as used herein refers to the number of different binding sites of an antibody for an antigen. A monovalent antibody comprises one binding site for an antigen. A bivalent antibody comprises two binding sites for the same antigen. A multivalent antibody comprises two or more binding sites for the same antigen. A trivalent antibody comprises three binding sites for the same antigen. A tetravalent antibody comprises four binding sites for the same antigen.

The term "avidity" as used herein in the context of antibody binding to an antigen refers to the combined binding strength of multiple binding sites of the antibody. Thus, "bivalent avidity" refers to the combined strength of two binding sites.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, e.g., the length of the two sequences, when compared and aligned for maximum correspondence over a comparison window or designated region. Alignment for purposes of determining percent amino acid sequence identity can be performed in various methods, including those using publicly available computer software such as BLAST, BLAST-2, ALIGN or Megalign (DNASTAR) software. Examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). Thus, for purposes of this invention, BLAST 2.0 can be used with the default parameters to determine percent sequence identity.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. The polypeptide that is aligned to the reference sequence need not be the same length as the reference sequence.

A "conservative" substitution as used herein refers to a substitution of an amino acid such that charge, polarity, hydropathy (hydrophobic, neutral, or hydrophilic), and/or size of the side group chain is maintained. Illustrative sets of amino acids that may be substituted for one another include (i) positively-charged amino acids Lys and Arg; and His at pH of about 6; (ii) negatively charged amino acids Glu and Asp; (iii) aromatic amino acids Phe, Tyr and Trp; (iv) nitrogen ring amino acids His and Trp; (v) aliphatic hydrophobic amino acids Ala, Val, Leu and Ile; (vi) hydrophobic sulfur-containing amino acids Met and Cys, which are not as hydrophobic as Val, Leu, and Ile; (vii) small polar uncharged amino acids Ser, Thr, Asp, and Asn (viii) small hydrophobic or neutral amino acids Gly, Ala, and Pro; (ix) amide-comprising amino acids Asn and Gln; and (xi) beta-branched amino acids Thr, Val, and Ile. Reference to the charge of an amino acid in this paragraph refers to the charge at pH 6-7.

The terms "nucleic acid" and "polynucleotide" are used interchangeably and as used herein refer to both sense and anti-sense strands of RNA, cDNA, genomic DNA, and synthetic forms and mixed polymers of the above. In particular embodiments, a nucleotide refers to a ribonucleotide, deoxynucleotide or a modified form of either type of nucleotide, and combinations thereof. The terms also include, but is not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids that encode the same polypeptide sequence.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. A "vector" as used here refers to a recombinant construct in which a nucleic acid sequence of interest is inserted into the vector. Certain vectors are capable of directing the expression of nucleic acids to which they are operatively linked. Such vectors are referred to herein as "expression vectors".

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody or fragment thereof" refers to one or more nucleic acid molecules encoding antibody heavy or light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Thus, a host cell is a recombinant host cells and includes the primary transformed cell and progeny derived therefrom without regard to the number of passages.

A polypeptide "variant," as the term is used herein, is a polypeptide that typically differs from one or more polypeptide sequences specifically disclosed herein in one or more substitutions, deletions, additions and/or insertions.

The term "cancer cell" or "tumor cell" as used herein refers to a neoplastic cell. The term includes cells from tumors that are benign as well as malignant. Neoplastic transformation is associated with phenotypic changes of the tumor cell relative to the cell type from which it is derived. The changes can include loss of contact inhibition, morphological changes, and unregulated cell growth.

"Inhibiting growth of a tumor" and "inhibiting growth of a cancer" as used herein are interchangeable and refer to slowing growth and/or reducing the cancer cell burden of a patient that has cancer. "Inhibiting growth of a cancer" thus includes killing cancer cells, as well as decreasing the rate of tumor growth, tumor size, invasion, and/or metastasis by direct or indirect effects on tumor cells.

As used herein, "therapeutic agent" refers to an agent that when administered to a patient suffering from a disease, in a therapeutically effective dose, will cure, or at least partially arrest the symptoms of the disease and complications associated with the disease.

As used herein, the term "a tumor overexpressing EphA2", or "a tumor that overexpresses EphA2", or "a cancer overexpressing EphA2" or "a cancer that overexpresses EphA2", refers to a tumor or cancer that expresses EphA2 or demonstrates EpA2 reactivity at a level that higher than the level of EphA2 expressed or EphA2 reactivity in normal tissue (e.g., tumor adjacent tissues or TAT). In certain embodiments, a tumor or cancer that overexpresses EphA2 is one that expresses EphA2 at a level that is at least 10%, at least 20%, at least 30%, at least 40%, at least 50%, at least 80%, or at 100% higher than the normal tissue (e.g., tumor adjacent tissues or TAT). In certain embodiments, a tumor or cancer that overexpresses EphA2 is one that demonstrates EphA2 reactivity at level that is at least 10%, at least 20%, at least 30%, at least 40%, at least 50%, at least 80%, or at 100% higher than the normal tissue (e.g., tumor adjacent tissues or TAT).

In some aspects, the disclosure additionally provides methods of identifying subjects who are candidates for treatment with an EphA2 antibody having tumor-targeting effects. Thus, in one embodiment, the invention provides a method of identifying a patient who can benefit from treatment with an EphA2 antibody of the present disclosure. In one embodiment, the patient has tumor that expresses EphA2. In one embodiment, the patient has tumor that overexpresses EphA2. In some embodiments, the tumor sample is from a primary tumor. In alternative embodiments, the tumor sample is a metastatic lesion. Binding of antibody to tumor cells through a binding interaction with the EphA2 can be measured using any assay, such as immunohistochemistry or flow cytometry. In some embodiments, binding of antibody to at least 0.2%, 0.5%, or 1%, or at least 5% or 10%, or at least 20%, 30%, or 50%, of the tumor cells in a sample may be used as a selection criterion for determining a patient to be treated with an EphA2 antibody as described herein. In other embodiments, analysis of components of the blood, e.g., circulating protein levels, is used to identify a patient whose tumor cells are overexpressing EphA2.

An EphA2 antibody disclosed herein can be used to treat a number of different cancers. In some embodiments, a cancer patient who can benefit from the treatment of the EphA2 antibody has a cancer expressing EphA2. In some embodiments, a cancer patient who can benefit from the treatment of the EphA2 antibody has a cancer overexpressing EphA2. In some embodiments, the cancer is a carcinoma or a sarcoma.

As used herein, the term "an antibody binds to an EphA2" or "an antibody binds to EphA2," means that the antibody binds to EphA2 under permissible conditions (e.g., in a suitable buffer), and the detected signal resulted from the binding is at least 2-fold, at least 5 fold, at least 10 fold, at least 20 fold, at least 100 fold, at least 150 fold, or at least 200 fold above a reference level. In some embodiments, the reference level is a detected signal produced by contacting a control antibody with the EphA2, or by contacting the antibody with a control protein.

As used herein, the term "sibling antibodies" refer to antibodies derived from the same B-cell clonal lineage. In some embodiments, sibling antibodies share sequence and structural properties as well as epitope specificity.

As used herein, the term "convergent antibodies" refer to that antibodies derived from different B-cell lineages that exhibit similar sequence and structural properties.

A number of anti-EphA2 comparator antibodies are referenced in this disclosure. AB-010018 is a mouse monoclonal antibody precursor of clinical candidate humanized DS-8895a (Daiichi Sankyo Company, Ltd.), as disclosed in U.S. Pat. No. 9,150,657, SEQ ID NO: 35 and 37, Hasegawa J. et al., Cancer Biol Ther. 2016 November; 17(11):1158-1167. doi: 10.1080/15384047.2016.1235663. Epub 2016 Sep. 21; Shitara K. et al., J Immunother Cancer, 2019 Aug. 14; 7(1):219. doi: 10.1186/s40425-019-0679-9)), AB-010016 is an anti-EphA2 antibody generated based on clinical candidate Medi-547 (MedImmune, Inc.) It was generated using the VH and VL amino acid sequences from Protein Data Bank code 3SKJ, Peng, L., et. al, (2011) J Mol Biol 413:390-405.

AB-010017 is an anti-EphA2 antibody generated based on clinical candidate MM-310 (Merrimack, Inc.) It was generated using VH and VL amino acid sequences from the scFv of SEQ ID NO: 40 in US20190070113A1; See also, Geddie et al., MAbs. 2017 January; 9(1):58-67; Kamoun et al., Nat Biomed Eng. 2019 April; 3(4):264-280. doi: 10.1038/s41551-019-0385-4. Epub 2019 Apr. 5.)

Overview

This application relates to tumor-targeting antibodies that bind to EphA2 and also bind preferentially to tumor tissues than normal tissues. In some embodiments, the EphA2 antibody binds to one or more epitopes in the FN2 domain of EphA2. The EphA2 antibodies disclosed herein can target a tumor in a variety of ways, for example, it can mediate antibody-dependent cell-mediated cytotoxicity (ADCC) and/or ADCP to target and kill tumor cells. These antibodies also demonstrated significant cytotoxicity towards tumor cells and show therapeutic potential in treating cancers. Some of the EphA2 antibodies are able to target both mouse tumor and human tumor cells. The EphA2 antibodies are also useful in detecting tumors suitable for treatment in diagnostic applications.

As compared to existing clinical candidates and commercial EphA2 antibodies, EphA2 antibodies provided in this disclosure showed a higher binding affinity to various tumors and lower binding to normal tissues (e.g., tumor adjacent tissues) and exhibit differential binding profile on various cancer tumor types. Unlike existing clinical candidates and commercial EphA2 antibodies, the EphA2 antibodies disclosed herein exhibit reduced agonistic or antagonistic effects on the EphA2 receptor. These properties render them ideal for use as cancer therapeutics.

EphA2

Ephrin receptor A2 (EphA2) is mainly expressed in proliferating epithelial cells in adults. Under normal conditions, EphA2 interacts with membrane proteins, ephrin A1, on the neighboring cell and induce diverse signaling networks following cell-to-cell contact. For example, EphA2 may decrease in cell-extracellular matrix (ECM) attachment upon phosphorylation.

EphA2 is overexpressed in many solid tumors including melanoma, glioma, prostate cancer, breast cancer, ovarian cancer, lung cancer, colon cancer, esophageal cancer, gastric cancer cervical cancer, bladder cancer. EphA2 contributes to cell adhesion and angiogenesis, and its expression is also linked to increased malignancy and poor prognosis.

Human EphA2 has a sequence of
(SEQ ID NO: 94)
MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKGDSNSYNVRRTEGFSVTLDDLAPD

TTYLVQVQALTQEGQGAGSKVHEFQTLSPEGSGNLAVIGGVAVGVVLLLV

LAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKA

GYTEKQRVDFLGEAGIIVIGQFSHHNIIRLEGVISKYKPMMIITEYMENG

ALDKFLREKDGEFSVLQLVGMLRGIAAGMKYLANMNYVHRDLAARNILVN

SNLVCKVSDFGLSRVLEDDPEATYTTSGGKIPIRWTAPEAISYRKFTSAS

DVWSFGIVMWEVMTYGERPYWELSNHEVMKAINDGFRLPTPMDCPSAIYQ

LMMQCWQQERARRPKFADIVSILDKLIRAPDSLKTLADFDPRVSIRLPST

SGSEGVPFRTVSEWLESIKMQQYTEHFMAAGYTAIEKVVQMTNDDIKRIG

VRLPGHQKRIAYSLLGLKDQVNTVGIPI

Human EphA2 comprises: a signal peptide having the sequence of:
(SEQ ID NO: 96)
MELQAARACFALLWGCALAAAAAA;

a ligand binding domain having the sequence of
(SEQ ID NO: 97)
QGKEVVLLDFAAAGGELGWLTHPYGKGWDLMQNIMNDMPIYMYSVCNVMS

GDQDNWLRTNWVYRGEAERIFIELKFTVRDCNSFPGGASSCKETFNLYYA

ESDLDYGTNFQKRLFTKIDTIAPDEITVSSDFEARHVKLNVEERSVGPLT

RKGFYLAFQDIGACVALLSVRVYYK;

a sushi domain having the sequence of
(SEQ ID NO: 98)
KCPELLQGLAHFPETIAGSDAPSLATVAGTCVDHAVVPPGGEEPRMHCAV

DGEWLVPIGQCL;

an EGF domain having the sequence of
(SEQ ID NO: 99)
CQAGYEKVEDACQACSPGFFKFEASESPCLECPEHTLPSPEGATSCECEE

GFFRAPQDPASMPCT;

an FN1 domain having the sequence of
(SEQ ID NO: 100)
RPPSAPHYLTAVGMGAKVELRWTPPQDSGGREDIVYSVTCEQCWPESGEC

GPCEASVRYSEPPHGLTRTSVTVSDLEPHMNYTFTVEARNGVSGLVTSRS

FRTASVSINQ;

and an FN2 domain having the sequence of
(SEQ ID NO: 95)
TEPPKVRLEGRSTTSLSVSWSIPPPQQSRVWKYEVTYRKKGDSNSYNVRR

TEGFSVTLDDLAPDTTYLVQVQALTQEGQGAGSKVHEFQTLSPEGSGN

EPHA2 comprises an ectodomain, an intracellular region, and a single transmembrane helix. The ectodomain of EphA2, consisting of amino acid residues 23-546 using SEQ ID NO: 94 as a reference, comprises a ligand binding domain (LBD), which interacts with ephrin A1, a Sushi domain, an epidermal growth factor like domain, and two fibronectin type III domains (FN1 and FN2). The intracellular region comprises a tyrosine kinase domain and a sterile □-motif domain. The transmembrane helix of the protein is flanked by juxtamembrane linkers, which connects the ectodomain and the intracellular domain. A membrane-binding motif FN2, located within amino acid residues 437-534 of SEQ ID NO: 94, includes positively charged residues, which can recruit negatively charged lipids to the site of membrane-protein interaction. The interactions of FN2 with lipids stabilize the otherwise flexible EphA2 ectodomain in two main conformations relative to the membrane.

The EphA2 ectodomain is highly conserved across species. The ectodomain of human EphA2 has sequence identity of 90.8%, 90.4%, 98.8%, and 98.8% to mouse, rat, macaque, and cyno, respectively.

EphA2 Antibodies

For purpose of this disclosure, an EphA2 antibody may be any one of AB-008873, the siblings and variants thereof, as further described below.

AB-008873 was discovered in antibody repertoires generated by Immune Repertoire Capture® (IRC™) technology from plasmablast B cells isolated from a non-small cell lung cancer patient with an active anti-tumor immune response after treatment with the anti-PD-1 antibody OPDIVO® (nivolumab) (Bristol Myers Squibb). The IRC™ technology and its use in antibody discovery is well known and disclosed in, e.g., WO 2012148497A2, the entire content of which is herein incorporated by reference. AB-008873 aligns to its closest human germline genes (IGHV4-34*02, IGHD2-8*01, IGHJ3*02, IGLV3-21*02, and IGLJ2*01), and also to its four known siblings AB-009805, AB-009806, AB-009807, and AB-009808. Structures of these antibodies are further disclosed below, e.g., in Tables 1-3.

Variants

In some embodiments, variants of any of the EphA2 antibodies disclosed herein can be generated by introducing mutations to the heavy chain and/or light chain sequences. In some embodiments, the mutation(s) are introduced into one or more of the CDRs of an EphA2 antibody disclosed herein, e.g., AB-008873, AB-010148, or AB-010363. In some embodiments, the mutation(s) are introduced in the framework regions. In some embodiments, an EphA2 antibody provided herein comprises a VH region of any one of SEQ ID NO 67-77 and 591-655, and/or a VL region of any one of SEQ ID NO: 78-88 and 656-720, or an antibody comprising a VH region with at least 80% identity to any one of SEQ ID NO 67-77 and 591-655 and a VL region having at least 80% identity to any one of SEQ ID NO: 78-88 and 656-720, with variations to the corresponding VH or VL regions present only in Framework regions.

In some embodiments, EphA2 antibody provided herein comprises an HCDR1 of any one of SEQ ID NOS: 1-11, and 201-265, an HCDR2 of any one of SEQ ID NOS: 12-22 and 266-330, an HCDR3 of any one of SEQ ID NOS: 23-33 and 331-395, an LCDR1 of any one of SEQ ID NOS: 34-44 and 396-460, an LCDR2 of any one of SEQ ID NOS: 45-55 and 461-525, an LCDR3 of any one of SEQ ID NOS: 56-66 and 526-590; and the FW regions in the VH region are at least 80% identical to the FW regions present in the VH region of SEQ ID NO 67-77 and 591-655, and wherein the FW regions in the VL region are at least 80% identical to the FW regions present in the VL region of SEQ ID NO: 78-88 and 656-720

In some embodiments, a variant is engineered to be as much like self as possible in order to minimize immunogenicity. One approach to do so is to identify a close germline sequence and mutate one of the EphA2 antibodies at as many mismatched positions (also known as "germline deviations") to the germline residue type as possible. In some embodiments, a variant (e.g., AB-009812) comprises a mutation H54RS relative to AB-008873 (heavy chain position 54 mutated from arginine to serine). In some embodiments, a variant (e.g., AB-009813) comprises a mutation H54RA relative to AB-008873 (heavy chain position 54 mutated from arginine to alanine). In some embodiments, a variant (e.g., AB-009814) comprises deletion of three residues, H61N-H62Y-H63N, relative to AB-008873. In some embodiments, a variant comprises one or more mutations selected from the group consisting of H54RS, H54RA, and deletions of three residues H61N-H62Y-H63N, relative to the sequence of the heavy chain variable region of AB-008873 (SEQ ID NO: 67). Variant antibodies AB-009812, AB-009813, and AB-009814 are described in Tables 1-3.

Additional variants antibodies may also be generated by introducing one or more mutations to any one of the AB-008873 and its siblings. In some embodiments, a variant comprises one or more mutations selected from the group consisting of H31DG, L31NS, L97LV, H51VI, H86TS, H129AS, and L60QR relative to AB-009815. Each using the HV and LV sequences of the AB-009815 (SEQ ID NO: 75 and 86) as references. For any the mutation disclosed in this application, the name indicates whether the mutation is a heavy chain or light chain, the position in the heavy chain or light chain of the mutation, the amino acid residue at the position before introduction of the mutation, and the amino acid at the position after introduction of the mutation. For example, H129AS, refers to that the alanine at heavy chain position 129 is mutated to a serine. Table 1 shows exemplary variants of AB-009815.

TABLE 1

Exemplary variants of AB-009815

| Antibody ID | Mutations relative to AB-009815 |
|---|---|
| AB-010141 | H31DG |
| AB-010142 | L31NS |
| AB-010143 | L97LV |
| AB-010144 | H51VI |
| AB-010145 | H86TS |
| AB-010146 | H129AS |
| AB-010147 | L60QR |
| AB-010148 | H51VI; H86TS |
| AB-010149 | H51VI; H129AS |
| AB-010150 | H86TS; H129AS |
| AB-010151 | H51VI, H86TS, H129AS |
| AB-010152 | H51VI, H86TS, H129AS, L60QR |

Further mutations can be introduced to any one of the AB-008873 variants listed in Table 1. For example, one or more mutations are introduced to AB-0010148 and exemplary variants resulted from the further mutagenesis are shown in in Table 2, below.

TABLE 2

Exemplary AB-0010148 variants

| Antibody ID | Mutations relative to AB-0010148 |
|---|---|
| AB-010357 | L97LV |
| AB-010358 | L60QR |
| AB-010359 | L97LV; L60QR |
| AB-010360 | H31DG |
| AB-010361 | H31DG; L97LV |
| AB-010362 | H31DG; L60QR |
| AB-010363 | H31DG; L60QR; L97LV |
| AB-010364 | H31DG; H54RA; L97LV |
| AB-010365 | H31DG; H54RA; L97LV; L60QR |
| AB-010366 | H31DG; H54RQ; L97LV |
| AB-010367 | H31DG; H54RQ; L97LV; L60QR |

Further mutations can be introduced to any one of the AB-0010148 variants listed in Table 2. For example, one or more mutations are introduced to AB-010357, AB-010361, AB-010363, and exemplary antibodies resulted from the further mutagenesis are shown in in Table 3, 4, 5, respectively.

TABLE 3

Exemplary variants of AB-010357

| Antibody ID | Mutations relative to AB-010357 |
|---|---|
| AB-010661 | H107TI; L23GR |
| AB-010662 | L23GR; L29SY |
| AB-010663 | L23GR; L30KM |
| AB-010664 | L23GR; L92SH |
| AB-010665 | H107T; L29SY |
| AB-010666 | L29SY; L30KM |
| AB-010667 | L29SY; L92SH |
| AB-010668 | H107TI; L30KM |
| AB-010669 | L30KM; L92SH |
| AB-010670 | H107TI; L92SH |
| AB-010671 | H107TI; L29SY; L92SH |
| AB-010672 | L93SR |
| AB-010673 | L93SE |
| AB-010674 | L29SY; L93SE |

TABLE 4

Exemplary variants of AB-010361

| Antibody ID | Mutations relative to AB-010361 |
|---|---|
| AB-010675 | H107TI; L23GR |
| AB-010676 | L23GR; L29SY |
| AB-010677 | L23GR;; L30KM |
| AB-010678 | L23GR; L92SH |
| AB-010679 | H107TI; L29SY |
| AB-010680 | L29SY; L30KM |
| AB-010681 | L29SY; L92SH |
| AB-010682 | H107TI; L30KM |
| AB-010683 | L30KM; L92SH |

TABLE 4-continued

Exemplary variants of AB-010361

| Antibody ID | Mutations relative to AB-010361 |
|---|---|
| AB-010684 | H107TI; L92SH |
| AB-010685 | H107TI; L29SY; L92SH |
| AB-010686 | L93SR |
| AB-010687 | L93SE |
| AB-010688 | L29SY; L93SE |

TABLE 5 shows exemplary variants of AB-010363

| Antibody ID | Mutations relative to AB-010363 |
|---|---|
| AB-010689 | H107TI; L23GR |
| AB-010690 | L23GR; L29SY |
| AB-010691 | L23GR; L30KM |
| AB-010692 | L23GR; L92SH |
| AB-010693 | H107TI; L29SY |
| AB-010694 | L29SY; L30KM |
| AB-010695 | L29SY; L92SH |
| AB-010696 | H107TI; L30KM |
| AB-010697 | L30KM; L92SH |
| AB-010698 | H107TI; L92SH |
| AB-010699 | H107TI; L29SY_L92SH |
| AB-010700 | L93SR |
| AB-010701 | L93SE |
| AB-010702 | L29SY; L93SE |

Methods of generating variants are further described in the section entitled "ENGINEERING VARIANTS" and Example 2 below.

Structures of the EphA2 Antibodies

In some embodiments, an EphA2 antibody that binds to EphA2 and comprises a heavy chain variable region comprising: an HCDR1 comprising a sequence (SEQ ID NO:1), or a variant HCDR1 in which 1, 2, 3, 4, or 5 amino acids are substituted relative to the sequence; an HCDR2 comprising a sequence (SEQ ID NO:12), or a variant HCDR2 in which 1, 2, 3, 4, or 5 amino acid is substituted relative to the sequence; and an HCDR3 comprising a sequence (SEQ ID NO: 23), or a variant HCDR3 in which 1, 2, 3, 4, or 5 amino acids are substituted relative to the sequence. In some embodiments, the antibody comprises a light chain variable region comprising: an LCDR1 comprising a sequence (SEQ ID NO:34), or a variant LCDR1 in which 1, 2, 3, 4, or 5 amino acid is substituted relative to the sequence; an LCDR2 comprising a sequence (SEQ ID NO:45), or variant LCDR2 in which 1, 2, or 3 amino acid is substituted relative to the sequence; and an LCDR3 comprising a sequence (SEQ ID NO:56), or a variant LCDR3 in which 1, 2, 3, 4, or 5 amino acid is substituted relative to the sequence.

In some embodiments, an antibody that binds to EphA2 comprises: a heavy chain variable region comprising: an HCDR1 of any one of SEQ ID NOS: 1-11 and 201-265 or a variant thereof in which 1, 2, 3, 4, or 5 amino acids are substituted relative to the sequence; an HCDR2 of any one of SEQ ID NOS: 12-22 and 266-330 or a variant thereof in which 1, 2, 3, 4, or 5 amino acid is substituted relative to the sequence; and an HCDR3 of any one of SEQ ID NOS: 23-33 and 331-395 or a variant thereof in which 1, 2, 3, 4, or 5 amino acids are substituted relative to the sequence. The antibody also comprises a light chain variable region comprising: an LCDR1 of any one of SEQ ID NOS: 34-44 and 396-460 or a variant thereof in which 1, 2, 3, 4, or 5 amino acid is substituted relative to the sequence; an LCDR2 of any one of SEQ ID NOS: 45-55 and 461-525 or a variant thereof in which 1, 2, or 3 amino acid is substituted relative to the sequence; and an LCDR3 of any one of SEQ ID NOS: 56-66 and 526-590 or a variant thereof in which 1, 2, 3, 4, or 5 amino acid is substituted relative to the sequence.

In some embodiments, an antibody that binds to EphA2 comprises (a) an HCDR1 sequence of GGSX$_1$X$_2$ X$_3$YX$_4$WS where X$_1$ is F or L, X$_2$ is S or N, and X$_3$ is D or G, and X$_4$ is Y or H (SEQ ID NO: 769); (b) an HCDR2 sequence of EX$_1$NHX$_2$GSX$_3$X$_4$YNNYNPSLKS, where X$_1$ is I or V, X$_2$ is A, Q, R or S, X$_3$ is I or T, and X$_4$ is N or S (SEQ ID NO: 770); and (c) an HCDR3 sequence of AKPX$_1$RPHC X$_2$NGVCX$_3$SGDAFDI, where X$_1$ is L or F, X$_2$ is I or T; and X$_3$ is Y or S (SEQ ID NO: 771). The antibody also comprises (d) an LCDR1 sequence of X$_1$GNNIGX$_2$ X$_3$ X$_4$VH, where X$_1$ is G or R, X$_2$ is S, T, or Y, X$_3$ is K or M, and X$_4$ is N or S (SEQ ID NO: 772); I an LCDR2 sequence of DDSDRPS (SEQ ID NO: 45); and (f) an LCDR3 sequence of QVWDX1 X2SDHX3V, where X1 is H or S, X2 is E, R, or S, and X3 is L or V (SEQ ID NO: 773).

In some embodiments, an antibody that binds to EphA2 comprises (a) an HCDR1 sequence of GGSX$_1$X$_2$ X$_3$YX$_4$WS where X$_1$ is F or L, X$_2$ is S or N, and X$_3$ is D or G, and X$_4$ is Y or H (SEQ ID NO: 769); (b) an HCDR2 sequence of EX$_1$NHX$_2$GSX$_3$X$_4$YNPSLKS, where X$_1$ is I or V, X$_2$ is A, Q, R or S, X$_3$ is I or T, and X$_4$ is N or S (SEQ ID NO: 774); or an HCDR2 sequence of EX$_1$NHX$_2$ GS X$_3$ X$_4$YNNYNPSLKS, where X$_1$ is I or V, X$_2$ is R or S, X$_3$ is I or T, and X$_4$ N or S (SEQ ID NO: 777); and (c) an HCDR3 sequence of AKPX$_1$RPHCX$_2$NGVCX$_3$SGDAFDI, where X$_1$ is L or F, X$_2$ is I or T; and X$_3$ is Y or S (SEQ ID NO: 771). The antibody also comprises (d) an LCDR1 sequence of X$_1$GNNIGX$_2$ X$_3$ X$_4$VH, where X$_1$ is G or R, X$_2$ is S, T, or Y, X$_3$ is K or M, and X$_4$ is N or I (SEQ ID NO: 780) (e) an LCDR2 sequence of DDSDRPS (SEQ ID NO: 45); and (f) an LCDR3 sequence of QVWDX1 X2SDHX3V, where X1 is H or S, X2 is E, R, or S, and X3 is L or V (SEQ ID NO: 773).

In some embodiments, an antibody that binds to EphA2 comprises a V$_H$ comprising an amino acid sequence having at least 95% identity to (SEQ ID NO: 67); and a V$_L$ comprising an amino sequence having at 95% identity to (SEQ ID NO: 78).

In some embodiments, an antibody that binds to EphA2 has a V$_H$ comprising an amino acid sequence having at least 95% identity to any one of SEQ ID NO: 67-77 and 591-655; and a V$_L$ comprising an amino sequence having at 95% identity to any one of SEQ ID NOs: 78-88 and 656-720.

In some embodiments, an antibody that binds to EphA2 comprises a heavy chain variable (V$_H$) region and a light chain variable (V$_L$) region. The V$_H$ region has at least 70% amino acid sequence identity to SEQ ID NO:67; and comprises a CDR1 of SEQ ID NO:1, or the CDR1 of SEQ ID NO: 1 in which 1, 2, 3, 4, or 5 amino acids are substituted; a CDR2 of SEQ ID NO: 83, or the CDR2 of SEQ ID NO: 12 in which 1, 2, 3, 4, or 5 amino acids are substituted; a CDR3 of SEQ ID NO:23 or the CDR3 of SEQ ID NO:23 in which 1, 2, 3, 4, or 5 are substituted. The V$_L$ region has at least 70% amino acid sequence identity to SEQ ID NO: 78, and comprises a CDR1 of SEQ ID NO:34 or the CDR1 of SEQ ID NO:34 in which 1, 2, 3, 4, or 5 amino acids are substituted; a CDR2 of SEQ ID NO:45, or the CDR2 of SEQ ID NO:45 in which 1, 2, 3, 4, or 5 amino acids are substituted; a CDR3 of SEQ ID NO:56 or the CDR3 of SEQ ID NO:56 in which 1, 2, 3, 4, or 5 are substituted.

In some embodiments, an antibody that binds to EphA2 comprises: a V$_H$ region comprising amino acid sequence SEQ ID NO:67 and a V$_L$ region comprising amino acid sequence SEQ ID NO:78; a V$_H$ region comprising amino acid sequence SEQ ID NO:68 and a V$_L$ region comprising amino acid sequence SEQ ID NO:79; a V$_H$ region comprising amino acid sequence SEQ ID NO:69 and a V$_L$ region comprising amino acid sequence SEQ ID NO:80; a V$_H$ region comprising amino acid sequence SEQ ID NO:70 and a V$_L$ region comprising amino acid sequence SEQ ID NO:81; a V$_H$ region comprising amino acid sequence SEQ ID NO:71 and a V$_L$ region comprising amino acid sequence SEQ ID NO:82; a V$_H$ region comprising amino acid sequence SEQ ID NO:72 and a V$_L$ region comprising amino acid sequence SEQ ID NO:83; a V$_H$ region comprising amino acid sequence SEQ ID NO:73 and a VI region comprising amino acid sequence SEQ ID NO:84; a V$_H$ region comprising amino acid sequence SEQ ID NO:74 and a V$_L$ region comprising amino acid sequence SEQ ID NO:85; a V$_H$ region comprising amino acid sequence SEQ ID NO:75 and a V$_L$ region comprising amino acid sequence SEQ ID NO:86; a V$_H$ region comprising amino acid sequence SEQ ID NO:76 and a V$_L$ region comprising amino acid sequence SEQ ID NO:87; or a V$_H$ region comprising amino acid sequence SEQ ID NO:77 and a V$_L$ region comprising amino acid sequence SEQ ID NO:88.

In some embodiments, an EphA2 antibody of the present invention has one, two, or three CDRs of a VL sequence in Table 2. In some embodiments, the EphA2 antibody has at least one mutation and no more than 10, 20, 30, 40 or 50 mutations in the VL amino acid sequences compared to a VL sequence set forth in Table 3. In some embodiments, the VL amino acid sequence may comprise 1, 2, 3, 4, 5, 6, 7, 8, 9, or 10 amino acid insertions or deletions compared to a VL sequence set forth in Table 3. In some embodiments, the VL amino acid sequence may comprise a deletion or insertion, e.g., a 1, 2, 3, 4, 5, 6, or 7 amino acid deletion or insertion, relative to a CDR sequence shown in Table 2. In some embodiments, the VL region comprises a CDR1 having 1 or 2 substitutions in relative to a CDR1 sequence shown in Table 2. In some embodiments, a CDR1 has 3, 4, or 5 substitutions relative to a CDR1 sequence shown in Table 2. In some embodiments, the VL region comprises a CDR2 that has 1 or 2; or 1, 2, or 3; substitutions relative to the CDR2 sequence shown in Table 2. In some embodiments, the VL region comprises a CDR3 that has 1, 2, or 3; or 1, 2, 3, or 4; substitutions relative to a CDR3 sequence shown in Table 2. In some embodiments, an EphA2 antibody of the present disclosure comprises a CDR1, CDR2, and CDR3, each having at least 70% identity to a CDR1, CDR2, and CDR3 as shown in Table 2. In some embodiments, an EphA2 antibody of the present invention comprises a CDR1, CDR2, and CDR3, each having at least 80% identity to a CDR1, CDR2, and CDR3 as shown in Table 2. In some embodiments, an anti-tumor antibody of the present invention comprises a CDR1, CDR2, and CDR3 as shown in Table 2. In some embodiments, an EphA2 antibody of the present invention comprises HCDR1, HCDR2, HCDR3, LCDR1, LCDR2, and LCDR3 of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702 in Table 2. In some embodiments, an EphA2 antibody of the present invention comprises a CDR1, CDR2, and CDR3 of the VL of an antibody designated as AB-010361 or AB-010699. Of these antibodies, AB-008873; AB-009805; AB-009806; AB-009807; AB-009808 are sibling antibodies as they are derived from the same lineage as AB-008873. See Example 1.

In some embodiments, the antibody comprises a heavy chain variable region and a light chain variable region of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702, or a variant thereof, wherein the variant comprises a heavy chain variable region having a sequence that is at least 95% identical to that of the corresponding heavy chain variable region and a light chain variable region having a sequence that is at least 95% identical to the corresponding light chain variable region.

In some embodiments, an EphA2 antibody of the present invention has one, two, or three CDRs of a VH sequence in Table 6. In some embodiments, the EphA2 antibody has at least one mutation and no more than 10, 20, 30, 40 or 50 mutations in the VH amino acid sequences compared to a VH sequence set forth in Table 3. In some embodiments, the VH amino acid sequence may comprise 1, 2, 3, 4, 5, 6, 7, 8, 9, or 10 amino acid insertions or deletions compared to a VH sequence set forth in Table 3. In some embodiments, the VH amino acid sequence may comprise a deletion or insertion, e.g., a 1, 2, 3, 4, 5, 6, or 7 amino acid deletion or insertion, relative to a CDR sequence shown in Table 6. In some embodiments, the VH region comprises a CDR1 having 1 or 2 substitutions in relative to a CDR1 sequence shown in Table 6. In some embodiments, a CDR1 has 3, 4, or 5 substitutions relative to a CDR1 sequence shown in Table 6. In some embodiments, the VH region comprises a CDR2 that has 1 or 2; or 1, 2, or 3; substitutions relative to the CDR2 sequence shown in Table 6. In some embodiments, the VH region comprises a CDR3 that has 1, 2, or 3; or 1, 2, 3, or 4; substitutions relative to a CDR3 sequence shown in Table 6. In some embodiments, an EphA2 antibody of the present disclosure comprises a CDR1, CDR2, and CDR3, each having at least 70% identity to a CDR1, CDR2, and CDR3 as shown in Table 6. In some embodiments, an EphA2 antibody of the present invention comprises a CDR1, CDR2, and CDR3, each having at least 80% identity to a CDR1, CDR2, and CDR3 as shown in Table 6. In some embodiments, an EphA2 antibody of the present invention comprises a CDR1, CDR2, and CDR3 as shown in Table 6. In some embodiments, an EphA2 antibody of the present invention comprises a CDR1, CDR2, and CDR3 of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702 in Table 6. In some embodiments, an EphA2 antibody of the present invention comprises a CDR1, CDR2, and CDR3 of the VH of an antibody designated as AB-010361 and AB-010699.

Exemplary EphA2 antibodies include AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702. In some embodiments, the EphA2 antibody is AB-010361 or AB-010699. These exemplary EphA2 antibodies have structures (HCDRs, LCDRs, VH and/or VL sequences) shown in Tables 6-8.

TABLE 6

Heavy chain CDRs

| Antibody ID | HCDR1 | HCDR2 | HCDR3 |
|---|---|---|---|
| AB-008873 | GGSFSDYYWS (SEQ ID NO: 1) | EVNHRGSINYNNYNPSLKS (SEQ ID NO: 12) | AKPLRPHCTNGVCYSGDAFDI (SEQ ID NO: 23) |
| AB-009805 | GGSLSDYHWS (SEQ ID NO: 2) | EINHSGSTNYNPSLKS (SEQ ID NO: 13) | AKPFRPHCTNGVCHSGDAFDI (SEQ ID NO: 24) |
| AB-009806 | GGSFSDYYWS (SEQ ID NO: 3) | EINHSGSTNYNPSLKS (SEQ ID NO: 14) | AKPFRPHCTNGVCYSGDAFDI (SEQ ID NO: 25) |
| AB-009807 | GGSFNDYYWS (SEQ ID NO: 4) | EVNHSGSTSYNPSLKS (SEQ ID NO: 15) | AKPFRPHCTNGVCYSGDAFDI (SEQ ID NO: 26) |
| AB-009808 | GGSFSDYYWS (SEQ ID NO: 5) | EINHSGSTNYNPSLKS (SEQ ID NO: 16) | AKPFRPHCTNGVCYSGDAFDI (SEQ ID NO: 27) |
| AB-009812 | GGSFSDYYWS (SEQ ID NO: 6) | EVNHSGSINYNNYNPSLKS (SEQ ID NO: 17) | AKPLRPHCTNGVCYSGDAFDI (SEQ ID NO: 28) |
| AB-009813 | GGSFSDYYWS (SEQ ID NO: 7) | EVNHAGSINYNNYNPSLKS (SEQ ID NO: 18) | AKPLRPHCTNGVCYSGDAFDI (SEQ ID NO: 29) |
| AB-009814 | GGSFSDYYWS (SEQ ID NO: 8) | EVNHRGSINYNPSLKS (SEQ ID NO: 19) | AKPLRPHCTNGVCYSGDAFDI (SEQ ID NO: 30) |
| AB-009815 | GGSFSDYYWS (SEQ ID NO: 9) | EVNHRGSINYNNYNPSKSL (SEQ ID NO: 20) | AKPLRPHCTNGVCYSGDAFDI (SEQ ID NO: 31) |
| AB-009816 | GGSFSDYYWS (SEQ ID NO: 10) | EVNHRGSINYNNYNPSLKS (SEQ ID NO: 21) | AKPLRPHCTNGVCYSGDAFDI (SEQ ID NO: 32) |
| AB-009817 | GGSFSDYYWS (SEQ ID NO: 11) | EVNHRGSINYNNYNPSLKS (SEQ ID NO: 22) | AKPLRPHCTNAVCYSGDAFDI (SEQ ID NO: 33) |
| AB-010141 | GGSFSGYYWS (SEQ ID NO: 201) | EVNHRGSINYNNYNPSLKS (SEQ ID NO: 266) | AKPLRPHCTNGVCYSGDAFDI (SEQ ID NO: 331) |
| AB-010142 | GGSFSDYYWS (SEQ ID NO: 202) | EVNHRGSINYNNYNPSLKS (SEQ ID NO: 267) | AKPLRPHCTNGVCYSGDAFDI (SEQ ID NO: 332) |
| AB-010143 | GGSFSDYYWS (SEQ ID NO: 203) | EVNHRGSINYNNYNPSLKS (SEQ ID NO: 268) | AKPLRPHCTNGVCYSGDAFDI (SEQ ID NO: 333) |
| AB-010144 | GGSFSDYYWS (SEQ ID NO: 204) | EINHRGSINYNNYNPSLKS (SEQ ID NO: 269) | AKPLRPHCTNGVCYSGDAFDI (SEQ ID NO: 334) |
| AB-010145 | GGSFSDYYWS (SEQ ID NO: 205) | EVNHRGSINYNNYNPSLKS (SEQ ID NO: 270) | AKPLRPHCTNGVCYSGDAFDI (SEQ ID NO: 335) |
| AB-010146 | GGSFSDYYWS (SEQ ID NO: 206) | EVNHRGSINYNNYNPSLKS (SEQ ID NO: 271) | AKPLRPHCTNGVCYSGDAFDI (SEQ ID NO: 336) |
| AB-010147 | GGSFSDYYWS (SEQ ID NO: 207) | EVNHRGSINYNNYNPSLKS (SEQ ID NO: 272) | AKPLRPHCTNGVCYSGDAFDI (SEQ ID NO: 337) |
| AB-010148 | GGSFSDYYWS (SEQ ID NO: 208) | EINHRGSINYNNYNPSLKS (SEQ ID NO: 273) | AKPLRPHCTNGVCYSGDAFDI (SEQ ID NO: 338) |
| AB-010149 | GGSFSDYYWS (SEQ ID NO: 209) | EINHRGSINYNNYNPSLKS (SEQ ID NO: 274) | AKPLRPHCTNGVCYSGDAFDI (SEQ ID NO: 339) |
| AB-010150 | GGSFSDYYWS (SEQ ID NO: 210) | EVNHRGSINYNNYNPSLKS (SEQ ID NO: 275) | AKPLRPHCTNGVCYSGDAFDI (SEQ ID NO: 340) |
| AB-010151 | GGSFSDYYWS (SEQ ID NO: 211) | EINHRGSINYNNYNPSLKS (SEQ ID NO: 276) | AKPLRPHCTNGVCYSGDAFDI (SEQ ID NO: 341) |
| AB-010152 | GGSFSDYYW (SEQ ID NO: 212) | SEINHRGSINYNNYNPSLK (SEQ ID NO: 277) | AKPLRPHCTNGVCYSGDAFDI (SEQ ID NO: 342) |
| AB-010357 | GGSFSDYYW (SEQ ID NO: 213) | SEINHRGSINYNNYNPSLK (SEQ ID NO: 278) | AKPLRPHCTNGVCYSGDAFDI (SEQ ID NO: 343) |
| AB-010358 | GGSFSDYYWS (SEQ ID NO: 214) | EINHRGSINYNNYNPSLKS (SEQ ID NO: 279) | AKPLRPHCTNGVCYSGDAFDI (SEQ ID NO: 344) |

TABLE 6-continued

| Heavy chain CDRs | | | |
|---|---|---|---|
| Antibody ID | HCDR1 | HCDR2 | HCDR3 |
| AB-010359 | GGSFSDYYWS (SEQ ID NO: 215) | EINHRGSINYNNYNPSLKS (SEQ ID NO: 280) | AKPLRPHCTNGVCYSGDAFDI (SEQ ID NO: 345) |
| AB-010360 | GGSFSGYYWS (SEQ ID NO: 216) | EINHRGSINYNNYNPSLKS (SEQ ID NO: 281) | AKPLRPHCTNGVCYSGDAFDI (SEQ ID NO: 346) |
| AB-010361 | GGSFSGYYWS (SEQ ID NO: 217) | EINHRGSINYNNYNPSLKS (SEQ ID NO: 282) | AKPLRPHCTNGVCYSGDAFDI (SEQ ID NO: 347) |
| AB-010362 | GGSFSGYYWS (SEQ ID NO: 218) | EINHRGSINYNNYNPSLKS (SEQ ID NO: 283) | AKPLRPHCTNGVCYSGDAFDI (SEQ ID NO: 348) |
| AB-010363 | GGSFSGYYWS (SEQ ID NO: 219) | EINHRGSINYNNYNPSLKS (SEQ ID NO: 284) | AKPLRPHCTNGVCYSGDAFDI (SEQ ID NO: 349) |
| AB-010364 | GGSFSGYYWS (SEQ ID NO: 220) | EINHAGSINYNNYNPSLKS (SEQ ID NO: 285) | AKPLRPHCTNGVCYSGDAFDI (SEQ ID NO: 350) |
| AB-010365 | GGSFSGYYWS (SEQ ID NO: 221) | EINHAGSINYNNYNPSLKS (SEQ ID NO: 286) | AKPLRPHCTNGVCYSGDAFDI (SEQ ID NO: 351) |
| AB-010366 | GGSFSGYYWS (SEQ ID NO: 222) | EINHQGSINYNNYNPSLKS (SEQ ID NO: 287) | AKPLRPHCTNGVCYSGDAFDI (SEQ ID NO: 352) |
| AB-010367 | GGSFSGYYWS (SEQ ID NO: 223) | EINHQGSINYNNYNPSLKS (SEQ ID NO: 288) | AKPLRPHCTNGVCYSGDAFDI (SEQ ID NO: 353) |
| AB-010661 | GGSFSDYYWS (SEQ ID NO: 224) | EINHRGSINYNNYNPSLKS (SEQ ID NO: 289) | AKPLRPHCINGVCYSGDAFDI (SEQ ID NO: 354) |
| AB-010662 | GGSFSDYYWS (SEQ ID NO: 225) | EINHRGSINYNNYNPSLKS (SEQ ID NO: 290) | AKPLRPHCTNGVCYSGDAFDI (SEQ ID NO: 355) |
| AB-010663 | GGSFSDYYWS (SEQ ID NO: 226) | EINHRGSINYNNYNPSLKS (SEQ ID NO: 291) | AKPLRPHCTNGVCYSGDAFDI (SEQ ID NO: 356) |
| AB-010664 | GGSFSDYYWS (SEQ ID NO: 227) | EINHRGSINYNNYNPSLKS (SEQ ID NO: 292) | AKPLRPHCTNGVCYSGDAFDI (SEQ ID NO: 357) |
| AB-010665 | GGSFSDYYWS (SEQ ID NO: 228) | EINHRGSINYNNYNPSLKS (SEQ ID NO: 293) | AKPLRPHCINGVCYSGDAFDI (SEQ ID NO: 358) |
| AB-010666 | GGSFSDYYWS (SEQ ID NO: 229) | EINHRGSINYNNYNPSLKS (SEQ ID NO: 294) | AKPLRPHCTNGVCYSGDAFDI (SEQ ID NO: 359) |
| AB-010667 | GGSFSDYYWS (SEQ ID NO: 230) | EINHRGSINYNNYNPSLKS (SEQ ID NO: 295) | AKPLRPHCTNGVCYSGDAFDI (SEQ ID NO: 360) |
| AB-010668 | GGSFSDYYWS (SEQ ID NO: 231) | EINHRGSINYNNYNPSLKS (SEQ ID NO: 296) | AKPLRPHCTNGVCYSGDAFDI (SEQ ID NO: 361) |
| AB-010669 | GGSFSDYYWS (SEQ ID NO: 232) | EINHRGSINYNNYNPSLKS (SEQ ID NO: 297) | AKPLRPHCTNGVCYSGDAFDI (SEQ ID NO: 362) |
| AB-010670 | GGSFSDYYWS (SEQ ID NO: 233) | EINHRGSINYNNYNPSLKS (SEQ ID NO: 298) | AKPLRPHCINGVCYSGDAFDI (SEQ ID NO: 363) |
| AB-010671 | GGSFSDYYWS (SEQ ID NO: 234) | EINHRGSINYNNYNPSLKS (SEQ ID NO: 299) | AKPLRPHCINGVCYSGDAFDI (SEQ ID NO: 364) |
| AB-010672 | GGSFSDYYWS (SEQ ID NO: 235) | EINHRGSINYNNYNPSLKS (SEQ ID NO: 300) | AKPLRPHCTNGVCYSGDAFDI (SEQ ID NO: 365) |
| AB-010673 | GGSFSDYYWS (SEQ ID NO: 236) | EINHRGSINYNNYNPSLKS (SEQ ID NO: 301) | AKPLRPHCTNGVCYSGDAFDI (SEQ ID NO: 366) |
| AB-010674 | GGSFSDYYWS (SEQ ID NO: 237) | EINHRGSINYNNYNPSLKS (SEQ ID NO: 302) | AKPLRPHCTNGVCYSGDAFDI (SEQ ID NO: 367) |
| AB-010675 | GGSFSGYYWS (SEQ ID NO: 238) | EINHRGSINYNNYNPSLKS (SEQ ID NO: 303) | AKPLRPHCINGVCYSGDAFDI (SEQ ID NO: 368) |
| AB-010676 | GGSFSGYYWS (SEQ ID NO: 239) | EINHRGSINYNNYNPSLKS (SEQ ID NO: 304) | AKPLRPHCTNGVCYSGDAFDI (SEQ ID NO: 369) |

TABLE 6-continued

| Heavy chain CDRs | | | |
|---|---|---|---|
| Antibody ID | HCDR1 | HCDR2 | HCDR3 |
| AB-010677 | GGSFSGYYWS (SEQ ID NO: 240) | EINHRGSINYNNYNPSLKS (SEQ ID NO: 305) | AKPLRPHCTNGVCYSGDAFDI (SEQ ID NO: 370) |
| AB-010678 | GGSFSGYYWS (SEQ ID NO: 241) | EINHRGSINYNNYNPSLKS (SEQ ID NO: 306) | AKPLRPHCTNGVCYSGDAFDI (SEQ ID NO: 371) |
| AB-010679 | GGSFSGYYWS (SEQ ID NO: 242) | EINHRGSINYNNYNPSLKS (SEQ ID NO: 307) | AKPLRPHCINGVCYSGDAFDI (SEQ ID NO: 372) |
| AB-010680 | GGSFSGYYWS (SEQ ID NO: 243) | EINHRGSINYNNYNPSLKS (SEQ ID NO: 308) | AKPLRPHCTNGVCYSGDAFDI (SEQ ID NO: 373) |
| AB-010681 | GGSFSGYYWS (SEQ ID NO: 244) | EINHRGSINYNNYNPSLKS (SEQ ID NO: 309) | AKPLRPHCTNGVCYSGDAFDI (SEQ ID NO: 374) |
| AB-010682 | GGSFSGYYWS (SEQ ID NO: 245) | EINHRGSINYNNYNPSLKS (SEQ ID NO: 310) | AKPLRPHCINGVCYSGDAFDI (SEQ ID NO: 375) |
| AB-010683 | GGSFSGYYWS (SEQ ID NO: 246) | EINHRGSINYNNYNPSLKS (SEQ ID NO: 311) | AKPLRPHCTNGVCYSGDAFDI (SEQ ID NO: 376) |
| AB-010684 | GGSFSGYYWS (SEQ ID NO: 247) | EINHRGSINYNNYNPSLKS (SEQ ID NO: 312) | AKPLRPHCINGVCYSGDAFDI (SEQ ID NO: 377) |
| AB-010685 | GGSFSGYYWS (SEQ ID NO: 248) | EINHRGSINYNNYNPSLKS (SEQ ID NO: 313) | AKPLRPHCINGVCYSGDAFDI (SEQ ID NO: 378) |
| AB-010686 | GGSFSGYYWS (SEQ ID NO: 249) | EINHRGSINYNNYNPSLKS (SEQ ID NO: 314) | AKPLRPHCINGVCYSGDAFDI (SEQ ID NO: 379) |
| AB-010687 | GGSFSGYYWS (SEQ ID NO: 250) | EINHRGSINYNNYNPSLKS (SEQ ID NO: 315) | AKPLRPHCTNGVCYSGDAFDI (SEQ ID NO: 380) |
| AB-010688 | GGSFSGYYWS (SEQ ID NO: 251) | EINHRGSINYNNYNPSLKS (SEQ ID NO: 316) | AKPLRPHCTNGVCYSGDAFDI (SEQ ID NO: 381) |
| AB-010689 | GGSFSGYYWS (SEQ ID NO: 252) | EINHRGSINYNNYNPSLKS (SEQ ID NO: 317) | AKPLRPHCINGVCYSGDAFDI (SEQ ID NO: 382) |
| AB-010690 | GGSFSGYYWS (SEQ ID NO: 253) | EINHRGSINYNNYNPSLKS (SEQ ID NO: 318) | AKPLRPHCTNGVCYSGDAFDI (SEQ ID NO: 383) |
| AB-010691 | GGSFSGYYWS (SEQ ID NO: 254) | EINHRGSINYNNYNPSLKS (SEQ ID NO: 319) | AKPLRPHCTNGVCYSGDAFDI (SEQ ID NO: 384) |
| AB-010692 | GGSFSGYYWS (SEQ ID NO: 255) | EINHRGSINYNNYNPSLKS (SEQ ID NO: 320) | AKPLRPHCTNGVCYSGDAFDI (SEQ ID NO: 385) |
| AB-010693 | GGSFSGYYWS (SEQ ID NO: 256) | EINHRGSINYNNYNPSLKS (SEQ ID NO: 321) | AKPLRPHCINGVCYSGDAFDI (SEQ ID NO: 386) |
| AB-010694 | GGSFSGYYWS (SEQ ID NO: 257) | EINHRGSINYNNYNPSLKS (SEQ ID NO: 322) | AKPLRPHCTNGVCYSGDAFDI (SEQ ID NO: 387) |
| AB-010695 | GGSFSGYYWS (SEQ ID NO: 258) | EINHRGSINYNNYNPSLKS (SEQ ID NO: 323) | AKPLRPHCINGVCYSGDAFDI (SEQ ID NO: 388) |
| AB-010696 | GGSFSGYYWS (SEQ ID NO: 259) | EINHRGSINYNNYNPSLKS (SEQ ID NO: 324) | AKPLRPHCINGVCYSGDAFDI (SEQ ID NO: 389) |
| AB-010697 | GGSFSGYYWS (SEQ ID NO: 260) | EINHRGSINYNNYNPSLKS (SEQ ID NO: 325) | AKPLRPHCINGVCYSGDAFDI (SEQ ID NO: 390) |
| AB-010698 | GGSFSGYYWS (SEQ ID NO: 261) | EINHRGSINYNNYNPSLKS (SEQ ID NO: 326) | AKPLRPHCINGVCYSGDAFDI (SEQ ID NO: 391) |
| AB-010699 | GGSFSGYYWS (SEQ ID NO: 262) | EINHRGSINYNNYNPSLKS (SEQ ID NO: 327) | AKPLRPHCINGVCYSGDAFDI (SEQ ID NO: 392) |
| AB-010700 | GGSFSGYYWS (SEQ ID NO: 263) | EINHRGSINYNNYNPSLKS (SEQ ID NO: 328) | AKPLRPHCINGVCYSGDAFDI (SEQ ID NO: 393) |
| AB-010701 | GGSFSGYYWS (SEQ ID NO: 264) | EINHRGSINYNNYNPSLKS (SEQ ID NO: 329) | AKPLRPHCTNGVCYSGDAFDI (SEQ ID NO: 394) |

TABLE 6-continued

| | Heavy chain CDRs | | |
|---|---|---|---|
| Antibody ID | HCDR1 | HCDR2 | HCDR3 |
| AB-010702 | GGSFSGYYWS (SEQ ID NO: 265) | EINHRGSINYNNYNPSLKS (SEQ ID NO: 330) | AKPLRPHCTNGVCYSGDAFDI (SEQ ID NO: 395) |

TABLE 7

| | Light chain CDR sequences | | |
|---|---|---|---|
| Antibody ID | LCDR1 | LCDR2 | LCDR3 |
| AB-008873 | GGNNIGSKNVH (SEQ ID NO: 34) | DDSDRPS (SEQ ID NO: 45) | QVWDSSSDHLV (SEQ ID NO: 56) |
| AB-009805 | GGNNIGSKNVH (SEQ ID NO: 35) | DDSDRPS (SEQ ID NO: 46) | QVWDSSSDHLV (SEQ ID NO: 57) |
| AB-009806 | GGNNIGTKNVH (SEQ ID NO: 36) | DDSDRPS (SEQ ID NO: 47) | QVWDSSSDHLV (SEQ ID NO: 58) |
| AB-009807 | GGNNIGSKNVH (SEQ ID NO: 37) | DDSDRPS (SEQ ID NO: 48) | QVWDSSSDHLV (SEQ ID NO: 59) |
| AB-009808 | GGNNIGSKNVH (SEQ ID NO: 38) | DDSDRPS (SEQ ID NO: 49) | QVWDSSSDHLV (SEQ ID NO: 60) |
| AB-009812 | GGNNIGSKNVH (SEQ ID NO: 39) | DDSDRPS (SEQ ID NO: 50) | QVWDSSSDHLV (SEQ ID NO: 61) |
| AB-009813 | GGNNIGSKNVH (SEQ ID NO: 40) | DDSDRPS (SEQ ID NO: 51) | QVWDSSSDHLV (SEQ ID NO: 62) |
| AB-009814 | GGNNIGSKNVH (SEQ ID NO: 41) | DDSDRPS (SEQ ID NO: 52) | QVWDSSSDHLV (SEQ ID NO: 63) |
| AB-009815 | GGNNIGSKNVH (SEQ ID NO: 42) | DDSDRPS (SEQ ID NO: 53) | QVWDSSSDHLV (SEQ ID NO: 64) |
| AB-009816 | GGNNIGSKNVH (SEQ ID NO: 43) | DDSDRPS (SEQ ID NO: 54) | QVWDSSSDHLV (SEQ ID NO: 65) |
| AB-009817 | GGNNIGSKNVH (SEQ ID NO: 44) | DDSDRPS (SEQ ID NO: 55) | QVWDSSSDHLV (SEQ ID NO: 66) |
| AB-010141 | GGNNIGSKNVH (SEQ ID NO: 396) | DDSDRPS (SEQ ID NO: 461) | QVWDSSSDHLV (SEQ ID NO: 526) |
| AB-010142 | GGNNIGSKSVH (SEQ ID NO: 397) | DDSDRPS (SEQ ID NO: 462) | QVWDSSSDHLV (SEQ ID NO: 527) |
| AB-010143 | GGNNIGSKNVH (SEQ ID NO: 398) | DDSDRPS (SEQ ID NO: 463) | QVWDSSSDHVV (SEQ ID NO: 528) |
| AB-010144 | GGNNIGSKNVH (SEQ ID NO: 399) | DDSDRPS (SEQ ID NO: 464) | QVWDSSSDHLV (SEQ ID NO: 529) |
| AB-010145 | GGNNIGSKNVH (SEQ ID NO: 400) | DDSDRPS (SEQ ID NO: 465) | QVWDSSSDHLV (SEQ ID NO: 530) |
| AB-010146 | GGNNIGSKNVH (SEQ ID NO: 401) | DDSDRPS (SEQ ID NO: 466) | QVWDSSSDHLV (SEQ ID NO: 531) |
| AB-010147 | GGNNIGSKNVH (SEQ ID NO: 402) | DDSDRPS (SEQ ID NO: 467) | QVWDSSSDHLV (SEQ ID NO: 532) |
| AB-010148 | GGNNIGSKNVH (SEQ ID NO: 403) | DDSDRPS (SEQ ID NO: 468) | QVWDSSSDHLV (SEQ ID NO: 533) |
| AB-010149 | GGNNIGSKNVH (SEQ ID NO: 404) | DDSDRPS (SEQ ID NO: 469) | QVWDSSSDHLV (SEQ ID NO: 534) |
| AB-010150 | GGNNIGSKNVH (SEQ ID NO: 405) | DDSDRPS (SEQ ID NO: 470) | QVWDSSSDHLV (SEQ ID NO: 535) |

TABLE 7-continued

Light chain CDR sequences

| Antibody ID | LCDR1 | LCDR2 | LCDR3 |
|---|---|---|---|
| AB-010151 | GGNNIGSKNVH (SEQ ID NO: 406) | DDSDRPS (SEQ ID NO: 471) | QVWDSSSDHLV (SEQ ID NO: 536) |
| AB-010152 | GGNNIGSKNVH (SEQ ID NO: 407) | DDSDRPS (SEQ ID NO: 472) | QVWDSSSDHLV (SEQ ID NO: 537) |
| AB-010357 | GGNNIGSKNVH (SEQ ID NO: 408) | DDSDRPS (SEQ ID NO: 473) | QVWDSSSDHVV (SEQ ID NO: 538) |
| AB-010358 | GGNNIGSKNVH (SEQ ID NO: 409) | DDSDRPS (SEQ ID NO: 474) | QVWDSSSDHLV (SEQ ID NO: 539) |
| AB-010359 | GGNNIGSKNVH (SEQ ID NO: 410) | DDSDRPS (SEQ ID NO: 475) | QVWDSSSDHVV (SEQ ID NO: 540) |
| AB-010360 | GGNNIGSKNVH (SEQ ID NO: 411) | DDSDRPS (SEQ ID NO: 476) | QVWDSSSDHLV (SEQ ID NO: 541) |
| AB-010361 | GGNNIGSKNVH (SEQ ID NO: 412) | DDSDRPS (SEQ ID NO: 477) | QVWDSSSDHVV (SEQ ID NO: 542) |
| AB-010362 | GGNNIGSKNVH (SEQ ID NO: 413) | DDSDRPS (SEQ ID NO: 478) | QVWDSSSDHLV (SEQ ID NO: 543) |
| AB-010363 | GGNNIGSKNVH (SEQ ID NO: 414) | DDSDRPS (SEQ ID NO: 479) | QVWDSSSDHVV (SEQ ID NO: 544) |
| AB-010364 | GGNNIGSKNVH (SEQ ID NO: 415) | DDSDRPS (SEQ ID NO: 480) | QVWDSSSDHVV (SEQ ID NO: 545) |
| AB-010365 | GGNNIGSKNVH (SEQ ID NO: 416) | DDSDRPS (SEQ ID NO: 481) | QVWDSSSDHVV (SEQ ID NO: 546) |
| AB-010366 | GGNNIGSKNVH (SEQ ID NO: 417) | DDSDRPS (SEQ ID NO: 482) | QVWDSSSDHVV (SEQ ID NO: 547) |
| AB-010367 | GGNNIGSKNVH (SEQ ID NO: 418) | DDSDRPS (SEQ ID NO: 483) | QVWDSSSDHVV (SEQ ID NO: 548) |
| AB-010661 | RGNNIGSKNVH (SEQ ID NO: 419) | DDSDRPS (SEQ ID NO: 484) | QVWDSSSDHVV (SEQ ID NO: 549) |
| AB-010662 | RGNNIGYKNVH (SEQ ID NO: 420) | DDSDRPS (SEQ ID NO: 485) | QVWDSSSDHVV (SEQ ID NO: 550) |
| AB-010663 | RGNNIGSMNVH (SEQ ID NO: 421) | DDSDRPS (SEQ ID NO: 486) | QVWDSSSDHVV (SEQ ID NO: 551) |
| AB-010664 | RGNNIGSKNVH (SEQ ID NO: 422) | DDSDRPS (SEQ ID NO: 487) | QVWDHSSDHVV (SEQ ID NO: 552) |
| AB-010665 | GGNNIGYKNVH (SEQ ID NO: 423) | DDSDRPS (SEQ ID NO: 488) | QVWDSSSDHVV (SEQ ID NO: 553) |
| AB-010666 | GGNNIGYMNVH (SEQ ID NO: 424) | DDSDRPS (SEQ ID NO: 489) | QVWDSSSDHVV (SEQ ID NO: 554) |
| AB-010667 | GGNNIGYKNVH (SEQ ID NO: 425) | DDSDRPS (SEQ ID NO: 490) | QVWDHSSDHVV (SEQ ID NO: 555) |
| AB-010668 | GGNNIGSMNVH (SEQ ID NO: 426) | DDSDRPS (SEQ ID NO: 491) | QVWDSSSDHVV (SEQ ID NO: 556) |
| AB-010669 | GGNNIGSMNVH (SEQ ID NO: 427) | DDSDRPS (SEQ ID NO: 492) | QVWDHSSDHVV (SEQ ID NO: 557) |
| AB-010670 | GGNNIGSKNVH (SEQ ID NO: 428) | DDSDRPS (SEQ ID NO: 493) | QVWDHSSDHVV (SEQ ID NO: 558) |
| AB-010671 | GGNNIGYKNVH (SEQ ID NO: 429) | DDSDRPS (SEQ ID NO: 494) | QVWDHSSDHVV (SEQ ID NO: 559) |
| AB-010672 | GGNNIGSKNVH (SEQ ID NO: 430) | DDSDRPS (SEQ ID NO: 495) | QVWDSRSDHVV (SEQ ID NO: 560) |

TABLE 7-continued

Light chain CDR sequences

| Antibody ID | LCDR1 | LCDR2 | LCDR3 |
|---|---|---|---|
| AB-010673 | GGNNIGSKNVH (SEQ ID NO: 431) | DDSDRPS (SEQ ID NO: 496) | QVWDSESDHVV (SEQ ID NO: 561) |
| AB-010674 | GGNNIGYKNVH (SEQ ID NO: 432) | DDSDRPS (SEQ ID NO: 497) | QVWDSESDHVV (SEQ ID NO: 562) |
| AB-010675 | RGNNIGSKNVH (SEQ ID NO: 433) | DDSDRPS (SEQ ID NO: 498) | QVWDSSSDHVV (SEQ ID NO: 563) |
| AB-010676 | RGNNIGYKNVH (SEQ ID NO: 434) | DDSDRPS (SEQ ID NO: 499) | QVWDSSSDHVV (SEQ ID NO: 564) |
| AB-010677 | RGNNIGSMNVH (SEQ ID NO: 435) | DDSDRPS (SEQ ID NO: 500) | QVWDSSSDHVV (SEQ ID NO: 565) |
| AB-010678 | RGNNIGSKNVH (SEQ ID NO: 436) | DDSDRPS (SEQ ID NO: 501) | QVWDHSSDHVV (SEQ ID NO: 566) |
| AB-010679 | GGNNIGYKNVH (SEQ ID NO: 437) | DDSDRPS (SEQ ID NO: 502) | QVWDSSSDHVV (SEQ ID NO: 567) |
| AB-010680 | GGNNIGYMNVH (SEQ ID NO: 438) | DDSDRPS (SEQ ID NO: 503) | QVWDSSSDHVV (SEQ ID NO: 568) |
| AB-010681 | GGNNIGYKNVH (SEQ ID NO: 439) | DDSDRPS (SEQ ID NO: 504) | QVWDHSSDHVV (SEQ ID NO: 569) |
| AB-010682 | GGNNIGSMNVH (SEQ ID NO: 440) | DDSDRPS (SEQ ID NO: 505) | QVWDSSSDHVV (SEQ ID NO: 570) |
| AB-010683 | GGNNIGSMNVH (SEQ ID NO: 441) | DDSDRPS (SEQ ID NO: 506) | QVWDHSSDHVV (SEQ ID NO: 571) |
| AB-010684 | GGNNIGSKNVH (SEQ ID NO: 442) | DDSDRPS (SEQ ID NO: 507) | QVWDHSSDHVV (SEQ ID NO: 572) |
| AB-010685 | GGNNIGYKNVH (SEQ ID NO: 443) | DDSDRPS (SEQ ID NO: 508) | QVWDHSSDHVV (SEQ ID NO: 573) |
| AB-010686 | GGNNIGSKNVH (SEQ ID NO: 444) | DDSDRPS (SEQ ID NO: 509) | QVWDSRSDHVV (SEQ ID NO: 574) |
| AB-010687 | GGNNIGSKNVH (SEQ ID NO: 445) | DDSDRPS (SEQ ID NO: 510) | QVWDSESDHVV (SEQ ID NO: 575) |
| AB-010688 | GGNNIGYKNVH (SEQ ID NO: 446) | DDSDRPS (SEQ ID NO: 511) | QVWDSESDHVV (SEQ ID NO: 576) |
| AB-010689 | RGNNIGSKNVH (SEQ ID NO: 447) | DDSDRPS (SEQ ID NO: 512) | QVWDSSSDHVV (SEQ ID NO: 577) |
| AB-010690 | RGNNIGYKNVH (SEQ ID NO: 448) | DDSDRPS (SEQ ID NO: 513) | QVWDSSSDHVV (SEQ ID NO: 578) |
| AB-010691 | RGNNIGSMNVH (SEQ ID NO: 449) | DDSDRPS (SEQ ID NO: 514) | QVWDSSSDHVV (SEQ ID NO: 579) |
| AB-010692 | RGNNIGSKNVH (SEQ ID NO: 450) | DDSDRPS (SEQ ID NO: 515) | QVWDHSSDHVV (SEQ ID NO: 580) |
| AB-010693 | GGNNIGYKNVH (SEQ ID NO: 451) | DDSDRPS (SEQ ID NO: 516) | QVWDSSSDHVV (SEQ ID NO: 581) |
| AB-010694 | GGNNIGYMNVH (SEQ ID NO: 452) | DDSDRPS (SEQ ID NO: 517) | QVWDSSSDHVV (SEQ ID NO: 582) |
| AB-010695 | GGNNIGYKNVH (SEQ ID NO: 453) | DDSDRPS (SEQ ID NO: 518) | QVWDHSSDHVV (SEQ ID NO: 583) |
| AB-010696 | GGNNIGSMNVH (SEQ ID NO: 454) | DDSDRPS (SEQ ID NO: 519) | QVWDSSSDHVV (SEQ ID NO: 584) |
| AB-010697 | GGNNIGSMNVH (SEQ ID NO: 455) | DDSDRPS (SEQ ID NO: 520) | QVWDHSSDHVV (SEQ ID NO: 585) |

TABLE 7-continued

Light chain CDR sequences

| Antibody ID | LCDR1 | LCDR2 | LCDR3 |
|---|---|---|---|
| AB-010698 | GGNNIGSKNVH (SEQ ID NO: 456) | DDSDRPS (SEQ ID NO: 521) | QVWDHSSDHVV (SEQ ID NO: 586) |
| AB-010699 | GGNNIGYKNVH (SEQ ID NO: 457) | DDSDRPS (SEQ ID NO: 522) | QVWDHSSDHVV (SEQ ID NO: 587) |
| AB-010700 | GGNNIGSKNVH (SEQ ID NO: 458) | DDSDRPS (SEQ ID NO: 523) | QVWDSRSDHVV (SEQ ID NO: 588) |
| AB-010701 | GGNNIGSKNVH (SEQ ID NO: 459) | DDSDRPS (SEQ ID NO: 524) | QVWDSESDHVV (SEQ ID NO: 589) |
| AB-010702 | GGNNIGYKNVH (SEQ ID NO: 460) | DDSDRPS (SEQ ID NO: 525) | QVWDSESDHVV (SEQ ID NO: 590) |

TABLE 8

Heavy and Light variable region sequences

| Antibody ID | VH | VL |
|---|---|---|
| AB-008873 | QVQLQQWGAGLLKPSETLSLTCAVYGGSFSDYYWSWIRQPPGKGLEWIGEVNHRGSINYNNYNPSLKSRVTISVDPSKNQFSLKLTSVTAADTAVYYCAKPLRPHCTNGVCYSGDAFDIWGQGTMVTVAS (SEQ ID NO: 67) | SYVLTQPPSVSVAPGQTARITCGGNNIGSKNVHWYQQKPGQAPVLVVYDDSDRPSGIPEQFSGSNSGNTATLTISRVEAGDEADYYCQVWDSSSDHLVFGGGTKLTVL (SEQ ID NO: 78) |
| AB-009805 | QVQLQQWGAGLLKPSETLSLTCAVYGGSLSDYHWSWIRQPPGKGLEWIGEINHSGSTNYNPSLKSRVTISVDTSKNQFSLKLSSVSAADTAVYYCAKPFRPHCTNGVCHSGDAFDIWGQGTMATVSS (SEQ ID NO: 68) | SYVLTQPPSVSVAPGQTARITCGGNNIGSKNVHWYQQKPGQAPVLVVYDDSDRPSGIPEQFSGSNSGNTATLTISRVEAGDEADYYCQVWDSSSDHLVFGGGTKLTVL (SEQ ID NO: 79) |
| AB-009806 | QVQLQQWGAGLLKPSETLSLTCAVYGGSFSDYYWSWIRQPPGKGLEWIGEINHSGSTNYNPSLKSRVTISVDPSKNQFSLKLTSVTAADTAVYYCAKPFRPHCTNGVCYSGDAFDIWGQGTMVTVSS (SEQ ID NO: 69) | SYVLTQPPSVSVAPGQTARITCGGNNIGTKNVHWYQQKPGQAPVLVVYDDSDRPSGIPEQFSGSNSGNTATLTISRVEAGDEADYYCQVWDSSSDHLVFGGGTKLTVL (SEQ ID NO: 80) |
| AB-009807 | QVQLQQWGAGLLKPSETLSLTCAVYGGSFNDYYWSWIRQPPGKGLEWIGEVNHSGSTSYNPSLKSRVTISVDTSKNQFSLKLSSVTAADTAVYYCAKPFRPHCTNGVCYSGDAFDIWGQGTMVTVSS (SEQ ID NO: 70) | SYVLTQPPSVSVAPGQTARITCGGNNIGSKNVHWYQQKPGQAPALVVYDDSDRPSGIPEQFSGSNSGNTATLTISRVEAGDEADYYCQVWDSSSDHLVFGGGTKLTVL (SEQ ID NO: 81) |
| AB-009808 | QVQLQQWGAGLLKPSETLSLTCAVYGGSFSDYYWSWIRQPPGKGLEWIGEINHSGSTNYNPSLKSRVTISVDPSKNQFSLKLTSVTAADTAVYYCAKPFRPHCTNGVCYSGDAFDIWGQGTMVTVSS (SEQ ID NO: 71) | SYVLTQPPSVSVAPGQTARITCGGNNIGSKNVHWYQQKPGQAPVLVVYDDSDRPSGIPEQFSGSNSGNTATLTISRVEAGDEADYYCQVWDSSSDHLVFGGGTKLTVL (SEQ ID NO: 82) |
| AB-009812 | QVQLQQWGAGLLKPSETLSLTCAVYGGSFSDYYWSWIRQPPGKGLEWIGEVNHSGSINYNNYNPSLKSRVTISVDPSKNQFSLKLTSVTAADTAVYYCAKPLRPHCTNGVCYSGDAFDIWGQGTMVTVAS (SEQ ID NO: 72) | SYVLTQPPSVSVAPGQTARITCGGNNIGSKNVHWYQQKPGQAPVLVVYDDSDRPSGIPEQFSGSNSGNTATLTISRVEAGDEADYYCQVWDSSSDHLVFGGGTKLTVL (SEQ ID NO: 83) |
| AB-009813 | QVQLQQWGAGLLKPSETLSLTCAVYGGSFSDYYWSWIRQPPGKGLEWIGEVNHAGSINYNNYNPSLKSRVTISVDPSKNQFSLKLTSVTAADTAVYYCAKPLRPHCTNGVCYSGDAFDIWGQGTMVTVAS (SEQ ID NO: 73) | SYVLTQPPSVSVAPGQTARITCGGNNIGSKNVHWYQQKPGQAPVLVVYDDSDRPSGIPEQFSGSNSGNTATLTISRVEAGDEADYYCQVWDSSSDHLVFGGGTKLTVL (SEQ ID NO: 84) |
| AB-009814 | QVQLQQWGAGLLKPSETLSLTCAVYGGSFSDYYWSWIRQPPGKGLEWIGEVNHRGSINYNPSLKSRVTISVDPSKNQFSLKLTS | SYVLTQPPSVSVAPGQTARITCGGNNIGSKNVHWYQQKPGQAPVLVVYDDSDRPSGIPEQFSGSNSGNTATLTISRVEAGDEADYYC |

TABLE 8-continued

Heavy and Light variable region sequences

| Antibody ID | VH | VL |
|---|---|---|
| | VTAADTAVYYCAKPLRPHCTNGVCYSGD<br>AFDIWGQGTMVTVAS<br>(SEQ ID NO: 74) | QVWDSSSDHLVFGGGTKLTVL<br>(SEQ ID NO: 85) |
| AB-009815 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LTSVTAADTAVYYCAKPLRPHCTNGVCY<br>SGDAFDIWGQGTMVTVAS<br>(SEQ ID NO: 75) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 86) |
| AB-009816 | QVQLQQWGAGLLKPSETLSLTCAVYGGS<br>FSDYYWSWIRQPPGKGLEWIGEVNHRGS<br>INYNNYNPSLKSRVTISVDASKNQFSLK<br>LTSVTAADTAVYYCAKPLRPHCTNGVCY<br>SGDAFDIWGQGTMVTVAS<br>(SEQ ID NO: 76) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 87) |
| AB-009817 | QVQLQQWGAGLLKPSETLSLTCAVYGGS<br>FSDYYWSWIRQPPGKGLEWIGEVNHRGS<br>INYNNYNPSLKSRVTISVDPSKNQFSLK<br>LTSVTAADTAVYYCAKPLRPHCTNAVCY<br>SGDAFDIWGQGTMVTVSS<br>(SEQ ID NO: 77) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 88) |
| AB-010141 | QVQLQQWGAGLLKPSETLSLTCAVYGGS<br>FSGYYWSWIRQPPGKGLEWIGEVNHRGS<br>INYNNYNPSLKSRVTISVDTSKNQFSLK<br>LTSVTAADTAVYYCAKPLRPHCTNGVCY<br>SGDAFDIWGQGTMVTVAS<br>(SEQ ID NO: 591) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 656) |
| AB-010142 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LTSVTAADTAVYYCAKPLRPHCTNGVCY<br>SGDAFDIWGQGTMVTVAS<br>(SEQ ID NO: 592) | SYVLTQPPSVSVAPGQTARITCGGNNIGS<br>KSVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 657) |
| AB-010143 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LTSVTAADTAVYYCAKPLRPHCTNGVCY<br>SGDAFDIWGQGTMVTVAS<br>(SEQ ID NO: 593) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 658) |
| AB-010144 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LTSVTAADTAVYYCAKPLRPHCTNGVCY<br>SGDAFDIWGQGTMVTVAS<br>(SEQ ID NO: 594) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 659) |
| AB-010145 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 595) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 660) |
| AB-010146 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LTSVTAADTAVYYCAKPLRPHCTNGVCY<br>SGDAFDIWGQGTMVTVSS<br>(SEQ ID NO: 596) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 661) |
| AB-010147 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LTSVTAADTAVYYCAKPLRPHCTNGVCY<br>SGDAFDIWGQGTMVTVAS<br>(SEQ ID NO: 597) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHLVFGGGTKLTVL<br>(SEQ ID NO: 662) |
| AB-010148 | QVQLQQWGAGLLKPSETLSLTCAVYGGS<br>FSDYYWSWIRQPPGKGLEWIGEINHRGS | SYVLTQPPSVSVAPGQTARITCGGNNIGS<br>KNVHWYQQKPGQAPVLVVYDDSDRPSGIP |

TABLE 8-continued

Heavy and Light variable region sequences

| Antibody ID | VH | VL |
|---|---|---|
| | INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 598) | EQFSGSNSGNTATLTISRVEAGDEADYYC<br>QVWDSSSDHLVFGGGTKLTVL<br>(SEQ ID NO: 663) |
| AB-010149 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LTSVTAADTAVYYCAKPLRPHCTNGVCY<br>SGDAFDIWGQGTMVTVSS<br>(SEQ ID NO: 599) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 664) |
| AB-010150 | QVQLQQWGAGLLKPSETLSLTCAVYGGS<br>FSDYYWSWIRQPPGKGLEWIGEVNHRGS<br>INYNNYNPSLKSRVTISVDTSKNQFSLK<br>LSSVTAADTAVYYCAKPLRPHCTNGVCY<br>SGDAFDIWGQGTMVTVSS<br>(SEQ ID NO: 600) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 665) |
| AB-010151 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVSS<br>(SEQ ID NO: 601) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLTVL<br>(SEQ ID NO: 666) |
| AB-010152 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVSS<br>(SEQ ID NO: 602) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHLVFGGGTKLTVL<br>(SEQ ID NO: 667) |
| AB-010357 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 603) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 668) |
| AB-010358 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 604) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHLVFGGGTKLTVL<br>(SEQ ID NO: 669) |
| AB-010359 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 605) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHVVFGGGTKLTVL<br>(SEQ ID NO: 670) |
| AB-010360 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 606) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHLVFGGGTKLVTVL<br>(SEQ ID NO: 671) |
| AB-010361 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 607) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 672) |
| AB-010362 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 608) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHLVFGGGTKLTVL<br>(SEQ ID NO: 673) |

TABLE 8-continued

Heavy and Light variable region sequences

| Antibody ID | VH | VL |
|---|---|---|
| AB-010363 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 609) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHVVFGGGTKLTVL<br>(SEQ ID NO: 674) |
| AB-010364 | QVQLQQWGAGLLKPSETLSLTCAVYGGS<br>FSGYYWSWIRQPPGKGLEWIGEINHAGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 610) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 675) |
| AB-010365 | QVQLQQWGAGLLKPSETLSLTCAVYGGS<br>FSGYYWSWIRQPPGKGLEWIGEINHAGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 611) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHVVFGGGTKLTVL<br>(SEQ ID NO: 676) |
| AB-010366 | QVQLQQWGAGLLKPSETLSLTCAVYGGS<br>FSGYYWSWIRQPPGKGLEWIGEINHQGS<br>INYNNYNPSLKSRVTISVDTSKNQFSLK<br>LSSVTAADTAVYYCAKPLRPHCTNGVCY<br>SGDAFDIWWGQGTMVTVAS<br>(SEQ ID NO: 612) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 677) |
| AB-010367 | QVQLQQWGAGLLKPSETLSLTCAVYGGS<br>FSGYYWSWIRQPPGKGLEWIGEINHQGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 613) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSSSDHVVFGGGTKLTVL<br>(SEQ ID NO: 678) |
| AB-010661 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 614) | SYVLTQPPSVSVAPGQTARITCRGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 679) |
| AB-010662 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 615) | SYVLTQPPSVSVAPGQTARITCRGNNIGY<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 680) |
| AB-010663 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 616) | SYVLTQPPSVSVAPGQTARITCRGNNIGS<br>MNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 681) |
| AB-010664 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 617) | SYVLTQPPSVSVAPGQTARITCRGNNIGS<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 682) |
| AB-010665 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 618) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 683) |
| AB-010666 | QVQLQQWGAGLLKPSETLSLTCAVYGGS<br>FSDYYWSWIRQPPGKGLEWIGEINHRGS | SYVLTQPPSVSVAPGQTARITCGGNNIGY<br>MNVHWYQQKPGQAPVLVVYDDSDRPSGIP |

TABLE 8-continued

Heavy and Light variable region sequences

| Antibody ID | VH | VL |
|---|---|---|
| | INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 619) | EQFSGSNSGNTATLTISRVEAGDEADYYC<br>QVWDSSSDHVVFGGGTKLTVL<br>(SEQ ID NO: 684) |
| AB-010667 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 620) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 685) |
| AB-010668 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 621) | SYVLTQPPSVSVAPGQTARITCGGNNIGS<br>MNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 686) |
| AB-010669 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 622) | SYVLTQPPSVSVAPGQTARITCGGNNIGS<br>MNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 687) |
| AB-010670 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 623) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 688) |
| AB-010671 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 624) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 689) |
| AB-010672 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 625) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSRSDHVVFGGGTKLTVL<br>(SEQ ID NO: 690) |
| AB-010673 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 626) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSESDHVVFGGGTKLTVL<br>(SEQ ID NO: 691) |
| AB-010674 | QVQLQQWGAGLLKPSETLSLTCAVYGGS<br>FSDYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 627) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDSESDHVVFGGGTKLTVL<br>(SEQ ID NO: 692) |
| AB-010675 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 628) | SYVLTQPPSVSVAPGQTARITCRGNNIGS<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 693) |
| AB-010676 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 629) | SYVLTQPPSVSVAPGQTARITCRGNNIGY<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 694) |

TABLE 8-continued

Heavy and Light variable region sequences

| Antibody ID | VH | VL |
|---|---|---|
| AB-010677 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 630) | SYVLTQPPSVSVAPGQTARITCRGNNIGS<br>MNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 695) |
| AB-010678 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 631) | SYVLTQPPSVSVAPGQTARITCRGNNIGS<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 696) |
| AB-010679 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 632) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 697) |
| AB-010680 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 633) | SYVLTQPPSVSVAPGQTARITCGGNNIGY<br>MNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 698) |
| AB-010681 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 634) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 699) |
| AB-010682 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 635) | SYVLTQPPSVSVAPGQTARITCGGNNIGS<br>MNVHWYQQKPGQAPVLVVYDDSDRPSGIP<br>EQFSGSNSGNTATLTISRVEAGDEADYYC<br>QVWDSSSDHVVFGGGTKLTVL<br>(SEQ ID NO: 700) |
| AB-010683 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 636) | SYVLTQPPSVSVAPGQTARITCGGNNIGS<br>MNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 701) |
| AB-010684 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 637) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 702) |
| AB-010685 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 638) | SYVLTQPPSVSVAPGQTARITCGGNNIGY<br>KNVHWYQQKPGQAPVLVVYDDSDRPSGIP<br>EQFSGSNSGNTATLTISRVEAGDEADYYC<br>QVWDHSSDHVVFGGGTKLTVL<br>(SEQ ID NO: 703) |
| AB-010686 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 639) | SYVLTQPPSVSVAPGQTARITCGGNNIGS<br>KNVHWYQQKPGQAPVLVVYDDSDRPSGIP<br>EQFSGSNSGNTATLTISRVEAGDEADYYC<br>QVWDSRSDHVVFGGGTKLTVL<br>(SEQ ID NO: 704) |

TABLE 8-continued

Heavy and Light variable region sequences

| Antibody ID | VH | VL |
|---|---|---|
| AB-010687 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 640) | SYVLTQPPSVSVAPGQTARITCGGNNIGS KNVHWYQQKPGQAPVLVVYDDSDRPSGIP EQFSGSNSGNTATLTISRVEAGDEADYYC QVWDSESDHVVFGGGTKLTVL (SEQ ID NO: 705) |
| AB-010688 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 641) | SYVLTQPPSVSVAPGQTARITCGGNNIGY KNVHWYQQKPGQAPVLVVYDDSDRPSGIP EQFSGSNSGNTATLTISRVEAGDEADYYC QVWDSESDHVVFGGGTKLTVL (SEQ ID NO: 706) |
| AB-010689 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCINGVCY SGDAFDIWGQGTMVTVAS (SEQ ID NO: 642) | SYVLTQPPSVSVAPGQTARITCRGNNIGS KNVHWYQQKPGQAPVLVVYDDSDRPSGIP ERFSGSNSGNTATLTISRVEAGDEADYYC QVWDSSSDHVVFGGGTKLTVL (SEQ ID NO: 707) |
| AB-010690 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 643) | SYVLTQPPSVSVAPGQTARITCRGNNIGY KNVHWYQQKPGQAPVLVVYDDSDRPSGIP ERFSGSNSGNTATLTISRVEAGDEADYYC QVWDSSSDHVVFGGGTKLTVL (SEQ ID NO: 708) |
| AB-010691 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 644) | SYVLTQPPSVSVAPGQTARITCRGNNIGS MNVHWYQQKPGQAPVLVVYDDSDRPSGIP ERFSGSNSGNTATLTISRVEAGDEADYYC QVWDSSSDHVVFGGGTKLTVL (SEQ ID NO: 709) |
| AB-010692 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 645) | SYVLTQPPSVSVAPGQTARITCRGNNIGS KNVHWYQQKPGQAPVLVVYDDSDRPSGIP ERFSGSNSGNTATLTISRVEAGDEADYYC QVWDHSSDHVVFGGGTKLTVL (SEQ ID NO: 710) |
| AB-010693 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCINGVCY SGDAFDIWGQGTMVTVAS (SEQ ID NO: 646) | SYVLTQPPSVSVAPGQTARITCGGNNIGY KNVHWYQQKPGQAPVLVVYDDSDRPSGIP ERFSGSNSGNTATLTISRVEAGDEADYYC QVWDSSSDHVVFGGGTKLTVL (SEQ ID NO: 711) |
| AB-010694 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 647) | SYVLTQPPSVSVAPGQTARITCGGNNIGY MNVHWYQQKPGQAPVLVVYDDSDRPSGIP ERFSGSNSGNTATLTISRVEAGDEADYYC QVWDSSSDHVVFGGGTKLTVL (SEQ ID NO: 712) |
| AB-010695 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 648) | SYVLTQPPSVSVAPGQTARITCGGNNIGY KNVHWYQQKPGQAPVLVVYDDSDRPSGIP ERFSGSNSGNTATLTISRVEAGDEADYYC QVWDHSSDHVVFGGGTKLTVL (SEQ ID NO: 713) |
| AB-010696 | QVQLQQWGAGLLKPSETLSLTCAVYGGS FSGYYWSWIRQPPGKGLEWIGEINHRGS INYNNYNPSLKSRVTISVDTSKNQFSLK LSSVTAADTAVYYCAKPLRPHCTNGVCY SGDAFDIWGQGTMVTVAS (SEQ ID NO: 649) | SYVLTQPPSVSVAPGQTARITCGGNNIGS MNVHWYQQKPGQAPVLVVYDDSDRPSGIP ERFSGSNSGNTATLTISRVEAGDEADYYC QVWDSSSDHVVFGGGTKLTVL (SEQ ID NO: 714) |

TABLE 8-continued

Heavy and Light variable region sequences

| Antibody ID | VH | VL |
|---|---|---|
| AB-010697 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 650) | SYVLTQPPSVSVAPGQTARITCGGNNIGS<br>MNVHWYQQKPGQAPVLVVYDDSDRPSGIP<br>ERFSGSNSGNTATLTISRVEAGDEADYYC<br>QVWDHSSDHVVFGGGTKLTVL<br>(SEQ ID NO: 715) |
| AB-010698 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 651) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDHSSDHVVFGGGTKLTVL<br>(SEQ ID NO: 716) |
| AB-010699 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCINGVCY<br>SGDAFDIWGQGTMVTVAS<br>(SEQ ID NO: 652) | SYVLTQPPSVSVAPGQTARITCGGNNIGY<br>KNVHWYQQKPGQAPVLVVYDDSDRPSGIP<br>ERFSGSNSGNTATLTISRVEAGDEADYYC<br>QVWDHSSDHVVFGGGTKLTVL<br>(SEQ ID NO: 717) |
| AB-010700 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 653) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSRSDHVVFGGGTKLTVL<br>(SEQ ID NO: 718) |
| AB-010701 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 654) | SYVLTQPPSVSVAPGQTARITCGGNNIGS<br>KNVHWYQQKPGQAPVLVVYDDSDRPSGIP<br>ERFSGSNSGNTATLTISRVEAGDEADYYC<br>QVWDSESDHVVFGGGTKLTVL<br>(SEQ ID NO: 719) |
| AB-010702 | QVQLQQWGAGLLKPSETLSLTCAVYGGS<br>FSGYYWSWIRQPPGKGLEWIGEINHRGS<br>INYNNYNPSLKSRVTISVDTSKNQFSLK<br>LSSVTAADTAVYYCAKPLRPHCTNGVCY<br>SGDAFDIWGQGTMVTVAS<br>(SEQ ID NO: 655) | SYVLTQPPSVSVAPGQTARITCGGNNIGY<br>KNVHWYQQKPGQAPVLVVYDDSDRPSGIP<br>ERFSGSNSGNTATLTISRVEAGDEADYYC<br>QVWDSESDHVVFGGGTKLTVL<br>(SEQ ID NO: 720) |

In some embodiments, the EphA2 antibody disclosed herein comprises a heavy chain variable region and a light chain variable region of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702 or a variant thereof. The variant comprises a heavy chain variable region having a sequence that is at least 95% identical to that of the corresponding heavy chain variable region and a light chain variable region having a sequence that is at least 95% identical to the corresponding light chain variable region. For example, the variant may comprise a VH that is at least 95% identical to that of AB-008873, AB-010148, AB-010363, or AB-010699 and/or a VL that is at least 95% identical to that of AB-008873, AB-010148, AB-010363, or AB-010699.

In some embodiments, the EphA2 antibody disclosed herein comprises a heavy chain variable region and a light chain variable region of an antibody designated as AB-010361 or AB-010699.

In some embodiments, the EphA2 antibody disclosed herein comprises an HCDR1, HCDR2, HCDR3, LCDR1, LCDR2, and LCDR3 of an antibody designated as AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702, or a variant thereof, and at least one, two, three, four, five, or all six of the CDRs of the variant contain 1 or 2 amino acid substitutions compared to the corresponding CDR. For example, at least one, two, three, four, five, or all six of the CDRs of the variant contain 1 or 2 amino acid substitutions compared to the CDRs of AB-008873, AB-010148, AB-010363, or AB-010699

In some embodiments, the EphA2 antibody disclosed herein comprises an HCDR1, HCDR2, HCDR3, LCDR1, LCDR2, and LCDR3 of an antibody designated as AB-010361 or AB-010699.

Epitope

An EphA2 antibody disclosed herein binds to an epitope in the EphA2 protein (SEQ ID NO: 94). In some embodiments, an EphA2 antibody disclosed herein binds to an epitope in the FN2 domain of the EphA2 protein. In some embodiments, the binding can be detected using yeast display experiments illustrated in FIG. 6. The FN2 domain consists of residues 437-534 of SEQ ID NO: 94 and has a sequence of SEQ ID NO: 95 (TEPPKVRLEGRSTT-SLSVSWSIPPPQQSRVWKYEVTYRKKGDSNSYN-VRRTEGFSVTLD DLAPDTTYLVQVQALTQEGQGAG-SKVHEFQTLSPEGSGN). In some embodiments, the epitope recognized by an EphA2 antibody disclosed herein overlaps with that of AB-010018.

Epitopes for the EphA2 antibodies disclosed herein can be determined by any method well known in the art, for example, by conventional immunoassays. In one example, the epitope to which the EphA2 antibody binds can be determined in a systematic screening by using overlapping peptides derived from the EphA2 sequence and determining binding by the antibody. In some cases, during the discovery process, the generation and characterization of antibodies may elucidate information about desirable epitopes. This information may allow screening for antibodies that compete for binding to the same epitope, e.g., an epitope in the FN2 domain of the EphA2 protein.

In some cases, an epitope binning method is performed, e.g., using Bio-layer interferometry (BLI) as described in Example 4. The underlying principle of epitope binning is that proteins with overlapping binding sites will sterically inhibit simultaneous binding. For each pair of antibodies, the antigen is pre-saturated with the 1st monoclonal antibody (mAb), the $2^{nd}$ mAb is applied and signal from the binding of the $2^{nd}$ mAb to the antigen is detected and quantified. A significantly reduced signal from binding of $2^{nd}$ mAb to the antigen indicates that there are overlapping binding sites between the two antibodies. Pair-wise interactions of the antibodies are scored and used to bin the antibodies into sets defined by mutual competition. Epitope binning is useful for antibody characterization because antibodies in a bin may exhibit similar MOAs. Binning with antibodies with antibodies of known reactivity can inform epitope identification.

An EphA2 antibody disclosed herein binds to at least one, at least two, at least three, at least four, at least five residues selected from the group consisting of Pro439, Lys441, Arg443, Leu444, Arg447, Lys476, Gly477, Leu504, Gln506, Ser519, Lys520, Val521, His522, Glu523, Phe524, and Gln525, with the residue numbering referring to the EphA2 amino acid sequence of SEQ ID NO: 94. In one embodiment, the EphA2 antibody binds to at least one, at least two, at least three, at least four, at least five residues, at least six residues, at least seven residues, at least eight residues, or at least nine residues selected from the group consisting of Leu444, Arg447, Lys476, Gln506, Ser519, Lys520, Val521, Glu523, Phe524, and Gln525. In one embodiment, the EphA2 antibody binds to all the residues Leu444, Arg447, Lys476, Gln506, Ser519, Lys520, Val521, Glu523, Phe524, and Gln525.

Figure 44:
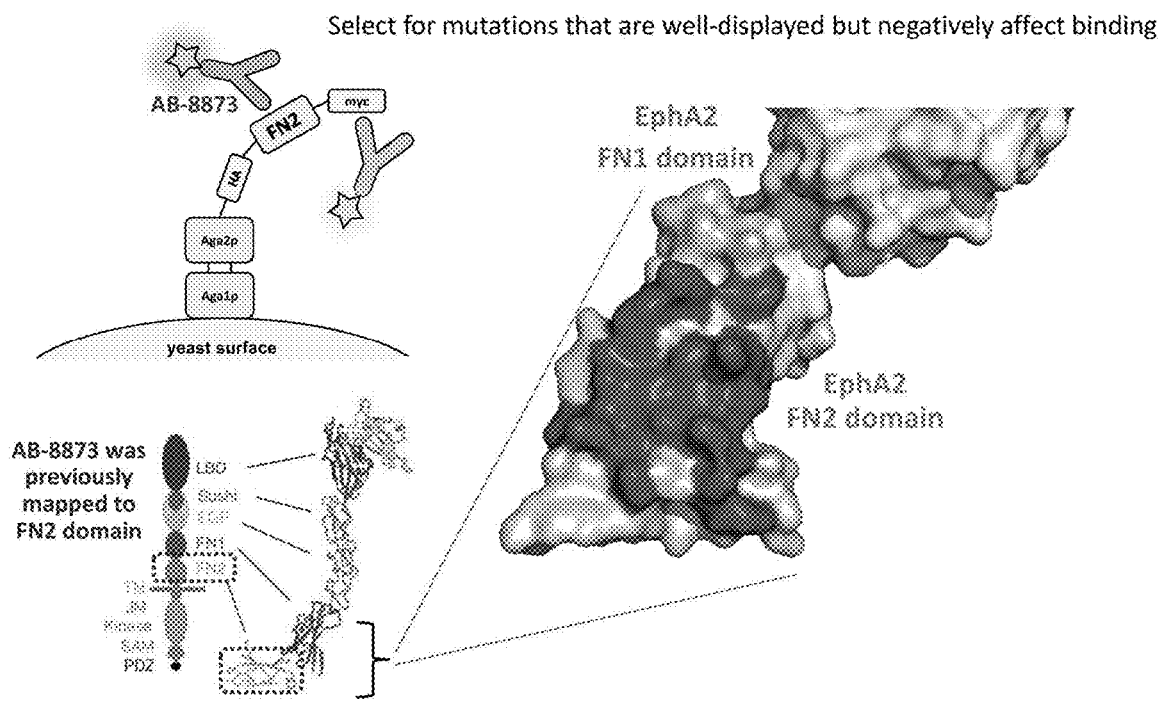
FIG. 44 shows identification of AB-008873 epitope residues by yeast display. The epitope residues identified by this method include Pro439, Lys441, Arg443, Leu444, Arg447, Lys476, Gly477, Leu504, Gln506, Ser519, Lys520, Val521, His522, Glu523, Phe524, and Gln525.
Figure 45:
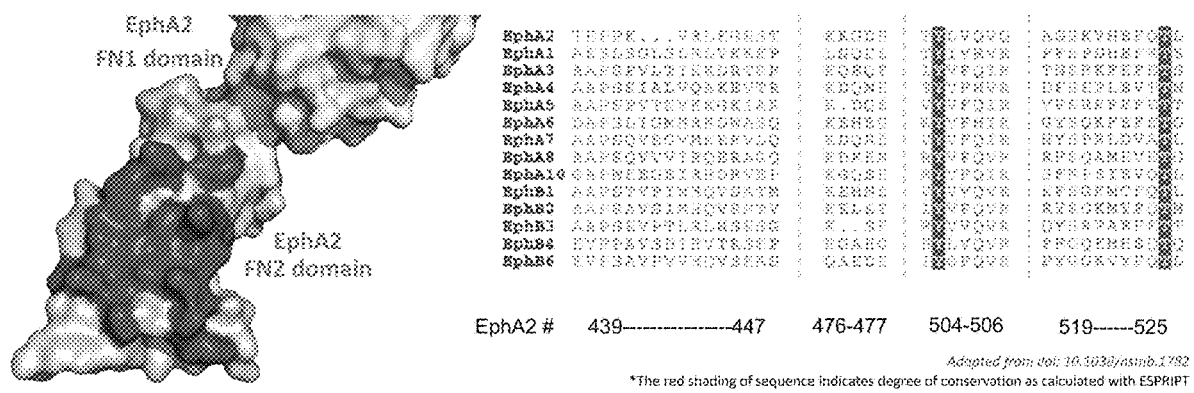
FIG. 45 shows the alignment of the epitope residues across the EphA/B family members. The results show that the residues are divergent across EphA/B family and the epitope is conformational.

In some embodiments, the EphA2 antibody bind to a conformational epitope that is located in one, two, three and/or four regions in the EphA2 protein: a first region consisting of amino acid residues 439-447, a second region consisting of amino acid residues 476-477, a third region consisting of amino acid residues 504-506, and a fourth region consisting of amino acid residues 519-525. In some embodiments, the epitope that the EphA2 antibody binds is conserved across species of cyno, rat, mouse and human, all of which are commonly used in toxicology studies. FIG. 46, FIGS. 44 and 45. Seiradake, et al., Nat Struct Mol Biol 17, 398-402 (2010).

Tumor-Binding Activity

The activity of the EphA2 antibodies as described herein can be assessed for binding in binding assays. Nonlimiting examples of suitable assays include surface plasmon resonance analysis using a biosensor system such as a Biacore® system or a flow cytometry assay, which are further described in the EXAMPLES section.

In some embodiments, binding to EphA2 protein is assessed in a competitive assay format with a reference antibody AB-008873 or a reference antibody having the variable regions of AB-008873. In some embodiments, a variant EphA2 antibody in accordance with the present disclosure may block binding of the reference antibody in a competition assay by about 50% or more.

In some embodiments, binding assays to assess variant activity are performed on tumor tissues or tumor cells ex vivo, e.g., on tumor cells that were grown as a tumor graft in a syngeneic (immune-matched) mouse in vivo then harvested and processed within 24-48 hrs. Binding can be assessed by any number of means including flow cytometry.

Figure 4:
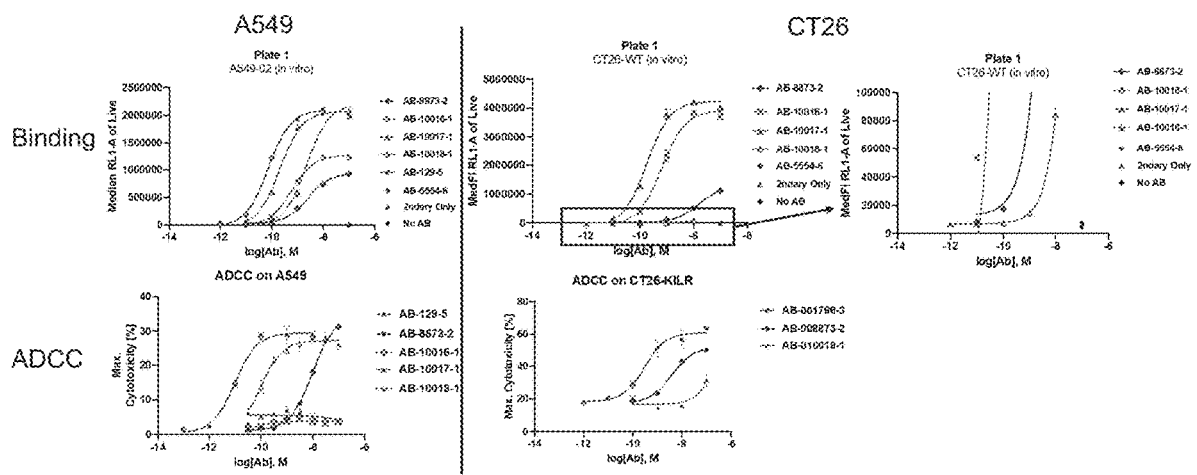
FIG. 4 compares the binding activity and functional activity of AB-008873 and other EphA2 antibodies on mouse and human cells.
Figure 20:
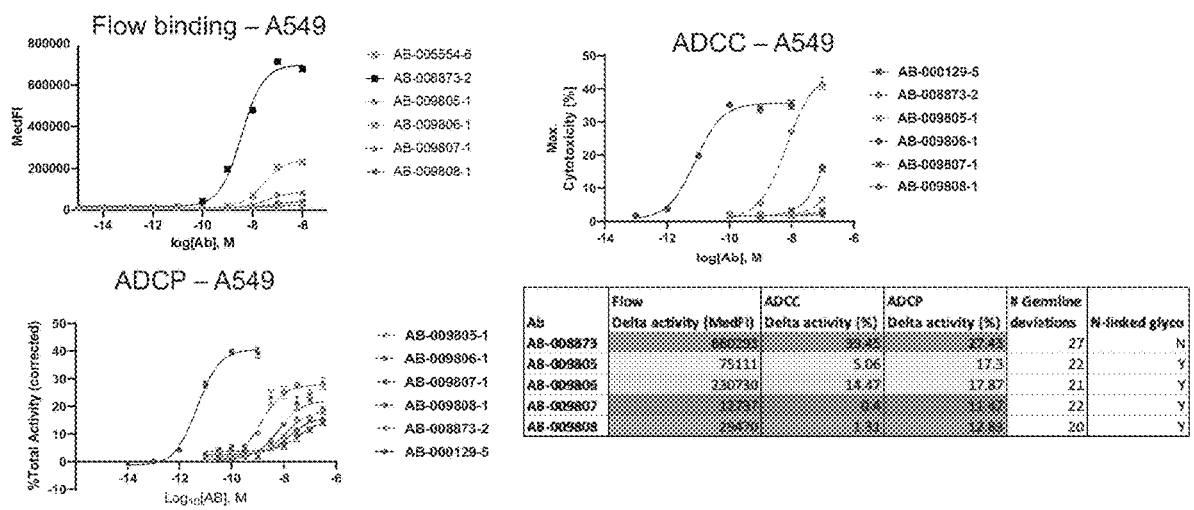
FIG. 20 shows the functional activity of AB-008873 siblings antibodies (antibodies that are derived from the same lineage as AB-008873)

The antibodies disclosed herein bind specifically to tumor cells. In some embodiments the antibody is added to a cancer cell line and the binding is analyzed using a flow cytometry. AB-008873 showed a strong binding to 786-O, A375, A549, H522, LoVo, MDA-MB-231, PC3, RKO, SKOV3, SW1116, and CT26. Additionally, AB-008873 is also capable of binding to CT26 ex vivo cells. FIG. 1, Tables 23 and 24. Its sibling antibodies AB-009805, AB-009806, AB-009807, and AB-009808 also showed binding activity to A549 cells, but less than that of AB-008873. FIG. 20. Unlike AB-010018 (mouse monoclonal antibody precursor of humanized DS-8895a. See U.S. Pat. No. 9,150,657, Sequences 35 and 37 Daiichi Sankyo (IgG)), which showed binding and ADCC activity on A549 cells (human lung cancer cells) but did not on CT26 cells (murine colon cancer cells), AB-008873 demonstrated binding and ADCC activity on both A549 cells and CT26 cells. FIG. 4.

Figure 27:
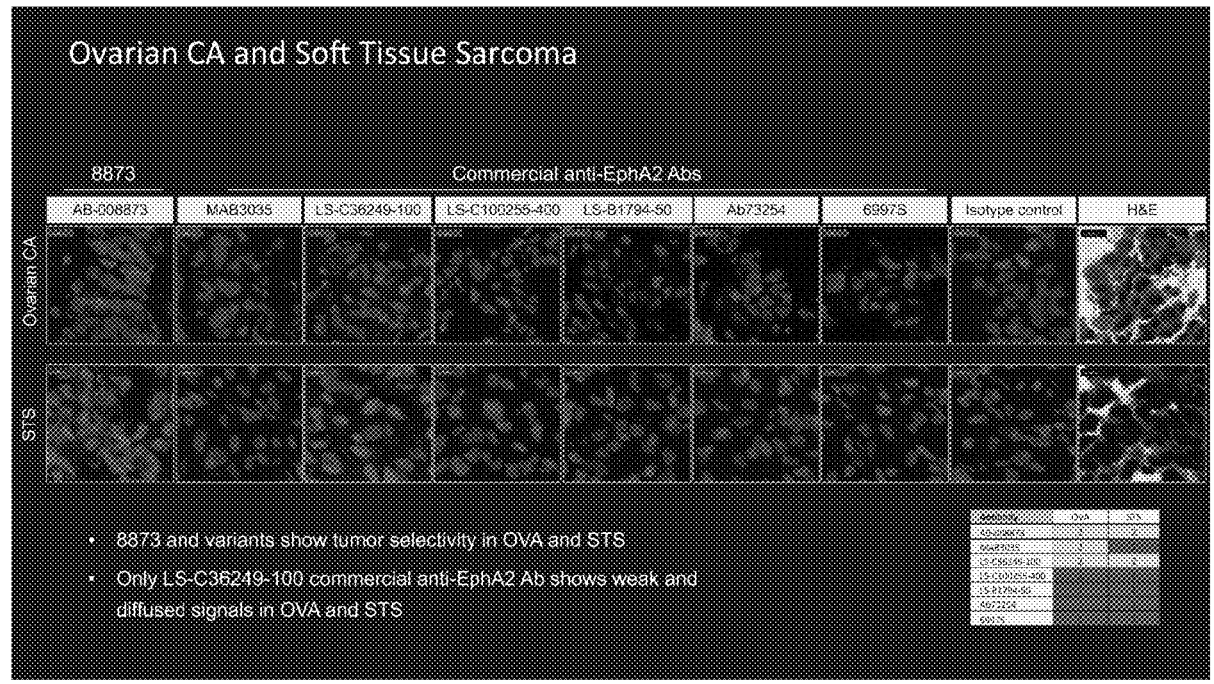
FIG. 27 shows comparison of AB-008873 with commercial anti-EphA2 antibodies in binding to ovarian cancer and soft tissue sarcoma cells.
Figure 28:
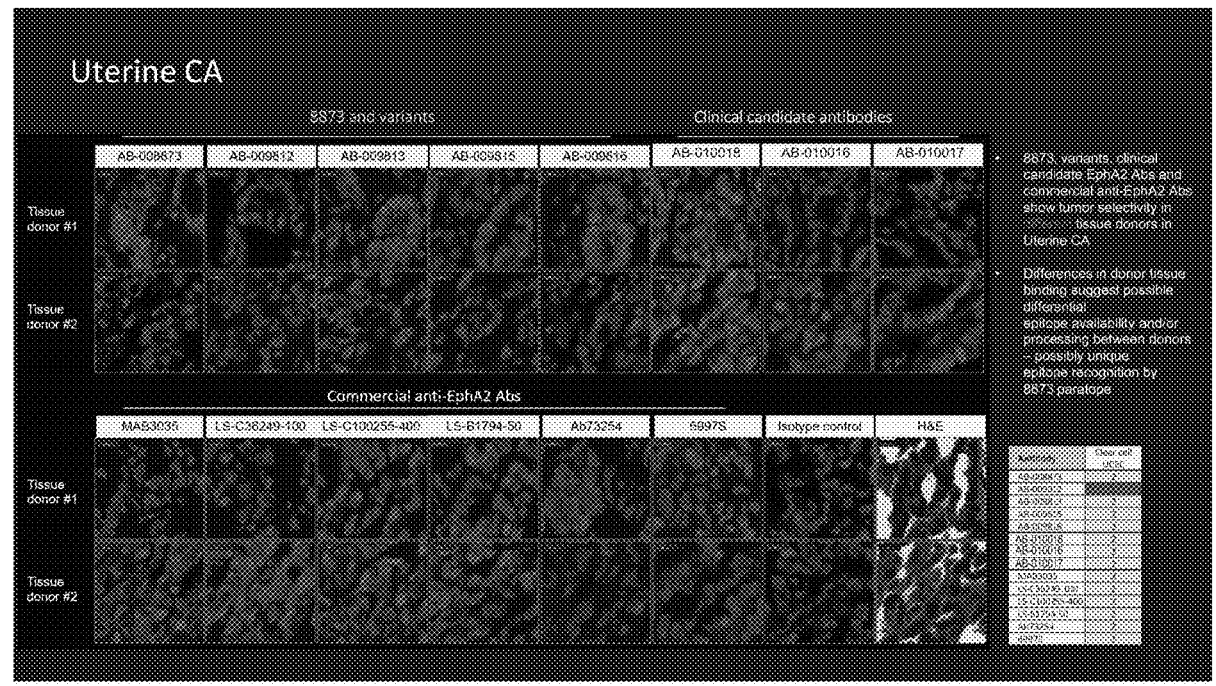
FIG. 28 compares the binding pattern of EphA2 antibodies in tumor tissues from different uterine cancer donors.
Figure 29:
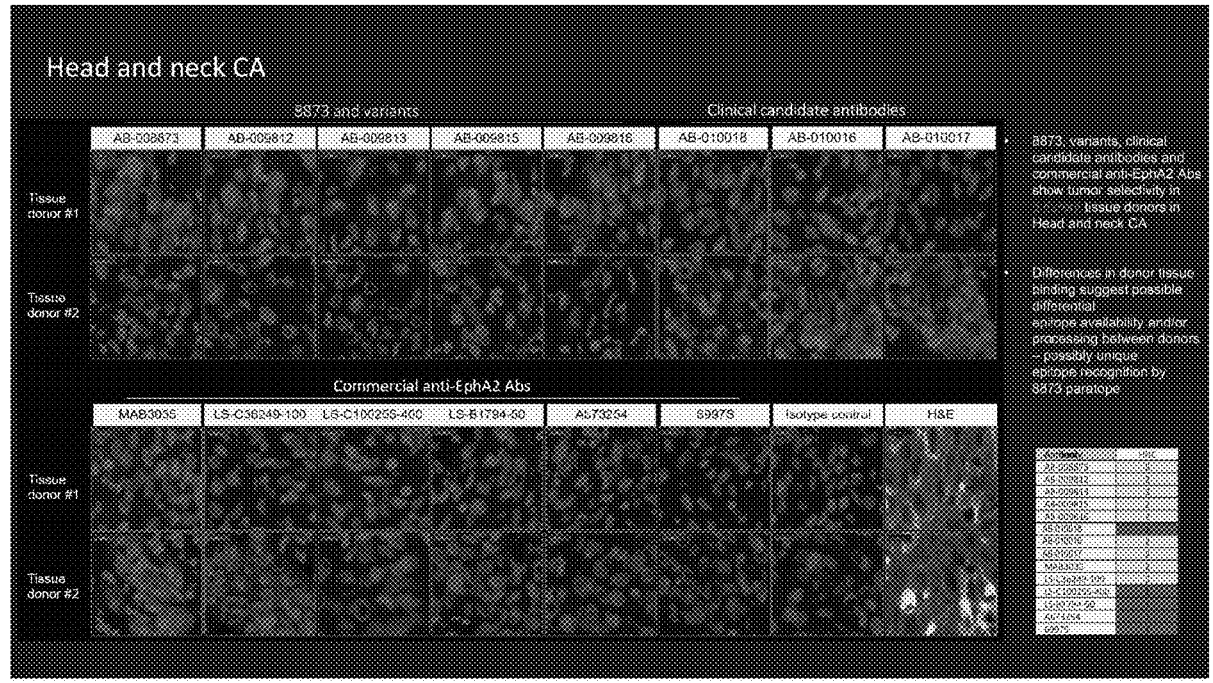
FIG. 29 shows the binding pattern of EphA2 antibodies in tumor tissues from different head and neck cancer donors.
Figure 30:
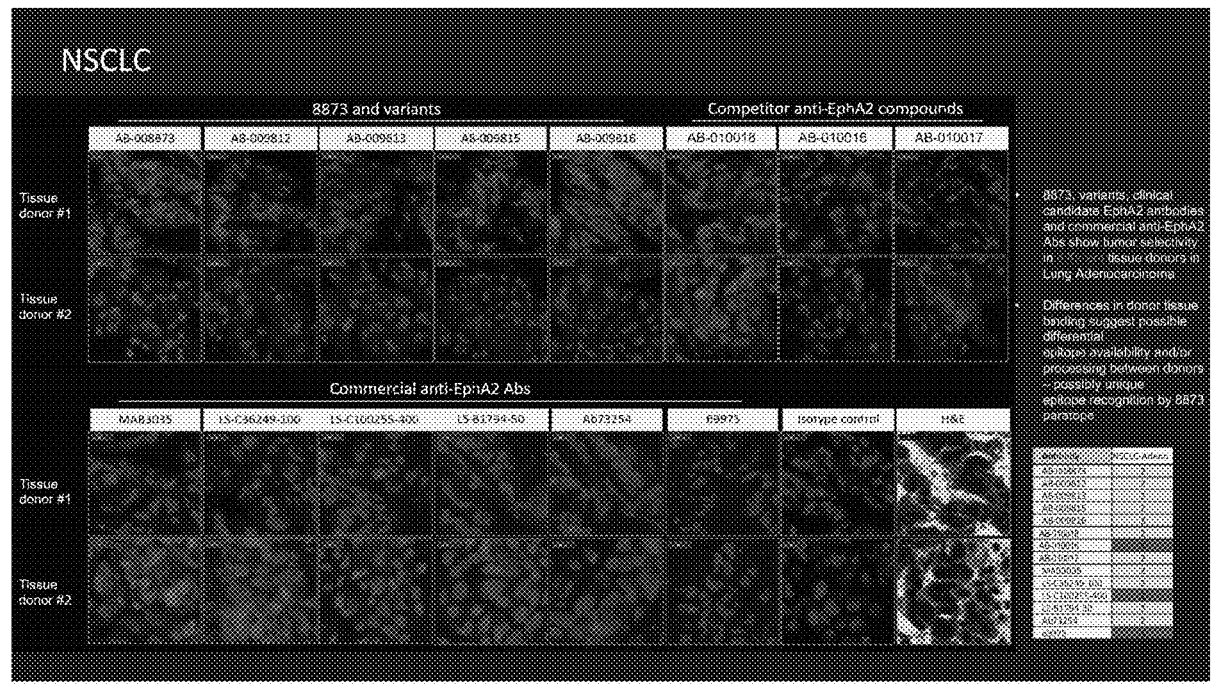
FIG. 30 shows the binding pattern of EphA2 antibodies in tumor tissues from different Non-small Cell Lung cancer (NSCLC) donors.

In some embodiments, the binding of the antibodies to bind to tumor cells are assessed by immunofluorescence methods, as described in the EXAMPLES. AB-008873 and its variants preferentially bind to various tumors but not to normal human tissues (FIGS. 27-34). As compared to AB-010018 and LS-C100255, AB-008873 advantageously showed less staining in normal tissues and a higher staining in tumor tissues. In one illustrative example, the AB-008873 showed preferential binding to ovarian cancer and soft tissue sarcoma (STS) than the respective tumor adjacent tissue (TATs); in contrast, all commercial anti-EphA2 antibodies tested, exception for LS-C 36249-100, did not show any detectable binding in these two tumors (FIG. 27). In some embodiments, for certain cancer types, such as uterine cancer, head and neck cancer, and NSCLS, an EphA2 antibody disclosed herein demonstrate tumor selectivity (i.e., preferentially bind to tumor tissue than TATs) in different donors. That is to say, the antibody shows tumor selectivity in some donors but not other donors. In one exemplary assay, AB-008873 and its variant antibodies, AB-009812, AB-009813, AB-009815, and AB-009816 showed tumor selectivity in different donors in uterine cancer, head and neck cancer, and NSCLS (FIG. 28-30). This suggests that there are possible differential epitope availability and/or processing between donors, or possibly a unique epitope recognition by the AB-008873 paratope.

In some embodiments, the antibody's binding activity of functional activity is assessed by determining $EC_{50}$ values, and in some embodiments additionally determining delta activity, i.e., the difference in specific activity between lower and upper plateaus of the activation curve expressed as percent of activity of a selected antibody having known in vitro activity. In typical embodiments, $EC_{50}$ values are compared to a reference antibody. For purposes of this disclosure, an antibody comprising the VH and VL regions of an EphA2 antibody disclosed herein and a mouse IgG2a Fc region when testing binding or functional activity using a tumor cell line, is employed as a reference antibody and included in an assay to assess variant activity relative to the reference antibody. The fold over $EC_{50}$ is calculated by dividing the $EC_{50}$ of the reference antibody by the $EC_{50}$ of the test antibody. Based on the resulting values, the antibodies were assigned to groups and given a ranking from 0-4 as follows: 0=(>500 nM); 1=<0.5; 2=0.5 to 2; 3=2 to 4; 4=>4.

EphA2 Signaling Effect

Figure 43A:
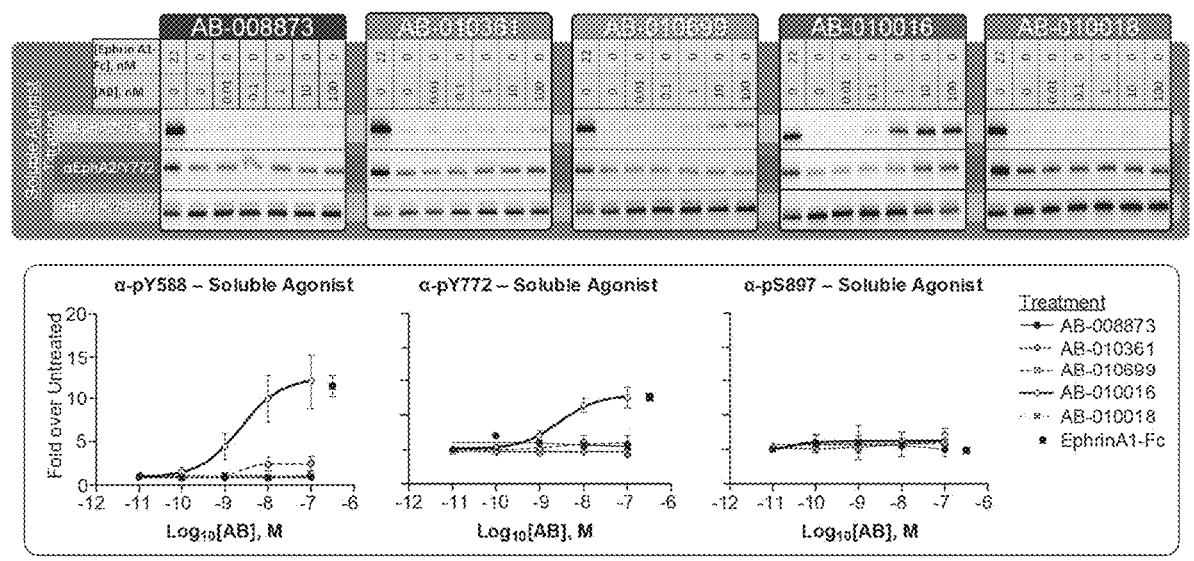
FIG. 43A and FIG. 43B show the phorphorylation of Y588 and S897 on EphA2 by anti-EphA2 antibodies AB-008873, AB-010361, AB-010699, AB-010016, AB-010018, and AB-010019 in angonist (FIG. 43A) and antagonist (FIG. 43B) assay.

In some embodiments, an EphA2 antibody of the present disclosure exhibits no measurable agonistic effect on the ephrinA1-EphA2 signaling axis. In some embodiments, an EphA2 antibody of the present disclosure exhibits less agonistic effect on the ephrinA1-EphA2 signaling axis than the ephrin-A1 ligand. In some embodiments, an EphA2 antibody of the present disclosure activates the ephrin A1-EphA2 signaling axis at least 99%, 98% 95%, 90%, 85%, 80%, 75%, 70%, 65%, 60%, 55%, or 50% less than ephrin-A1 activates the ephrin A1-EphA2 signaling axis. In some embodiments, an EphA2 antibody of the present disclosure activates the ephrin A1-EphA2 signaling axis at least 99%, 98%, 95%, 90%, 85%, or 80% less than ephrin-A1 activates the ephrin A1-EphA2 signaling axis. FIG. 43A.

In some embodiments, an EphA2 antibody of the present disclosure shows weak agonistic effect on the ephrinA1-EphA2 signaling axis, with the effect occurring at a potency less than the potency of the ADCC of the antibody. In some embodiments, an EphA2 antibody of the present disclosure has an EC50 for activation of the ephrinA1-EphA2 signaling axis that is at least 10-, 20-, 50-, 100-, 200-, 500-fold less potent than the ADCC EC50 of the antibody.

Figure 43B:
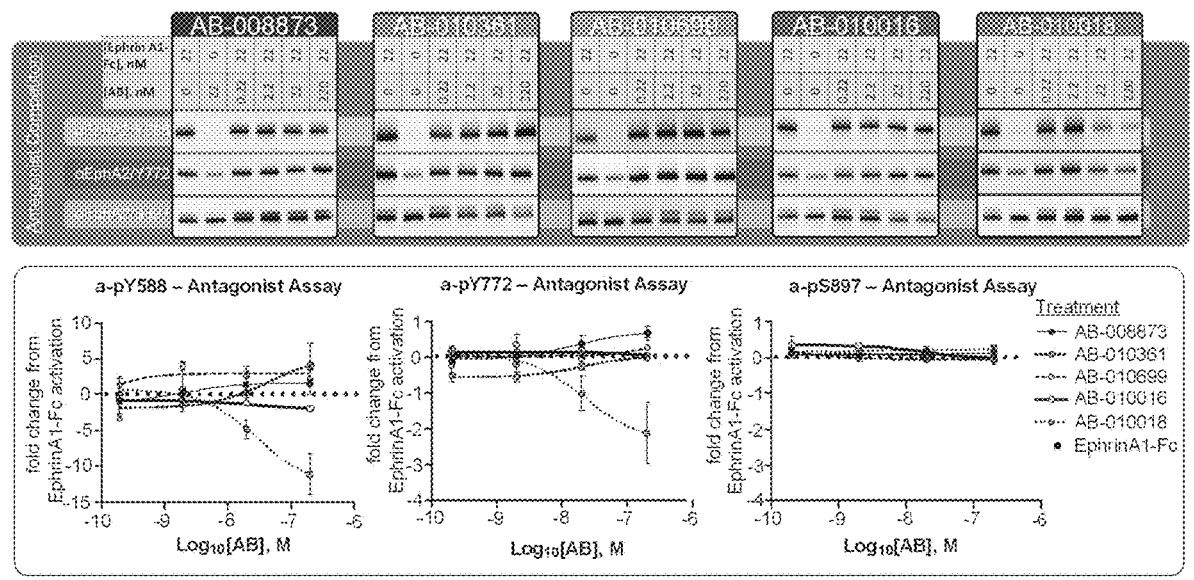

In some embodiments, an EphA2 antibody of the present disclosure exhibits no antagonistic effect on the ephrinA1-EphA2 signaling axis. In some embodiments, an EphA2 antibody of the present disclosure exhibits less antagonistic effect on the ephrinA1-EphA2 signaling axis than AB-010018. FIG. 43B. Methods for measuring ephrinA1-EphA2 signaling axis and the effect of the EphA2 antibodies described herein are well known. In some embodiments, it can be accomplished by detecting the phosphorylation of EphA2 protein. The degree of phosphorylation can be quantified using methods such as Western Blot analysis. One exemplary method of measuring ephrinA1-EphA2 signaling axis is disclosed in Example 5.

The limited effect on EphaA2 signaling provides a therapeutic advantage over other EphA2 antibodies that act as agonists or antagonists of the ephrin A1-EphA2 signaling axis by increasing the therapeutic index. For example, an EphaA2 antibody, or an immunoconjugate or bispecific version thereof, with limited effect on EphA2 signaling may be dosed at a level that provides both efficacy and safety while an EphaA2 antibody, or an immunoconjugate or bispecific version thereof, that agonizes the ephrin A1-EphA2 signaling axis could show a smaller, and potentially non-viable, therapeutic index.

Fc Effector Function

In some embodiments, an EphA2 antibody of the present disclosure comprises an Fc region that has effector function. Examples of effector functions include, but are not limited to, C1q binding and complement-dependent cytotoxicity (CDC), Fc receptor binding (e.g., FcγR binding), ADCC, antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, the Fc region of the EphA2 antibodies disclosed herein may be an Fc region engineered to alter one or more functional properties of the antibody, such as serum half-life, complement fixation, Fc receptor binding, and/or ADCC. Accordingly, an Fc region can comprise additional mutations to increase or decrease effector functions, i.e., the ability to induce certain biological functions upon binding to an Fc receptor expressed on an immune cell. Immune cells include, but are not limited to, monocytes, macrophages, neutrophils, dendritic cells, eosinophils, mast cells, platelets, B cells, large granular lymphocytes, Langerhans' cells, natural killer (NK) cells, and cytotoxic T cells. In some embodiments, an antibody of the present disclosure has enhanced ADCC and/or serum stability compared to antibody AB-008873 when the antibodies are assayed in a human IgG1 isotype format.

The EphA2 antibodies of the present disclosure may be evaluated in various assays for their ability to mediate FcR-dependent activity. In one assay, the binding activity of an EphA2 antibody is evaluated in an Fc receptor engagement assay. For purposes of testing variants, "engagement" of an Fc receptor occurs when a variant antibody binds to both a target tumor cell via its Fv region and an FcγR present on an immune cell via the antibody Fc region in such as manner so as to transduce a signal. If the Fc region is kept constant among variants that differ in their Fv regions, then the assay allows an evaluation of tumor binding activity across such variants in the context of potential signal transduction through a particular Fc region binding a particular Fc receptor. In some embodiments, binding of the antibody Fc region can result in clustering and/or internalization of the FcR, resulting in a luminescence signal in cells harbouring a NFAT-RE-Luciferase reporter construct.

ADCC Activity

Figure 52:
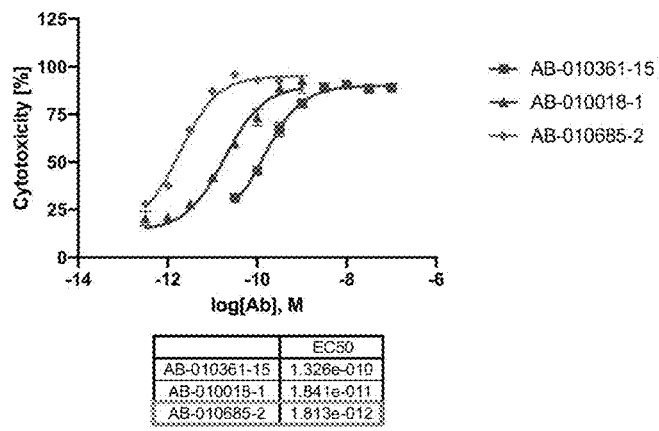
FIG. 52 compares the cytotoxicity of AB-010361 ("AB-010361-15"), AB-010018 (AB-010018-1"), and AB-010685 ("AB-010685-2") on PC3-KILR cells in an ADCC assay.

In some embodiments, an EphA2 antibody of the present disclosure has ADCC when the antibodies are assayed in a mouse IgG2a isotype format. In some embodiments, an EphA2 antibody of the present disclosure has ADCC activity that is comparable to that of AB-008873. The term "comparable activity," refers to the ADCC activity of the EphA2 antibody in a range of 40% to 200% of the activity of a reference antibody that exhibits ADCC when evaluated under the same assay conditions. In one exemplary assay, AB-008873 showed dose dependent ADCC on A549, MDA-MB-231, CT26, and to a small extent EMT6. See FIGS. 2A-2B and Table 25. Its sibling antibodies AB-009805, AB-009806, AB-009807, and AB-009808 also showed ADCC activity on A549 cells, but less than that of AB-008873. Certain variants exhibited improved ADCC activity, including AB-010699, AB-010361 and AB-010685. FIGS. 50A-50B and FIG. 52.

ADCP Activity

In some embodiments, ADCP activity of an EphA2 antibody (e.g., a variant of AB-008873) is assessed using fluorescently-labeled, in vitro cultured tumor cells and Raw264.7 murine macrophages.1. In certain embodiments, opsonization of the tumor cell by the antibody leads to phagocytosis detected by flow cytometry. Variations of this assay have been described and can include co-labeling of tumor and effector cells or assessment of phagocytosis through FcγRIIa engagement (e.g., FcγRIIa-H ADCP Reporter Bioassay from Promega).

Figure 2A:
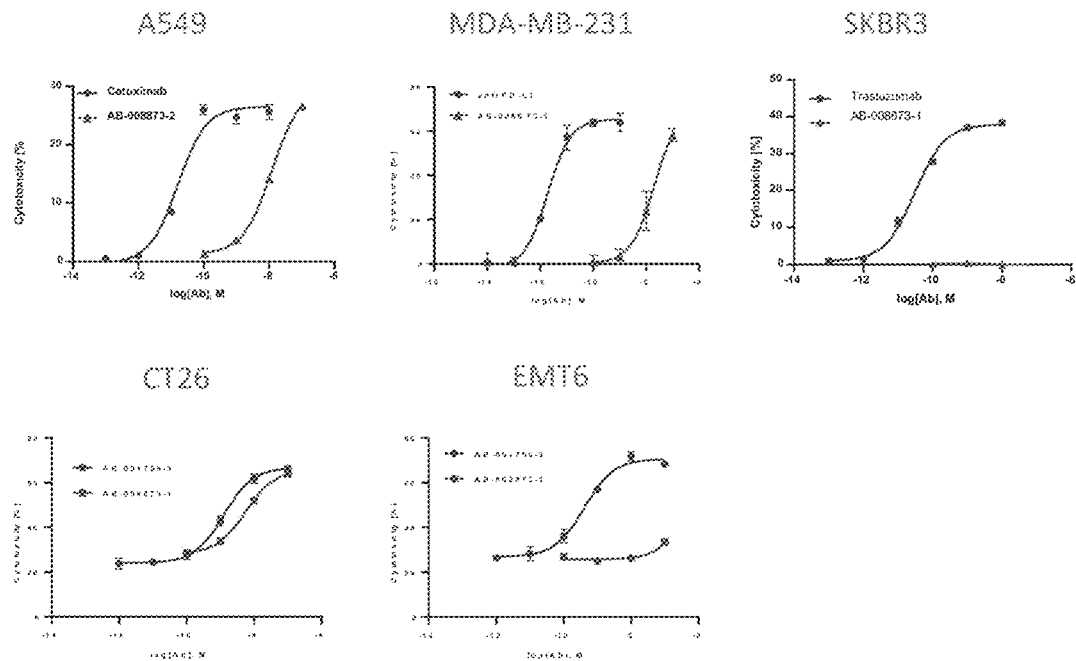
FIG. 2A and FIG. 2B shows results of assessing the ADCC activity (FIG. 2A) and ADCP activity (FIG. 2B) of AB-008873 in vitro functional assays.
Figure 2B:
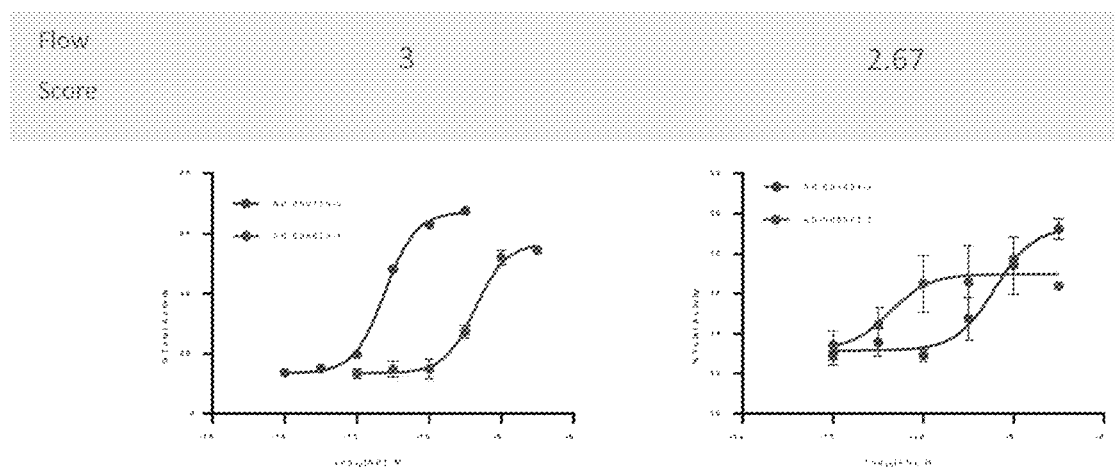

In one illustrative embodiment, The ADCP activity of an EphA2 antibody is evaluated using the method described above and in more detail in EXAMPLE 3. In one illustrative example, AB-008873 showed strong ADCP activity on A549 cells. FIG. 2B and FIG. 20. The sibling antibodies AB-009805, AB-009806, AB-009807, and AB-009808 also showed ADCP activity, but less than that of AB-008873. In one illustrative example, AB-008873 showed strong ADCP activity on A549 cells. FIG. 2A-2B, Table 25, and FIG. 20. The sibling antibodies AB-009805, AB-009806, AB-009807, and AB-009808 also showed ADCP activity, but less than that of AB-008873.

In Vivo Activity

In some embodiments, activity of an EphA2 antibody variant is evaluated in vivo in a suitable animal tumor model. A reduction in tumor load reflects the anti-tumor function of an antibody.

In some embodiments, a variant of an antibody as described herein has at least 50%, or at least 60%, or 70%, or greater, of the anti-tumor activity of a reference antibody as shown in Tables 1-4 when evaluated under the same assay conditions to measure the anti-tumor activity in vivo. In some embodiments, an anti-tumor antibody exhibits improved activity, i.e., greater than 100% activity, compared to the reference antibody.

Antibody Formats

In a further aspect of the invention, an EphA2 antibody in accordance with the disclosure may be an antibody fragment, e.g., a Fv, Fab, Fab', scFv, diabody, or F(ab')$_2$ fragment. In another embodiment, the antibody is a substantially full-length antibody, e.g., an IgG antibody or other antibody class or isotype as defined herein. For a review of certain antibody fragments, see Hudson et al. Nat. Med. 9:129-134 (2003). Antibody fragments can be made by various techniques, including but not limited to proteolytic digestion of an intact antibody as well as production by recombinant host cells.

In some embodiments, an EphA2 antibody according to the present disclosure that is administered to a patient is an IgG of the IgG1 subclass. In some embodiments, such an antibody is an IgG of the IgG2, IgG3, or IgG4 subclass. In some embodiments, such an antibody is an IgM. In some embodiments, such an antibody has a lambda light chain constant region. In some embodiments, such an antibody has a kappa light chain constant region.

In some embodiments an EphA2 antibody in accordance with the present disclosure is in a monovalent format. In some embodiments, the tumor-targeting antibody is in a fragment format, e.g., a Fv, Fab, Fab', scFv, diabody, or F(ab')$_2$ fragment.

In some embodiments, EphA2 antibodies disclosed herein, including antibody fragments, of the present disclosure comprises an Fc region that has effector function, e.g., exhibits antibody-dependent cellular cytotoxicity (ADCC), antibody-dependent cellular phagocytosis (ADCP), and/or complement-dependent cytotoxicity (CDC). In some embodiments, the Fc region may be an Fc region engineered to alter one or more functional properties of the antibody, such as serum half-life, complement fixation, Fc receptor binding, and/or ADCC. Accordingly, an Fc region can comprise additional mutations to increase or decrease effector functions, i.e., the ability to induce certain biological functions upon binding to an Fc receptor expressed on an immune cell. Immune cells include, but are not limited to, monocytes, macrophages, neutrophils, dendritic cells, eosinophils, mast cells, platelets, B cells, large granular lymphocytes, Langerhans' cells, natural killer (NK) cells, and cytotoxic T cells.

In some embodiments, an Fc region described herein can include additional modifications that modulate effector function. Examples of Fc region amino acid mutations that modulate an effector function include, but are not limited to, one or more substitutions at positions 228, 233, 234, 235, 236, 237, 238, 239, 243, 265, 269, 270, 297, 298, 318, 326, 327, 329, 330, 331, 332, 333, and 334 (EU numbering scheme) of an Fc region.

Illustrative substitutions that decrease effector functions include the following: position 329 may have a mutation in which proline is substituted with a glycine or arginine or an amino acid residue large enough to destroy the Fc/Fcγ receptor interface that is formed between proline 329 of the Fc and tryptophan residues Trp 87 and Trp 110 of FcγRIII. Additional illustrative substitutions that decrease effector functions include S228P, E233P, L235E, N297A, N297D, and P331S. Multiple substitutions may also be present, e.g., L234A and L235A of a human IgG1 Fc region; L234A, L235A, and P329G of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region, to decrease effectors functions. Examples of substitutions that increase effector functions include, e.g., E333A, K326W/E333S, S239D/I332E/G236A, S239D/A330L/I332E, G236A/S239D/A330L/I332E, F243L, G236A, and S298A/E333A/K334A. In some embodiments, the Fc mutations include P329G, L234A, L235A, or a combination thereof. Descriptions of amino acid mutations in an Fc region that can increase or decrease effector functions can be found in, e.g., Wang et al., Protein Cell. 9(1):63-73, 2018; Saunders, Front Immunol. June 7, eCollection, 2019; Kellner et al., Transfus Med Hemother. 44(5):327-336, 2017; and Lo et al., J Biol Chem. 292(9):3900-3908, 2017.

In some embodiments, an Fc region may have one or more amino acid substitutions that modulate ADCC, e.g., substitutions at positions 298, 333, and/or 334 of the Fc region, according to the EU numbering scheme. Specifically, S298A, E333A, and K334A can be introduced to an Fc region to increase the affinity of the Fc region to FcγRIIIa and decrease the affinity of the Fc region to FcγRIIa and FcγRIIb.

An Fc region can also comprise additional mutations to increase serum half-life. Through enhanced binding to the neonatal Fc receptor (FcRn), such mutations in an Fc region can improvpharmacokineticsentics of the antibody. Examples of substitutions in an Fc region that increase the serum half-life of an antibody include, e.g., M252Y/S254T/T256E, T250Q/M428L, N434A, N434H, T307A/E380A/N434A, M428L/N434S, M252Y/M428L, D259I/V308F, N434S, V308W, V308Y, and V308F. Descriptions of amino acid mutations in an Fc region that can increase the serum half-life of an antibody can be found in, e.g., Dumet et al., MAbs. 26:1-10, 2019; Booth et al., MAbs. 10(7):1098-1110, 2018; and Dall'Acqua et al., J Biol Chem. 281(33):23514-24, 2006.

Furthermore, in some embodiments, an antibody of the disclosure may be chemically modified (e.g., one or more chemical moieties can be attached to the antibody) or be modified, e.g., produced in cell lines and/or in cell culture conditions to alter its glycosylation (e.g., hypofucosylation, afucosylation, or increased sialylation), to alter one or more functional properties of the antibody. For example, the antibody can be linked to one of a variety of polymers, for example, polyethylene glycol. In some embodiments, an antibody may comprise mutations to facilitate linkage to a chemical moiety and/or to alter residues that are subject to post-translational modifications, e.g., glycosylation.

In some embodiments, an EphA2 antibody described herein comprise an Fc region having altered glycosylation that increases the ability of the antibody to recruit NK cells and/or increase ADCC. In some embodiments, the Fc region comprises glycan containing no fucose (i.e., the Fc region is afucosylated). Afucosylated antibodies can be produced using cell lines that express a heterologous enzyme that depletes the fucose pool inside the cell (e.g., GlymaxX® by ProBioGen AG, Berlin, Germany). Non-fucosylated antibodies can also be produced using a host cell line in which the endogenous α-1,6-fucosyltransferase (FUT8) gene is deleted. See Satoh, M. et al., "Non-fucosylated therapeutic antibodies as next-generation therapeutic antibodies," Expert Opinion on Biological Therapy, 6:11, 1161-1173, DOI: 10.1517/14712598.6.11.1161.

In some embodiments, an EphA2 antibody is constructed as a multivalent antibody. In some embodiments, an EphA2 antibody is constructed as a tetravalent molecule, comprising four EphA2 binding arms per molecule. Such constructs exhibit increased ADCC activity, as well as increased binding to tumor cells a measured by flow cytometry.

In some embodiments, an EphA2 antibody of the present disclosure is employed in a bispecific or multi-specific format, e.g., a tri-specific format. For example, in some embodiments, the antibody may be incorporated into a bispecific or multi-specific antibody that comprises a further binding domain that binds to the same or a different antigen.

There are a variety of possible formats that can be used in bispecific or multi-specific antibodies. The formats can vary elements such as the number of binding arms, the format of each binding arm (e.g., Fab, scFv, scFab, or VH-only), the number of antigen binding domains present on the binding arms, the connectivity and geometry of each arm with respect to each other, the presence or absence of an Fc domain, the Ig class (e.g., IgG or IgM), the Fc subclass (e.g., hIgG1, hIgG2, or hIgG4), and any mutations to the Fc (e.g., mutations to reduce or increase effector function or extend serum half-life). Also see Speiss, et al., Alternative Molecular Formats and Therapeutic Applications for Bispecific Antibodies, Mol Immunol, 67, 95-106 (2015), in particular FIG. 1, for examples of bispecific and multispecific formats.

Illustrative antigens that can be targeted by a further binding domain in a bispecific or multi-specific antibody that comprises an antigen binding domain of an EphA2 antibody described herein, include, but are not limited to, antigens on T cells to enhance T cell engagement and/or activate T cells. Illustrative examples of such an antigen include, but are not limited to, CD3, CD2, CD4, CD5, CD6, CD8, CD28, CD40L, CD44, IL-15Rα, CD122, CD132, or CD25. In some embodiments, the antigen is CD3. In some embodiments, the antigen is in a T cell activating pathway, such as a 4-1BB/CD137, 4-1BBL/CD137L, OX40, OX40L, GITRL, GITR, CD27, CD70, CD28, ICOS, HVEM, or LIGHT antigen.

In some embodiments, an EphA2 antibody is incorporated into a bispecific or multi-specific antibody that comprises a binding domain that binds to a T-cell antigen. These bispecific antibodies or multi-specific antibodies can direct T cells to attach and lyse targeted tumor cells, i.e., the EphA2 expressing tumor cells. In some embodiments, the bispecific or multispecific antibody comprises a binding domain that binds to CD3. In some embodiments, the bispecific or multispecific antibody comprises a binding domain that binds to human CD3 comprising the anti-tumor antibodies described herein.

Figure 53:
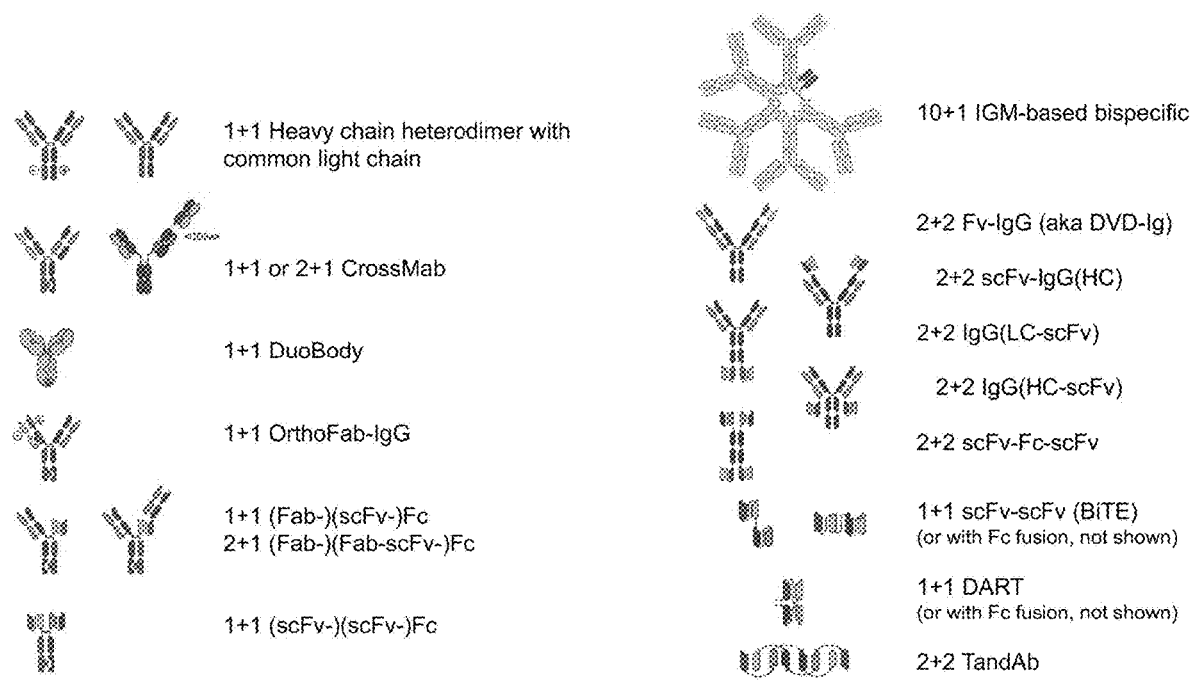
FIG. 53 shows representative anti-CD3 bispecific antibody constructs.

Table 9 provides specific examples of anti-CD3 binding arms that can be combined with any of the anti-EphA2 antibodies described herein. FIG. 53 provides examples of a variety of formats according to which anti-EphA2/anti-CD3 bispecific constructs that can be generated.

TABLE 9

CD3 heavy chain (VH) and light chain (VL) sequences.

| AB ID | VH | VL |
|---|---|---|
| AB-008703 | EVQLVESGGGLVQPKGSLKLSCAASG FTFNTYAMNWVRQAPGKGLEWVARI RSKYNNYATYYADSVKDRFTISRDDS QSILYLQMNNLKTEDTAMYYCVRHG NFGNSYVSWFAYWGQGTLVTVSA (SEQ ID NO: 133) | QAVVTQESALTTSPGETVTLTCR SSTGAVTTSNYANWVQEKPDHL FTGLIGGTNKRAPGVPARFSGSLI GDKAALTITGAQTEDEAIYFCAL WYSNLWVFGGGTKLTVL (SEQ ID NO: 134) |
| AB-008704 | EVQLVESGGGLVQPGGSLKLSCAASG FTFNKYAMNWVRQAPGKGLEWVARI RSKYNNYATYYADSVKDRFTISRDDS | QTVVTQEPSLTVSPGGTVTLTCG SSTGAVTSGNYPNWVQQKPGQA PRGLIGGTKFLAPGTPARFSGSLL |

TABLE 9-continued

CD3 heavy chain (VH) and light chain (VL) sequences.

| AB ID | VH | VL |
|---|---|---|
| | KNTAYLQMNNLKTEDTAVYYCVRHG NFGNSYISYWAYWGQGTLVTVSS (SEQ ID NO: 135) | GGKAALTLSGVQPEDEAEYYCV LWYSNRWVFGGGTKLTVL (SEQ ID NO: 136) |
| AB-0087 05 | EVQLVESGGGLVQPGGSLRLSCAASG FTFSTYAMNWVRQAPGKGLEWVGRI RSKYNNYATYYADSVKGRFTISRDDS KNSLYLQMNSLKTEDTAVYYCVRHG NFGNSYVSWFAYWGQGTLVTVSS (SEQ ID NO: 137) | QAVVTQEPSLTVSPGGTVTLTCR SSTGAVTTSNYANWVQQKPGQ APRGLIGGTNKRAPWTPARFSGS LLGGKAALTITGAQAEDEADYY CALWYSNLWVFGGGTKLTVL (SEQ ID NO: 138) |
| AB-0087 06 | EVQLVESGGGLVQPGGSLRLSCAASG FTFSTYAMNWVRQAPGKGLEWVGRI RSKYNNYATYYADSVKDRFTISRDDS KNSLYLQMNSLKTEDTAVYYCVRHG NFGNSYVSWFAYWGQGTLVTVSS (SEQ ID NO: 139) | QAVVTQEPSLTVSPGGTVTLTCR SSTGAVTTSNYANWVQQKPGQ APRGLIGGTNKRAPWTPARFSGS LLGGKAALTITGAQAEDEADYY CALWYSNLWVFGGGTKLTVL (SEQ ID NO: 140) |
| AB-0087 07 | EVQLVESGGGLVQPGGSLRLSCAASG FTFSTYAMNWVRQAPGKGLEWVGRI RSKYNNYATYYADSVKGRFTISRDDS KNTLYLQMNSLRAEDTAVYYCVRHG NFGDSYVSWFAYWGQGTLVTVSS (SEQ ID NO: 141) | QAVVTQEPSLTVSPGGTVTLTCG SSTGAVTTSNYANWVQQKPGKS PRGLIGGTNKRAPGVPARFSGSL LGGKAALTISGAQPEDEADYYC ALWYSNHWVFGGGTKLTVL (SEQ ID NO: 142) |
| AB-0087 08 | EVQLVESGGGLVQPGGSLRLSCAASG FTFSTYAMSWVRQAPGKGLEWVGRI RSKYNNYATYYADSVKGRFTISRDDS KNTLYLQMNSLRAEDTAVYYCVRHG NFGDSYVSWFAYWGQGTLVTVSS (SEQ ID NO: 143) | QAVVTQEPSLTVSPGGTVTLTCG SSTGAVTTSNYANWVQQKPGKS PRGLIGGTNKRAPGVPARFSGSL LGGKAALTISGAQPEDEADYYC ALWYSNHWVFGGGTKLTVL (SEQ ID NO: 144) |
| AB-0087 09 | EVQLVESGGGLVQPGGSLRLSCAASG FTFSTYAMNWVRQAPGKGLEWVGRI RSKANNYATYYADSVKGRFTISRDDS KNTLYLQMNSLRAEDTAVYYCVRHG NFGDSYVSWFAYWGQGTLVTVSS (SEQ ID NO: 145) | QAVVTQEPSLTVSPGGTVTLTCG SSTGAVTTSNYANWVQQKPGKS PRGLIGGTNKRAPGVPARFSGSL LGGKAALTISGAQPEDEADYYC ALWYSNHWVFGGGTKLTVL (SEQ ID NO: 146) |
| AB-0087 10 | EVQLVESGGGLVQPGGSLRLSCAASG FTFSTYAMNWVRQAPGKGLEWVGRI RSKYNNYATYYADSVKGRFTISRDDS KNTLYLQMNSLRAEDTAVYYCVRHG NFGDSYVSWFDYWGQGTLVTVSS (SEQ ID NO: 147) | QAVVTQEPSLTVSPGGTVTLTCG SSTGAVTTSNYANWVQQKPGKS PRGLIGGTNKRAPGVPARFSGSL LGGKAALTISGAQPEDEADYYC ALWYSNHWVFGGGTKLTVL (SEQ ID NO: 148) |
| AB-0087 11 | EVQLVESGGGLVQPGGSLRLSCAASG FTFNTYAMNWVRQAPGKGLEWVARIR SKYNNYATYYADSVKGRFTISRDDS KNTLYLQMNSLRAEDTAVYYCVRHG NFGNSYVSYFAYWGQGTTVTVSS (SEQ ID NO: 149) | E1VVTQSPATLSVSPGERATLSCR SSTGAVTESNYANWVQEKPGQA FRGLIGGANKRAPGVPARFSGSL SGDEATLTISSLQSEDFAVYYCA LFYSNTWVFGQGTKLEIK (SEQ ID NO: 150) |
| AB-0087 12 | EVQLLESGGGLVQPGGSLRLSCAASG FTFSTYAMNWVRQAPGKGLEWVSRI RSKYNNYATYYADSVKGRFTISRDDS KNTLYLQMNSLRAEDTAVYYCVRHG NFGNSYVSWFAYWGQGTLVTVSS (SEQ ID NO: 151) | QAVVTQEPSLTVSPGGTVTLTCG SSTGAVTTSNYANWVQEKPGQA FRGLIGGTNKRAPGTPARFSGSL LGGKAALTLSGAQPEDEAEYYC ALWYSNLWVFGGGTKLTVL (SEQ ID NO: 152) |
| AB-0087 13 | EVQLVQSGAEVKKPGASVKVSCKAS GYTFTNYYIHWVRQAPGQGLEWIGWI YPGDGNTKYNEKFKGRATLTADTSTS TAYLELSSLRSEDTAVYYCARDSYSN YYFDYWGQGTLVTVSS (SEQ ID NO: 153) | DIVMTQSPDSLAVSLGERATINC KSSQSLLNSRTRKNYLAWYQQK PGQPPKLLIYWASTRESGVPDRF SGSGSGTDFTLTISSLQAEDVAV YYCTQSFILRTFGQGTKVEIK (SEQ ID NO: 154) |
| AB-0087 14 | EVQLVQSGAEVKKPGASVKVSCKAS GFTFTSYYIHWVRQAPGQGLEWIGWI YPENDNTKYNEKFKDRVTITADTSTST AYLELSSLRSEDTAVYYCARDGYSRY YFDYWGQGTLVTVSS (SEQ ID NO: 155) | DIVMTQSPDSLAVSLGERATINC KSSQSLLNSRTRKNYLAWYQQK PGQSPKLLIYWTSTRKSGVPDRF SGSGSGTDFTLTISSLQAEDVAV YYCKQSFILRTFGQGTKVEIK (SEQ ID NO: 156) |

TABLE 9-continued

CD3 heavy chain (VH) and light chain (VL) sequences.

| AB ID | VH | VL |
|---|---|---|
| AB-0087 15 | EVQLVQSGAEVKKPGASVKVSCKAS GFTFTSYYIHWVRQAPGQGLEWIGWI YPENDNTKYNEKFKDRVTITADTSTST AYLELSSLRSEDTAVYYCARDGYSRY YFDYWGQGTLVTVSS (SEQ ID NO: 157) | DIVMTQSPDSLAVSLGERATINC KSSQSLLNSRTRKNYLAWYQQK PGQSPKLLIYWTSTRKSGVPDRF SGSGSGTDFTLTISSLQAEDVAV YYCTQSFILRTFGQGTKVEIK (SEQ ID NO: 158) |
| AB-0087 16 | QVQLVQSGPEVKKPGSSVKVSCKASG YTFSRSTMHWVRQAPGQGLEWIGYIN PSSAYTNYNQKFKDRVTITADKSTSTA YMELSSLRSEDTAVYYCARPQVHYD YNGFPYWGQGTLVTVSS (SEQ ID NO: 159) | DIQMTQSPSTLSASVGDRVTMTC SASSSVSYMNWYQQKPGKAPKR WIYDSSKLASGVPSRFSGSGSGT DYTLTISSLQPDDFATYYCQQWS RNPPTFGGGTKVEIK (SEQ ID NO: 160) |
| AB-0087 17 | QVQLQQSGAELARPGASVKMSCKAS GYTFTRYTMHWVKQRPGQGLEWIGY INPSRGYTNYNQKFKDKATLTTDKSSS TAYMQLSSLTSEDSAVYYCARYYDD HYCLDYWGQGTTLTVSS (SEQ ID NO: 161) | QIVLTQSPAIMSASPGEKVTMTC SASSSVSYMNWYQQKSGTSPKR WIYDTSKLASGVPAHFRGSGSGT SYSLTISGMEAEDAATYYCQQW SSNPFTFGSGTKLEIN (SEQ ID NO: 162) |
| AB-0087 18 | QVQLQQSGAELARPGASVKMSCKAS GYTFTRYTMHWVKQRPGQGLEWIGY INPSRGYTNYNQKFKDKATLTTDKSSS TAYMQLSSLTSEDSAVYYCARYYDD HYSLDYWGQGTTLTVSS (SEQ ID NO: 163) | QIVLTQSPAIMSASPGEKVTMTC SASSSVSYMNWYQQKSGTSPKR WIYDTSKLASGVPAHFRGSGSGT SYSLTISGMEAEDAATYYCQQW SSNPFTFGSGTKLEIN (SEQ ID NO: 164) |
| AB-0087 19 | QVQLQQSGAELARPGASVKMSCKAS GYTFTRYTMHWVKQRPGQGLEWIGY INPSRGYTNYNQKFKDKATLTTDKSSS TAYMQLSSLTSEDSAVYYCARYYDD HYCLDYWGQGTTLTVSS (SEQ ID NO: 165) | QIVLTQSPAIMSASPGEKVTMTC SASSSVSYMNWYQQKSGTSPKR WIYDTSKLASGVPAHFRGSGSGT SYSLTISGMEAEDAATYYCQQW SSNPFTFGCGTKLEIN (SEQ ID NO: 166) |
| AB-0087 20 | QVQLQQSGAELARPGASVKMSCKAS GYTFTRYTMHWVKQRPGQGLEWIGY INPSRGYTNYNQKFKDKATLTTDKSSS TAYMQLSSLTSEDSAVYYCARYYDD HYSLDYWGQGTTLTVSS (SEQ ID NO: 167) | QIVLTQSPAIMSASPGEKVTMTC SASSSVSYMNWYQQKSGTSPKR WIYDTSKLASGVPAHFRGSGSGT SYSLTISGMEAEDAATYYCQQW SSNPFTFGCGTKLEIN (SEQ ID NO: 168) |
| AB-0087 21 | QVQLQQSGAELARPGASVKMSCKAS GYTFTRYTMHWVKQRPGQGLEWIGY INPSRGYTNYNQKFKDKATLTTDKSSS TAYMQLSSLTSEDSAVYYCARYYDD HYCLDYWGQGTTLAVSS (SEQ ID NO: 169) | QIVLTCSPAIMSASPGEKVTMTC RASSSVSYMNWYQQKSGTSPKR WIYDTSKVASGVPYRFSGSGSGT SYSLTISSMEAEDAATYYCQQW SSNPLTFGSGTKLEIN (SEQ ID NO: 170) |
| AB-0087 22 | DIKLQQSGAELARPGASVKMSCKTSG YTFTRYTMHWVKQRPGQGLEWIGYI NPSRGYTNYNQKFKDKATLTTDKSSS TAYMQLSSLTSEDSAVYYCARYYDD HYCLDYWGQGTTLTVSS (SEQ ID NO: 171) | DIQLTQSPAIMSASPGEKVTMTC RASSSVSYMNWYQQKSGTSPKR WIYDTSKVASGVPYRFSGSGSGT SYSLTISSMEAEDAATYYCQQW SSNPLTFGAGTKLELK (SEQ ID NO: 172) |
| AB-0087 23 | DVQLVQSGAEVKKPGASVKVSCKAS GYTFTRYTMHWVRQAPGQGLEWIGY INPSRGYTNYADSVKGRFTITTDKSTS TAYMELSSLRSEDTATYYCARYYDDH YCLDYWGQGTTVTVSS (SEQ ID NO: 173) | DIVLTQSPATLSLSPGERATLSCR ASQSVSYMNWYQQKPGKAPKR WIYDTSKVASGVPARFSGSGSGT DYSLTINSLEAEDAATYYCQQW SSNPLTFGGGTKVEIK (SEQ ID NO: 174) |
| AB-0087 24 | QVQLVQSGGGVVQPGRSLRLSCKASG YTFTRYTMHWVRQAPGKGLEWIGYI NPSRGYTNYNQKVKDRFTISRDNSKN TAFLQMDSLRPEDTGVYFCARYYDD HYCLDYWGQGTPVTVSS (SEQ ID NO: 175) | DIQMTQSPSSLSASVGDRVTITCS ASSSVSYMNWYQQTPGKAPKR WIYDTSKLASGVPSRFSGSGSGT DYTFTISSLQPEDIATYYCQQWS SNPFTFGQGTKLQIT (SEQ ID NO: 176) |
| AB-0087 25 | EVQLVESGGGLVQPGGSLRLSCAASG YTFTRYTMHWVRQAPGKGLEWIGYI NPSRGYTYYADSVKGRFTLSTDKSKN TAYLQMSSLRAEDTAVYYCARYYDD | DIQLTQSPSSLSASVGDRVTITCR ASSSVSYVAWYQQKPGKAPKR WIYDTSKLYSGVPSRFSGSGSGT DYTLTISSLQPEDFATYYCQQWS |

TABLE 9-continued

CD3 heavy chain (VH) and light chain (VL) sequences.

| AB ID | VH | VL |
|---|---|---|
| | HYCLDYWGQGTLVTVSS (SEQ ID NO: 177) | SNPPTFGQGTKVEIK (SEQ ID NO: 178) |
| AB-0087 26 | QVQLVQSGGGVVQPGRSLRLSCKASG YTFTRYTMHWVRQAPGKGLEWIGYI NPSRGYTNYNQKFKDRFTISRDNSKN TAFLQMDSLRPEDTGVYFCARYYDD HYSLDYWGQGTPVTVSS (SEQ ID NO: 179) | DIQMTQSPSSLSASVGDRVTITCS ASSSVSYMNWYQQTPGKAPKR WIYDTSKLASGVPSRFSGSGSGT DYTFTISSLQPEDIATYYCQQWS SNPFTFGQGTKLQIT (SEQ ID NO: 180) |
| AB-0087 27 | QVQLVQSGGGVVQPGRSLRLSCKASG YTFTRYTMHWVRQAPGKCLEWIGYI NPSRGYTNYNQKFKDRFTISRDNSKN TAFLQMDSLRPEDTGVYFCARYYDD HYSLDYWGQGTPVTVSS (SEQ ID NO: 181) | DIQMTQSPSSLSASVGDRVTITCS ASSSVSYMNWYQQTPGKAPKR WIYDTSKLASGVPSRFSGSGSGT DYTFTISSLQPEDIATYYCQQWS SNPFTFGCGTKLQIT (SEQ ID NO: 182) |
| AB-0087 28 | QVQLVQSGGGVVQPGRSLRLSCKASG YTFTRYTMHWVRQAPGKGLEWIGYI NPSRGYTNYNQKFKDRFTISRDNSKN TAFLQMDSLRPEDTGVYFCARYYDD HYCLDYWGQGTPVTVSS (SEQ ID NO: 183) | DIQMTQSPSSLSASVGDRVTITCS ASSSVSYMNWYQQTPGKAPKR WIYDTSKLASGVPSRFSGSGSGT DYTFTISSLQPEDIATYYCQQWS SNPFTFGCGTKLQIT (SEQ ID NO: 184) |
| AB-0087 29 | EVQLQQSGPELVKPGASMKISCKASG YSFTGYTMNWVKQSHGKNLEWMGLI NPYKGVSTYNQKFKDKATLTVDKSSS TAYMELLSLTSEDSAVYYCARSGYYG DSDWYFDVWGQGTTLTVFS (SEQ ID NO: 185) | DIQMTQTTSSLSASLGDRVTISCR ASQDIRNYLNWYQQKPDGTVKL LIYYTSRLHSGVPSKFSGSGSGT DYSLTISNLEQEDIATYFCQQGN TLPWTFAGGTKLEIK (SEQ ID NO: 186) |
| AB-0087 30 | EVQLVESGGGLVQPGGSLRLSCAASG YSFTGYTMNWVRQAPGKGLEWVALI NPYKGVSTYNQKFKDRFTISVDKSKN TAYLQMNSLRAEDTAVYYCARSGYY GDSDWYFDVWGQGTLVTVSS (SEQ ID NO: 187) | AIQMTQSPSSLSASVGDRVTITC RASQDIRNYLNWYQQKPGKAPK LLIYYTSRLESGVPSRFSGSGSGT DYTLTISSLQPEDFATYYCQQGN TLPWTFGQGTKVEIK (SEQ ID NO: 188) |
| AB-0087 31 | QLQLQESGPGLVKPSQTLSLTCSVSGG SIRSGGHYWSWIRQHPGKGLEWIGYI HHSGSTYYNPSLKSRVIISVDTSKNQF SLKLRSVTAADTAIYYCARWRHDIFT TYPYYYYGMDVWGQGTLVTVSS (SEQ ID NO: 189) | EIVMTQSPATLSVSPGERATLSC RASQSVSSNLAWYQQKPGQAPR LLIYGASTRATGIPARFSGSGSGT EFTLTISSLQSEDFAVYYCQQYN NWPWTFGQGTKVEIK (SEQ ID NO: 190) |
| AB-0087 32 | QLQLQESGPGLVKPSQTLSLTCSVSGG SIRSGGHYWSWIRQHPGKGLEWIGYIS YSGSTYYNPSLKSRVTISVDTSKNQFS LKLSSVTAADTAVYYCARWRHDILTA YPYYYYGMDVWGQGTLVTVSS (SEQ ID NO: 191) | EIVMTQSPATLSVSPGERATLSC RASQSVSSNLAWYQQKPGQAPR LLIYGASTRATGIPARFSGSGSGT EFTLTISSLQSEDFAVYYCQQYN NWPWTFGQGTKVEIK (SEQ ID NO: 192) |
| AB-0087 33 | EVQLVESGGGLVQPGRSLRLSCAASG FTFDDYAMHWVRQAPGKGLEWVSGI SWNSGSIGYADSVKGRFTISRDNAKN SLYLQMNSLRAEDTALYYCAKDSRG YGDYRLGGAYWGQGTLVTVSS (SEQ ID NO: 193) | EIVMTQSPATLSVSPGERATLSC RASQSVSSNLAWYQQKPGQAPR LLIYGASTRATGIPARFSGSGSGT EFTLTISSLQSEDFAVYYCQQYN NWPWTFGQGTKVEIK (SEQ ID NO: 194) |
| AB-0087 34 | EVQLVESGGGLVQPGRSLRLSCAASG FTFDNYAMHWVRQAPGKGLEWVSGI SWNSGSIGYADSVKGRFTISRDNAKN SLYLQMNSLRAEDTALYYCAKDSRG YGDYSRGGAYWGQGTLVTVSS (SEQ ID NO: 195) | EIVMTQSPATLSVSPGERATLSC RASQSVSSNLAWYQQKPGQAPR LLIYGASTRATGIPARFSGSGSGT EFTLTISSLQSEDFAVYYCQQYN NWPWTFGQGTKVEIK (SEQ ID NO: 196) |
| AB-0087 35 | EVQLVESGGGLVQPGRSLRLSCAASG FTFDDYSMHWVRQAPGKGLEWVSGI SWNSGSKGYADSVKGRFTISRDNAKN SLYLQMNSLRAEDTALYYCAKYGSG YGKFYHYGLDVWGQGTTVTVSS (SEQ ID NO: 197) | DIQMTQSPSSLSASVGDRVTITC RASQSISSYLNWYQQKPGKAPK LLIYAASSLQSGVPSRFSGSGSGT DPTLTISSLQPEDFATYYCQQSYS TPPITFGQGTRLEIK (SEQ ID NO: 198) |
| AB-0087 | EVQLVESGGGLVQPGRSLRLSCAASG FTFDDYSMHWVRQAPGKGLEWVSGI | DIQMTQSPSSLSASVGDRVTITC RASQSISSYLNWYQQKPGKAPK |

TABLE 9-continued

CD3 heavy chain (VH) and light chain (VL) sequences.

| AB ID | VH | VL |
|---|---|---|
| 36 | SWNSGSIGYADSVKGRFTISRDNAKN SLYLQMNSLRAEDTALYYCAKDGSG YGKFYYYGMDVWGQGTTVTVSS (SEQ ID NO: 199) | LLIYAASSLQSGVPSRFSGSGSGT DFTLTISSLQPEDFATYYCQQSYS TPPITFGQGTRLEIK (SEQ ID NO: 200) |

Figure 54:
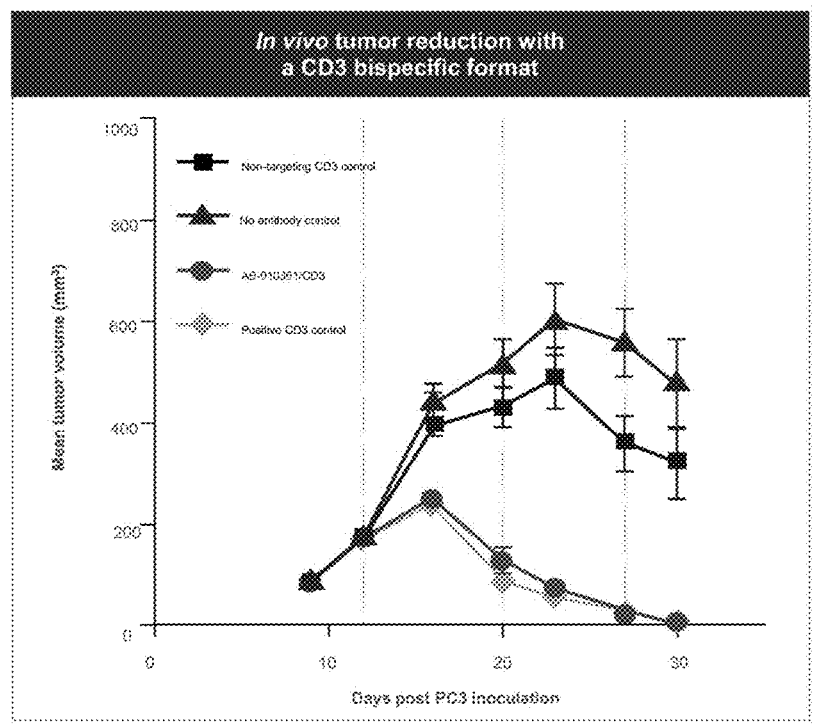
FIG. 54 shows measurements of tumor growth of NSG-DKO mice carrying PC3 tumor cells upon treatment of a bispecific antibody comprised of AB-010361 and an anti-CD3 binding arm.

FIG. 54 shows treatment of mice carrying the tumors formed by PC3 tumor cells using an exemplary bispecific antibody led to tumor burden reduction and/or elimination of tumors in mice. Said bispecific antibody was generated using a 1+1 (Fab-)(scFv-) Fc format (shown in FIG. 53) and the CD3 arm of which comprises the VH/VL sequence of AB-008707.

Additional antigens that can be targeted by a further binding domain in a bispecific or multi-specific antibody that comprises an antigen binding domain of an EphA2 antibody described herein, include, but are not limited to, antigens on NK cells to activate or inhibit NK cell pathways.

Illustrative examples of such an antigen include activating NK cell receptors such as activating human Killer Immunoglobulin-like Receptor (KIR) family members, activating Ly49 family members, CD94-NKG2C/E/H heterodimeric receptors, NKG2D, SLAM family receptors including 2B4/CD244, CRACC/SLAMF7, NTB-A/SLAMF6, Fc gamma RIIIA/CD16a, CD27, CD100/Semaphorin 4D, CD160, natural cytotoxicity receptors, including NKp30, NKp44, and NKp46, DNAM-1/CD226, IL-2 receptor subunit beta (IL-2RB), IL-2 receptor subunit gamma (IL-2RG), 4-1BB/CD137, and CRTAM. Illustrative examples of such an antigen include inhibiting NK cell receptors such as inhibiting human KIR family members, inhibiting Ly49 family members, CD94/NKG2A, TIGIT and CD96, sialic acid-binding Siglecs (Siglec-3, -7, and -9), ILT2/LILRB1, KLRG1, LAIR-1, CD161/NKR-P1A, and CEACAM-1.

In some embodiments, an EphA2 antibody is incorporated into a bispecific or multi-specific antibody that comprises a binding domain from an agonist antibody that binds to 4-1BB.

In one embodiment the 4-1BB agonist antibody is a bispecific antibody that is capable of binding to both EphA2 and 4-1BB. For purposes of this application, the term "4-1BB engager," refers to the portion of a molecule (e.g., a bispecific antibody capable of binding to both 4-1BB and EphA2) that binds to 4-1BB. In some embodiments, the 4-1BB engager is an antibody or an antibody fragment (e.g., scFv) that binds to 4-1BB. In some embodiments, the 4-1BB engager is a multimeric 4-1BB ligand ("4-1BBL"), for example, a 4-1BBL trimer. In some embodiments, as further described below, the bispecific antibody comprises one or more scFv fragments of an anti 4-1BB antibody and an EphA2 antibody disclosed herein. In one embodiment, the 4-1BB agonist antibody is a trispecific antibody. Examples of bispecific and trispecific antibody constructs are described in US20190010248, FIG. 1; WO2020025659, FIG. 1; Berczhnoy A, et al. Converting PD-L1-induced T-lymphocyte Inhibition into CD137-mediated Costimulation via PD-L1×CD137 Bispecific DART® Molecules. Poster presented at 30th EORTC/AACR/NCI Symposium, Nov. 13-16, 2018, Dublin, Ireland, Compte, M., et al. A tumor-targeted trimeric 4-1BB-agonistic antibody induces potent tumor-targeting immunity without systemic toxicity. Nat Com 9, 4809 (2018), FIG. 1; U.S. Pat. No. 10,239,949, FIG. 10; and WO2019/092452, Example 2.

Non-limiting examples of the scFv of the anti 4-1BB antibodies that can be used in the fusion proteins are shown in Table 10. Exemplary linkers that can be used to connect the heavy chain or light chain of the EphA2 antibody and the 4-1BB ligand domains in the fusion are shown in Table 14. Various fusion proteins comprising the 4-1BBL and the EphA2 antibodies are shown in Table 14.

TABLE 10 scFv4-1BB sequences used in the fusion construct

| Part Name | Description | Part Sequence |
|---|---|---|
| SCFV-009036-01 | Anti-4-1BB SCFV | QVQLQQSGAELAKPGTSVKL SCKASGYTFTSYYIYWVKQR PGQGLEWIGNIWPGNGGTFY GEKFMGKATFTADTSSSTAY MLLGSLTPEDSAYYFCARRP DYSGDDYFDYWGQGVLVTVS SGGGGSGGGGSGGGGSGGGG SQVVLTQPKSVSTSLKSTVK LSCKLNSGNIGSYYVHWYQQ HAGRSPTTMIYRDDKRPDGV PDRFSGSIDSSSNSAFLTIN NVQTEDDAIYFCHSYDSTIT PVFGGGTKLTVL (SEQ ID NO: 111) |
| SCFV-009036-02 | Anti-4-1BB SCFV | QVVLTQPKSVSTSLKSTVKL SCKLNSGNIGSYYVHWYQQH AGRSPTTMIYRDDKRPDGVP DRFSGSIDSSSNSAFLTINN VQTEDDAIYFCHSYDSTITP VFGGGTKLTVLGGGGSGGGG SGGGGSGGGGSQVQLQQSGA ELAKPGTSVKLSCKASGYTF TSYYIYWVKQRPGQGLEWIG NIWPGNGGTFYGEKFMGKAT FTADTSSSTAYMLLGSLTPE DSAYYFCARRPDYSGDDYFD YWGQGVLVTVSS (SEQ ID NO: 112) |
| SCFV-009365-01 | Anti-4-1BB SCFV | EVQLLESGGGLVQPGGSLRL SCAASGFTFSSYAMSWVRQA PGKGLEWVSAISGSGGSTYY ADSVKGRFTISRDNSKNTLY LQMNSLRAEDTAVYYCAKDS PFLLDDYYYYYMDVWGKGT TVTVSSGGGGSGGGGSGGGG SGGGGSDIQMTQSPSSVSAS VGDRVTITCRASQGISSWLA WYQQKPGKAPKLLIYAASSL QSGVPSRFSGSGSGTDFTLT ISSLQPEDFATYYCQQGHLF PITFGGGTKVEIK (SEQ ID NO: 113) |
| SCFV-009365-02 | Anti-4-1BB SCFV | DIQMTQSPSSVSASVGDRVT ITCRASQGISSWLAWYQQKP GKAPKLLIYAASSLQSGVPS |

TABLE 10-continued scFv4-1BB sequences used in the fusion construct

| Part Name | Description | Part Sequence |
|---|---|---|
| | | RFSGSGSGTDFTLTISSLQP EDFATYYCQQGHLFPITFGG GTKVEIKGGGGSGGGGSGGG GSGGGGSEVQLLESGGGLVQ PGGSLRLSCAASGFTFSSYA MSWVRQAPGKGLEWVSAISG SGGSTYYADSVKGRFTISRD NSKNTLYLQMNSLRAEDTAV YYCAKDSPFLLDDYYYYYYM DVWGKGTTVTVSS (SEQ ID NO: 114) |
| SCFV-009366-01 | Anti-4-1BB SCFV | EVQLLESGGGLVQPGGSLRL SCAASGFTFRNYAMSWVRQA PGKGLEWVSAISGSGDTTYY ADSVKGRFTISRDNSKNTLY LQMNSLRAEDTAVYYCAKDS PFLLDDYYYYYMDVWGKGT TVTVSSGGGGSGGGGSGGGG SGGGGSDIQMTQSPSSVSAS VGDRVTITCRASQGISSWLA WYQQKPGKAPKLLIYAASSL QSGVPSRFSGSGSGTDFTLT ISSLQPEDFATYYCQQGHLF PITFGGGTKVEIK (SEQ ID NO: 115) |
| SCFV-009366-02 | Anti-4-1BB SCFV | DIQMTQSPSSVSASVGDRVT ITCRASQGISSWLAWYQQKP GKAPKLLIYAASSLQSGVPS RFSGSGSGTDFTLTISSLQP EDFATYYCQQGHLFPITFGG GTKVEIKGGGGSGGGG SGGGGSGGGGSEVQLLESGG GLVQPGGSLRLSCAASGFTF RNYAMSWVRQAPGKGLEWVS AISGSGDTTYYADSVKGRFT ISRDNSKNTLYLQMNSLRAE DTAVYYCAKDSPFLLDDYYY YYMDVWGKGTTVTVSS (SEQ ID NO: 116) |
| SCFV-009037-01 | Anti-4-1BB SCFV | QVKLVQSGAALVKPGASVKM SCKASDYTFNDYWVSWVKQR HGESLEWIGEIYPNSGATNF NGKFRGKATLTVDNPTSTAY MELSRLTSEDSAIYYCTREY TRDWFAYWGQGTLVTVSSGG GGSGGGGSGGGGSGGGGSDV VLTQTPSILSATIGQSVSIS CRSSQSLLDSDGNTYLYWFL QRPGQSPQRLIYLVSNLGSG VPNRFSGSGSGTDFTLKISG VEAEDLGIYYCMQPTHAPYT FGAGTKLELK (SEQ ID NO: 117) |
| SCFV-009037-02 | Anti-4-1BB SCFV | DVVLTQTPSILSATIGQSVS ISCRSSQSLLDSDGNTYLYW FLQRPGQSPQRLIYLVSNLG SGVPNRFSGSGSGTDFTLKI SGVEAEDLGIYYCMQPTHAP YTFGAGTKLELKGGGGSGGG GSGGGGSGGGGSQVKLVQSG AALVKPGASVKMSCKASDYT FNDYWVSWVKQRHGESLEWI GEIYPNSGATNFNGKFRGKA TLTVDNPTSTAYMELSRLTS EDSAIYYCTREYTRDWFAYW GQGTLVTVSS (SEQ ID NO: 118) |
| SCFV-009809-01 | Anti-4-1BB SCFV | QVQLQQSGAEVIKPGASVKL SCKASGYTFSSYMHWVRQA PGQGLEWIGEINPGNGHTNY NEKFKSRATLTGDTSTSTVY MELSSLRSEDTAVYYCARSF TTARAFAYWGQGTLVTVSSG GGGSGGGGSGGGGSGGGGSD IVMTQSPAFLSVTPGEKVTI TCRASQTISDYLHWYQQKPD QAPKLLIKYASQSISGIPSR FSGSGSGTDFTFTISSLEAE DAATYYCQDGHSFPPTFGQG TKLEIK (SEQ ID NO: 119) |
| SCFV-009809-02 | Anti-4-1BB SCFV | DIVMTQSPAFLSVTPGEKVT ITCRASQTISDYLHWYQQKP DQAPKLLIKYASQSISGIPS RFSGSGSGTDFTFTISSLEA EDAATYYCQDGHSFPPTFGQ GTKLEIKGGGGSGGGGSGGG GSGGGGSQVQLQQSGAEVIK PGASVKLSCKASGYTFSSYW MHWVRQAPGQGLEWIGEINP GNGHTNYNEKFKSRATLTGD TSTSTVYMELSSLRSEDTAV YYCARSFTTARAFAYWGQGT LVTVSS (SEQ ID NO: 120) |
| SCFV-009810-01 | Anti-4-1BB SCFV | EVQLVESGGGLVQPGGSLRL SCAASGFTFSDYWMSWVRQA PGKGLEWVADIKNDGSYTNY APSLTNRFTISRDNAKNSLY LQMNSLRAEDTAVYYCAREL TGTWGQGTMVTVSSGGGGSG GGGSGGGGSGGGGSDIVMTQ SPDSLAVSLGERATINCKSS QSLLSSGNQKNYLAWYQQKP GQPPKLLIYYASTRQSGVPD RFSGSGSGTDFTLTISSLQA EDVAVYYCLQYDRYPFTFGQ GTKLEIK (SEQ ID NO: 121) |
| SCFV-009810-02 | Anti-4-1BB SCFV | DIVMTQSPDSLAVSLGERAT INCKSSQSLLSSGNQKNYLA WYQQKPGQPPKLLIYYASTR QSGVPDRFSGSGSGTDFTLT ISSLQAEDVAVYYCLQYDRY PFTFGQGTKLEIKGGGGSGG GGSGGGGSGGGGSEVQLVES GGGLVQPGGSLRLSCAASGF TFSDYWMSWVRQAPGKGLEW VADIKNDGSYTNYAPSLTNR FTISRDNAKNSLYLQMNSLR AEDTAVYYCARELTGTWGQG TMVTVSS (SEQ ID NO: 122) |

TABLE 11

Heavy Chain Sequences Used in 4-1BB Bispecific antibody

| IgG Identifier | Sequence of CH123 fused to 4-1BB engager | Sequence of CH123 not fused (if applicable) |
|---|---|---|
| HIgG1 | STKGPSVFPLAPSSK STSGGTAALGCLVKD YFPEPVTVSWNSGAL TSGVHTFPAVLQSSG LYSLSSVVTVPSSSL | N/A |

TABLE 11-continued

Heavy Chain Sequences Used in 4-1BB Bispecific antibody

| IgG Identifier | Sequence of CH123 fused to 4-1BB engager | Sequence of CH123 not fused (if applicable) |
|---|---|---|
| | GTQTYICNVNHKPSN<br>TKVDKRVEPKSCDKT<br>HTCPPCPAPELLGGP<br>SVFLFPPKPKDTLMI<br>SRTPEVTCVVVDVSH<br>EDPEVKFNWYVDGVE<br>VHNAKTKPREEQYNS<br>TYRVVSVLTVLHQDW<br>LNGKEYKCKVSNKAL<br>PAPIEKTISKAKGQP<br>REPQVYTLPPSREEM<br>TKNQVSLTCLVKGFY<br>PSDIAVEWESNGQPE<br>NNYKTTPPVLDSDGS<br>FFLYSKLTVDKSRWQ<br>QGNVFSCSVMHEALH<br>NHYTQKSLSLSPG<br>(SEQ ID NO: 123) | |
| hIgG4_<br>S22<br>8P_<br>R409K | STKGPSVFPLAPCSR<br>STSESTAALGCLVKD<br>YFPEPVTVSWNSGAL<br>TSGVHTFPAVLQSSG<br>LYSLSSVVTVPSSSL<br>GTKTYTCNVDHKPSN<br>TKVDKRVESKYGPPC<br>PPCPAPEFLGGPSVF<br>LFPPKPKDTLMISRT<br>PEVTCVVVDVSQEDP<br>EVQFNWYVDGVEVHN<br>AKTKPREEQFNSTYR<br>VVSVLTVLHQDWLNG<br>KEYKCKVSNKGLPSS<br>IEKTISKAKGQPREP<br>QVYTLPPSQEEMTKN<br>QVSLTCLVKGFYPSD<br>IAVEWESNGQPENNY<br>KTTPPVLDSDGSFFL<br>YSKLTVDKSRWQEGN<br>VFSCSVMHEALHNHY<br>TQKSLSLSLG<br>(SEQ ID NO: 124) | N/A |
| hIgG1_<br>P32<br>9G_<br>L234A<br>L235A | STKGPSVFPLAPSSK<br>STSGGTAALGCLVKD<br>YFPEPVTVSWNSGAL<br>TSGVHTFPAVLQSSG<br>LYSLSSVVTVPSSSL<br>GTQTYICNVNHKPSN<br>TKVDKRVEPKSCDKT<br>HTCPPCPAPEAAGGP<br>SVFLFPPKPKDTLMI<br>SRTPEVTCVVVDVSH<br>EDPEVKFNWYVDGVE<br>VHNAKTKPREEQYNS<br>TYRVVSVLTVLHQDW<br>LNGKEYKCKVSNKAL<br>GAPIEKTISKAKGQP<br>REPQVYTLPPSREEM<br>TKNQVSLTCLVKGFY<br>PSDIAVEWESNGQPE<br>NNYKTTPPVLDSDGS<br>FFLYSKLTVDKSRWQ<br>QGNVFSCSVMHEALH<br>NHYTQKSLSLSPG<br>(SEQ ID NO: 125) | N/A |
| mIgG1 | KTTPPSVYPLAPGSA<br>AQTNSMVTLGCLVKG<br>YFPEPVTVTWNSGSL<br>SSGVHTFPAVLQSDL<br>YTLSSSVTVPSSTWP | N/A |

TABLE 11-continued

Heavy Chain Sequences Used in 4-1BB Bispecific antibody

| IgG Identifier | Sequence of CH123 fused to 4-1BB engager | Sequence of CH123 not fused (if applicable) |
|---|---|---|
| | SETVTCNVAHPASST<br>KVDKKIVPRDCGCKP<br>CICTVPEVSSVFIFP<br>PKPKDVLTITLTPKV<br>TCVVVDISKDDPEVQ<br>FSWFVDDVEVHTAQT<br>QPREEQFNSTFRSVS<br>ELPIMHQDWLNGKEF<br>KCRVNSAAFPAPIEK<br>TISKTKGRPKAPQVY<br>TIPPPKEQMAKDKVS<br>LTCMITDFFPEDITV<br>EWQWNGQPAENYKNT<br>QPIMDTDGSYFVYSK<br>LNVQKSNWEAGNTFT<br>CSVLHEGLHNHHTEK<br>SLSHSPG<br>(SEQ ID NO: 126) | |
| hIgG1_<br>kih | STKGPSVFPLAPSSK<br>STSGGTAALGCLVKD<br>YFPEPVTVSWNSGAL<br>TSGVHTFPAVLQSSG<br>LYSLSSVVTVPSSSL<br>GTQTYICNVNHKPSN<br>TKVDKRVEPKSCDKT<br>HTCPPCPAPELLGGP<br>SVFLFPPKPKDTLMI<br>SRTPEVTCVVVDVSH<br>EDPEVKFNWYVDGVE<br>VHNAKTKPREEQYNS<br>TYRVVSVLTVLHQDW<br>LNGKEYKCKVSNKAL<br>PAPIEKTISKAKGQP<br>REPQVYTLPPSREEM<br>TKNQVSLTCAVKGFY<br>PSDIAVEWESNGQPE<br>NNYKTTPPVLDSDGS<br>FFLVSKLTVDKSRWQ<br>QGNVFSCSVMHEALH<br>NHYTQKSLSLSPG<br>(SEQ ID NO: 127) | STKGPSVFPLAPSSK<br>STSGGTAALGCLVKD<br>YFPEPVTVSWNSGAL<br>TSGVHTFPAVLQSSG<br>LYSLSSVVTVPSSSL<br>GTQTYICNVNHKPSN<br>TKVDKRVEPKSCDKT<br>HTCPPCPAPELLGGP<br>SVFLFPPKPKDTLMI<br>SRTPEVTCVVVDVSH<br>EDPEVKFNWYVDGVE<br>VHNAKTKPREEQYNS<br>TYRVVSVLTVLHQDW<br>LNGKEYKCKVSNKAL<br>PAPIEKTISKAKGQP<br>REPQVYTLPPSREEM<br>TKNQVSLWCLVKGFY<br>PSDIAVEWESNGQPE<br>NNYKTTPPVLDSDGS<br>FFLYSKLTVDKSRWQ<br>QGNVFSCSVMHEALH<br>NHYTQKSLSLSPG<br>(SEQ ID NO: 128) |
| hIgG4_<br>S22<br>8P_<br>R409K_<br>kih | STKGPSVFPLAPCSR<br>STSESTAALGCLVKD<br>YFPEPVTVSWNSGAL<br>TSGVHTFPAVLQSSG<br>LYSLSSVVTVPSSSL<br>GTKTYTCNVDHKPSN<br>TKVDKRVESKYGPPC<br>PPCPAPEFLGGPSVF<br>LFPPKPKDTLMISRT<br>PEVTCVVVDVSQEDP<br>EVQFNWYVDGVEVHN<br>AKTKPREEQFNSTYR<br>VVSVLTVLHQDWLNG<br>KEYKCKVSNKGLPSS<br>IEKTISKAKGQPREP<br>QVYTLPPSQEEMTKN<br>QVSLSCAVKGFYPSD<br>IAVEWESNGQPENNY<br>KTTPPVLDSDGSFFL<br>VSKLTVDKSRWQEGN<br>VFSCSVMHEALHNHY<br>TQKSLSLSLG<br>(SEQ ID NO: 129) | STKGPSVFPLAPCSR<br>STSESTAALGCLVKD<br>YFPEPVTVSWNSGAL<br>TSGVHTFPAVLQSSG<br>LYSLSSVVTVPSSSL<br>GTKTYTCNVDHKPSN<br>TKVDKRVESKYGPPC<br>PPCPAPEFLGGPSVF<br>LFPPKPKDTLMISRT<br>PEVTCVVVDVSQEDP<br>EVQFNWYVDGVEVHN<br>AKTKPREEQFNSTYR<br>VVSVLTVLHQDWLNG<br>KEYKCKVSNKGLPSS<br>IEKTISKAKGQPREP<br>QVYTLPPSQEEMTKN<br>QVSLWCLVKGFYPSD<br>IAVEWESNGQPENNY<br>KTTPPVLDSDGSFFL<br>YSKLTVDKSRWQEGN<br>VFSCSVMHEALHNHY<br>TQKSLSLSLG<br>(SEQ ID NO: 130) |
| hIgG1-<br>Xmab | STKGPSVFPLAPSSK<br>STSGGTAALGCLVKD<br>YFPEPVTVSWNSGAL<br>TSGVHTFPAVLQSSG<br>LYSLSSVVTVPSSSL | STKGPSVFPLAPSSK<br>STSGGTAALGCLVKD<br>YFPEPVTVSWNSGAL<br>TSGVHTFPAVLQSSG<br>LYSLSSVVTVPSSSL |

TABLE 11-continued

Heavy Chain Sequences Used in 4-1BB Bispecific antibody

| IgG Identifier | Sequence of CH123 fused to 4-1BB engager | Sequence of CH123 not fused (if applicable) |
|---|---|---|
| | GTQTYICNVNHKPSD TKVDKKVEPKSCDKT HTCPPCPAPPVAGPS VFLFPPKPKDTLMIS RTPEVTCVVVDVKHE DPEVKFNWYVDGVEV HNAKTKPREEQYNST YRVVSVLTVLHQDWL NGKEYKCKVSNKALP APIEKTISKAKGQPR EPQVYTLPPSREQMT KNQVKLTCLVKGFYP SDIAVEWESNGQPEN NYKTTPPVLDSDGSF FLYSKLTVDKSRWQQ GNVFSCSVMHEALHN HYTQKSLSLSPGK (SEQ ID NO: 131) | GTQTYICNVNHKPSD TKVDKKVEPKSCDKT HTCPPCPAPPVAGPS VFLFPPKPKDTLMIS RTPEVTCVVVDVKHE DPEVKFNWYVDGVEV HNAKTKPREEEYNST YRVVSVLTVLHQDWL NGKEYKCKVSNKALP APIEKTISKAKGQPR EPQVYTLPPSREEMT KNQVSLTCDVSGFYP SDIAVEWESDGQPEN NYKTTPPVLDSDGSF FLYSKLTVDKSRWEQ GDVFSCSVMHEALHN HYTQKSLSLSPGK (SEQ ID NO: 132) |

Note:
"CH123" refers to an IgG heavy chain constant region comprising CH1-CH2-hinge-CH3.

Additional 4-1BB antibody sequences suitable for use in generating bispecific constructs that are capable of binding to both EphA2 and 4-1BB are provided in Table 12.

TABLE 12

4-1BB antibody sequences sutiable for generating bispecific constructs

| 4-1BB antibody | VH | VL |
|---|---|---|
| hu106-1 | EVQLVQSGAEVKKPG SSVKVSCKASGYTFT SYYIYWVRQAPGQGL EWIGNIWPGNGGTFY GEKFMGRATFTADTS TSTAYMELSSLRSED TAVYYCARRPDYSGD DYFDYWGQGTLVTVS S (SEQ ID NO: 721) | NVMLTQPHSVSESPG KTVTISCKLNSGNIG SYYVHWYQQRPGSSP TTMIYRDDKRPDGVP DRFSGSIDSSSNSAS LTISGLKTEDEADYY CHSYDSTITPVFGGG TKLTVL (SEQ ID NO: 743) |
| TABBY 106 | QVQLQQSGAELAKPG TSVKLSCKASGYTFT SYYIYWVKQRPGQGL EWIGNIWPGNGGTFY GEKFMGKATFTADTS SSTAYMLLGSLTPED SAYYFCARRPDYSGD DYFDYWGQGVLVTVS S (SEQ ID NO: 722) | QVVLTQPKSVSTSLK STVKLSCKLNSGNIG SYYVHWYQQHAGRSP TTMIYRDDKRPDGVP DRFSGSIDSSSNSAF LTINNVQTEDDAIYF CHSYDSTITPVFGGG TKLTVL (SEQ ID NO: 744) |
| TABBY 107 | QVKLVQSGAALVKPG ASVKMSCKASDYTFN DYWVSWVKQRHGESL EWIGEIYPNSGATNF NGKFRGKATLTVDNP TSTAYMELSRLTSED SAIYYCTREYTRDWF AYWGQGTLVTVSS (SEQ ID NO: 723) | DVVLTQTPSILSATI GQSVSISCRSSQSLL DSDGNTYLYWFLQRP GQSPQRLIYLVSNLG SGVPNRFSGSGSGTD FTLKISGVEAEDLGI YYCMQPTHAPYTFGA GTKLELK (SEQ ID NO: 745) |
| BBK4 | QVQLQQSGAEVIKPG ASVKLSCKASGYTFS SYWMHWVRQAPGQGL EWIGEINPGNGHTNY | DIVMTQSPAFLSVTP GEKVTITCRASQTIS DYLHWYQQKPDQAPK LLIKYASQSISGIPS |

TABLE 12-continued 4-1BB antibody sequences sutiable for generating bispecific constructs

| 4-1BB antibody | VH | VL |
|---|---|---|
| | NEKFKSRATLTGDTS TSTVYMELSSLRSED TAVYYCARSFTTARA FAYWGQGTLVTVSS (SEQ ID NO: 724) | RFSGSGSGTDFTFTI SSLEAEDAATYYCQD GHSFPPTFGQGTKLE IK (SEQ ID NO: 746) |
| hu39E3G.4 | EVQLVESGGGLVQPG GSLRLSCAASGFTFS DYWMSWVRQAPGKGL EWVADIKNDGSYTNY APSLTNRFTISRDNA KNSLYLQMNSLRAED TAVYYCARELTGTWG QGTMVTVSS (SEQ ID NO: 725) | DIVMTQSPDSLAVSL GERATINCKSSQSLL SSGNQKNYLAWYQQK PGQPPKLLIYYASTR QSGVPDRFSGSGSGT DFTLTISSLQAEDVA VYYCLQYDRYPFTFG QGTKLEIK (SEQ ID NO: 747) |
| Urelumab | QVQLQQWGAGLLKPS ETLSLTCAVYGGSFS GYYWSWIRQSPEKGL EWIGEINHGGYVTYN PSLESRVTISVDTSK NQFSLKLSSVTAADT AVYYCARDYGPGNYD WYFDLWGRGTLVTVS S (SEQ ID NO: 726) | EIVLTQSPATLSLSP GERATLSCRASQSVS SYLAWYQQKPGQAPR LLIYDASNRATGIPA RFSGSGSGTDFTLTI SSLEPEDFAVYYCQQ RSNWPPALTFGGGTK VEIK (SEQ ID NO: 748) |
| CTX-471 | EVQLLESGGGLVQPG GSLRLSCAASGFTFS SYAMSWVRQAPGKGL EWVSAISGSGGSTYY ADSVKGRFTISRDNS KNTLYLQMNSLRAED TAVYYCAKDSPFLLD DYYYYYMDVWGKGT TVTVSS (SEQ ID NO: 727) | DIQMTQSPSSVSASV GDRVTITCRASQGIS SWLAWYQQKPGKAPK LLIYAASSLQSGVPS RFSGSGSGTDFTLTI SSLQPEDFATYYCQQ GHLFPITFGGGTKVE IK (SEQ ID NO: 749) |
| CTX-471AF | EVQLLESGGGLVQPG GSLRLSCAASGFTFR NYAMSWVRQAPGKGL EWVSAISGSGDTTYY ADSVKGRFTISRDNS KNTLYLQMNSLRAED TAVYYCAKDSPFLLD DYYYYYMDVWGKGT TVTVSS (SEQ ID NO: 728) | DIQMTQSPSSVSASV GDRVTITCRASQGIS SWLAWYQQKPGKAPK LLIYAASSLQSGVPS RFSGSGSGTDFTLTI SSLQPEDFATYYCQQ GHLFPITFGGGTKVE IK (SEQ ID NO: 750) |
| MOR-6032 | QVQLVQSGAEVKKPG SSVKVSCKASGGTFN SYAISWVRQAPGQGL EWMGGIIPGFGTANY AQKFQGRVTITADES TSTAYMELSSLRSED TAVYYCARKNEEDGG FDHWGQGTLVTVSS (SEQ ID NO: 729) | DIELTQPPSVSVAPG QTARISCGDNLGDY YASWYQQKPGQAPVL VIYDDSNRPSGIPER FSGSNSGNTATLTIS GTQAEDEADYYCQTW DGTLHFVFGGGTKLT VL (SEQ ID NO: 751) |
| MOR-7361 | QVQLVESGGGLVQPG GSLRLSCAASGFTFS DYYMHWVRQAPGKGL EWVSVISGSGSNTYY ADSVKGRFTISRDNS KNTLYLQMNSLRAED TAVYYCARLYAQFEG DFWGQGTLVTVSS (SEQ ID NO: 730) | DIELTQPPSVSVAPG QTARISCGDNIGSK YVSWYQQKPGQAPVL VIYSDSERPSGIPER FSGSNSGNTATLTIS GTQAEDEADYYCQSW DGSISRVFGGGTKLT VL (SEQ ID NO: 752) |
| MOR-7480 | QVQLVQSGAEVKKPG ESLKISCKGSGYSFS TYWISWVRQMPGKGL EWMGKIYPGDSYTNY SPSFQGQVTISADKS | DIELTQPPSVSVAPG QTARISCGDNIGDQ YAHWYQQKPGQAPVV VIYQDKNRPSGIPER FSGSNSGNTATLTIS |

TABLE 12-continued

4-1BB antibody sequences sutiable for generating bispecific constructs

| 4-1BB antibody | VH | VL |
|---|---|---|
|  | ISTAYLQWSSLKASD TAMYYCARGYGIFDY WGQGTLVTVSS (SEQ ID NO: 731) | GTQAEDEADYYCATY TGFGSLAVFGGGTKL TVL (SEQ ID NO: 753) |
| MOR-7480.1/ Utomilumab | EVQLVQSGAEVKKPG ESLRISCKGSGYSFS TYWISWVRQMPGKGL EWMGKIYPGDSYTNY SPSFQGQVTISADKS ISTAYLQWSSLKASD TAMYYCARGYGIFDY WGQGTLVTVSS (SEQ ID NO: 732) | SYELTQPPSVSVSPG QTASITCSGDNIGDQ YAHWYQQKPGQSPVL VIYQDKNRPSGIPER FSGSNSGNTATLTIS GTQAMDEADYYCATY TGFGSLAVFGGGTKL TVL (SEQ ID NO: 754) |
| MOR-7483 | QVQLVQSGAEVKKPG ESLKISCKGSGYSFS TYWISWVRQMPGKGL EWMGKIYPGDSYTNY SPSFQGQVTISADKS ISTAYLQWSSLKASD TAMYYCARGYGIFDY WGQGTLVTVSS (SEQ ID NO: 733) | DIELTQPPSVSVAPG QTARISCSGDNIGDQ YAHWYQQKPGQAPVV VIYQDKNRPSGIPER FSGSNSGNTATLTIS GTQAEDEADYYCSTY TFVGFTTVFGGGTKL TVL (SEQ ID NO: 755) |
| Utomilumab | EVQLVQSGAEVKKPG ESLRISCKGSGYSFS TYWISWVRQMPGKGL EWMGKIYPGDSYTNY SPSFQGQVTISADKS ISTAYLQWSSLKASD TAMYYCARGYGIFDY WGQGTLVTVSS (SEQ ID NO: 734) | SYELTQPPSVSVSPG QTASITCSGDNIGDQ YAHWYQQKPGQSPVL VIYQDKNRPSGIPER FSGSNSGNTATLTIS GTQAMDEADYYCATY TGFGSLAVFGGGTKL TVL (SEQ ID NO: 756) |
| EU-101 | QVQLVQSGAEVKKPG ASVKLSCKASGYTFS SYWMHWVRQAPGQGL EWIGEINPGNGHTNY NEKFKSRVTMTRDTS TSTAYMELSSLRSED TAVYYCARSFKTARA FAYWGQGTLVTVSS (SEQ ID NO: 735) | DIVMTQSPAFLSVTP GEKVTITCRASQTIS DYLHWYQQKPDQAPK LLIKYASQSISGIPS RFSGSGSGTDFTFTI SSLEAEDAATYYCQD GHSWPPTFGQGTKLE IK (SEQ ID NO: 757) |
| STA-551 | EVQLVESGGGLVKPG GSLRLSCAASGFTFS TFTMNWVRQAPGKGL EWVSSISSKSTYIEY ADSFKVRFTISRDNA KNSLYLQMNSLRAED TAVYYCARYGAKNFL NWVFDYWGQGTLVTV SS (SEQ ID NO: 736) | QSALTQPPSASGSPG QTVTISCTGTRYDVG YYEVVSWYQQHPGKA PKLMIYETSKRLSGV PDRFSGSKSGNTASL TVSGLQAEDEADYYC SSYRYEHQVSFGGGT KLTVL (SEQ ID NO: 758) |
| LVGN-6051 | QVQLVQSGAEVKKPG ASVKVSCKASGYTFA GFEMHWVRQAPGQGL EWMGAIDPKTGGTDY NQKFKDRVTMTRDTS ISTAYMELSRLSDD TAVYYCARDLGYFDV WGQGTLVTVSS (SEQ ID NO: 737) | DIQMTQSPSSLSASV GDRVTITCRASQDIR SNLNWYQQKPGGAVK LLIYYTSRLHSGVPS RFSGSGSGTDYTLTI SSLQPEDFATYFCQQ SEKLPRTFGGGTKVE IR (SEQ ID NO: 759) |
| AGEN-2373 | XVQLVQSGAEVKKPG ASVKVSCKASGYTFT GYYMHWVRQAPGQGL EWMGWINPNSGGTNY AQKFQGRVTMTRDTS ISTAYMELSRLSDD | SYVLTQPPSVSVAPG ETARITCGGDDIGDK RVHWYQKKPDQAPVL VVYEDRYRPSGIPER ISGSNSGNTATLTLS RVEAGDEADYYCQVW |
|  | TAVYYCAREPGYYGS GLDYWGQGTLVTVSS (SEQ ID NO: 738) | DSSSDHPGVFGGGTQ LIIL (SEQ ID NO: 760) |
| ADG-106/ AG10131 | EVQLVESGGGLVQPG GSLRLSCAASGFSLS TGGVGVGWIRQAPGK GLEWLALIDWADDKY YSPSLKSRLTISRDN SKNTLYLQLNSLRAE DTAVYYCARGGSDTV IGDWFAYWGQGTLVT VSS (SEQ ID NO: 739) | DIQLTQSPSSLSASVG DRVTITCRASQSIGSY LAWYQQKPGKAPKLL IYDASNLETGVPSRF SGSGSGTDFTLTISS LQPEDFATYYCQQGY YLWTFGQGTKVEIK (SEQ ID NO: 761) |
| ATOR-1017 | EVQLLESGGGLVQPG GSLRLSCAASGFNFG YSYMSWVRQAPGKGL EWVSSIGSTSSHTYY ADSVKGRFTISRDNS KNTLYLQMNSLRAED TAVYYCARVYSSPGI DYWGQGTLVTVSS (SEQ ID NO: 740) | DIQMTQSPSSLSASV GDRVTITCRASQSIG STLNWYQQKPGKAPK LLIYGASSLQSGVPS RFSGSGSGTDFTLTI SSLQPEDFATYYCQQ YYTWVPFTGQGTKL EIK (SEQ ID NO: 762) |
| Hz4B4-1 | QVQLVQSGAEWKPGA SVKLSCKASGYTFSS YWMHWVKQAPGQVLE WIGEINPGNGHTNYN EKFKSKATLTVDKSA STAYMELSSLRSEDT AVYYCARSFTTARAF AYWGQGTLVTVSS (SEQ ID NO: 741) | DIVMTQSPATQSVSP GERVTLSCRASQTIS DYLHWYQQKPGQSPR LLIKYASQSISGIPS RFSGSGSGSDFTLTI SSVEPEDFGVYYCQD GHSFPPTFGGGTKLE IK (SEQ ID NO: 763) |
| Hz4B4-2 | QVQLVQSGAEVKKPG ASVKVSCKASGYTFS SYWMHWVRQAPGQRL EWMGEINPGNGHTNY SQKFQGRVTITVDKS ASTAYMELSSLRSED TAVYYCARSFTTARA FAYWGQGTLVTVSS (SEQ ID NO: 742) | DIVMTQSPPTLSLSP GERVTLSCRASQSIS DYLHWYQQKPGQSPR LLIKYASQSISGIPA RFSGSGSGTD FTLTISSLEPEDFAV YYCQDGHSFPPTFGG GTKVEIK (SEQ ID NO: 764) |

Figure 49:
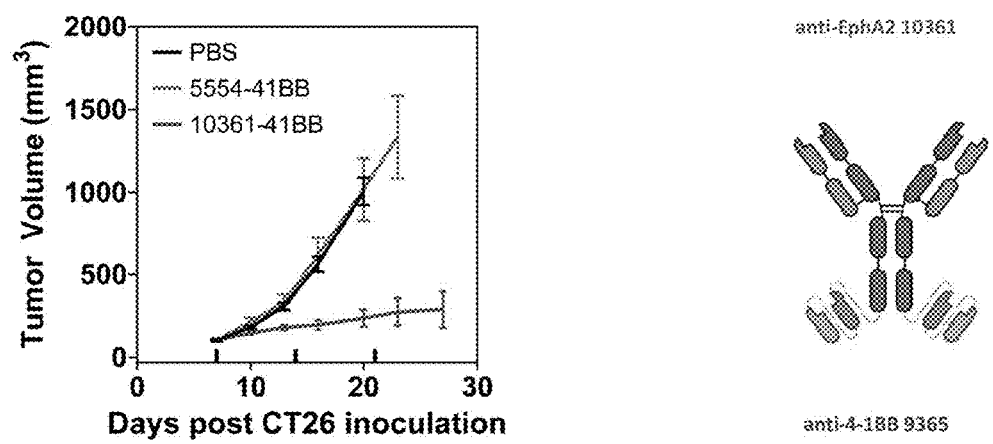
FIG. 49 shows measurements of tumor growth in mice inoculated with CT26 cells upon treatment of a bispecific antibody comprising scFv of the anti-4-1BB antibody 9365 and AB-010361.

As shown in FIG. 49, one exemplary bispecific antibody that comprises two scFv fragments of anti-4-1BB antibody linked to the HC of the EphA2 antibody AB-010361 showed capability of reducing tumor growth in mice carrying tumors formed from CT26 cells.

In one embodiment, the fusion molecule comprises a silenced human IgG1 with three human 4-1BB ligand ectodomains attached via flexible linkers. See WO2019086499, FIGS. 1-3. Other 4-1BBL fusion molecules can be utilized with the tumor-targeting antibodies described herein, see Zhang et al., Targeted and Untargeted CD137L Fusion Proteins for the Immunotherapy of Experimental Solid Tumors, Clin Cancer Res, 2758-2767 (2007), FIG. 1; (Kermer et al., Combining Antibody-Directed Presentation of IL-15 and 4-1BBL in a Trifunctional Fusion Protein for Cancer Immunotherapy, Mol Cancer Ther, 112-121 (2014), FIG. 1.

In some embodiments, an EphA2 antibody is incorporated into a fusion molecule comprising one or more 4-1BB ligands (4-1BBL). In one embodiment, a trimer of 4-1BBL is C-terminally fused to either the light chain or heavy chain of an EphA2 antibody. In one embodiment, one or more individual 4-1BBL domains are connected via linkers, with one of the domains additionally fused to the EphA2 antibody via a linker. The 4-1BBL domains comprise entire ECD portion of the molecule or truncated forms that can still bind and activate 4-1BB. See WO2019086499, FIGS. 1-3. Non-limiting examples of the 4-1BBL domains that can be used in the fusion proteins are shown in Table 13. Exemplary linkers that can be used to connect the heavy chain or light chain of the EphA2 antibody and the 4-1BB ligand domains in the fusion are shown in Table 14 Various fusion proteins comprising the 4-1BBL and the EphA2 antibodies are shown in Table 14.

TABLE 13

4-1BBL domains used in the fusion constructs

| Part Name | Description | Part Sequence |
|---|---|---|
| h4-1BBL (THD) | Human 4-1BB ligand, residues 89-242 of ECD | QGMFAQLVAQNVLLIDGPLSWYSDP GLAGVSLTGGLSYKEDTKELVVAKA GVYYVFFQLELRRVVAGEGSGSVSL ALHLQPLRSAAGAAALALTVDLPPA SSEARNSAFGFQGRLLHLSAGQRLG VHLHTEARARHAWQLTQGATVLGLF RVTP (SEQ ID NO: 106) |
| h4-1BBL (THD)3-10 | Human 4-1BB Ligand (89-242) Trimer with (GGGGG)2 linkers (SEQ ID NO: 781) between protomers | QGMFAQLVAQNVLLIDGPLSWYSDP GLAGVSLTGGLSYKEDTKELVVAKA GVYYVFFQLELRRVVAGEGSGSVSL ALHLQPLRSAAGAAALALTVDLPPA SSEARNSAFGFQGRLLHLSAGQRLG VHLHTEARARHAWQLTQGATVLGLF RVTPGGSGGGGSGGQGMFAQLVAQN VLLIDGPLSWYSDPGLAGVSLTGGL SYKEDTKELVVAKAGVYYVFFQLEL RRVVAGEGSGSVSLALHLQPLRSAA GAAALALTVDLPPASSEARNSAFGF QGRLLHLSAGQRLGVHLHTEARARH AWQLTQGATVLGLFRVTPGGSGGGG SGGQGMFAQLVAQNVLLIDGPLSWY SDPGLAGVSLTGG LSYKEDTKELVVAKAGVYYVFFQLE LRRVVAGEGSGSVSLALHLQPLRSA AGAAALALTVDLPPASSEARNSAFG FQGRLLHLSAGQRLGVHLHTEARAR HAWQLTQGATVLGLFRVTP (SEQ ID NO: 107) |
| h41BBL (THD)3-2 | Human 4-1BB Ligand (89-242) Trimer with GG linkers | QGMFAQLVAQNVLLIDGPLSWYSDP GLAGVSLTGGLSYKEDTKELVVAKA GVYYVFFQLELRRVVAGEGSGSVSL ALHLQPLRSAAGAAALALTVDLPPA SSEARNSAFGFQGRLLHLSAGQRLG VHLHTEARARHAWQLTQGATVLGLF RVTPGGQGMFAQLVAQNVLLIDGPL SWYSDPGLAGVSLTGGLSYKE DTKELVVAKAGVYYVFFQLELRRVV AGEGSGSVSLALHLQPLRSAAGAAA LALTVDLPPASSEARNSAFGFQGRL LHLSAGQRLGVHLHTEARARHAWQL TQGATVLGLFRVTPGGQGMFAQLVA QNVLLIDGPLSWYSDPGLAGVSLTG GLSYKEDTKELVVAKAGVYYVFFQL ELRRVVAGEGSGSVSLALHLQPLRS AAGAAALALTVDLPPASSEARNSAF GFQGRLLHLSAGQRLGVHLHTEARA RHAWQLTQGATVLGLFRVTP (SEQ ID NO: 108) |
| h4-1BBL (71-248) | Human 4-1BB ligand, residues 71-248 of ECD | REGPELSPDDDPAGLLDLRQGMFAQL VAQNVLLIDGPLSWYSDPGLAGVSL TGGLSYKEDTKELVVAKAGVYYVFF QLELRRVVAGEGSGSVSLALHLQPL RSAAGAAALALTVDLPPASSEARNS AFGFQGRLLHLSAGQRLGVHLHTEA RARHAWQLTQGATVLGLFRVTPEIP AGL (SEQ ID NO: 109) |
| h4-1BBL (71-248)3-10 | Human 4-1BB Ligand (71-248) Trimer with (GGGGG)2 linkers (SEQ ID NO: 781) between promomers | REGPELSPDDDPAGLLDLRQGMFAQL VAQNVLLIDGPLSWYSDPGLAGVSL TGGLSYKEDTKELVVAKAGVYYVFF QLELRRVVAGEGSGSVSLALHLQPL RSAAGAAALALTVDLPPASSEARNS AFGFQGRLLHLSAGQRLGVHLHTEA RARHAWQLTQGATVLGLFRVTPEIP AGLGGSGGGGSGGREGPELSPDDPA GLLDLRQGMFAQLVAQNVLLIDGPL SWYSDPGLAGVSLTGGLSYKEDTKE LVVAKAGVYYVFFQLELRRVVAGEG SGSVSLALHLQPLRSAAGAAALALT VDLPPASSEARNSAFGFQGRLLHLS AGQRLGVHLHTEARARHAWQLTQGA TVLGLFRVTPEIPAGLGGSGGGGSG GREGPELSPDDPAGLLDLRQGMFAQ LVAQNVLLIDGPLSWYSDPGLAGVS LTGGLSYKEDTKELVVAKAGVYYVF FQLELRRVVAGEGSGSVSLALHLQP LRSAAGAAALALTVDLPPASSEARN SAFGFQGRLLHLSAGQRLGVHLHTE ARARHAWQLTQGATVLGLFRVTPEI PAGL (SEQ ID NO: 110) |

Note:
Part names are comprised of the 4-1BBL domain, number of domains, and length of linker between domains.

TABLE 14

4-1BB fusion constructs

| Molecule Name | IgG Identifier | Valency (tumor:4-1BB) | Fusion Location | Linker to 4-1BB-engaging Part | 4-1BB Engager* |
|---|---|---|---|---|---|
| h1-2p2-LC-h41BBL(THD)3-2 | hIgG1 | 2:2 | LC-Cter | TS(G4S)3 (SEQ ID NO: 105) | h41BBL(THD)3-2 |
| h1-2p2-LC-h41BBL(THD)3-10 | hIgG1 | 2:2 | LC-Cter | TS(G4S)3 (SEQ ID NO: 105) | h41BBL(THD)3-10 |
| h1-2p2-LC-h41BBL(71-248)3-10 | hIgG1 | 2:2 | LC-Cter | TS(G4S)3 (SEQ ID NO: 105) | h41BBL(71-248)3-10 |
| h4-2p2-LC-h41BBL(THD)3-2 | hIgG4_S228P_R409K | 2:2 | LC-Cter | TS(G4S)3 (SEQ ID NO: 105) | h41BBL(THD)3-2 |
| h4-2p2-LC-h41BBL(THD)3-10 | hIgG4_S228P_R409K | 2:2 | LC-Cter | TS(G4S)3 (SEQ ID NO: 105) | h41BBL(THD)3-10 |

TABLE 14-continued 4-1BB fusion constructs

| Molecule Name | IgG Identifier | Valency (tumor:4-1BB) | Fusion Location | Linker to 4-1BB-engaging Part | 4-1BB Engager* |
|---|---|---|---|---|---|
| | | | | 105) | |
| h4-2p2-LC-h41BBL(71-248)3-10 | hIgG4_S228P_R409K | 2:2 | LC-Cter | TS(G4S)3 (SEQ ID NO: 105) | h41BBL(71-248)3-10 |
| h1s-2p2-LC-h41BBL(THD)3-2 | hIgG1_P329G_L234A_L235A | 2:2 | LC-Cter | TS(G4S)3 (SEQ ID NO: 105) | h41BBL(THD)3-2 |
| h1s-2p2-LC-h41BBL(THD)3-10 | hIgG1_P329G_L234A_L235A | 2:2 | LC-Cter | TS(G4S)3 (SEQ ID NO: 105) | h41BBL(THD)3-10 |
| h1s-2p2-LC-h41BBL(71-248)3-10 | hIgG1_P329G_L234A_L235A | 2:2 | LC-Cter | TS(G4S)3 (SEQ ID NO: 105) | h41BBL(71-248)3-10 |
| h4-2p2-HC-SCFV9365-02 | hIgG4_S228P_R409K | 2:2 | HC-Cter | (G4S)3 (SEQ ID NO: 91) | SCFV9365-02 |
| m1-2p2-HC-SCFV9365-02 | mIgG1 | 2:2 | HC-Cter | (G4S)3 (SEQ ID NO: 91) | SCFV9365-02 |
| h4-2p2-HC-SCFV9036-02 | hIgG4_S228P_R409K | 2:2 | HC-Cter | (G4S)3 (SEQ ID NO: 91) | SCFV9036-02 |
| m1-2p2-HC-SCFV9036-02 | mIgG1 | 2:2 | HC-Cter | (G4S)3 (SEQ ID NO: 91) | SCFV9036-02 |
| h4-2p2-HC-SCFV9809-01 | hIgG4_S228P_R409K | 2:2 | HC-Cter | (G4S)3 (SEQ ID NO: 91) | SCFV9809-01 |
| m1-2p2-HC-SCFV9809-01 | mIgG1 | 2:2 | HC-Cter | (G4S)3 (SEQ ID NO: 91) | SCFV9809-01 |
| h4-2p2-HC-SCFV9810-01 | hIgG4_S228P_R409K | 2:2 | HC-Cter | (G4S)3 (SEQ ID NO: 91) | SCFV9810-01 |
| m1-2p2-HC-SCFV9810-01 | mIgG1 | 2:2 | HC-Cter | (G4S)3 (SEQ ID NO: 91) | SCFV9810-01 |
| h1-2p1-HC-h41BBL(THD)3-2 | hIgG1_kih | 2:1 | HC-Cter | (G4S)3 (SEQ ID NO: 91) | h41BBL(THD)3-2 |
| h1-2p1-HC-h41BBL(THD)3-10 | hIgG1_kih | 2:1 | HC-Cter | (G4S)3 (SEQ ID NO: 91) | h41BBL(THD)3-10 |
| h1-2p1-HC-h41BBL(71-248)3-10 | hIgG1_kih | 2:1 | HC-Cter | (G4S)3 (SEQ ID NO: 91) | h41BBL(71-248)3-10 |
| h4-2p1-HC-h41BBL(THD)3-2 | hIgG4_S228P_R409K_kih | 2:1 | HC-Cter | (G4S)3 (SEQ ID NO: 91) | h41BBL(THD)3-2 |
| h4-2p1-HC-h41BBL(THD)3-10 | hIgG4_S228P_R409K_kih | 2:1 | HC-Cter | (G4S)3 (SEQ ID NO: 91) | h41BBL(THD)3-10 |
| h4-2p1-HC-h41BBL(71-248)3-10 | hIgG4_S228P_R409K_kih | 2:1 | HC-Cter | (G4S)3 (SEQ ID NO: 91) | h41BBL(71-248)3-10 |
| h1-Xmab-2p1-HC-h41BBL(THD)3-2 | hIgG1-Xmab | 2:1 | HC-Cter | (G4S)3 (SEQ ID NO: 91) | h41BBL(THD)3-2 |
| h1-Xmab-2p1-HC-h41BBL(THD)3-10 | hIgG1-Xmab | 2:1 | HC-Cter | (G4S)3 (SEQ ID NO: 91) | h41BBL(THD)3-10 |
| h1-Xmab-2p1-HC-h41BBL(71-248)3-10 | hIgG1-Xmab | 2:1 | HC-Cter | (G4S)3 (SEQ ID NO: 91) | h41BBL(71-248)3-10 |

*Terminology is as follows, using "h42BBL(THD)3-2" as an illustrative example:
1. h stands for "human" and m stands for "mouse" (or m = mouse)
2. 41BBL stand for 4-1BB ligand (native sequence)
3. THD stand for "TNF homology domain" portion of 41BBL. In instances where a number range in parentheses after 41BBL, e.g., h41BBL(71-248)3-10, refers to that residue numbers 71-248 of the 4-1BB ligand were used.
4. "3" refers to three copies connected by polypeptide linker
5. "-2" typically refers to the length of the linker used to connect the ligands together. In one example, h41BBL(THD)3-2 represent h41BBL(THD) + GG + h41BBL(THD) + GG + h41BBL(THD); In another example, h41BBL(71-248)3-10 represents h41BBL(71-248) + (GGSGG)2 (SEQ ID NO: 781) + h41BBL (71-248) + (GGSGG)2 (SEQ ID NO: 781) + h41BBL(71-248)

In some embodiments, the tumor-targeting antibody is conjugated to one or more TLR agonists. In one embodiment, the tumor-targeting antibody conjugated to a TLR agonist is a bispecific or multispecific antibody. In some embodiments, the tumor-targeting antibody is a bispecific or multispecific antibody comprising an antigen binding domain of an antibody described herein that further comprises a TLR agonist.

In some embodiments, a bispecific or multispecific antibody comprising an antigen binding domain of an antibody described herein further comprises a binding domain that binds to a checkpoint antigen, PD1, PDL1, CTLA-4, ICOS, PDL2, IDO1, IDO2, B7-H3, B7-H4, BTLA, HVEM, TIM3, GAL9, GITR, HAVCR2, LAG3, KIR, LAIR1, LIGHT, MARCO, OX-40, SLAM, 2B4, CD2, CD27, CD28, CD30, CD40, CD70, CD80, CD86, CD137, CD160, CD39, VISTA, TIGIT, CGEN-15049, 2B4, CHK 1, CHK2, A2aR, or a B-7 family ligand or its receptor.

In some embodiments, a bispecific or multispecific antibody comprising an antigen binding domain of an antibody described herein further comprises a binding domain that targets a tumor-associated antigen. Illustrative tumor-associate antigens include, but are not limited to, EpCAM, HER2/neu, HER3/neu, G250, CEA, MAGE, proteoglycans, VEGF, VEGFR, EGFR, ErbB2, ErbB3, MET, IGF-1R, PSA, PSMA, EphA2, EphA3, EphA4, folate binding protein αVβ3-integrin, integrin α5β1 HLA, HLA-DR, ASC, CD1, CD2, CD4, CD6, CD7, CD8, CD1 1, CD1 3, CD14, CD19, CD20, CD21, CD22, CD23, CD24, CD30, CD33, CD37, CD40, CD41, CD47, CD52, c-erb-2, CALLA, MHCII, CD44v3, CD44v6, p97, ganglioside GM1, GM2, GM3, GD1 a, GD1 b, GD2, GD3, GT1 b, GT3, GQ1, NY-ESO-1, NFX2, SSX2, SSX4 Trp2, gp100, tyrosinase, Muc-1, telomerase, survivin, SLAMF7 EphG250, p53, CA125 MUC, Wue antigen, Lewis Y antigen, HSP-27, HSP-70, HSP-72, HSP-90, Pgp, PMEL17, MCSP, and cell surface targets GC182, GT468 or GT512.

In some embodiments, a binding domain of an antibody described herein may be incorporated into a chimeric antigen receptor (CAR-T) construct, an engineered TCR-T cell construct, or a combined CAR-T/TCR-T construct comprising the complete TCR complex (see Hardy et al. "Implications of T cell receptor biology on the development of new T cell therapies for cancer, Immunotherapy Vol. 12, No. 1. Published Online: 6 Jan. 2020 https://doi.org/10.2217/imt-2019-0046). Such constructs can be used to generate a modified immune cell such as a T-cell, NK-cell, or monocyte/macrophage comprising the binding domain of an antibody described herein. For example, in some embodiments, a first-generation CAR joins a single-chain variable region from the antibody to a CD3zeta (ζ) intracellular signaling domain of a CD3 T-cell receptor through hinge and transmembrane domains. In some embodiments, the CAR may contain co-stimulating domains, e.g., a second or third generation CAR may include an additional one or two-co-stimulating domains, such as 4-1BB, CD28, or OX-40). In additional embodiments, a CAR-containing cell, e.g., a CAR-T cell, may additionally be engineered to with an inducible expression component such as a cytokine, e.g., IL-12 or IL-15 to increase activation of CAR-T cells and also activate innate immune cells.

In one embodiment of any of the above bispecific or multispecific antibody constructs, the tumor-targeting binding domain comprises all six CDRs (HCDR1, HCDR2, HCDR3, LCDR1, LCDR2, and LCDR3) sequences from the individual antibodies disclosed in Tables 6 and 7.

In one embodiment of any of the above bispecific or multispecific antibody constructs, the tumor-targeting binding domain comprises the VH and VL sequences from the individual antibodies disclosed in Table 8.

In one embodiment of any of the above bispecific or multispecific antibody constructs, the tumor-targeting binding domain comprises all six CDRs (HCDR1, HCDR2, HCDR3, LCDR1, LCDR2, and LCDR3) sequences from any one of antibodies AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702. In some embodiments, in any of the above bispecific or multispecific antibody constructs, the tumor-targeting binding domain comprises all six CDRs (HCDR1, HCDR2, HCDR3, LCDR1, LCDR2, and LCDR3) sequences from AB-010361 or AB-010699.

In one embodiment of any of the above bispecific or multispecific antibody constructs, the tumor-targeting binding domain comprises the VH and VL sequences any one of AB-008873; AB-009805; AB-009806; AB-009807; AB-009808; AB-009812; AB-009813; AB-009814; AB-009815; AB-009816; and AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702. In one embodiment of any of the above bispecific or multispecific antibody constructs, the tumor-targeting binding domain comprises the VH and VL sequences of AB-010361 or AB-010699.

Generation of Antibodies

EphA2 antibodies as disclosed herein are commonly produced using vectors and recombinant methodology well known in the art (see, e.g., Sambrook & Russell, Molecular Cloning: A Laboratory Manual, Cold Spring Harbor Laboratory Press; Ausubel, Current Protocols in Molecular Biology). Reagents, cloning vectors, and kits for genetic manipulation are available from commercial vendors. Accordingly, in a further aspect of the invention, provided herein are isolated nucleic acids encoding a $V_H$ and/or $V_L$ region, or fragment thereof, of any of the tumor-targeting antibodies as described herein; vectors comprising such nucleic acids and host cells into which the nucleic acids are introduced that are used to replicate the antibody-encoding nucleic acids and/or to express the antibodies. Such nucleic acids may encode an amino acid sequence containing the VI, and/or an amino acid sequence containing the $V_H$ of the tumor-targeting antibody (e.g., the light and/or heavy chains of the antibody). In some embodiments, the host cell contains (1) a vector containing a polynucleotide that encodes the $V_L$ amino acid sequence and a polynucleotide that encodes the $V_H$ amino acid sequence, or (2) a first vector containing a polynucleotide that encodes the $V_L$ amino acid sequence and a second vector containing a polynucleotide that encodes the $V_H$ amino acid sequence.

In a further aspect, the invention provides a method of making an EphA2 antibody as described herein. In some embodiments, the method includes culturing a host cell as described in the preceding paragraph under conditions suitable for expression of the antibody. In some embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mpl8, mpl9, pBR322, pMB9, ColE1 plasmids, pCR1, RP4, phage DNAs, and shuttle vectors. These and many other cloning vectors are available from commercial vendors.

Expression vectors generally are replicable polynucleotide constructs that contain a nucleic acid of the present disclosure. The expression vector can be replicable in the host cells either as episomes or as an integral part of the chromosomal DNA. Suitable expression vectors include but are not limited to plasmids and viral vectors, including adenoviruses, adeno-associated viruses, retroviruses, and any other vector.

Suitable host cells for expressing an EphA2 antibody as described herein include both prokaryotic or eukaryotic cells. For example, an EphA2 antibody may be produced in bacteria, in particular when glycosylation and Fc effector function are not needed. After expression, the antibody may be isolated from the bacterial cell paste in a soluble fraction and can be further purified. Alternatively, the host cell may be a eukaryotic host cell, including eukaryotic microorganisms, such as filamentous fungi or yeast, including fungi and yeast strains whose glycosylation pathways have been "humanized," resulting in the production of an antibody with a partially or fully human glycosylation pattern, vertebrate, invertebrate, and plant cells. Examples of invertebrate cells include insect cells. Numerous baculoviral strains have been identified which may be used in conjunction with insect cells. Plant cell cultures can also be utilized as host cells.

In some embodiments, vertebrate host cells are used for producing an EphA2 antibody of the present disclosure. For example, mammalian cell lines such as a monkey kidney CV1 line transformed by SV40 (COS-7); human embryonic kidney line (293 or 293 cells as described, e.g., in Graham et al., *J. Gen Virol.* 36:59, 1977; baby hamster kidney cells (BHK); mouse sertoli cells (TM4 cells as described, e.g., in Mather, *Biol. Reprod.* 23:243-251, 1980 monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68, 1982; MRC 5 cells; and FS4 cells may be used to express an tumor-targeting antibodies. Other useful mammalian host cell lines include Chinese hamster ovary (CHO) cells, including DHFR-CHO cells (Urlaub et al., *Proc. Natl. Acad. Sci. USA* 77:4216, 1980); and myeloma cell lines such as Y0, NS0 and Sp2/0. Host cells of the present disclosure also include, without limitation, isolated cells, in vitro cultured cells, and ex vivo cultured cells. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268, 2003.

In some embodiments, an EphA2 antibody of the present invention is produced by a CHO cell line, e.g., the CHO-K1 cell line. One or more expression plasmids can be introduced that encode heavy and light chain sequences. For example, in one embodiment, an expression plasmid encoding a heavy chain disclosed herein, e.g., SEQ ID NO: 67, and an expression plasmid encoding a light chain disclosed herein, e.g., SEQ ID NO: 68 are transfected into host cells as linearized plasmids at a ratio of 1:1 in the CHO-K1 host cell line using reagents such as Freestyle Max reagent. Fluorescence-activated cell sorting (FACS) coupled with single cell imaging can be used as a cloning method to obtain a production cell line.

A host cell transfected with an expression vector encoding an EphA2 antibody of the present disclosure, or fragment thereof, can be cultured under appropriate conditions to allow expression of the polypeptide to occur. The polypeptides may be secreted and isolated from a mixture of cells and medium containing the polypeptides. Alternatively, the polypeptide may be retained in the cytoplasm or in a membrane fraction and the cells harvested, lysed, and the polypeptide isolated using a desired method.

In some embodiments, an EphA2 antibody of the present disclosure can be produced by in vitro synthesis (see, e.g., Sutro Biopharma biochemical protein synthesis platform).

In some embodiments, provided herein is a method of generating variants of an EphA2 antibody as disclosed herein. Thus, for example, a construct encoding a variant of a $V_H$ CDR3 as described herein can be modified and the $V_H$ region encoded by the modified construct can be tested for binding activity to CT26 cells and/or in vivo tumor-targeting activity in the context of a $V_H$ region as described herein, that is paired with a $V_L$ region or variant region as described herein. Similarly, a construct encoding a variant of a $V_L$ CDR3 as described herein can be modified and the $V_L$ region encoded by the modified construct can be tested for binding to CT26 cells, or other tumor cells, and/or in vivo tumor-targeting activity efficacy. Such an analysis can also be performed with other CDRs or framework regions and an antibody having the desired activity can then be selected.

Tumor-Targeting Antibody Conjugates/Co-Stimulatory Agents

In a further aspect, an EphA2 antibody of the present invention may be conjugated or linked to therapeutic, imaging/detectable moieties, or enzymes. For example, the tumor-targeting antibody may be conjugated to a detectable marker, a cytotoxic agent, an immunomodulating agent, an imaging agent, a therapeutic agent, an oligonucleotide, or an enzyme. Methods for conjugating or linking antibodies to a desired molecule are well known in the art. The moiety may be linked to the antibody covalently or by non-covalent linkages.

In some embodiments, the antibody is conjugated, either directly or via a cleavable or non-cleavable linker, to a cytotoxic moiety or other moiety that inhibits cell proliferation. In some embodiments, the antibody is conjugated to a cytotoxic agent including, but not limited to, e.g., ricin A chain, doxorubicin, daunorubicin, a maytansinoid, taxol, ethidium bromide, mitomycin, etoposide, tenoposide, vincristine, vinblastine, colchicine, dihydroxy anthracin dione, methotrexate, actinomycin, a diphtheria toxin, exotoxin A from *Pseudomonas, Pseudomonas* exotoxin40, abrin, abrin A chain, modeccin A chain, alpha sarcin, gelonin, mitogellin, restrictocin, cobran venom factor, a ribonuclease, engineered Shiga toxin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, or a cisplatin. In some embodiments, the antibody may be linked to an agent such as an enzyme inhibitor, a proliferation inhibitor, a lytic agent, a DNA or RNA synthesis inhibitors, a membrane permeability modifier, a DNA metabolite, a dichloroethylsulfide derivative, a protein production inhibitor, a ribosome inhibitor, or an inducer of apoptosis. In some embodiments, the antibody is conjugated to a drug such as a topoisomerase inhibitor, e.g., a topoisomerase I inhibitor.

In some embodiments, an EphA2 antibody as described herein is joined to a molecule that facilitates transport of the antibody across a biological membrane, e.g., by enhancing penetration of the membrane, facilitating protein translocation across membranes. Thus, for example, the antibody may be linked to a cell penetration agent, such as a cell-penetrating peptide. Examples of cell penetrating peptides include TAT, penetrating, polyarginine molecules, Kunitz domain-derived peptides, e.g., Angiopep-2, SynB, buforin, transportan, amphipathic peptides and others. In some embodiments, the antibody may be conjugated with a cationic molecule such as a polyamine. In some embodiments, the antibody may be conjugated to an agent that facilitates transport across the blood brain barrier, e.g., transcytosis. Thus, for example, the antibody may be conjugated to an agent that binds to endothelial cell receptors that are internalized, e.g., transferrin receptor, insulin receptor, insulin-like growth factor receptor, or a low-density lipoprotein receptor, and the like. In some embodiments, the antibody may be conjugated to a toxin facilitating entry of the antibody into the cytoplasm, e.g., Shiga toxin. In some embodiments, an EphA2 antibody as described herein can be conjugated to an engineered toxin body (ETBs) to facilitate internalization of the antibody into a cell.

In some embodiments, an EphA2 antibody described herein is conjugated or administered with a polypeptide immunomodulating agent, e.g., an adjuvant. Examples of immunomodulating agents include, but are not limited to, cytokines (e.g., transforming growth factor-β (TGFβ)), growth factors, lymphotoxins, tumor necrosis factor (TNF), hematopoietic factors, interleukins (e.g., interleukin-1 (IL-1), IL-2, IL-3, IL-6, IL-10, IL-12, IL-15, an IL-15/IL-15Rα, e.g., sushi domain, complex, IL-18, and IL-21), colony stimulating factors (e.g., granulocyte-colony stimulating factor (G-CSF) and granulocyte macrophage-colony stimulating factor (GM-CSF), interferons (e.g., interferon-α, -β or -γ, erythropoietin and thrombopoietin, or a combination thereof. In some embodiments, the antibody is linked or administered with a compound that stimulates the innate immune system, such as an adjuvant, a Toll-like receptor (TLR) agonist, a C-type lectin receptor (CLR) agonist, a retinoic acid-inducible gene I-like receptor (RLR) agonist, a saponin, a polysaccharide such as chitin, chitosan, β-glucan, an ISCOM, QS-21, a stimulator of interferon genes (STING) agonist, or another immunopotentiating agent.

In some embodiments, an EphA2 antibody described herein is conjugated to or administered with an IL-15 receptor agonist, such as an IL-15 fusion construct, an IL-15:IL-15Rα fusion construct or a single-chain IL-15:IL-15Rα (sushi) fusion construct. In one embodiment, the tumor-targeting antibody conjugated to an IL-15 receptor agonist is a bispecific or multispecific antibody. In some embodiments, the antibody is a bispecific or multispecific antibody comprising an antigen binding domain described herein that further comprises an IL-15 receptor agonist.

In one embodiment, an EphA2 antibody described herein is administered with a single-chain IL-15:IL-15Rα (sushi) fusion construct. In some embodiments, an EphA2 antibody is administered with a polymer-conjugated IL-15 construct, such as NKTR-255.

The IL-15:IL-15Rα single chain constructs can be administered to a subject comprising a therapeutically effective dose, for example in the range of less than 0.01 mg/kg body weight to about 25 mg/kg body weight, or 0.1-10 mg/kg, or in the range 1 mg-2 g per patient, or approximately 50 mg-1000 mg/patient.

In one embodiment, the single-chain IL-15 fusion construct comprises IL-15 joined to IL-15Rα (sushi) with a polypeptide linker. In one embodiment, the single-chain IL-15 fusion construct is joined via a polypeptide linker to another protein, such as an Fc for long half-life. See, for example, FIG. 9B in WO2018071919A1 (corresponding to U.S. patent Ser. No. 10/550,185). In one embodiment, the IL-15 is joined or fused to the N-terminus of the heavy chain of an Fc, and IL-15Rx (sushi) is joined or fused to the other Fc heavy chain N-terminus, using a heavy chain heterodimerization technology to form the desired hybrid Fc. See, for example, FIG. 9A in WO2018071919A1.

Figure 36:
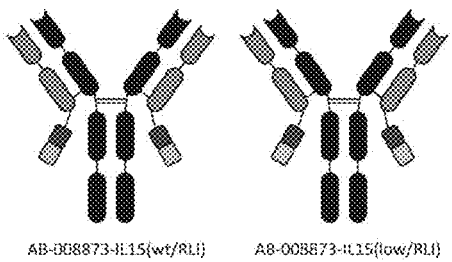
FIG. 36 is a schematic illustration of AB-008873-IL15 fusions.

In one embodiment, the IL-15:IL-15Rα (sushi) single chain constructs are fused to the C-terminus of an antibody light chain, or the C-terminus of an antibody heavy chain, in both cases producing a molecule with two tumor-targeting binding sites (the Fab arms), and two IL15:IL15Rα units. Illustrative configurations of the fusion construct is shown in FIG. 36. In another embodiment, one copy of an IL15:IL15Rα fusion construct is fused to an EphA2 antibody, thereby producing an antibody molecule comprising two tumor-targeting binding sites (the Fab arms) and only one IL15:IL15Rα unit, for example using a knob-in-holes approach to heavy chain heterodimerization, or other heterodimerization technology.

In some embodiments, the IL-15:IL-15Rα (sushi) fusion constructs or the antibodies comprising the fusion constructs comprise a low affinity IL-15 variant having improved pharmacokinetics (PK). In some embodiments, the IL-15:IL-15Rα (sushi) fusion constructs comprise a high affinity IL-15 variant having increased agonist activity. In some embodiments, the high affinity IL-15 variant has an N72D mutation. In some embodiments, the high affinity variant is fused to a dimeric IL-15Rα sushi domain-IgG1 Fc fusion protein. In some embodiments, the IL-15:IL-15Rα (sushi) fusion construct is ALT-803. See Liu B, et al. (November 2016). "A Novel Fusion of ALT-803 (Interleukin (IL)-15 Superagonist) with an Antibody Demonstrates Antigen-specific Antitumor Responses". The Journal of Biological Chemistry. 291 (46): 23869-23881. doi: 10.1074/jbc.M116.733600. Sequences of the IL-15:IL-15Rα fusion constructs and linkers are provided in the Examples.

In some embodiments, antibodies comprising the IL15:IL15Rα fusion construct comprise one or more mutations in the Fc region described herein, for example E333A, K326W/E333S, S239D/I332E/G236A, S239D/A330L/I332E, G236A/S239D/A330L/I332E, F243L, G236A, and S298A/E333A/K334A. In some embodiments, antibodies comprising the IL15:IL15Rα fusion comprise one or more mutations in the Fc region that increase binding of the antibody to tumor cells, for example the mutations P329G, L234A, L235A, or a combination thereof.

In some embodiments, antibodies comprising the IL15:IL15Rα fusion construct comprises one or more sequences shown in Table 15. In some embodiments, the fusion protein comprises or consists of SEQ ID NO: 89, SEQ ID NO: 90, SEQ ID NO: 91, and SEQ ID NO: 92. In some embodiments, the fusion protein comprises or consists of SEQ ID NO: 89, SEQ ID NO: 90, SEQ ID NO: 91, and SEQ ID NO: 93.

TABLE 15

Sequences in antibodies comprising the IL15:IL15Rα fusion construct

| Description | Sequence |
|---|---|
| AB-008873 mIgG2a Heavy Chain | QVQLQQWGAGLLKPSETLSL TCAVYGGSFSDYYWSWIRQP PGKGLEWIGEVNHRGSINYN NYNPSLKSRVTISVDPSKNQ FSLKLTSVTAADTAVYYCAK PLRPHCTNGVCYSGDAFDIW GQGTMVTVASAKTTAPSVYP LAPVCGDTTGSSVTLGCLVK GYFPEPVTLTWNSGSLSSGV HTFPAVLQSDLYTLSSSVTV TSSTWPSOSITCNVAHPASS TKVDKKIEPRGPTIKPCPPC KCPAPNLLGGPSVFIFPPKI KDVLMISLSPIVTCVVVDVS EDDPDVQISWFVNNVEVHTA QTQTHREDYNSTLRVVSALP IQHQDWMSGKEFKCKVNNKD LPAPIERTISKPKGSVRAPQ VYVLPPPEEEMTKKQVTLTC MVTDFMPEDIYVEWTNNGKT ELNYKNTEPVLDSDGSYFMY SKLRVEKKNWVERNSYSCSV VHEGLHNHHTTKSFSRTPG (SEQ ID NO: 89) |
| AB-008873 mIgG2a Light Chain | SYVLTQPPSVSVAPGQTARI TCGGNNIGSKNVHWYQQKPG QAPVLVVYDDSDRPSGIPEQ FSGSNSGNTATLTISRVEAG DEADYYCQVWDSSSDHLVFG GGTKLTVLGQPKSSPSVTLF PPSSEELETNKATLVCTITD FYPGVVTVDWKVDGTPVTQG METTQPSKQSNNKYMASSYL TLTARAWERHSSYSCQVTHE GHTVEKSLSRADCS (SEQ ID NO: 90) |
| Linker (G4S)3 | GGGGSGGGGSGGGGS (SEQ ID NO: 91) |
| Linker TS(G4S)3 | TSGGGGSGGGGSGGGGS (SEQ ID NO: 105) |
| IL15 (wt/RLI) | ITCPPPMSVEHADIWVKSYS LYSRERYICNSGFKRKAGTS SLTECVLNKATNVAHWTTPS LKCIRDPALVHQRPAPPGGG GSGGGGSGGGSGGGGSLQNW VNVISDLKKIEDLIQSMHID ATLYTESDVHPSCKVTAMKC FLLELQVISLESGDASIHDT VENLIILANNSLSSNGNVTE SGCKECEELEEKNIKEFLOS FVHIVOMFINTS (SEQ ID NO: 92) |
| IL15 (low/RLI) | ITCPPPMSVEHADIWVKSYS LYSRERYICNSGFKRKAGTS SLTECVLNKATNVAHWTTPS LKCIRDPALVHQRPAPPGGG GSGGGGSGGGSGGGGSLQNW VNVISDLKKIEDLIQSMHID ATLYTESNVHPSCKVTAMKC FLLELQVISLESGDASIHDT VQDLIILANNSLSSNGNVTE SGCKECEELEEKNIKEFLQS FVHIVOMFINTS (SEQ ID NO: 93) |

In some embodiments, an EphA2 antibody described herein is conjugated to or administered with an IL-2 receptor agonist. In one embodiment, the tumor-targeting antibody conjugated to an IL-2 receptor agonist is a bispecific or multispecific antibody. In some embodiments, the antibody is a bispecific or multispecific antibody comprising an antigen binding domain of an antibody described herein that further comprises an IL-2 receptor agonist. In some embodiments, the IL-2 receptor agonist is pegylated IL-2.

In some embodiments, an EphA2 antibody described herein is conjugated to or administered with a construct that can act as a trap for transforming growth factor-β (TGFβ). In one embodiment, the TGFβ trap comprises the extracellular domain (ECD) of TGFβ. In one embodiment, the TGFβ trap comprises the extracellular domain (ECD) of TGFβRII. In one embodiment, the TGFβ trap is in the form of a bispecific antibody (see US2018/0118832A1, FIG. 1). The TGFβRII ECD can preferably trap TGFβ1, and its low affinity to TGFβ2 may mitigate potential cardiac toxicity.

Thus, in another aspect, an EphA2 antibody described herein comprises an extracellular domain (ECD) of the TGFβ Receptor fused to the C-terminus of the heavy chain or to the C-terminus of the light chain. In some embodiments, the TGFβ trap is a single trap construct. In some embodiments, the single TGFβ trap is a bispecific tumor-targeting TGFβ trap comprising a TGFβ RII ECD fused to any one of the antibodies disclosed herein via a flexible linker to the C-terminus of the heavy chain or to the C-terminus of the light chain.

In some embodiments, the TGFβ trap is a tandem trap construct. In some embodiments, the tandem TGFβ trap comprises an IgG fused to two TGFβRII ECDs. In some embodiments, the tandem TGFβ trap comprises two TGFβ2RII ECDs. In some embodiments, the two TGFβ2RII ECDs are fused in series and are linked by a short linker (for example L10 or L25). In some embodiments, the two TGFβ2RII ECDs are fused directly in series without a linker (L0). In some embodiments, the tandem TGFβRII ECDs are fused to the C-terminus of the heavy chain (HC-Cter), and the heavy chains were designed as an asymmetric pair such that the tandem-Trap is on only one heavy chain. In some embodiments, the asymmetric pair of heavy chains comprise knob-in-hole mutation that promote pairing of the heavy chains. For example, in some embodiments, one heavy chain comprises the amino acid substitutions T366S+L368A+Y407V (and optionally Y349C), and the other heavy chain comprises the amino acid substitution T336W (and optionally S354C). In some embodiments, the asymmetric single heavy chain C-ter fusion improves steric access of the Fc region to Fc gamma receptors and thereby improve function.

In some embodiments, the tandem TGFβ trap is fused to the C-terminus of the light chain (LC-Cter), such that both light chains comprise two TGFβRII ECDs. In these embodiments, the net molecule exhibits twice the TGFβ trapping capacity per molecule, and therefore may exhibit improved function.

In some embodiments, the bispecific TGFβ trap construct comprises human variable regions. In some embodiments, the bispecific TGFβ trap construct comprises a IgG1 or IgG2 constant region. In some embodiments, the bispecific TGFβ trap construct comprises a human IgG1 constant region. In some embodiments, the bispecific TGFβ trap construct comprises a mouse IgG2a constant region. In some embodiments, the variable regions of the TGFβ trap construct are fused in frame to the IgG constant regions.

Binding of the TGFβ trap construct can be determined using an ELISA assay, as described in the Examples. The ability of TGFβ trap constructs to bind to target tumor cells can be determined, for example, using flow-cytometry, as described in the Examples. The ability of TGFβ trap constructs to engage and stimulate Fc-gamma Receptor in the presence of target tumor cells can be determined using a reporter bioassay, as described in the Examples. The ability of TGFβ trap constructs to inhibit tumor growth can be determined, for example, in a syngeneic mouse model, as described in the Examples.

In some embodiments, the antibody may be linked to a radionuclide, an iron-related compound, a dye, a fluorescent agent, or an imaging agent. In some embodiments, an antibody may be linked to agents, such as, but not limited to, metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores.

In one embodiment of any of the above constructs, the EphA2 antibody is any one of AB-008873; AB-009805; AB-009806; AB-009807; AB-009808; AB-009812; AB-009813; AB-009814; AB-009815; AB-009816; AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010361, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010699, AB-010700, AB-010701, or AB-010702. In one embodiment of any of the above constructs, the tumor-targeting binding domain comprises the VH and VL sequences of AB-010361 or AB-010699.

Methods of Inducing an Immune Response

In a further aspect, provided herein are methods of inducing an immune response by administering an EphA2 antibody as described herein to a subject that has a tumor. In some embodiments, the EphA2 antibody is an antibody set forth in Tables 6-8, or a variant thereof as described above. In some embodiments, the antibody or variant thereof comprises a modified Fc region comprising mutations described herein. For example, in some embodiments, the antibody comprises an Fc mutation that increases effect function selected from E333A, K326W/E333S, S239D/I332E/G236A, S239D/A330L/I332E, G236A/S239D/A330L/I332E, F243L, G236A, S298A/E333A/K334A, and P329G/L234A/L235A, or a combination thereof. In some embodiments, the antibody comprises a modified Fc region that is a-fucosylated. In some embodiments, the antibody is conjugated to or administered with an IL-15 receptor agonist, a TGFβ trap, a TLR agonist, or an agonist anti-4-1BB antibody. In some embodiments, the antibody is a bispecific or multispecific antibody described herein.

An immune response induced by administration of an antibody as described herein can be either an innate or adaptive immune response. In some embodiments, the antibody activates an immune response directly, e.g., via binding of the antibody to a target tumor cell and engagement with an Fc receptor on an effector cell such that the effector cell is activated. In some embodiments, the antibody indirectly activates an immune response by inducing immune responses that are initiated by antibody binding to the target cell and an effector cell with subsequent induction of downstream immune responses. In some embodiments, the antibody activates monocytes, myeloid cells, and/or NK cells, e.g., macrophages, neutrophils, dendritic cells, mast cells, basophils, eosinophil, and/or NK cells. In some embodiments, the antibody activates T lymphocytes and/or B cells.

Treatment of Cancer

In a further aspect, an EphA2 antibody as provided herein, or a variant thereof as described herein, can be used and a therapeutic agent to treat cancer. In some embodiments, the antibody or variant thereof comprises a modified Fc region comprising mutations described herein. For example, in some embodiments, the antibody comprises an Fc mutation that increases effector function selected from E333A, K326W/E333S, S239D/I332E/G236A, S239D/A330L/I332E, G236A/S239D/A330L/I332E, F243L, G236A, S298A/E333A/K334A, and P329G/L234A/L235A, or a combination thereof. In some embodiments, the antibody comprises a modified Fc region that is afucosylated. In some embodiments, the antibody is conjugated to or administered with an IL-15 receptor agonist, a TGFβ trap, a TLR agonist, or an agonist anti-4-1BB antibody. In some embodiments, the antibody is a bispecific or multispecific antibody described herein.

In some aspects, the disclosure additionally provides methods of identifying subjects who are candidates for treatment with an EphA2 antibody having tumor-targeting effects. Thus, in one embodiment, the invention provides a method of identifying a patient who can benefit from treatment with an EphA2 antibody of the present disclosure. In one embodiment, the patient has tumor that expresses EphA2. In one embodiment, the patient has tumor that overexpresses EphA2. In some embodiments, the tumor sample is from a primary tumor. In alternative embodiments, the tumor sample is a metastatic lesion. Binding of antibody to tumor cells through a binding interaction with the EphA2 can be measured using any assay, such as immunohistochemistry or flow cytometry. In some embodiments, binding of antibody to at least 0.2%, 0.5%, or 1%, or at least 5% or 10%, or at least 20%, 30%, or 50%, of the tumor cells in a sample may be used as a selection criterion for determining a patient to be treated with an EphA2 antibody as described herein. In other embodiments, analysis of components of the blood, e.g., circulating exosomes and/or extracellular RNA-protein complex and/or extracellular protein, is used to identify a patient whose tumor cells are overexpressing EphA2.

An EphA2 antibody disclosed herein can be used to treat a number of different cancers. In some embodiments, a cancer patient who can benefit from the treatment of the EphA2 antibody has a cancer that expresses EphA2In some embodiments, a cancer patient who can benefit from the treatment of the EphA2 antibody has a cancer overexpressing EphA2. In some embodiments, the cancer is a carcinoma or a sarcoma. In some embodiments, the cancer is a hematological cancer. In some embodiments, the cancer is breast cancer, prostate cancer, testicular cancer, renal cell cancer, bladder cancer, ovarian cancer, cervical cancer, endometrial cancer, lung cancer, colorectal cancer, anal cancer, pancreatic cancer, gastric cancer, esophageal cancer, hepatocellular cancer, head and neck cancer, a brain cancer, e.g., glioblastoma, melanoma, or a bone or soft tissue sarcoma. In one embodiment, the cancer is acral melanoma. In some embodiments, the cancer is acute lymphoblastic leukemia, acute myeloid leukemia, adrenocortical carcinoma, astrocytoma, basal-cell carcinoma, bile duct cancer, bone tumor, brainstem glioma, cerebellar astrocytoma, cerebral astrocytoma, ependymoma, medulloblastoma, supratentorial primitive neuroectodermal tumors, visual pathway and hypothalamic glioma, bronchial adenomas, Burkitt's lymphoma, central nervous system lymphoma, cerebellar astrocytoma, chondrosarcoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, epitheliod hemangioendothelioma (EHE), esophageal cancer, Ewing's sarcoma, extracranial germ cell tumor, extragonadal germ cell tumor, extrahepatic bile duct cancer, a cancer of the eye, intraocular melanoma, retinoblastoma, gallbladder cancer, gastrointestinal carcinoid tumor, gastrointestinal stromal tumor (GIST), germ cell tumor, gestational trophoblastic tumor, gastric carcinoma, hairy cell leukemia, hepatocellular carcinoma, Hodgkin lymphoma, hypopharyngeal cancer, hypothalamic and visual pathway glioma, childhood, intraocular melanoma, islet cell carcinoma, Kaposi sarcoma, kidney cancer, laryngeal cancer, leukaemias, lip and oral cavity cancer, liposarcoma, liver cancer, non-small cell lung cancer, small-cell lung cancer, lymphomas, macroglobulinemia, male breast cancer, malignant fibrous histiocytoma of bone, medulloblastoma, Merkel cell cancer, mesothelioma, metastatic squamous neck cancer, mouth cancer, multiple endocrine neoplasia syndrome, multiple myeloma, mycosis fungoides, myelodysplastic syndromes, myelogenous leukemia, myeloid leukemia, adult acute, myeloproliferative disorders, chronic, myxoma, nasal cavity and paranasal sinus cancer, nasopharyngeal carcinoma, neuroblastoma, non-Hodgkin lymphoma, oligodendroglioma, oral cancer, oropharyngeal cancer, osteosarcoma, ovarian epithelial cancer, ovarian germ cell tumor, ovarian low malignant potential tumor, paranasal sinus and nasal cavity cancer, parathyroid cancer, penile cancer, pharyngeal cancer, pheochromocytoma, pineal astrocytoma, pineal germinoma, pineoblastoma, supratentorial primitive neuroectodermal tumors, pituitary adenoma. plasma cell neoplasia, pleuropulmonary blastoma, primary central nervous system lymphoma, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sézary syndrome, non-melanoma skin cancer, melanoma, small intestine cancer, squamous cell carcinoma, squamous neck cancer, stomach cancer, cutaneous T-Cell lymphoma, throat cancer, thymoma, thyroid cancer, transitional cell cancer of the renal pelvis and ureter, trophoblastic tumor, gestational, urethral cancer, uterine cancer, vaginal cancer, vulvar cancer, Waldenström macroglobulinemia, or Wilms tumor.

In some embodiments, the cancer is lung cancer, e.g., non-small cell lung adenocarcinoma or squamous cell carcinoma; breast cancer, e.g., Triple$^-$, ER/PR$^+$Her2$^-$, ER/PR$^-$Her2$^+$, or Triple$^-$; colorectal cancer, e.g., adenocarcinoma, mucinous adenocarcinoma, or papillary adenocarcinoma; esophageal cancer; stomach cancer; kidney cancer, e.g., kidney clear cell cancer; ovarian cancer, e.g., ovarian endometrioid carcinoma, ovarian mucinous cystadenocarcinoma, or ovarian serous cystadenocarcinoma; melanoma, e.g., acral melanoma, cutaneous melanoma, or mucosal melanoma; uterine or cervical cancer; liver cancer, e.g., hepatocellular carcinoma or bile duct carcinoma; bladder cancer, e.g., transitional or urothelial bladder cancer; or testicular cancer.

In some embodiments, an EphA2 antibody disclosed herein can be used to a gastric cancer, ovarian cancer, or soft tissue sarcoma. As discussed above, the EphA2 antibody, e.g., AB-008873 showed better tumor selectivity than a number of EphA2 antibodies derived from clinical candidates and commercial EphA2 antibodies.

In one aspect, methods of the disclosure comprise administering an EphA2 antibody disclosed herein, or a variant thereof, as a pharmaceutical composition to a cancer patient in a therapeutically effective amount using a dosing regimen suitable for treatment of the cancer. The composition can be formulated for use in a variety of drug delivery systems. One or more physiologically acceptable excipients or carriers can also be included in the compositions for proper formulation. Suitable formulations for use in the present invention are found, e.g., in Remington: The Science and Practice of Pharmacy, 21st Edition, Philadelphia, PA. Lippincott Williams & Wilkins, 2005.

The tumor-targeting antibody is provided in a solution suitable for administration to the patient, such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

Administration

The pharmaceutical compositions are administered to a patient in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose includes the amelioration of symptoms of the disease in the patient. Amounts effective for this use will depend upon the severity of the disease and the general state of the patient's health, including other factors such as age, weight, gender, administration route, and the like Single or multiple administrations of the antibody may be administered depending on the dosage and frequency as required and tolerated by the patient. In any event, the methods provide a sufficient quantity of tumor-targeting antibody to effectively treat the patient.

An EphA2 antibody can be administered by any suitable means, including, for example, parenteral, intrapulmonary, and intranasal, administration, as well as local administration, such as intratumor administration. Parenteral infusions include intramuscular, intravenous, intraarterial, intraperitoneal, or subcutaneous administration. In some embodiments, the antibody may be administered by insufflation. In an illustrative embodiment, the antibody may be stored at 10 mg/ml in sterile isotonic aqueous saline solution for injection at 4° C. and is diluted in either 100 ml or 200 ml 0.9% sodium chloride for injection prior to administration to the patient. In some embodiments, the antibody is administered by intravenous infusion over the course of 1 hour at a dose of between 0.01 and 25 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.01 mg/kg body weight to about 25 mg/kg body weight or in the range 1 mg-2 g per patient. Preferably the dose is in the range 0.1-10 mg/kg or approximately 50 mg-1000 mg/patient. The dose may be repeated at an appropriate frequency which may be in the range once per day to once every three months, or every six months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months or once every 6 months. In other embodiments, the antibody is administered approximately once per month.

In an illustrative embodiment, the antibody may be stored at 10 mg/ml or 20 mg/ml in a sterile isotonic aqueous solution. The solution can comprise agents such as buffering agents and stabilizing agents. For example, in some embodiments, a buffering agent such as histidine is included to maintain a formulation pH of about 5.5. Additional reagents such as sucrose or alternatives can be added to prevent aggregation and fragmentation in solution and during freezing and thawing. Agents such as polysorbate 80 or an alternative can be included to lower surface tension and stabilizes the antibody against agitation-induced denaturation and air-liquid and ice-liquid surface denaturation. In some embodiments, the solution for injection is stored at 4° C. and is diluted in either 100 ml or 200 ml 0.9% sodium chloride for injection prior to administration to the patient.

In some embodiments, antibody for IV administration is formulated at a target concentration of 20 mg/mL in 20 mM histidine buffer, 8% (w/v) sucrose and 0.02% (w/v) polysorbate 80, pH 5.5.

Combination Therapy

An EphA2 antibody of may be administered with one or more additional therapeutic agents, e.g., radiation therapy, chemotherapeutic agents and/or immunotherapeutic agents.

In some embodiments, an EphA2 antibody can be administered in conjunction with an agent that targets an immune checkpoint antigen. In one aspect, the agent is a biologic therapeutic or a small molecule. In another aspect, the agent is a monoclonal antibody, a humanized antibody, a human antibody, a fusion protein or a combination thereof. In certain embodiments, the agents inhibit, e.g., by blocking ligand binding to receptor, a checkpoint antigen that may be PD1, PDL1, CTLA-4, ICOS, PDL2, IDO1, IDO2, B7-H3, B7-H4, BTLA, HVEM, TIM3, GAL9, GITR, HAVCR2, LAG3, KIR, LAIR1, LIGHT, MARCO, OX-40, SLAM, 2B4, CD2, CD27, CD28, CD30, CD40, CD70, CD80, CD86, CD137 (4-1BB), CD160, CD39, VISTA, TIGIT, a SIGLEC, CGEN-15049, 2B4, CHK1, CHK2, A2aR, B-7 family ligands or their receptors, or a combination thereof. In some embodiments, the agent targets PD-1, e.g., an antibody that blocks PD-L1 binding to PD-1 or otherwise inhibits PD-1. In some embodiments, the agent targets CTLA-4. In some embodiments, the agent targets LAG3. In some embodiments, the agent targets TIM3. In some embodiments, the agents target ICOS.

In some embodiments, an EphA2 antibody can be administered in conjunction with a therapeutic antibody, such as an antibody that targets a tumor cell antigen. Examples of therapeutic antibodies include as rituximab, trastuzumab, tositumomab, ibritumomab, alemtuzumab, atezolizumab, avelumab, durvalumab, pidilizumab, AMP-224, AMP-514, PDR001, cemiplimab, BMS-936559, CK-301, epratuzumab, bevacizumab, elotuzumab, necitumumab, blinatumomab, brentuximab, cetuximab, daratumumab, denosumab, dinutuximab, gemtuzumab ibritumomab ipilimumab, nivolumab, obinutuzumab, ofatumumab, ado-trastuzumab, panitumumab, pembrolizumab, pertuzumab, ramucirumab, and ranibizumab. In some embodiments, an EphA2 antibody can be administered in conjunction with a therapeutic antibody that binds an extracellular RNA-protein complex comprising polyadenylated RNA, such as the antibody designated ATRC-101, see WO2020168231 incorporated herein in its entirety.

In some embodiments, an EphA2 antibody as described herein is administered with an agonist anti-4-1BB antibody such as urelumab (Bristol Meyers Squibb, BMS-663513, U.S. Pat. No. 7,288,638), utomilumab, (Pfizer, PF-05082566, WO2012145183), 1D8 and 5B9 (US20100279932), hu106-1, TABBY 101-TABBY 110 (WO2017205745, FIGS. 2A-2F), Hz4B4-1 (U.S. Pat. No. 6,458,934), BBK-1 and BBK-4 (U.S. Pat. No. 6,559,997), hu39E3.G4 (U.S. Pat. No. 6,887,673), CTX-471 and CTX-471AF (U.S. Pat. No. 10,279,038), MOR-6032, MOR-7361, MOR-7480 and MOR-7483 (U.S. Pat. No. 8,337,850), LVGN-6051 (US20210246218), AGEN-2373 (US 2021/0106693), ADG-106/AG10131 (US20200369776), ATOR-1017 (US20190352414).

In some embodiments, an EphA2 antibody is administered with a chemotherapeutic agent. Examples of cancer chemotherapeutic agents include alkylating agents such as thiotepa and cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside; cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylomithine (DMFO); retinoic acid derivatives such as bexarotene, alitretinoin; denileukin diftitox; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, mifepristone, aromatase inhibiting 4(5)-imidazoles, 4-hydroxytamoxifen, trioxifene, keoxifene, LY 1 17018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, crizotinib, dasatinib, erlotinib, fostamatinib, gefitinib, imatinib, lapatinib, lenvatinib, mubritinib, nilotinib, pazopanib, pegaptanib, ruxolitinib, vandetanib, vemurafenib, and sunitinib; sirolimus (rapamycin), everolimus and other mTOR inhibitors. Examples of additional chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitabine, gemcitabine, fludarabine, cytarabine, mercaptopurine, thioguanine, pentostatin, and hydroxyurea). Illustrative chemotherapeutic agents additionally include paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinasel and other inhibitors of proteins or enzymes known to be upregulated, over-expressed or activated in cancers, the inhibition of which down regulates cell replication. Additional agents include asparaginase and a Bacillus Calmete-Guérin preparation.

In some embodiments, an EphA2 antibody as described herein is administered after, or at the same time, as a therapeutic agent, e.g., a chemotherapeutic agent, such as doxorubicin, that induces stress granules ("SG-inducing agent"). Increasing the amount of stress granules in cancer cells can promote targeting the tumor cells by the tumor-targeting antibody. Other exemplary therapeutic agents that can induce stress granules include pyrimidine analogs (e.g., 5-FU, under trade names of Adrucil®, Carac®, Efudex®, Efudix®); protease inhibitors (e.g., Bortezomib, under the trade name of Velcade®); kinase inhibitors (e.g, Sorafenib and Imatinib, under the trade names of Nexavar® and Gleevec®, respectively); Arsenic compounds (e.g., Arsenic trioxide, under the trade name of Trisenox®); Platinum-based compounds that induce DNA damage (e.g., Cisplatin and Oxaliplatin®, under the trade names of Platinol® and Eloxatin®, respectively); agents that disrupt microtubules (e.g., Vinblastin, under the trade name of Velban® or alkabban-AQ®; vincristin, under the trade name of Vincasar®, Marqibo®, or Oncovin®; Vinorelbin, under the trade name of Navelbin®); topoisomerase II inhibitor (e.g., Etoposide, under the trade name of Etopophos, Toposar®, VePesid®); and agents that induce DNA damage, e.g., irradiation. A number of exemplary therapeutic agents that can induce stress granules formation are disclosed in Mahboubi et al., *Biochimica et Biophysica Acta* 1863 (2017) 884-895.

Various combinations with the tumor-targeting antibody and the SG-inducing agent (or a combination of such agents) described herein may be employed to treat a cancer patient. By "combination therapy" or "in combination with", it is not intended to imply that the therapeutic agents must be administered at the same time and/or formulated for delivery together, although these methods of delivery are within the scope described herein. The tumor-targeting antibody and the SG-inducing agent can be administered following the same or different dosing regimen. In some embodiments, the tumor-targeting antibody and the SG-inducing agent is administered sequentially in any order during the entire or portions of the treatment period. In some embodiments, the tumor-targeting antibody and the SG-inducing agent is administered simultaneously or approximately simultaneously (e.g., within about 1, 5, 10, 15, 20, or 30 minutes of each other). In still other embodiments, the SG-inducing agent may be administered 1, 2, 3, 4, 5, 6, 7, 8, 9, 10, or more days before administration of the tumor-targeting antibody. In some embodiments, the SG-inducing agent is administered from 1 to 4 weeks, or longer, before the tumor-targeting antibody is administered.

An EphA2 antibody may also be administered to a cancer patient in conjunction with a cell based therapy, such as natural killer (NK) cell therapy or a cancer vaccine. In some instances, a cancer vaccine is a peptide-based vaccine, a nucleic acid-based vaccine, a cell-based vaccine, a virus-based or viral fragment-based vaccine or an antigen presenting cell (APC) based vaccine (e.g. dendritic cell based vaccine). Cancer vaccines include Gardasil®, Cervarix®, sipuleucel-T (Provenge®), NeuVax™, HER-2 ICD peptide-based vaccine, HER-2/neu peptide vaccine, AdHER2/neu dendritic cell vaccine, HER-2 pulsed DC1 vaccine, Ad-sig-hMUC-l/ecdCD40L fusion protein vaccine, MVX-ONCO-1, hTERT/survivin/CMV multipeptide vaccine, E39, J65, P10s-PADRE, rV-CEA-Tricom, GVAX®, Lucanix®, HER2 VRP, AVX901, ONT-10, ISA1O1, ADXS1 1-001, VGX-3100, INO-9012, GSK1437173A, BPX-501, AGS-003, IDC-G305, HyperAcute®-Renal (HAR) immunotherapy, Prevenarl3, MAGER-3.A1, NA17.A2, DCVax-Direct, latent membrane protein-2 (LMP2)-loaded dendritic cell vaccine (NCT02115126), HS410-101 (NCT02010203, Heat Biologies), EAU RF 2010-01 (NCT01435356, GSK), 140036 (NCT02015104, Rutgers Cancer Institute of New Jersey), 130016 (NCTO 1730118, National Cancer Institute), MVX-201101 (NCT02193503, Maxivax SA), ITL-007-ATCR-MBC (NCT01741038, Immunovative Therapies, Limited), CDR0000644921 (NCT00923143, Abramson cancer center of the University of Pennsylvania), SuMo-Sec-01 (NCT00108875, Julius Maximilians Universitaet Hospital), or MCC-15651 (NCT01176474, Medarex, Inc, BMS).

In some embodiments, an EphA2 antibody of the present invention may be administered with an agent, e.g., a corticosteroid, that mitigates side-effects resulting from stimulation of the immune system.

In the context of the present invention a therapeutic agent that is administered in conjunction with an EphA2 antibody of the present invention can be administered prior to administrations of the tumor-targeting antibody or after administration of the tumor-targeting antibody. In some embodiments, an EphA2 antibody may be administered at the same time as the additional therapeutic agent. In some embodiments, an EphA2 antibody and an additional therapeutic agent described above can be administered following the same or different dosing regimens. In some embodiments, the tumor-targeting antibody and the therapeutic agent are administered sequentially in any order during the entire treatment period or portions thereof. In some embodiments, the tumor-targeting antibody and the therapeutic agent are administered simultaneously or approximately simultaneously (e.g., within about 1, 5, 10, 15, 20, or 30 minutes of each other). In still other embodiments, the therapeutic agent may be administered 1, 2, 3, 4, 5, 6, 7, 8, 9, 10, or more days before the administration of the tumor-targeting antibody. In still other embodiments, the therapeutic agent may be administered 1, 2, 3, 4, 5, 6, 7, 8, 9, 10, or more days after the administration of the tumor-targeting antibody.

Functional Assays

Also described herein are functional assays that can be used to determine the ability of the antibodies described herein to mediate FcR-dependent activity. In some embodiments, the assay measures antibody dependent cellular cytotoxicity (ADCC), antibody dependent cellular phagocytosis (ADCP), or complement-dependent cytoxicity (CDC).

In Vivo Assays

In some embodiments, the activity of the antibodies is evaluated in vivo in an animal model that is known for specific human tumors. One exemplary model is the CT26 mouse model, as described in the EXAMPLES. Tumor-targeting activity of these antibodies in vivo may be assessed by using a number of assays, including but not limited to using flow cytometry to analyse the immune profiling of the blood and tumor, monitoring tumor growth, and performing immunofluorescence to semi-quantitative estimate tumor infiltratration. In some embodiments, the effect of the antibody can be assessed using Survival, a normalized area above the curve metric (NAAC), and a normalized growth rate metric (NGRM), where NAAC and NGRM were both developed at Atreca. An "in vivo active" determination can be based on the in vivo activity was assessed by a p-value≤0.05 in at least one of the analyses of survival, NAAC, and NGRM, i.e., if an antibody exhibited a p-value of less than or equal to 0.05 for survival, NAAC, and/or NGRM (any one alone being sufficient), the antibody is considered "in vivo active".

In one aspect, provided herein are antibodies that exhibit inhibitory effects on tumors, including decreasing rate of tumor growth, size, tumor invasion and/or metastasis. Such antibodies exhibit tumor-targeting effects in vivo, e.g., when administered to subjects that has a tumor expressing or overexpressing EphA2.

Engineering Variants

In some embodiments, an antibody or variant thereof described herein is modified to have improved developability (i.e., reduced development liabilities), including but not limited to, decreased heterogeneity, increased yield, increased stability, improved net charges to improve pharmacokinetics, and or/reduced immunogenicity. In some embodiments, antibodies having improved developability can be obtained by introducing mutations to reduce or eliminate potential development liabilities. In some embodiments, antibodies having improved developability possess modifications as compared to a reference or control antibody in their amino acid sequence.

In some embodiments, the antibodies or variants thereof disclosed herein have improved developability while maintaining comparable or improved binding affinity to the target antigen as compared to a reference or control (unmodified) antibody. In some embodiments, the antibodies or variants thereof disclosed herein have improved developability while maintaining activities that are similar to a reference or control (unmodified) antibody.

In some embodiments, the antibodies or variants thereof have improved developability, e.g., as identified through various in vitro assays, such as aggregation assessment by HPLC or UPLC, hydrophobic interaction chromatography (HIC), polyspecificity assays (e.g., baculovirus particle binding), self-interaction nanoparticle spectroscopy (SINS), or mass spec analysis after incubation in an accelerated degradation condition such as high temperature, low pH, high pH, or oxidative $H_2O_2$. Mutations are successful if activity is maintained (or enhanced) while removing or reducing the severity of the liability.

Improved properties of antibodies or variants thereof as described herein include: (1) fits a standard platform (expression, purification, formulation); (2) high yield; (3) low heterogeneity (glycosylation, chemical modification, and the like); (4) consistent manufacturability (batch-to-batch, and small-to-large scale); (5) high stability (years in liquid formulation), e.g., minimal chemical degradation, fragmentation, and aggregation; and (6) long PK (in vivo half-life), e.g., no off-target binding, no impairment of FcRn recycling, and stable. Antibody liabilities are further described in Table 16.

TABLE 16

Description of potential development liabilities

| | | Sequence comprises an odd number of cysteines | |
|---|---|---|---|
| Free cysteine[6] | Yield, heterogeneity, stability, activity | odd number of cysteines | High |
| N-linked glycosylation | Yield, heterogeneity, activity | N(~P)(S, T)[1] | High |
| Abnormal net charge | Platform fit, PK | Sharma 2014[2] | High |
| Patches of hydrophobicity | Stability, PK | Sharma 2014 | High |
| Patches of same charge | Stability, PK | N/A (based on structure) | Medium |
| Proteolysis | Stability, PK | (K, R)(K, R)[3] | Medium |
| Proteolysis | Stability, PK | DP | Medium |
| Asparagine deamidation | Heterogeneity, stability, activity | NG; N(A, N, S, T)[4] | Medium; Low |
| Aspartate isomerization | Heterogeneity, stability, activity | DG; D(A, D, S, T)[5] | Medium; Low |

TABLE 16-continued

Description of potential development liabilities

| | | Sequence comprises an odd number of cysteines | High |
|---|---|---|---|
| Free cysteine[6] | Yield, heterogeneity, stability, activity | | |
| Lysine glycation | Heterogeneity, stability, activity | K | Low |
| Methionine oxidation | Heterogeneity, stability, activity | M | Low |
| Tryptophan oxidation | Heterogeneity, stability, activity | W | Low |

Note:
[1]The N-linked glycosylation site is N-X-S/T, where X is any residue other than proline.
[2]Sharma et al., Proc. Natl. Acad. Sci. USA 111:18601-18606, 2014
[3]This motif consists of a K or R, followed by a K or R. Stated differently, the motif can be KK, KR, RK, or RR.
[4]The dipeptide NG poses a medium risk of development liability. The dipeptides NA, NN, NS, and NT pose a low risk of development liability. N may also exhibit low risk of liability for other successor residues, e.g., D, H, or P. Stated differently, dipeptide ND, NH, or NP poses a low risk of development liability.
[5]Similarly to the above, the dipeptide DG poses a medium risk of development liability. The dipeptides DA, DD, DS, and DT pose a low risk of development liability. D may also exhibit low risk of development liability for other successor residues, e.g., N, H, or P.
[6]"Free cysteine" refers to a cysteine that does not form a disulfide bond with another cysteine and thus is left "free" as thiols. The presence of free cysteines in the antibody can be a potential development liability. Typically, an odd net number of cysteines in the protein shows a likelihood there is a free cysteine.

Figure 35:
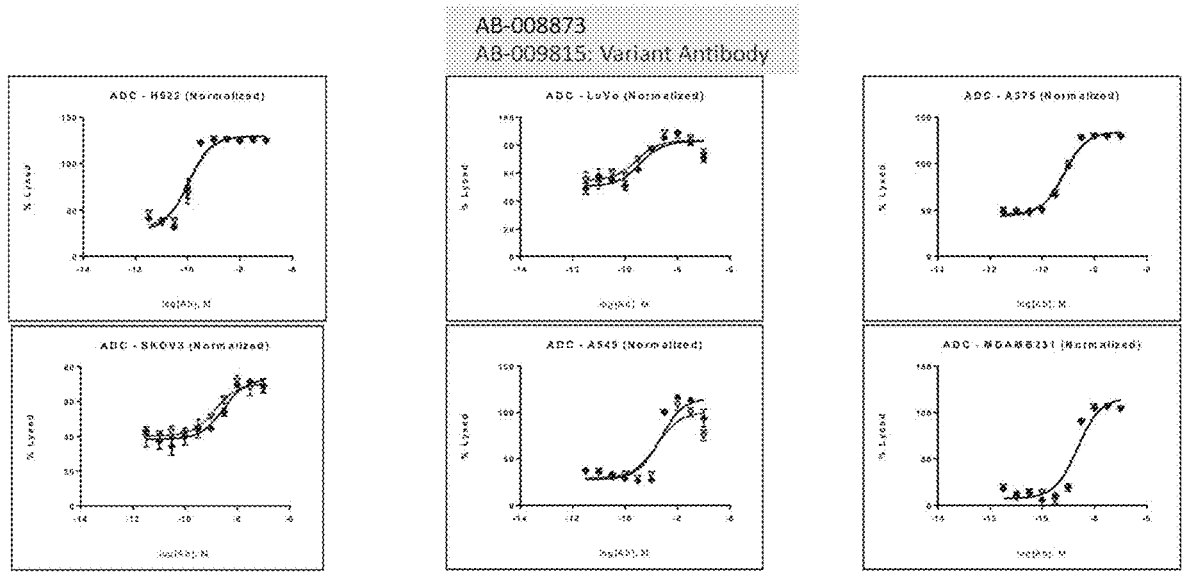
FIG. 35 shows a comparison of the ADC activity of AB-008873 with AB-009815 (comprising an H76PT mutation relative to AB-008873). This mutation removes a medium risk DP proteolytic cleavage site that could cause AB degradation in the serum which decreases half-life after injection in mice/humans. The results showed that the ADC activity of AB-009815 is substantially similar to that of AB-008873 in H522, LoVo, A375, SKOV3, A549, and MDAMB231 cells.

As one illustrative example, a variant was generated by introducing H76PT mutation to the heavy chain variable region of AB-009815 (SEQ ID NO: 75). This mutation removes a medium risk DP proteolytic cleavage site that could cause AB degradation during production, while in storage, or in the serum which decreases half-life after injection in mice/humans. The variant retains the ADC activity of AB-009815 in tumor cells, e.g., H522, LoVo, A375, SKOV3, A549, and MDAMB231 cells (FIG. 35)

Another goal for engineering variants is to reduce the risk of clinical immunogenicity: the generation of anti-drug antibodies against the therapeutic antibody. To reduce risk, the antibody sequences are evaluated to identify residues that can be engineered to increase similarity to the intended population's native immunoglobulin variable region sequences.

The factors that drive clinical immunogenicity can be classified into two groups. First are factors that are intrinsic to the drug, such as: sequence; post-translational modifications; aggregates; degradation products; and contaminants. Second are factors related to how the drug is used, such as: dose level; dose frequency; route of administration; patient immune status; and patient HLA type.

One approach to engineering a variant to be as much like self as possible is to identify a close germline sequence and mutate as many mismatched positions (also known as "germline deviations") to the germline residue type as possible. This approach applies for germline genes IGHV, IGHJ, IGKV, IGKJ, IGLV, and IGLJ, and accounts for all of the variable heavy (VH) and variable light (VL) regions except for part of H-CDR3. Germline gene IGHD codes for part of the H-CDR3 region but typically exhibits too much variation in how it is recombined with IGHV and IGHJ (e.g., forward or reverse orientation, any of three translation frames, and 5' and 3' modifications and non-templated additions) to present a "self" sequence template from a population perspective.

Each germline gene can present as different alleles in the population. The least immunogenic drug candidate, in terms of minimizing the percent of patients with an immunogenic response, would likely be one which matches an allele commonly found in the patient population. Single nucleotide polymorphism (SNP) data from the human genome can be used to approximate the frequency of alleles in the population.

Another approach to engineering a lead for reduced immunogenicity risk is to use in silico predictions of immunogenicity, such as the prediction of T cell epitopes, or use in vitro assays of immunogenicity, such as ex vivo human T cell activation. For example, services such as those offered by Lonza, United Kingdom, are available that employ platforms for prediction of HLA binding and in vitro assessment to further identify potential epitopes.

Antibody variants can be designed to enhance the efficacy of the antibody. In some embodiments, design parameters can focus on CDRs, e.g., CDR3. Positions to be mutated can be identified based on structural analysis of antibody-antigen co-crystals (Oyen et al., Proc. Natl. Acad Sci. USA 114: E10438-E10445, 2017; Epub Nov. 14, 2017) and based on sequence information of other antibodies from the same lineage.

Approaches to Mutation Design

Development liabilities can be removed or reduced by one or more mutations. Mutations are designed to preserve antibody structure and function while removing or reducing development liabilities and to improve function. In some embodiments, mutations to chemically similar residues can be identified that maintain size, shape, charge, and/or polarity. Illustrative mutations are described in Table 17.

TABLE 17

Preferred mutations to remove development liabilities

| | | | |
|---|---|---|---|
| Free cysteine | Odd # C | High | C→(A, S) |
| N-linked glycosylation | N(~P)(S, T) | High | N→(Q, D, S, A); (S, T)→(A, N) |
| Proteolytic cleavage | (K, R)(K, R) | Medium | K, R→(Q, S, A) |
| Proteolytic cleavage | DP | Medium | D→(E, S, A) |

TABLE 17-continued

Preferred mutations to remove development liabilities

| | | | |
|---|---|---|---|
| Asparagine deamidation | NG; N(A, N, S, T)* | Medium; Low | N→(Q, S, A); G→(A, S) |
| Aspartate isomerization | DG; D(A, D, S, T)* | Medium; Low | D→(E, S, A); G→(A, S) |
| Lysine glycation | K | Low | K→(R, Q, S, A) |
| Methionine oxidation | M | Low | M→(Q, L, S, A) |
| Tryptophan oxidation | W | Low | W→(Y, F) |

Note:
the last column of Table 4 shows preferred mutations. For example, C→(A, S) refers to C can be mutated to either A or S in order to remove development liabilities.

Methods for Altering the Glycosylation of an Antibody

In another aspect, the antibodies described herein comprise an Fc region having altered glycosylation that increase the ability of the antibody to recruit NK cells and/or increase ADCC. In some embodiments, the Fc region comprises glycan containing no fucose (i.e., the Fc region is afucosylated). Fucosylated antibodies can be produced using cell lines that express a heterologous enzyme that depletes the fucose pool inside the cell (e.g., GlymaxX® by ProBioGen AG, Berlin, Germany). Non-fucosylated antibodies can also be produced using a host cell line in which the endogenous α-1,6-fucosyltransferase (FUT8) gene is deleted. See Satoh, M. et al., "Non-fucosylated therapeutic antibodies as next-generation therapeutic antibodies," Expert Opinion on Biological Therapy, 6:11, 1161-1173, DOI: 10.1517/14712598.6.11.1161.

Diagnosis of Cancer

The EphA2 antibodies disclosed herein can also be used for diagnosing a patient having a cancer suitable for treatment. In one aspect, the method comprises contacting a tumor sample from the patient with an antibody disclosed above and detecting binding of the antibody to the tumor sample. In some cases, the antibodies are conjugated to a detectable label that produces fluorescent, luminescent or colorimetric signals, and detecting the signal from the label indicates that tumor is suitable for treatment with an EphA2 antibody disclosed herein. In some cases, after the antibodies are contacted with the tumor sample, a labeled secondary antibody is added to the tumor sample that have been contacted with the antibody disclosed herein and detecting the signal from the secondary antibody indicates that the tumor expressing or overexpressing EphA2.

As discussed above, in some tumor types, e.g., uterine cancer, head and neck cancer, and NSCLC, an EphA2 antibody may display donor-specific tumor selectivity, i.e., the antibody may show tumor selectivity in some donors but not other donors. In these cases, it is desirable to determine the binding of the tumor to the EphA2 antibody before treating the patient.

Screening Antibodies

Also disclosed herein is a method for selecting a tumor-targeting antibody. The method comprises contacting an antibody disclosed above with a polypeptide comprising SEQ ID NO: 94 or SEQ ID NO: 95 and contacting the antibody with a tumor cell, and selecting the antibody if the antibody binds to the polypeptide and also binds preferentially to the tumor cell as compared to normal cell.

The following examples are offered for illustrative purposes and are not intended to limit the invention. Those of skill in the art will readily recognize a variety of non-critical parameters that can be changed or modified to yield essentially the same results.

EXAMPLES

Example 1. AB-008873

AB-008873 was discovered in antibody repertoires generated by Immune Repertoire Capture® (IRC™) technology from plasmablast B cells isolated a non-small cell lung cancer patient with an active anti-tumor immune response after treatment with the anti-PD-1 antibody OPDIVO® (nivolumab) (Bristol Myers Squibb). AB-008873 was tested for cell surface binding to 6,000 human membrane proteins expressed on the surface of HEK293 cells by flow cytometry. Two membrane proteins showed binding over the background: EphA2 and FcGR1. No other ephrin type-A or type-B receptors had a binding signal above the background.

AB-008873 was further shown to bind the extracellular domain of EphA2 via an indirect and reverse indirect ELISA. The ELISAs also confirmed binding to mouse EphA2.

Next, AB-008873 was tested to determine if the previously observed the in vitro surface binding to A549 of the antibody was mediated by interaction with EphA2. 3 EphA2 guide RNAs were introduced into Cas9 overexpressing A549 cells. The EphA2 guide RNAs were designed by Synthego and Chop CRISPR tool. Exact sequences were selected based on low off-target score. The designed sgRNAs were synthesized and modified by Synthego. Electroporations of guide RNA was performed using the Neon™ Transfection System 10 µL Kit #MPK1096 according to manufacturer protocol. Final concentrations of the sgRNA were 100 µM (100 pmol/µl). This resulted in a knockout of EphA2 gene in >90% of cells. The polyclonal EphA2 KO A549 cell population was then cultured for ~4 days and assayed for cell surface binding by AB-008873. The fraction of cells in the AB-008873 positive gate was reduced from ~98% (irrelevant guide RNA) to ~10%, thus confirming EphA2 is the primary driver of AB-008873 A549 binding.

Example 2. Ab-008873 Variants

The sequence of AB-008873 was analyzed for potential liabilities. There are no high-risk liabilities. There is a medium-risk proteolytic cleavage site at H75D-H76P (i.e., heavy chain position 75 aspartate followed by heavy chain position 76 proline) and a medium-risk deamidation site at H108N-H109G. Low-risk liabilities include tryptophan oxidation at H34W and L90W; asparagine deamidation at H60N-H61N and L25N-L26N; lysine glycation at H67K, H100K, and L30K; and aspartate isomerization at H115D-H116A, L49D-L50D, L50D-L51S, and L91D-L92S.

AB-008873 was aligned to its closest human germline genes (IGHV4-34*02, IGHD2-8*01, IGHJ3*02, IGLV3-21*02, and IGLJ2*01), and to four of its known siblings (AB-009805, AB-009806, AB-009807, and AB-009808). Three variants were designed to explore differences between AB-008873 and its siblings. AB-009812 was designed with mutation H54RS to AB-008873 (heavy chain position 54 mutated from arginine to serine), in order to match H54S as found in the siblings and germline, and to create the N-linked glycosylation motif found in the siblings and germline (H52N-H53H-H54S). AB-009813 was designed with mutation H54RA to AB-008873, in order to remove the H54 arginine from AB-008873, but not create and N-linked glycosylation motif (ie, H52N-H53H-H54A is not an N-linked glycosylation motif). AB-009814 was designed with deletion of three residues, H61N-H62Y-H63N, in order to match the siblings and germline in that region. Note that AB-009814 could equivalently be described as a deletion of H60N-H61N-H62Y, H59Y-H60N-H61N, or H58N-H59Y-H60N and the resulting sequence is the same.

AB-009815 and AB-009816 were designed to remove the medium-risk proteolytic cleavage liability in AB-008873 at H75D-H76P. The variants make the mutation H76PT or H76PA, respectively. AB-009815 with H76PT also changes the sequence to germline.

AB-009817 was designed to remove the medium-risk deamidation site at H108N-H109G. The variant makes the mutation H109GA, to reduce the liability to a low-risk deamidation site (i.e., NG is medium risk but NA is low risk). H106C and H111C are predicted to form an intra-H3 disulfide bond, with H107-H110 in a 4-residue turn. Alternative approaches to removing the medium-risk deamidation site include H108NS, H108NA, H108NQ, H108NL, or H108NY.

AB-008873, siblings AB-009805 through AB-009808, and variants AB-009812 through AB-009817, were synthesized on a mouse IgG2a framework. All siblings show less binding, less ADCC, and less ADCP activity than AB-008873. See, FIG. 20. Variants AB-009815 and AB-009816, which remove the same medium-risk cleavage site, show similar levels of binding and activity as AB-008873. AB-009817 completely loses binding (tested up to 1 uM) and functional activity (tested up to 100 nM). Variants AB-009812, AB-009813, and AB-009814 show some binding ADCC and activity, though less than AB-008873, which shows that N-linked glycosylation motif and 3-aa insertion in H2 region affect binding but not essential. The ADC (antibody-drug conjugate) activity of AB-009815 is the same as that of AB-008873. See, FIGS. 21A-C and Table 18.

TABLE 18

Functional activity of engineered AB-008873 variants

| Reg ID | Mutation | Flow EC50 (nM) | Delta | ADCC EC50 (nM) | Delta | Rationale |
|---|---|---|---|---|---|---|
| AB-008873 | | 3.6 | 680293 | 8.9 | 46.8 | |
| AB-009812 | H54RS | 9.6 | 567759 | 51.0 | 41.1 | Re-create NHS glycosylation motif as found in sibs and germline |
| AB-009813 | H54RA | 6.8 | 578049 | 26.0 | 39.9 | Keep glycosylation motif out bt via alanine instead of arginine |
| AB-009814 | H61NYNxxx | 11.5 | 407293 | 62.8 | 36 | Undo 3-residue insertion, back to as found in sibs and germline |
| AB-009815 | H76PT | 5.5 | 745456 | 10.4 | 59.8 | Remove medium-risk DP proteolytic cleavage site |
| AB-009816 | H76PA | 5.5 | 670105 | 12.5 | 58 | Remove medium-risk DP proteolytic cleavage site |
| AB-009817 | H109GA | inactive | 0 | inactive | 0 | Remove medium-risk NG asparagine deamidation site (leave as low-risk NA) |

The 12 variants AB-010141, AB-010142, AB-010143, AB-010144, AB-010145, AB-010146, AB-010147, AB-010148, AB-010149, AB-010150, AB-010151, and AB-010152 were designed to mutate AB-009815 closer to germline. Each variant exhibits 1 to 4 mutations at positions that differ from the closest germline. Some positions are framework; some are CDR. AB-010141 makes H31DG. AB-010142 makes L31NS. AB-010143 makes L97LV. AB-010144 makes H51VI. AB-010145 makes H86TS. AB-010146 makes H129AS. AB-010147 makes L60QR. AB-010148 combines H51VI and H86TS. AB-010149 combines H51VI and H129AS. AB-010150 combines H86TS and H129AS. AB-010151 combines H51VI, H86TS, and H129AS. AB-010152 combines H51VI, H86TS, H129AS, and L60QR. Further combinations of mutations to germline are of interest.

Anti-EphA2 Variants AB-010141-AB-010152 were synthesized on a mouse IgG2a framework and assayed for ADCC, both by EC50 and delta-activity as compared AB-008873 and melting temperature (Tm) measured using UNcle instrument. The results of these assays are shown in Table 19.

TABLE 19

Properties of anti-EphA2 antibodies

| AB regid | Parent | Mutations | Tm | ADCC EC50 (nM) | dAct (%) |
|---|---|---|---|---|---|
| AB-008873 | N/A | N/A | 64.1 | 29.0 | 18.6 |
| AB-010141 | AB-009815 | H31DG | 63.1 | 4.6 | 24.2 |

TABLE 19-continued

Properties of anti-EphA2 antibodies

| AB regid | Parent | Mutations | Tm | ADCC EC50 (nM) | dAct (%) |
|---|---|---|---|---|---|
| AB-010142 | AB-009815 | L31NS | 64.2 | | |
| AB-010143 | AB-009815 | L97LV | 65.4 | 25.1 | 21.6 |
| AB-010144 | AB-009815 | H51VI | 64.5 | 35.8 | 17.1 |
| AB-010145 | AB-009815 | H86TS | 64.1 | 48.9 | 19.2 |
| AB-010146 | AB-009815 | H129AS | 63.9 | 66.8 | 17.3 |
| AB-010147 | AB-009815 | L60QR | 66.5 | 79.4 | 15.8 |
| AB-010148 | AB-009815 | H51VI_H86TS | 64.4 | 45 | 17.4 |
| AB-010149 | AB-009815 | H51VI_H129AS | 64.6 | | |
| AB-010150 | AB-009815 | H86TS_H129AS | 64.4 | 65.9 | 17.1 |
| AB-010151 | AB-009815 | H51_H86_H129 | 64.6 | 33.3 | 17.5 |
| AB-010152 | AB-009815 | H51_H86_H129_L60 | 67.0 | | |

AB-010141 with H31DG exhibits improved ADCC EC50 but decreases Tm by approximately 1° C. AB-010143 with L97LV exhibits improved Tm by approximately 1° C. AB-010147 with L60QR exhibits improved Tm by approximately 2° C. but might exhibit somewhat decreased ADCC activity. AB-010148 with H51VI and H86TS exhibits maintained Tm and ADCC activity as compared to AB-008873.

Additional variants were made based on AB-010148 and were designated as AB-010357, AB-010358, AB-010359, AB-010360, AB-010361, AB-010362, AB-010363, AB-010364, AB-010365, AB-010366, and AB-010367.

AB-010148 was selected based on Tm and ADCC activity similar to that of AB-008873, while incorporating H76PT to remove the medium-risk DP proteolytic cleavage site and incorporating H51VI and H86TS to remove germline deviations to reduce potential immunogenicity. Combinations of L31DG, L97LV, and/or L60QR were added to AB-010148 in order to improve Tm, improve ADCC activity, and/or remove germline deviations.

H31DG is predicted to remove an intramolecular salt bridge between H31D and H54R. To potentially compensate for this removal, H31DG was combined with either H54RA or H54RQ, along with L97LV and optionally L60QR, in variants AB-010364, AB-010365, AB-010366, and AB-010367.

Antibody variants AB-010357-AB-010367 were synthesized on a mouse IgG2a framework and assayed for ADCC, both by EC50 and delta-activity as compared AB-008873 and melting temperature (Tm) measured using UNcle instrument. The results of these assays are shown in Table 20.

TABLE 20

Properties of Anti-EphA2 antibodies

| AB regid | Parent | Mutations | Tm | EC50 (nM) | Fold-improved | dAct (%) |
|---|---|---|---|---|---|---|
| AB-008873 | N/A | N/A | | 34.8 | 1.00 | 19.3 |
| AB-010357 | AB-010148 | L97LV | 65.3 | 11.6 | 3.00 | 23.1 |
| AB-010358 | AB-010148 | L60QR | 66.9 | 73.3 | 0.47 | 15.7 |
| AB-010359 | AB-010148 | L97LV_L60QR | 67.6 | 25.3 | 1.38 | 16.9 |
| AB-010360 | AB-010148 | H31DG | 64.0 | 4.3 | 8.09 | 26.1 |
| AB-010361 | AB-010148 | H31DG_L97LV | 65.0 | 3.1 | 11.23 | 24.1 |
| AB-010362 | AB-010148 | H31DG_L60QR | 65.9 | 12.8 | 2.72 | 19.6 |

TABLE 20-continued

Properties of Anti-EphA2 antibodies

| AB regid | Parent | Mutations | Tm | EC50 (nM) | Fold-improved | dAct (%) |
|---|---|---|---|---|---|---|
| AB-010363 | AB-010148 | H31DG_L60QR_L97LV | 66.5 | 9.5 | 3.66 | 27.8 |
| AB-010364 | AB-010148 | H31DG_H54RA_L97LV | 64.5 | 14.5 | 2.40 | 26.3 |
| AB-010365 | AB-010148 | H31DG_H54RA_L97LV_L60QR | 66.7 | 34.6 | 1.01 | 21.3 |
| AB-010366 | AB-010148 | H31DG_H54RQ_L97LV | 64.7 | 28.9 | 1.20 | 25.9 |
| AB-010367 | AB-010148 | H31DG_H54RQ_L97LV_L60QR | 67.6 | 42.7 | 0.81 | 21.3 |

Multiple variants exhibit improvements in both Tm and ADCC activity relative to AB-008873.

Antibodies AB-010357, AB-010361, and AB-010363 were then used as the basis for further variants. AB-010357 was mutated to generate AB-010661, AB-010662, AB-010663, AB-010664, AB-010665, AB-010666, AB-010667, AB-010668, AB-010669, AB-010670, AB-010671, AB-010672, AB-010673, and AB-010674.

AB-010361 was mutated to generate AB-010675, AB-010676, AB-010677, AB-010678, AB-010679, AB-010680, AB-010681, AB-010682, AB-010683, AB-010684, AB-010685, AB-010686, AB-010687, and AB-010688. AB-010363 was mutated to generate AB-010689, AB-010690, AB-010691, AB-010692, AB-010693, AB-010694, AB-010695, AB-010696, AB-010697, AB-010698, AB-010699, AB-010700, AB-010701, and AB-010702.

Example 3. In Vitro Studies

Immunophenotyping

Peripheral blood was blocked with 1:100 TruStain FcX PLUS Antibody (BioLegend 156604) for 10 min at 4° C. and stained for 30 min at 4° C. with a mastermix of antibodies for each panel. Next, 1.6 ml of 1× fix/lyse solution prepared according to manufacturer's protocol (BD 558049) was added to each sample and incubated for 10 min at RT. Samples were centrifuged at 500×g for 5 min, supernatant removed and transferred to a 96-well plate. Samples were centrifuged at 300×g for 5 min, washed with 200 ul of PBS, and resuspended in 100 ul of 1% FBS/5 mM EDTA/PBS for analysis on Beckman Coulter's Cytoflex flow cytometer. Resulting data was analyzed using FlowJo_v10.7.1. Reagents for immunophenotyping are provided in Table 21.

TABLE 21

Reagents for immunophenotyping

| Lymphoid Panel | BioLegend | Myeloid Panel | BioLegend |
|---|---|---|---|
| CD45-PerCP | 103129 | CD45-PerCP | 103129 |
| CD3-APC | 152306 | Ly6C-APC | 128016 |
| CD8-AF700 | 100730 | F4/80-AF700 | 123130 |
| CD4-APCCy7 | 100414 | B220-APCCy7 | 103224 |
| CD25-PE | 101904 | Tim3-PE | 119704 |
| Tim3-PEDazzle594 | 134014 | CD11c-PEDazzle594 | 117348 |
| CD49b-PECy7 | 108922 | CD103-PECy7 | 121426 |
| CD62L-BV421 | 104436 | MHCII-BV421 | 107632 |
| PD1-BV510 | 135241 | CD24-BV510 | 101831 |

TABLE 21-continued

Reagents for immunophenotyping

| Lymphoid Panel | BioLegend | Myeloid Panel | BioLegend |
|---|---|---|---|
| CD44-BV605 | 103047 | Ly6G-BV605 | 127639 |
| CD19-BV650 | 115541 | CD11b-BV650 | 101259 |
| Lymphoid Panel | BioLegend | Myeloid Panel | BioLegend |

Tumors were digested using Miltenyi's gentleMACS Octo Dissociator with heaters and Tumor Dissociation Kit, mouse (130-096-730) according to the manufacturer's instructions and cryopreserved in 10% FBS/DMSO. Dissociated cells were thawed using pre-warmed 2% FBS/RPMI dropwise, centrifuged at 300×g for 10 min, with supernatant decanted. Cells are blocked TruStain FcX PLUS Antibody (BioLegend 156604) for 10 min at 4° C. and stained with a mastermix of antibodies for 30 min at 4° C. Next, 100 ul of PBS was added, cells were centrifuged at 300×g for 5 min, supernatant decanted, and washed with another 200 ul PBS. Cells were resuspended in 100 ul of 1% FBS/5 mM EDTA/PBS with 1:500 Membrane integrity Dye (Intellicyt 90365) for analysis on Beckman Coulter's Cytoflex flow cytometer. Resulting data was analyzed using FlowJo_v10.7.1. Reagents for immunophenotyping in tumor cells are provided in Table 22.

TABLE 22

Reagents for immunophenotyping in tumor cells

| Lymphoid Panel | BioLegend | Myeloid Panel | BioLegend |
|---|---|---|---|
| CD3-APC | 152306 | Ly6C-APC | 128016 |
| CD8-AF700 | 100730 | F4/80-AF700 | 123130 |
| CD4-APCCy7 | 100414 | B220-APCCy7 | 103224 |
| CD25-PE | 101904 | CD45-PE | 103106 |
| NKG2D-PEDazzle594 | 130214 | CD11c-PEDazzle594 | 117348 |
| CD49b-PECy7 | 108922 | CD103-PECy7 | 121426 |
| PD1-BV421 | 135221 | MHCII-BV421 | 107632 |
| Gr1-BV510 | 108457 | CD24-BV510 | 101831 |
| CD45-BV605 | 103155 | Ly6G-BV605 | 127639 |
| CD19-BV650 | 115541 | CD11b-BV650 | 101259 |

Figure 8:
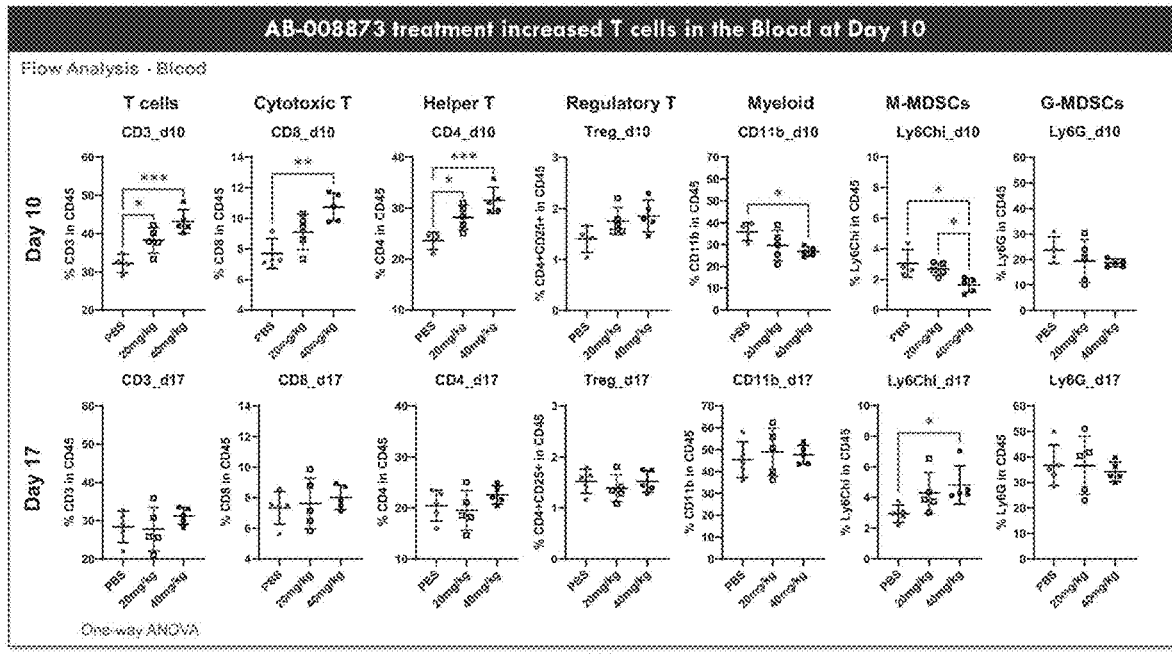
FIG. 8 shows that AB-008873 treatment increased T cells in the blood.

Immunophenotyping Results Summary:

Early increases in total T cells, cytotoxic T cells, and helper T cells observed in the blood 2 days after 1st dose. At the same time, decreases in overall myeloid, monocytes, or M-MDSCs was detected after treatment with 40 mg/kg AB-008873. These changes were longer detected 9 days after 1$^{st}$ dose and instead, an increase in CD11b+Ly6Chi monocytes or M-MDSCs was observed. FIG. 8

Figure 10:
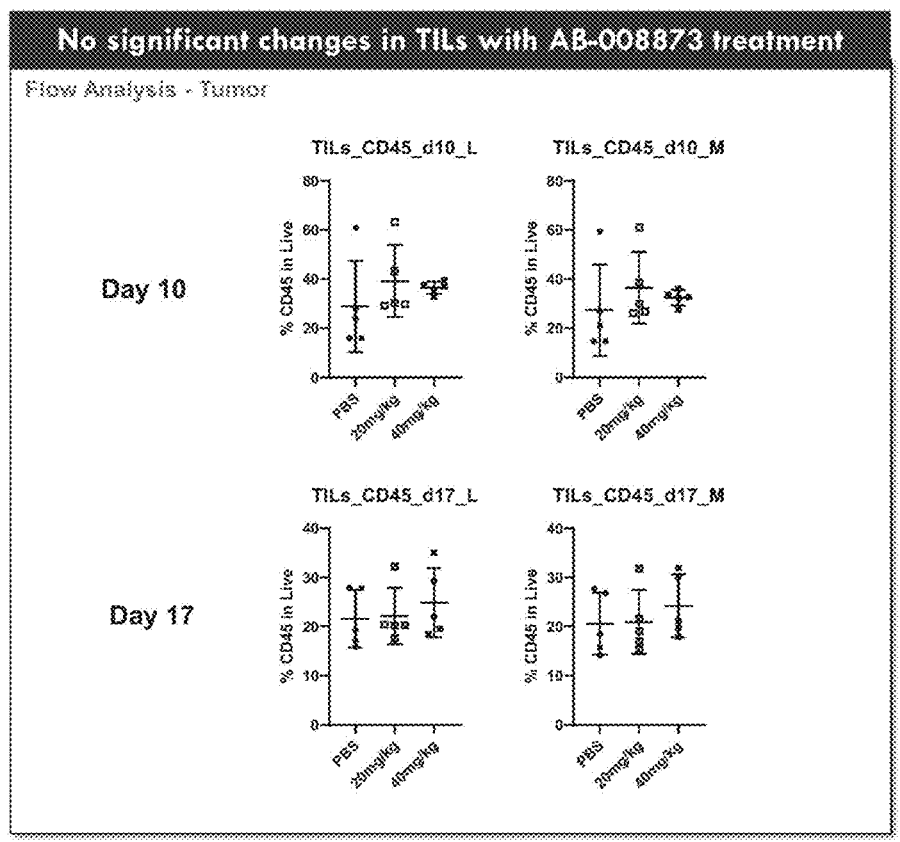
FIG. 10 shows that AB-008873 treatment did not result in significant changes in TIL number.
Figure 11:
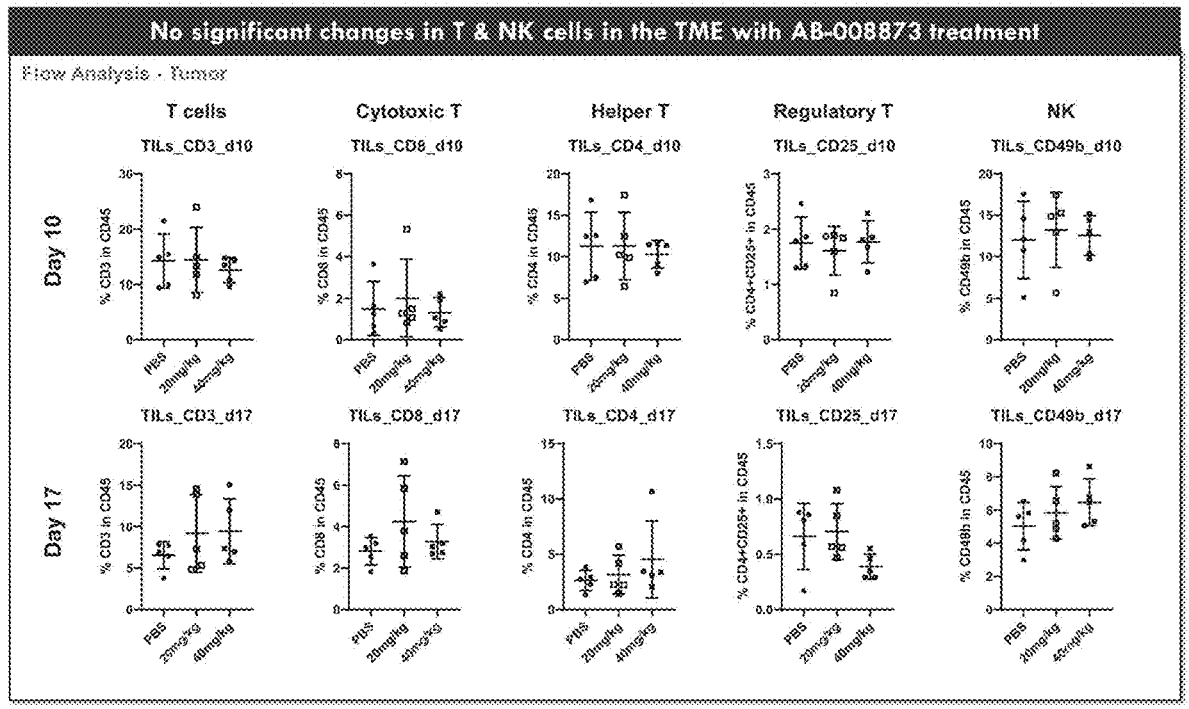
FIG. 11 shows that AB-008873 treatment did not result in significant changes in T & NK cell number in the TME.
Figure 12:
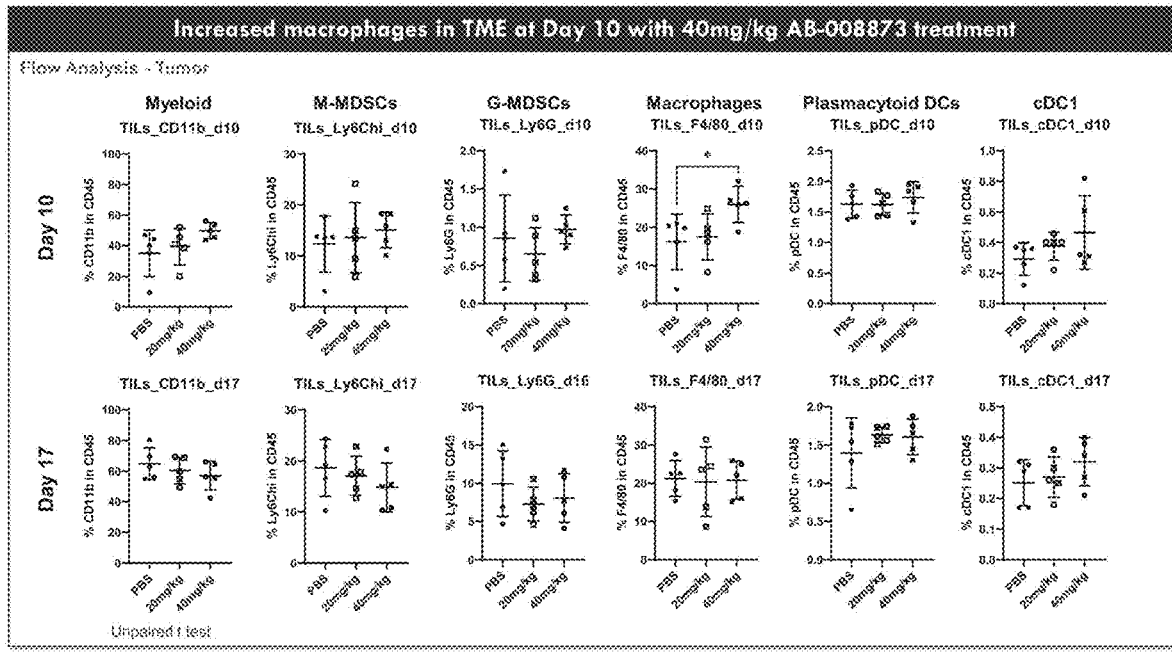
FIG. 12 shows increased macrophage numbers in TME at Day 10 with 40 mg/kg AB-008873 treatment.
Figure 17:
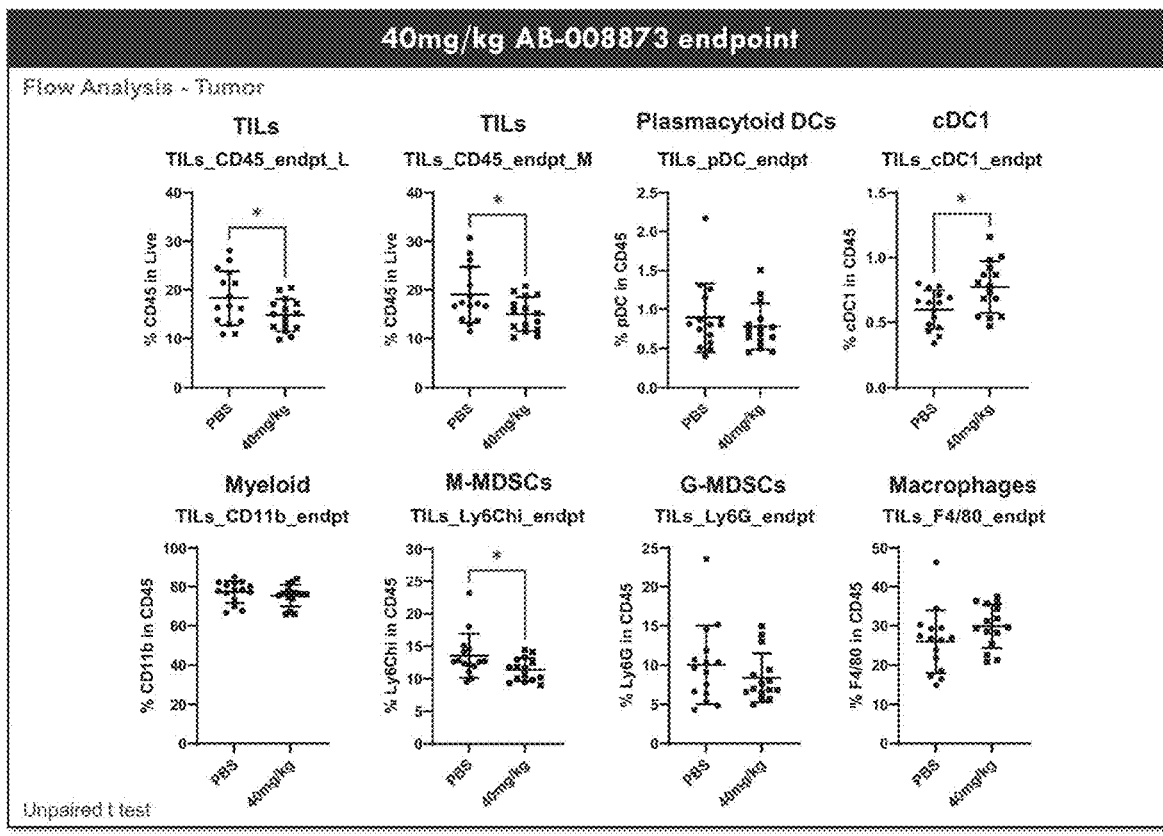
FIG. 17 shows flow cytometry analysis of total tumor-infiltrating leukocytes (TIL) and myeloid cells from tumors in mice inoculated with CT26 cells. The mice were treated with 40 mg/kg AB-008873 or PBS.
Figure 18:
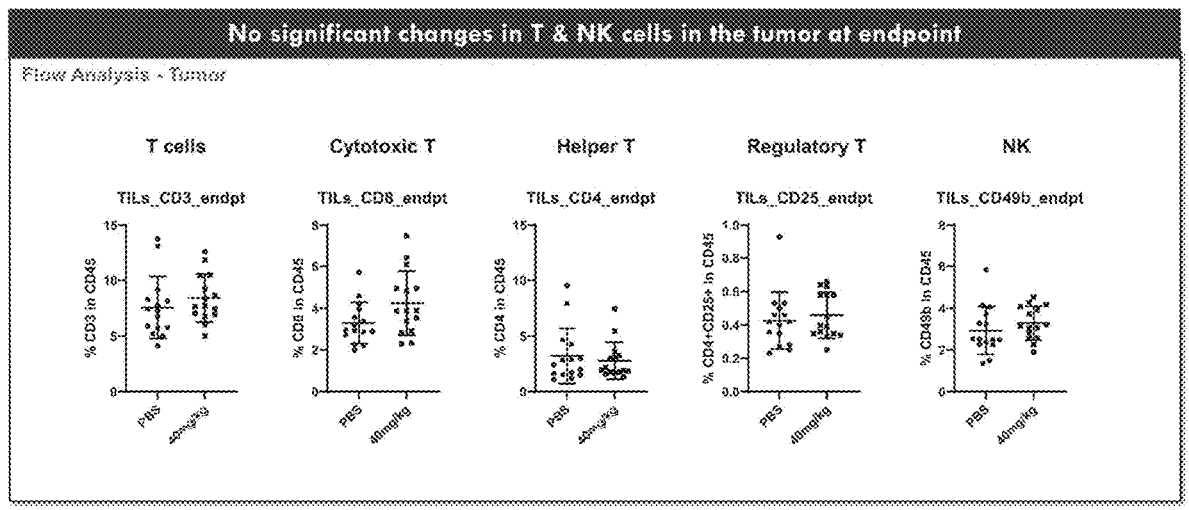
FIG. 18 shows flow cytometry analysis of lymphoid cells from tumors in mice inoculated with CT26 cells. The mice were treated with 40 mg/kg AB-008873 or PBS.

Tumors treated with AB-008873 showed no significant changes in the percentage of tumor infiltrating leukocytes (TILs) by flow cytometer at days 10 and 17 post inoculation compared to PBS treated controls. FIG. 10. Similarly, no significant changes in T cells, NK cells, monocytes/M-MDSCs, granulocytes/G-MDSCs was detected in the tumor at days 10 and 17 (FIG. 11 and FIG. 18) while total macrophages were increased at day 10 in mice treated with 40 mg/kg AB-008873. Tumors collected at endpoint and treated with 40 mg/kg AB-008873 show possible signs of decreased TILs, M-MDSCs, and slight increases in cDC1. FIG. 12 and FIG. 17.

Binding Assays

Flow Screen (In Vitro) Method:

Surface binding of the antibodies to in vitro grown cell lines was assessed by flow cytometry. Tumor cells were detached from their culture plate using Versene and counted. Cells were staining in BSA-containing buffer with primary antibody for 30 minutes at 4° C. with shaking. Following, cells were washed and stained with secondary PE-labeled antibody for 30 minutes at 4° C. with shaking. Before analysis on an Intellicyt iQue3 scanner, cells were counterstained with DAPI. MedFI values from live, single cells was expressed as fold over isotype control.

Flow Screen (Ex Vivo) Method:

AB-008873 was conjugated using Thermo's SiteClick™ R-PE Antibody Labeling Kit for testing on dissociated CT26 ex vivo cells. Dissociated cells were thawed and cells were blocked with TruStain FcX™ (anti-mouse CD16/32) Antibody and stained with PE-conjugated antibodies and CD45-BV605 for 30 min at 4° C. Cells were washed 3 times with 200 ul 1% FBS/1 mM EDTA/PBS and resuspended in assay buffer containing DAPI. Cells were analyzed using the Cytoflex and FlowJo_v10.7.1.

Surface binding of AB-008873 on a number of in vitro mouse and human tumor cell lines was assessed using flow cytometry. Among the cell lines screened, AB-008873 show binding on 786-O, A375, A549, H522, LoVo, MDA-MB-231, PC3, RKO, SKOV3, SW1116, and CT26. Additionally, AB-008873 bound CT26 ex vivo cells. FIG. 1, Tables 23 and 24.

TABLE 23

Surface binding profile of AB-008873 in human cell lines
Secondary Screens: In Vitro Cell Lines
Flow-Based Binding Assay

| 293T | 786O | A375 | A549 | BT474 | COLO205 | H522 | LoVo | MDAMB231 | PC3 | RKO | SKBR3 | SKMEL28 | SKOV3 | SW1116 | T84 |
|---|---|---|---|---|---|---|---|---|---|---|---|---|---|---|---|
| 2 | 3 | 2 | 3 | 0 | 0 | 3 | 3 | 3 | 4 | 4 | 0 | 0 | 3 | 2 | 1 |

TABLE 24

Surface binding profile of AB-008873 in mouse cell lines
Secondary Screens: In Vitro Cell Lines
Flow-Based Binding Assay

| CT26 | EMT6 | MC38 | RENCA |
|---|---|---|---|
| 2.66667 | 0.2 | 0 | 0 |

ADCC

For Antibody-dependent cellular cytotoxicity (ADCC), KILR™-transfected target cells were opsonized with different concentrations of the antibody at room temperature for 20 minutes. Following, NK92 cells carrying a mouse extracellular-human intracellular CD16 chimera were added at a 5:1 ratio of effector to target cells. After a 4 h co-culture at 37° C. and 5% $CO_2$, pre-mixed KILR™ detection reagent was added to each well at equal volume and allowed to incubate for 30 min at room temperature in the dark before reading luminescence on a pate reader. Cytotoxicity was calculated after background (spontaneous release) subtraction and expressed as percent of a maximum lysis control.

ADCC activity of AB-008873 was assessed on a number of in vitro human and mouse tumor cell lines. Among the cell lines screened, AB-008873 showed dose-dependent ADCC on A549, MDA-MB-231, CT26, and to a small extent EMT6. AB-008873 did not show any ADCC up to 100 nM on SKBR3. FIGS. 2A-2B and Table 25.

TABLE 25

Results of assessing the ADCC activity (FIG. 2A) and ADCP activity (FIG. 2B) of AB-008873 in vitro functional assays.

|  | n | EC50 (nM) | Delta Toxicity (%) | NAUC (%) |
|---|---|---|---|---|
| A549 | 15 | 15.3 ± 11.8 | 37.8 ± 19.2 | 30.7 ± 13.1 |
| MDAMB231 | 2 | 18.7 ± 1.4 | 53.2 ± 5.7 | 17.1 ± 1.7 |
| SKBR3 | 2 | >100 | 0 | 0 |
| CT26 | 4 | 10.2 ± 9.5 | 37.5 ± 5.9 | 52.6 ± 15.4 |
| EMT6 | 2 | >100 | 15.1 ± 10.6 | 7.9 ± 4.9 |

Note:
Table 25 summarizes the results in FIG. 2A. The values are shown as mean + SD.
N = number of biological replicates;
delta toxicity (%) = difference between lower and upper plateau of the sigmoidal dose response curve;
NAUC (%) = Normalized Area Under the Curve, internal metric quantifying area under the curve of the sigmoidal dose response normalized to a known positive control.

Antibodies derived from the same lineage as AB-008873 (sibling antibodies) were tested for binding and for ADCC and ADCP activity on tumor cell line A549. Compared with AB-008873, all sibling antibodies showed less potent and less maximum binding and less ADCC and ADCP activity. Out of the sibling antibodies, AB-009806 showed the best binding and functional activity, followed by AB-009805. AB-009807 and AB-009808 showed little binding and ADCC activity but some ADCP activity. FIG. 20.

Engineered variant antibodies of AB-0008873 were tested for binding and for ADCC activity on tumor cell line A549. Compared with AB-008873, AB-009815 and AB-009816 showed similar levels of binding and ADCC activity as AB-008873. AB-009812 and AB-009813 showed weaker binding and ADCC activity, followed by AB-009814. AB-009817 did not show any substantial binding or ADCC activity on A549 up to 100 nM. FIG. 21.

Figure 40:
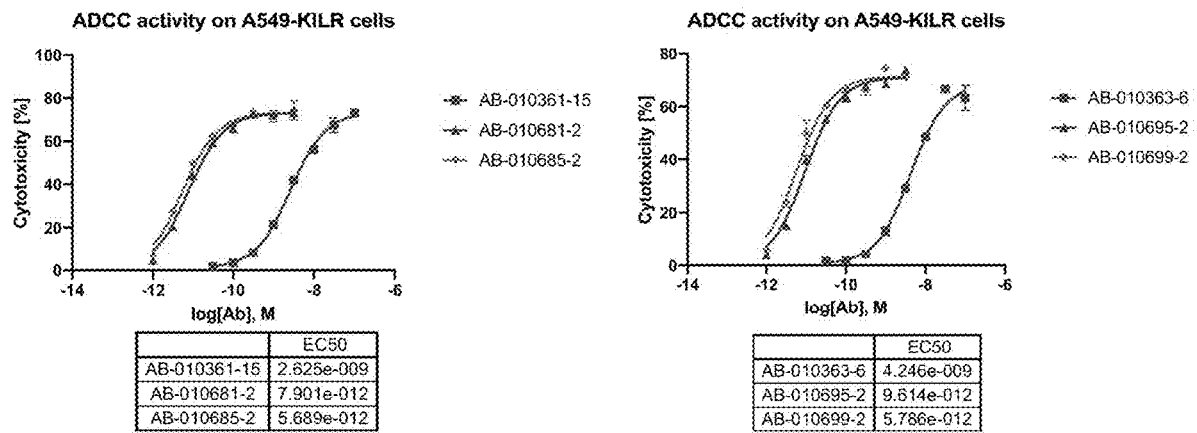
FIG. 40 compares the ADCC activity of a number of anti-EphA2 antibodies AB-010361 ("AB-010361-15"), AB-010681 ("AB-010681-2"), and AB-010685 ("AB-010681-2") on A549 cells.
Figure 41:
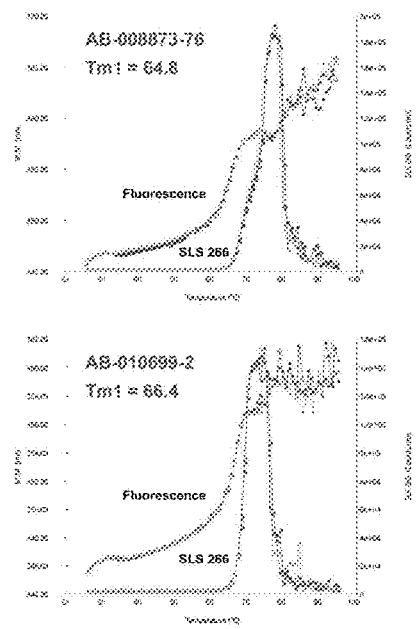
FIG. 41 shows the results of thermostability analysis of the anti-EphA2 antibodies AB-008873 and AB-010699.

AB-010357, AB-010361, and AB-010363 and variants (Table 27) based on those antibodies exhibited ADCC activity greater than AB-008873 on the tumor cell line A549. All of the variants tested exhibited ADCC activity at least as good as their parental antibody. Many variants showed a 10-to-100-fold increase in potency as compared to their parent, with some variants showed a greater than 700-fold increase. AB-010685, AB-010671, and AB-010699 had EC50s under these assay conditions of approximately 6 pM. AB-010681 and AB-010695 had EC50s of approximately 8 pM and 10 pM, respectively. FIG. 40 and Table 26. It is notable that both AB-010685 and AB-010699 have the same double mutations L29SY and L92SH. See Table 28.

TABLE 26

ADCC of anti-EphA2 antibodies

| | | ADCC-EC50 (nM) | | ADCC-dAct rel. parent (%) | |
|---|---|---|---|---|---|
| AB ID | Mutations | Trial 1 | Trial 2 | Trial 1 | Trial 2 |
| AB-008873 | N/A | 24 | | | |
| AB-010357 | | 12.3 | 9.6 | 100.0 | 100.0 |
| AB-010661 | 10357_H107TI_L23GR | 5.7 | | 160.1 | |
| AB-010662 | 10357_L23GR_L29SY | 0.57 | | 166.4 | |
| AB-010663 | 10357_L23GR_L30KM | 4.7 | | 163.1 | |
| AB-010664 | 10357_L23GR_L92SH | 0.54 | | 167.7 | |
| AB-010665 | 10357_H107TI_L29SY | ~0.23 | 0.14 | 177.0 | 120.5 |
| AB-010666 | 10357_L29SY_L30KM | ~0.19 | 0.16 | 193.7 | 132.8 |
| AB-010667 | 10357_L29SY_L92SH | <0.03 | 0.012 | 154.8 | 108.9 |
| AB-010668 | 10357_H107TI_L30KM | 3.7 | | 162.9 | |
| AB-010669 | 10357_L30KM_L92SH | 0.44 | | 177.7 | |
| AB-010670 | 10357_H107TI_L92SH | 0.36 | | 178.2 | |
| AB-010671 | 10357_H107TI_L29SY_L92SH | <0.03 | 0.0064 | 157.1 | 106.7 |
| AB-010672 | 10357_L93SR | 12.4 | | 162.9 | |
| AB-010673 | 10357_L93SE | 3.9 | | 166.4 | |
| AB-010674 | 10357_L29SY_L93SE | ~0.13 | 0.10 | 171.2 | 97.2 |
| AB-010361 | | 4.0 | 2.2 | 100.0 | 100.0 |
| AB-010675 | 10361_H107TI_L23GR | 1.5 | | 122.5 | |
| AB-010676 | 10361_L23GR_L29SY | ~0.1 | 0.039 | 121.6 | 88.7 |
| AB-010677 | 10361_L23GR_L30KM | 1.6 | | 165.5 | |
| AB-010678 | 10361_L23GR_L92SH | ~0.14 | 0.047 | 154.2 | 93.9 |
| AB-010679 | 10361_H107TI_L29SY | ~0.15 | 0.040 | 171.5 | 102.9 |
| AB-010680 | 10361_L29SY_L30KM | ~0.081 | 0.031 | 161.1 | 106.1 |
| AB-010681 | 10361_L29SY_L92SH | <0.03 | 0.0079 | 152.1 | 104.6 |
| AB-010682 | 10361_H107TI_L30KM | 3.2 | | 147.9 | |
| AB-010683 | 10361_L30KM_L92SH | ~0.14 | 0.046 | 174.8 | 100.0 |
| AB-010684 | 10361_H107TI_L92SH | ~0.14 | 0.048 | 166.6 | 115.4 |
| AB-010685 | 10361_H107TI_L29SY_L92SH | <0.03 | 0.0057 | 161.1 | 106.4 |
| AB-010686 | 10361_L93SR | 6.4 | | 132.3 | |
| AB-010687 | 10361_L93SE | 2.8 | | 166.8 | |
| AB-010688 | 10361_L29SY_L93S | ~0.052 | 0.032 | 129.9 | 108.0 |
| AB-010363 | | 5.1 | 4.2 | 100.0 | 100.0 |
| AB-010689 | 10363_H107TI_L23R | 2.5 | | 88.0 | |
| AB-010690 | 10363_L23GR_L29S | 0.19 | | 112.4 | |
| AB-010691 | 10363_L23GR_L30K | 2.2 | | 85.3 | |
| AB-010692 | 10363_L23GR_L92S\ | 0.21 | | 105.0 | |
| AB-010693 | 10363_H107TI_L29 | 0.15 | | 129.0 | |
| AB-010694 | 10363_L29SY_L30K | 0.14 | | 131.3 | |
| AB-010695 | 10363_L29SY_L92SH | ~0.021 | 0.0096 | 148.3 | 118.8 |

TABLE 26-continued

ADCC of anti-EphA2 antibodies

| AB ID | Mutations | ADCC-EC50 (nM) Trial 1 | ADCC-EC50 (nM) Trial 2 | ADCC-dAct rel. parent (%) Trial 1 | ADCC-dAct rel. parent (%) Trial 2 |
|---|---|---|---|---|---|
| AB-010696 | 10363_H107TI_L30KM | 1.9 | | 114.7 | |
| AB-010697 | 10363_L30KM_L92SH | 0.30 | | 147.1 | |
| AB-010698 | 10363_H107TI_L92SH | 0.23 | | 142.1 | |
| AB-010699 | 10363_H107TI_L29SY_L92SH | ~0.014 | 0.0058 | 152.5 | 114.6 |
| AB-010700 | 10363_L93SR | 9.5 | | 75.7 | |
| AB-010701 | 10363_L93SE | 3.0 | | 99.2 | |
| AB-010702 | 10363_L29SY_L93SE | 0.065 | | 124.7 | |

TABLE 27

Sequence features of selected anti-EphA2 antibody variants

| | Variant based on AB-010357 | Variant based on AB-010361 | Variant based on AB-010363 |
|---|---|---|---|
| H107TI_L23GR | AB-010661 | AB-010675 | AB-010689 |
| L23GR_L29SY | AB-010662 | AB-010676 | AB-010690 |
| L23GR_L30KM | AB-010663 | AB-010677 | AB-010691 |
| L23GR_L92SH | AB-010664 | AB-010678 | AB-010692 |
| H107TI_L29SY | AB-010665 | AB-010679 | AB-010693 |
| L29SY_L30KM | AB-010666 | AB-010680 | AB-010694 |
| L29SY_L92SH | AB-010667 | AB-010681 | AB-010695 |
| H107TI_L30KM | AB-010668 | AB-010682 | AB-010696 |
| L30KM_L92SH | AB-010669 | AB-010683 | AB-010697 |
| H107TI_L92SH | AB-010670 | AB-010684 | AB-010698 |
| H107TI_L29SY_L92SH | AB-010671 | AB-010685 | AB-010699 |
| L93SR | AB-010672 | AB-010686 | AB-010700 |
| L93SE | AB-010673 | AB-010687 | AB-010701 |
| L29SY_L93SE | AB-010674 | AB-010688 | AB-010702 |

TABLE 28

Activities of anti-EphA2 antibodies

| Mutations | Variant based on AB-010357 EC50 (nM) | Variant based on AB-010361 EC50 (nM) | Variant based on AB-010363 EC50 (nM) |
|---|---|---|---|
| Parent (AB-010357, AB-010361, or AB-010363) | 10.95 | 3.1 | 4.65 |
| H107TI_L23GR | 5.7 | 1.5 | 2.5 |
| L23GR_L29SY | 0.57 | 0.039 | 0.19 |
| L23GR_L30KM | 4.7 | 1.6 | 2.2 |
| L23GR_L92SH | 0.54 | 0.047 | 0.21 |
| H107TI_L29SY | 0.14 | 0.04 | 0.15 |
| L29SY_L30KM | 0.16 | 0.031 | 0.14 |
| L29SY_L92SH | 0.012 | 0.0079 | 0.0096 |
| H107TI_L30KM | 3.7 | 3.2 | 1.9 |
| L30KM_L92SH | 0.44 | 0.046 | 0.30 |
| H107TI_L92SH | 0.36 | 0.048 | 0.23 |
| H107TI_L29SY_L92SH | 0.0064 | 0.0057 | 0.0058 |
| L93SR | 12.4 | 6.4 | 9.5 |
| L93SE | 3.9 | 2.8 | 3.0 |
| L29SY_L93SE | 0.10 | 0.032 | 0.065 |

AB-010699 and AB-010361 exhibited greater ADCC activity on A549 cells than AB-010018, while both AB-010699 and AB-010695 were more toxic than cetuximab on A549 cells. FIGS. 50A and 50B. AB-010699 showed several thousand-fold higher ADCC activity on A549 cells and higher thermostability (as reflected in a 2.0° C. higher Tm1) as compared to AB-008873. AB-010685 was also highly potent on PC3-KILR cells and exhibited a 10-fold improvement in ADCC as compared to AB-010018. FIG. 52.

ADCP

For antibody-dependent cellular phagocytosis (ADCP), the cell membrane of a target cell was labeled with green fluorescent membrane dye preceding opsonization with different concentrations of antibody at room temperature for 30 minutes. RAW264.7 mouse macrophage (effector) cells were then added at a 1:1 ratio with the target cells and co-cultured at 37° C. and 5% $CO_2$ for 2 hours. After incubation, the cell mixture was dissociated with 2 mM ethylenediaminetetraacetic acid (EDTA, pH 7.4). The cell suspension was then washed several times in an isotonic salt solution and probed with a commercially available anti-CD11b antibody, conjugated with Allophycocyanin (APC). After a 30-minute incubation at 4° C. with this antibody, the cell suspension was washed again before being analyzed by flow cytometry. Cytotoxicity was calculated as the fraction of effector cells recorded that also displayed signal for green fluorescent dye and was expressed as a percentage of the total effector cell population.

The activity of AB-008873 was tested on A549 and CT26 cells. The results, as shown in FIG. 2B, demonstrated dose-dependent activity in both of these models.

AB-008873 was tested for ADCP activity on A549 cells alongside its siblings. All siblings showed reduced activity compared to AB-008873. FIG. 20.

ADC

AB-008873 was tested for its antibody-drug conjugate activity using a secondary, toxin-conjugated antibody. In brief, target cells were detached from the culture plate and cell concentration was adjusted to 31,250 cells/mL in assay media. 2,500 cells were added to each well of a 96 well plate and incubated with different concentrations of primary antibody for 15 min at room temperature. Following, secondary Fab anti-mouse IgG Fc conjugated to Duocarmycin with a cleavable linker (Moradec, #AM-202-DD) was added at a final concentration of 250 ng/mL. Cells were incubated for 72 h at 37° C. and 5% $CO_2$. At the end of the incubation period, 100 µl CellTiter-Glo® was added to each well and allowed to incubate for 5-10 min at room temperature before reading luminescence in a BMG ClarioSTAR plate reader. Data was then normalized to a maximum lysis control and plotted using graph pad prism.

Figure 3:
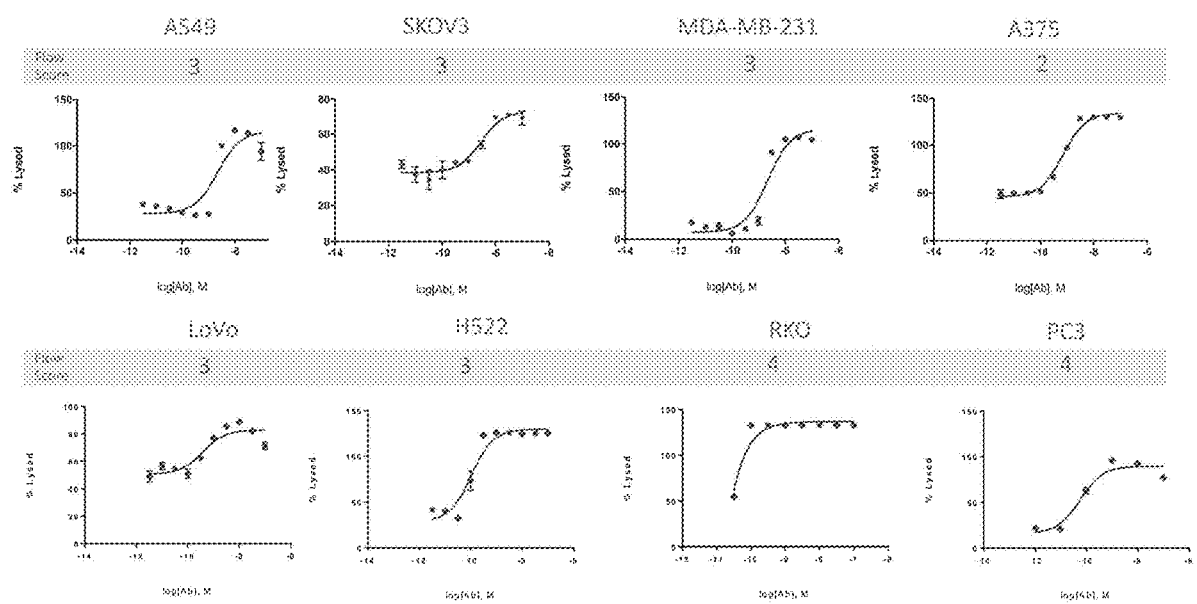
FIG. 3 shows the ADC activity of AB-008873 on in vitro cell lines.

The ADC activity of AB-008873 was assessed on a number of in vitro human and mouse tumor cell lines. Among the cell lines screened, AB-008873 showed dose dependent ADC on A549, SKOV3, MDA-MB-231, A375, LoVo, H522, RKO, and PC3. As shown in FIG. 3, AB-008873 demonstrated ADC activity on these tumor cells.

The ADC activity of AB-008873 was compared to the engineered variant AB-009815 (H76PT mutation) on H522, LoVo, A375, SKOV3, A549, and MDA-MB-231 cells. AB-009815 showed similar activity compared to AB-008873 in all cell lines tested. As shown in FIG. 35 show that the ADC activity of AB-009815 is substantially identical to AB-008873 on these tumor cells.

Figure 51:
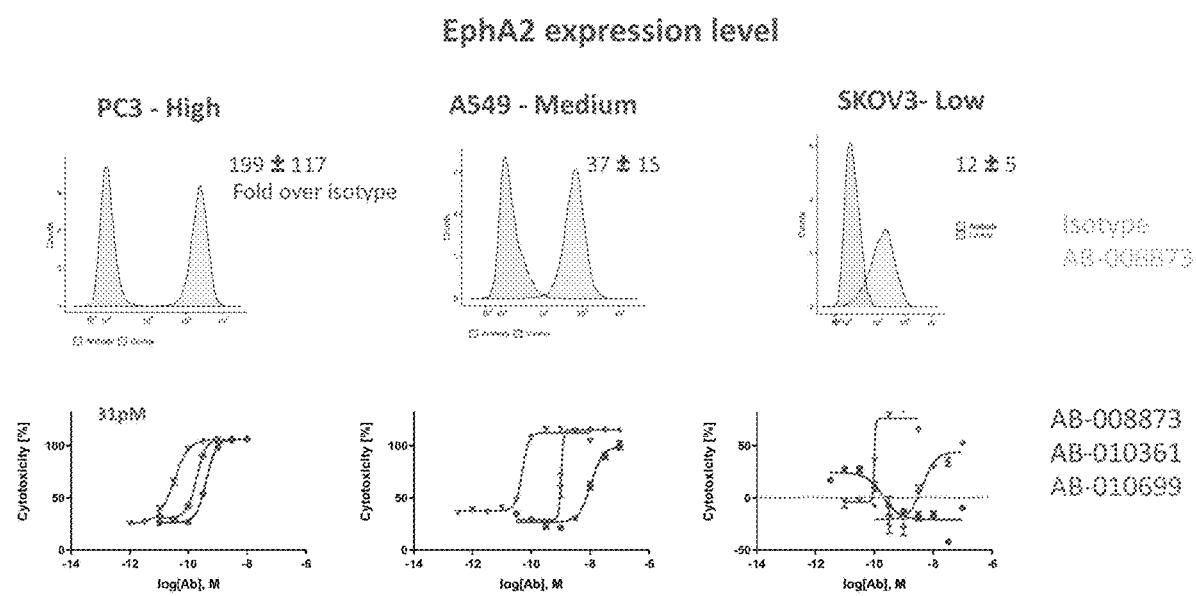
FIG. 51 compares the cytotoxicity of AB-008873, AB-010361, and AB-010699 in an ADC assay.

The ADC activity of AB-010361 and AB-010699 was assayed as described above and was compared to that of AB-008873, with the results shown in FIG. 51. Both AB-010361 and AB-010699 had similar ADC activity as AB-008873 in cells expressing high levels of EphA2 and exhibited enhanced ADC activity in cells expressing low levels of EphA2.

Thermostability

AB-010357, AB-010361, and AB-010363 and variants based on those antibodies were assayed for thermostability using an Unchained Labs UNcle instrument. The concentration of purified antibodies was adjusted as needed to between 0.2 mg/ml and 0.5 mg/ml in PBS immediately prior to analysis. To determine melting temperature (Tm) intrinsic protein fluorescence was measured at 473 nm every 1.1° C. as temperature was increased linearly from 25° C. to 95° C. at a rate of 0.3° C./min. The UNcle Analysis software (version 4.01) was used to find the Tm as the first derivative of the barycentric mean (BCM). All antibodies tested were at least as stable as AB-008873, with AB-010363 and variants thereof exhibiting improved thermostability as indicated by the increased Tm1. Table 29 provides thermostability of anti-EphA2 antibodies.

TABLE 29

Thermostability of anti-EphA2 antibodies

| Mutations | Variant based on AB-010357 Average Tm1 (° C.) | Variant based on AB-010361 Average Tm1 (° C.) | Variant based on AB-010363 Average Tm1 (° C.) |
|---|---|---|---|
| Parent (AB-010357, AB-010361, or AB-010363) | 64.8 | 64.7 | 68.0 |
| H107TI_L23GR | 66.7 | 65.5 | 66.5 |
| L23GR_L29SY | 64.7 | 65.5 | 66.4 |
| L23GR_L30KM | 64.5 | 64.7 | 67.0 |
| L23GR_L92SH | 64.4 | 64.1 | 65.8 |
| H107TI_L29SY | 64.3 | 63.6 | 65.8 |
| L29SY_L30KM | 64.5 | 63.9 | 65.7 |
| L29SY_L92SH | 64.0 | 64.4 | 65.9 |
| H107TI_L30KM | 64.5 | 64.4 | 66.8 |
| L30KM_L92SH | 64.5 | 64.2 | 66.5 |
| H107TI_L92SH | 65.0 | 64.4 | 66.9 |
| H107TI_L29SY_L92SH | 64.9 | 64.2 | 66.4 |
| L93SR | 64.7 | 65.2 | 66.8 |
| L93SE | 65.3 | 64.9 | 67.7 |
| L29SY_L93SE | 64.9 | 64.5 | 66.7 |

Example 4. In Vivo Studies

Tumor Cell Implantation/Inoculation

Mouse CT26 tumor cells were propagated in culture by passaging cells every 2 to 3 days (1:10 subcultures) for 6 passages. On the day of inoculation, cells were collected, counted, and diluted to $5 \times 10^6$ cells/mL in RPMI medium without supplements. Cell viability was recorded as 86.8% at time of inoculation.

Female, 6-week-old BALB/c mice were inoculated in the right hind flank by subcutaneous injection with $1 \times 10^6$ CT26 cells/mouse in 0.2 mL Waymouth's media without supplements. The day of cell inoculation was designated as Study Day 0.

Randomization

Mice were inoculated with CT26 tumor cells on Study Day 0. To achieve study groups with consistent and homogenous tumor volumes an overage of approximately 50% was included. Mouse tumors routinely became visible and palpable five days after cell inoculation. Tumor volumes were measured twice prior to randomization. On Study Day 9, mice were randomized to ensure homogenous tumor volumes using the 'matched distribution' randomization function of the StudyLog lab animal management software. Mice with pre-ulcerated tumors, irregular shaped tumors, or multiple tumors were excluded from randomization. Animal IDs were assigned randomly within each treatment group on the day of randomization.

Test Article Dosing

Test article AB-008873 was administered starting on Day 8 by intraperitoneal (IP) injection twice weekly at 20 or 40 mg/kg based on group mean body weight. Mice received either 1 or 3 doses before they were removed from study for analysis two days after dosing (Day 10 or Day 17, respectively).

Mice in the vehicle control groups were dosed at 10 mL/kg DPBS based on group mean body weight using the same dosing schedule as the test article.

Termination

Mice were euthanized by carbon dioxide asphyxiation followed by cervical dislocation or by isoflurane inhalation and cardiac puncture followed by cervical dislocation at predetermined time points (i.e., Day 10 or Day 17).

A number of assays were performed to analyze the effect of the antibody. Flow cytometry was used to analyse the immune profiling of the blood and tumor. Tumor volume was measured. Immunofluorescence is used to semi-quantitative estimates of tumor infiltrates using immunofluorescence.

Tissue Harvest for Immunofluorescence

Mice were euthanized by carbon dioxide asphyxiation followed by cervical dislocation. Tumors were excised from the mice, weighed, and placed in pre-filled tubes containing 10% neutral buffered formalin (Caplugs). Tumors were fixed for 24 hours at room temperature and then transferred to 80% ethanol prior to slicing and embedding in paraffin.

Immunofluorescence Analysis

Tumor Processing for Immunofluorescence Analysis

Figure 7:
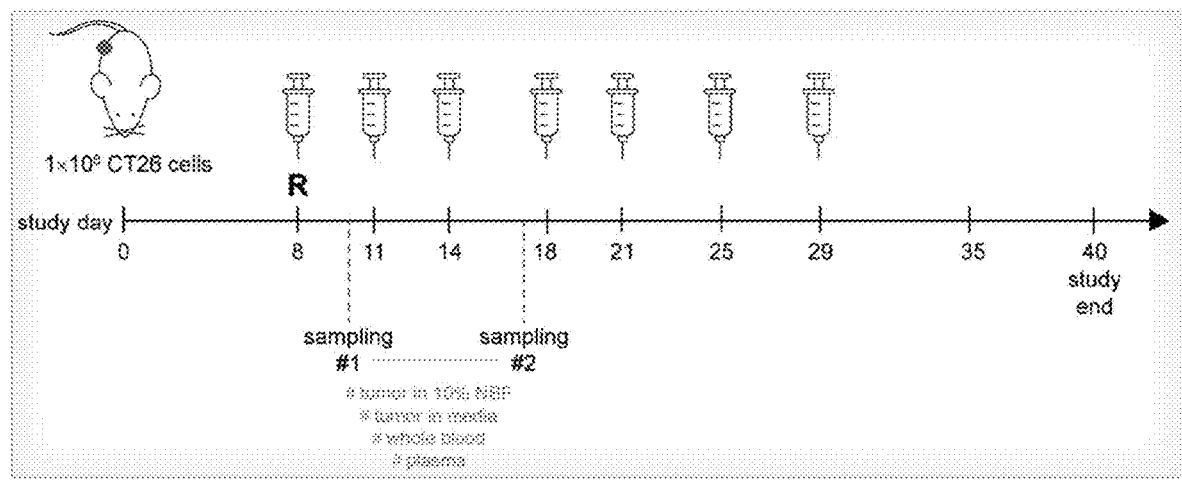
FIG. 7 shows the design of an in vivo study to assess the effect of the AB-008873 treatment.

Each fixed tumor was dissected using a slicer matrix with 2.0 or 3.0 mm section slide intervals (Zivic 5526 or 5527), to allow for assessment of tumor microenvironment at 3 to 6 evenly spaced locations to account for tumor heterogeneity. The resultant tissue slices from each tumor were placed in tissue cassettes (up to three tumors in one cassette; including a piece of mouse spleen as a landmark for orientation) and subsequently processed in graded alcohols and xylene and embedded in paraffin per manufacturer's instructions using a Tissue Tek VIP® 6 AI Vacuum Infiltration Processor (Sakura) and Tissue-Tek® TEC™ 5 embedding console system (Sakura). Blocks containing tumors were sectioned at 5 μm using a Accu-Cut® SRM™ 200 Rotary Microtome (Sakura). Sections were mounted to slide and dried. In one exemplary procedure, samples (e.g., tumor samples) were sectioned by longitudinal slicing into 2 or 3 mm thick slices using a mold. Sections are then embedded face down for examination. This approach is ideal for assessing infiltrates across the tumor and fitting multiple tumors per block. FIG. 7 and Table 30 show the procedures and reagents used in an in vivo study to assess the effect of the AB-008873 treatment to mice.

TABLE 30

Reagents and dosing information

| n | Test Art. | Lot# | dose level (mg/kg) | Dose Freq. | # of Doses | Route | MODEL |
|---|---|---|---|---|---|---|---|
| 15 | AB-008873 | 2 | 40 | 2/Wk | 7 | i.p. | CT26 |
| 15 | PBS | 12620008 | 0 | 2/Wk | 7 | i.p. | CT26 |

TABLE 30-continued

Reagents and dosing information

| n | Test Art. | Lot# | dose level (mg/kg) | Dose Freq. | # of Doses | Route | MODEL |
|---|---|---|---|---|---|---|---|
| 5 | AB-008873 | 2 | 20 | 2/Wk | 1 | i.p. | CT26 |
| 5 | AB-008873 | 2 | 40 | 2/Wk | 1 | i.p. | CT26 |
| 5 | PBS | 12020008 | 0 | 2/Wk | 1 | i.p. | CT26 |
| 5 | AB-008873 | 2 | 20 | 2/Wk | 3 | i.p. | CT26 |
| 5 | AB-008873 | 2 | 40 | 2/Wk | 3 | i.p. | CT26 |
| 5 | PBS | 12620008 | 0 | 2/Wk | 3 | i.p. | CT26 |

Immunofluorescence Staining

Immunofluorescence staining was performed on 5 μm formalin-fixed paraffin-embedded tissue sections of mouse CT26 tumors following standard immunostaining protocols. The primary antibodies were utilized with species-specific secondary antibodies and detected using standard tyramide signaling amplification methodology.

The tissue sections were baked at 65° C. for 30 minutes, dewaxed in xylene and rehydrated. Antigen retrieval was performed under high pressure either at 95° C. for 20 minutes or 110° C. for 15 minutes using Target Retrieval Solution (Dako) in Decloaking Chamber NxGen (Biocare Medical). The sections were blocked for 15 minutes at room temperature with Bloxall (Vector Labs).

T Cell Marker Protocol

Dual labeling for cytotoxic T cells ("$T_{cyt}$ cells", which are CD3+CD8+) and regulatory T cells ($T_{reg}$ cells, i.e., CD4+/ forkhead-box protein P3; FoxP3+) populations was performed as follows. Following antigen retrieval and blocking with Bloxall, tissue sections were blocked in blocking buffer (3% bovine serum albumin with 3% normal donkey serum in 1× phosphate-buffered saline) for 30 minutes or 1 hour at room temperature. After blocking, the slides were incubated with primary antibodies against CD8 for 1 hour at room temperature, FoxP3 overnight at 4° C., or with species-appropriate isotype controls at corresponding times and temperatures. The slides were subsequently washed with Wash Buffer (Thermo-Fisher Scientific), incubated with species-specific secondary PowerVision Poly-HRP (Leica) for 30 minutes at room temperature followed by incubation with CF Tyramide 647 (for CD8) or 488 (for FoxP3) Working Solution (Biotium) for 3 minutes at room temperature, respectively.

To provide signal in distinct channels for the second primary antibody, elution immunofluorescence was utilized through pressure and heat application. After washing and block steps, the second primary antibody against CD3 and CD4 or species-appropriate isotype control was applied to sections as describe in the previous paragraph. The slides were subsequently washed with Wash Buffer (Thermo-Fisher Scientific), incubated with species-specific secondary PowerVision Poly-HRP (Leica) for 30 minutes at room temperature followed by incubation with CF Tyramide 488 (for CD3) or 647 (for CD4) Working Solution (Biotium) for 3 minutes at room temperature, respectively.

All tissue slides were counterstained with Hoechst dye, mounted in PermaFluor Aqueous Mounting Medium (ThermoFisher Scientific), and coverslipped. Images were acquired using an AxioScan whole slide scanner (Carl Zeiss Microscopy).

Dendritic Cell Marker Protocol

Dual labeling for dendritic cells (DC cells, i.e., CD3-CD103+) populations was performed as follows. Following antigen retrieval and blocking with Bloxall, tissue sections were blocked in blocking buffer (3% bovine serum albumin with 3% normal donkey serum in 1× phosphate-buffered saline) for 30 minutes or 1 hour at room temperature. After blocking, the slides were incubated with the primary antibody against CD103 for 1 hour at room temperature or with the species-appropriate isotype control at corresponding time and temperature. The slides were subsequently washed with Wash Buffer (Thermo-Fisher Scientific), incubated with species-specific secondary Power Vision Poly-HRP (Leica) for 30 minutes at room temperature followed by incubation with CF Tyramide 488 (for CD103) Working Solution (Biotium) for 3 minutes at room temperature.

To provide signal in distinct channels for the second primary antibody, elution immunofluorescence was utilized through pressure and heat application. After washing and block steps, the second primary antibody against CD3 or species-appropriate isotype control was applied to sections and incubated overnight at 4° C. The slides were subsequently washed with Wash Buffer (Thermo-Fisher Scientific), incubated with species-specific secondary PowerVision Poly-HRP (Leica) for 30 minutes at room temperature followed by incubation with CF Tyramide 647 (for CD3) Working Solution (Biotium) for 3 minutes at room temperature.

All tissue slides were counterstained with Hoechst dye, mounted in PermaFluor Aqueous Mounting Medium (ThermoFisher Scientific), and coverslipped. Images were acquired using an AxioScan whole slide scanner (Carl Zeiss Microscopy).

Macrophage Marker Protocol

Following antigen retrieval and blocking with Bloxall, tissue sections were successively blocked for 15 minutes with Avidin block (Biocare), Biotin block (Biocare), and blocking buffer (3% bovine serum albumin with 3% normal donkey serum in 1×PBS) for 1 hour at room temperature. After blocking, the slides were incubated with primary antibodies against F4/80 and inducible nitric oxide synthase (iNOS), F4/80 and Arginase-1 (Arg-1), or species-appropriate isotype controls overnight at 4° C. The next day, slides were washed with Wash Buffer (Thermo-Fisher Scientific), incubated for 30 minutes at room temperature with species-specific (for F4/80 and IgG) secondary antibody conjugated to biotin and then 5 minutes at room temperature with Streptavidin Conjugate CF® 647 Working Solution (Biotium). The slides were subsequently washed twice with Wash Buffer, incubated with species-specific (for iNOS/Arg-1 and IgG) secondary PowerVision Poly-HRP for 30 minutes at room temperature followed by incubation with CF Tyramide 488 Working Solution (Biotium) for 3 minutes at room temperature.

All tissue slides were counterstained with Hoechst dye, mounted in PermaFluor Aqueous Mounting Medium (ThermoFisher Scientific), and coverslipped. Images were acquired using an AxioScan whole slide scanner (Carl Zeiss Microscopy).

Algorithm-Based Digital Image Analysis

Positive immunoreactivity was assessed by analyzing whole slide images (Zeiss AxioScan) using Indica Labs HALO software through application of the HighPlex FL v3.2.1 algorithm to identify the double positive cell populations (Table 31). For each of the two to six tumor tissue sections per tumor, regions of interest were manually annotated, while peripheral tissues such as skin, adipose, and connective tissues as well as tissue folds and other artifacts were excluded. Individual cells were detected based on HOECHST nuclear stain. Detection thresholds for fluorescent signals were adjusted based on antibody-specific signal strength and nonspecific background signal for each experiment. Cell count estimates were determined for each tumor and normalized to cell counts observed in the corresponding IgG antibody control-stained tumor.

TABLE 31

Marker Phenotype for Immune Cell Subsets

| Cell Type | Marker Phenotype |
|---|---|
| $T_{cyt}$ cells | $CD3^+ CD8^+$ |
| $T_{reg}$ cells | $CD4^+ FoxP3^+$ |
| Dendritic cells | $CD3- CD103+$ |
| M1 macrophages | $F4/80^+ iNOS^+$ |
| M2 macrophages | $F4/80^+ Arg-1^+$ |

Figure 9:
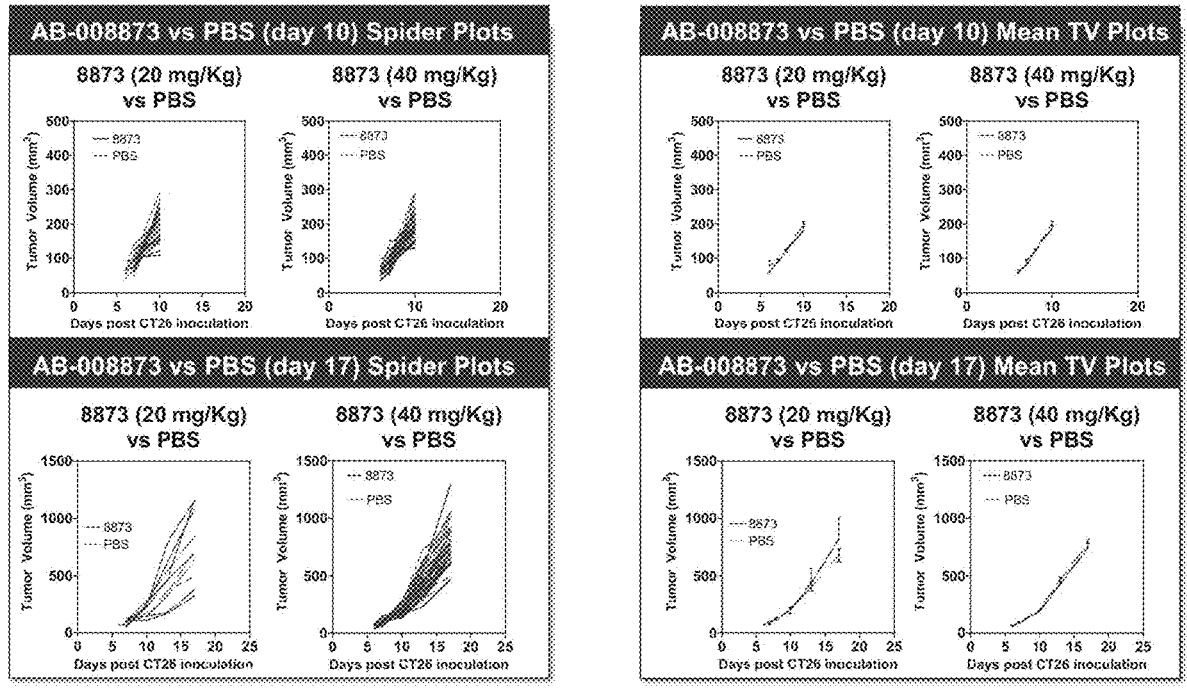
FIG. 9 shows the effects on tumor growth of treatment of AB-008873 on mice inoculated with CT26 cells.
Figure 13:
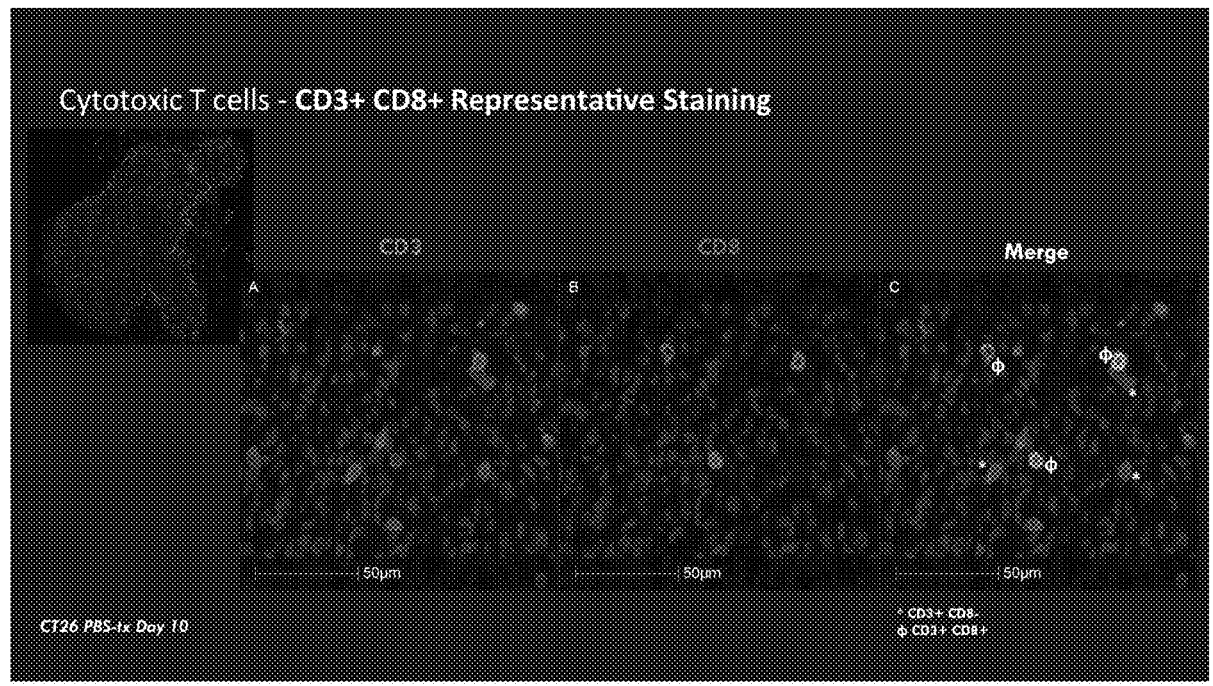
FIG. 13 shows representative CD3+ CD8+ staining of cytotoxic T cells.
Figure 14:
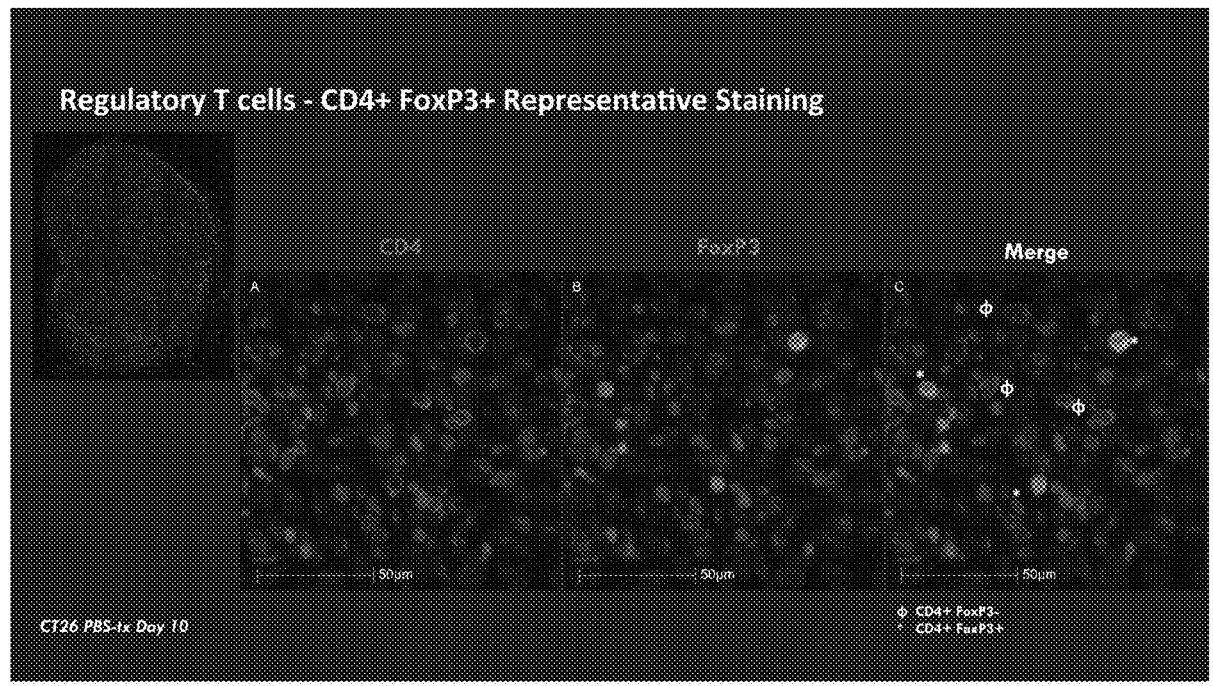
FIG. 14 shows representative CD4+ FoxP3+ staining of regulatory T cells.
Figure 15:
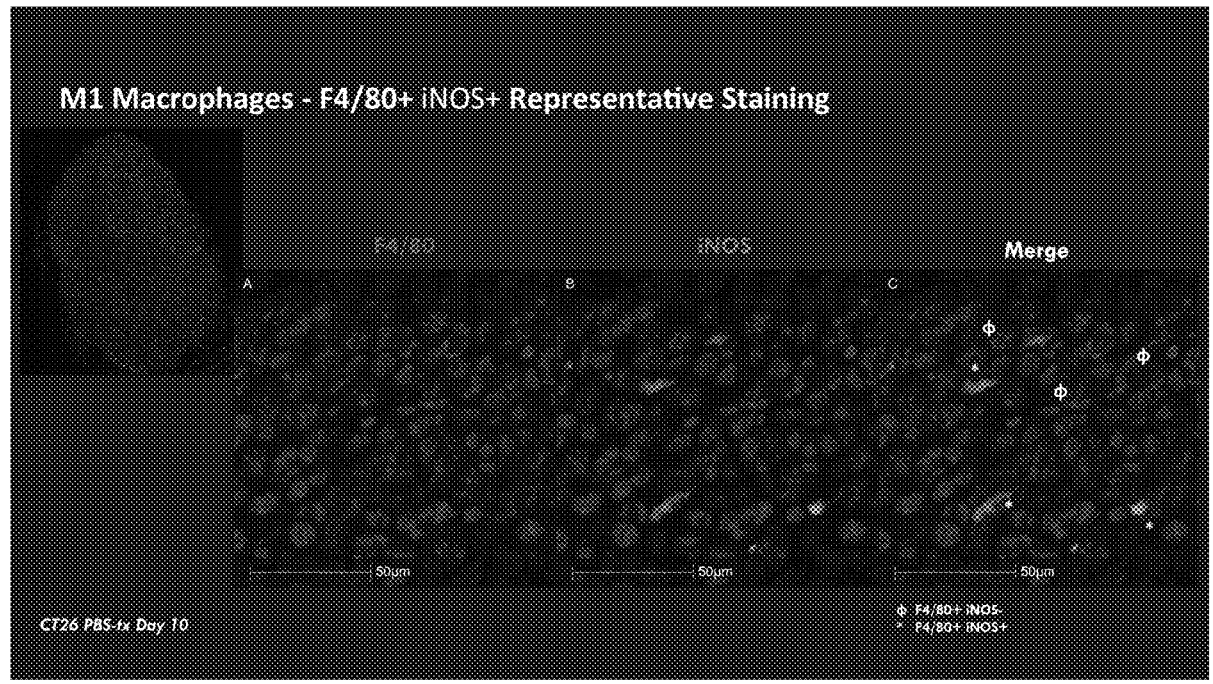
FIG. 15 shows representative F4/80+ iNOS+ staining on M1 macrophages.
Figure 16:
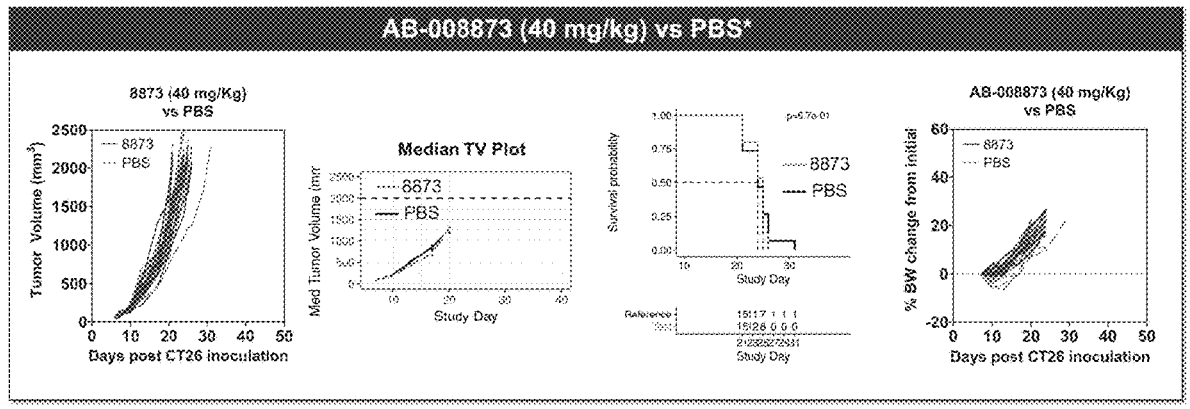
FIG. 16 shows the effect of administration of 40 mg/kg AB-00 8873 on tumor growth and body weight in mice inoculated with CT26 cells (murine colon carcinoma cells).

Arg-1 = arginase-1;
CD = cluster of differentiation;
FoxP3 = forkhead-box protein P3;
iNOS = inducible nitric oxide synthase;
M1 = M1-type (classically activated) macrophage;
M2 = M2-type (alternatively activated) macrophage;
$T_{cyt}$ cell = cytotoxic T cell;
$T_{reg}$ cell = regulatory T cell Results A significant increase in CD3+ and CD4+ cell populations with a concomitant decrease in Treg cells was observed in CT26 tumors from mice treated with 40 mg/kg AB-008873 vs PBS by 10 days after administration of the antibody. FIGS. 13-15. By Day 17, a significant increase in cytotoxic T cells and M1 macrophages (i.e., pro-inflammatory macrophages) were noted in CT26 tumors from mice treated with AB-008873 vs. PBS. The results are summarized in Tables 32 and 33. AB-008873 did not demonstrate significant anti-tumor activity vs PBS at either 20 mg/kg or 40 mg/kg. The results also show that AB-008873 treatment showed early transient changes in blood and AB-008873 treatment induces TME changes associated with anti-tumorigenic, pro-inflammatory changes vs PBS in the CT26 model. FIG. 9 and FIG. 16.

TABLE 32

Changes in % of CD45 by Flow cytometry with AB-008873 treatment

| 40 mg/kg | Day | TILs | $T_{cyt}$ | $T_{help}$ | $T_{reg}$ | NK | M-MDSCs | G-MDSCs | MΦ | pDC | cDC1 |
|---|---|---|---|---|---|---|---|---|---|---|---|
| Blood | 10 | — | ↑* | ↑* | ns | — | ↓* | ns | — | — | — |
| | 17 | — | ns | ns | ns | — | ↑* | ns | — | — | — |
| Tumor | 10 | ns | ns | ns | ns | ns | ns | ns | ↑* | ns | ns |
| | 17 | ns | ns | ns | ns | ns | ns | ns | ns | ns | ns |
| | end | ↓* | ns | ns | ns | ns | ↓* | ns | ns | ns | ↑* |

TABLE 33

Changes by IF with AB-008873 treatment

| | Day | CD3+ | $T_{cyt}$ | CD4+ | $T_{reg}$ | DC | MΦ | M1 | M2 |
|---|---|---|---|---|---|---|---|---|---|
| AB-008873 40 mg/kg | 10 | ↑* | ns | ↑* | ↓* | ns | ns | ns | ns |
| | 17 | ns | ↑* | ns | ns | ns | ns | ↑* | ns |
| AB-008873 20 mg/kg | 10 | ns | ns | ns | ns | ns | ns | ns | ns |
| | 17 | ns | ns | ns | ns | ns | ns | ↑* | ns |

Tissue Reactivity

Figure 23:
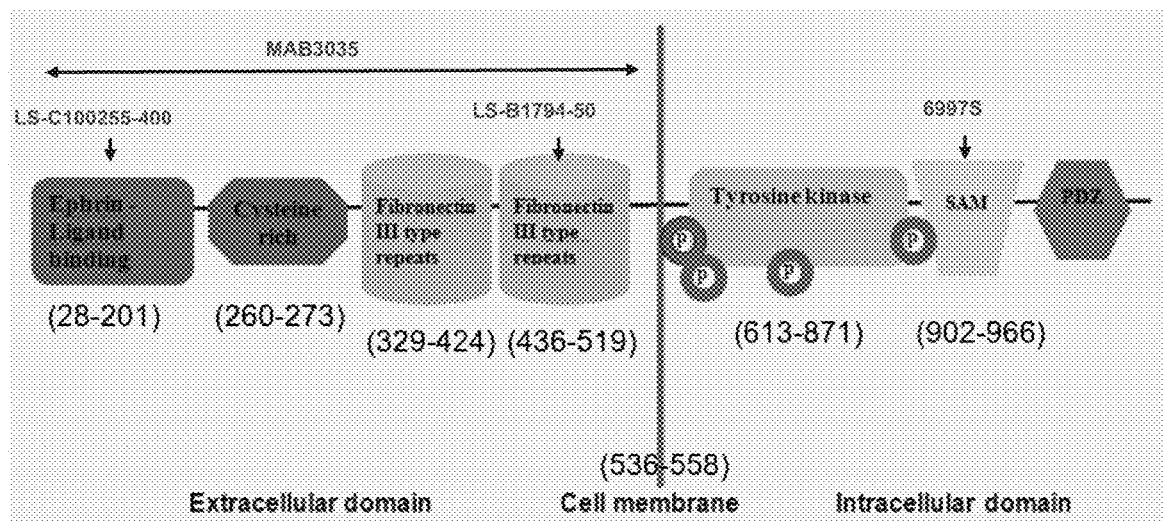
FIG. 23 shows the binding sites of various commercial EphA2 antibodies.

AB-008873, its variants, AB-010016, AB-010017, and AB-010018 and MAB 3035, LS-C36249-100, LS-C100255-400, LS-B1794-50, and AB-0073254 derived against distinct EphA2 epitopes (Table 34) were tested on human tumor and tumor adjacent tissues (TAT). FIG. 23 depicts binding sites of commercial anti-EphA2 antibodies. Typically, commercial anti-EphA2 antibodies bind to the extracellular domain or intracellular domain of Eph2A. For instance, MAB3035 (a.a. Gln25-Asn534), LS-C36249-100 (extracellular domain), LS-C100255-400 (a.a. 30-60), LS-B1794-50 (a.a. 450-500), and Ab73254 (extracellular domain) bind to sites in the extracellular domain, while 6997S (around a.a. Arg907) binds to sites in the intracellular domain. Briefly, fixed tissues were washed with 2.5% donkey serum to block non-specific binding. Sections were incubated with a primary antibody in 2.5% donkey serum diluent. Sections were incubated with Cγ5 conjugated secondary antibody and counterstained with Hoechst, mounted in anti-fade mountant and stained using H&E. Tumor types and their related TAT (n=2-6 per indication) used include non-small cell lung cancer (NSCLC)-squamous cell carcinoma, NSCLC-adenocarcinoma, renal cell carcinoma (i.e., clear cell and papillary subtypes), melanoma, esophageal cancer, breast cancer (i.e., triple negative, hormone receptor-positive, and HER2-positive molecular phenotypes), colorectal cancer, soft tissue sarcoma, and pancreatic, prostate, and urothelial cancers.

TABLE 34

Antibodies tested on human tumor and tumor adjacent tissues in immunofluorescence studies

| Category | Name | | |
|---|---|---|---|
| 8873 and variants | AB-008873 | | |
| | AB-009812 | | |
| | AB-009813 | | |
| | AB-009815 | | |
| | AB-009816 | | |
| EphA2 antibodies derived from clinical candidates | AB-010016 | | |
| | AB-010017 | | |
| | AB-010018 | | |
| Commercial anti-EphA2 Abs | Extracellular | MAB3035 (Gln25-Asn534) | |
| | | LS-C36249-100 (extracellular domain) | |

TABLE 34-continued

Antibodies tested on human tumor and tumor adjacent tissues in immunofluorescence studies

| Category | Name | |
|---|---|---|
| | | LS-C100255-400 (AA 30-60) |
| | | LS-B1794-50 (AA 450-500) |
| | | Ab73254 (extracellular domain) |
| | Cytoplasmic | 6997S (around Arg907) |

In brief, commercially obtained frozen resected tumor samples and tumor adjacent tissue from non-autologous patients were sectioned to slide and lightly fixed using 4% paraformaldehyde. Following a buffer wash, the slides were incubated in a blocking reagent containing 2.5% normal donkey serum in phosphate-buffered saline (PBS), pH 7.0, at room temperature and then incubated overnight at 4° C. in primary antibody diluted in 2.5% donkey serum in PBS (concentration range of 0.1-30 ug/mL). The primary antibody is a chimeric sequence comprised of a human Fv derived from the Atreca library and a mouse IgG2a Fc sequence. After the primary antibody and subsequent wash in buffer solution, the slide is incubated in donkey anti-mouse secondary antibody conjugated to AlexaFluor 647 at room temperature. Following a wash step, the tissue is counterstained with Hoescht dye which ubiquitously labels cell nuclei, washed again, and coverslipped.

Figure 25:
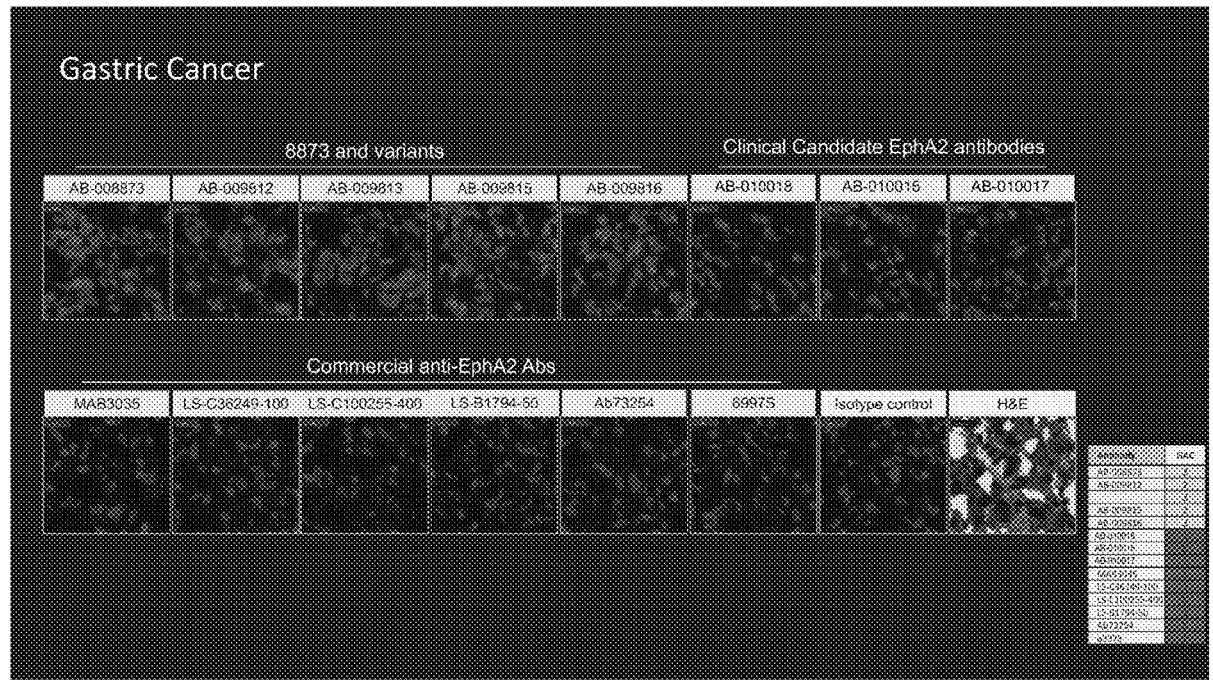
FIG. 25 shows the results of immunofluorescence study which demonstrates a possible unique epitope of AB-008873 in gastric cancer.
Figure 26:
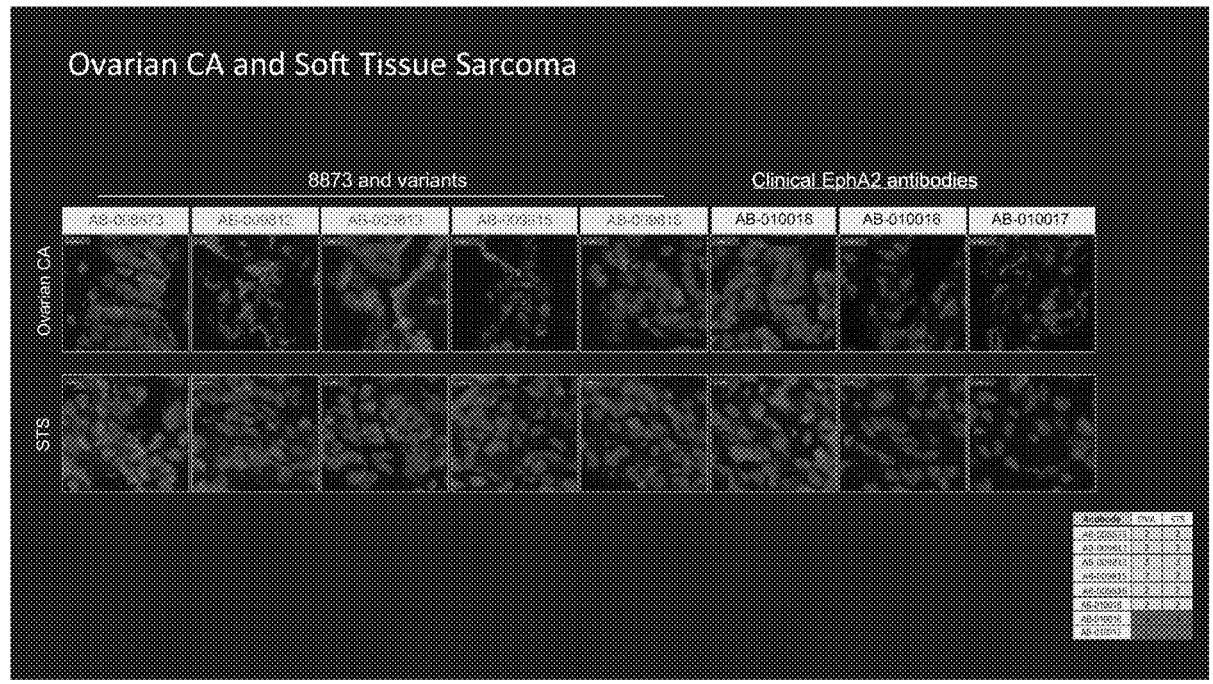
FIG. 26 shows comparison of EphA2 antibodies in binding ovarian cancer and a soft tissue sarcoma cells.

AB-008873 immunoreactivity was detected in NSCLC adenocarcinoma, melanoma, esophageal cancer, ovarian cancer, HER2+ breast cancer, soft tissue sarcoma, anal cancer, gastric cancer, uterine cancer, and head and neck cancer. FIGS. 25-30. Nearly identical profiles were detected for its engineered variant antibodies. FIGS. 25-27. AB-008873 showed approximately 80% overlap of immunoreactive tumor cores with the AB-010018 and 90% with the commercial antibody derived against the EphA2 extracellular domain. Table 35. Interestingly, in these experiments, AB-008873 signal, and that of all engineered variants, was detectable in gastric cancer whereas no reactivity was noted with anti-EphA2 compounds (i.e., antibodies AB-010018 (mouse monoclonal antibody precursor of clinical candidate humanized DS-8895a. See U.S. Pat. No. 9,150,657, SEQ ID NO: 35 and 37), AB-010016 (derived from MedImmune's clinical candidate Medi-547), and AB-010017 (derived from Merrimack's clinical candidate MM-310)) nor the commercial anti-EphA2s. FIG. 25. Furthermore, AB-008873 and its engineered variants demonstrated a punctate binding pattern across multiple cancer types including ovarian and uterine cancers and soft tissue sarcoma while any labeling by antibodies AB-010018, AB-010016, and AB-010017 or commercial antibodies was diffuse with cytoplasmic signal predominant. FIGS. 26-28.

TABLE 35

IHC score of AB-008873 and its variants on 21 types of fresh frozen human tumor and TAT

| | Ab Info | | NSCLC-SQ | NSCLC-Adeno | RCC-clear cell | RCC-papillary | MELA | ESC | OVA | TNBC | ER+ BRC | Her2+ BRC | CRC | PANC | PROC |
|---|---|---|---|---|---|---|---|---|---|---|---|---|---|---|---|
| 8873 and variants | AB-008873 | | 1 | 2 | 1 | 1 | 2 | 2 | 2 | 1 | 1 | 2 | 1 | 1 | 1 |
| | AB-009812 | | 1 | 2 | 1 | 1 | 2 | 2 | 2 | 1 | 1 | 2 | 1 | 1 | 1 |
| | AB-009813 | | 1 | 2 | 1 | 1 | 2 | 2 | 2 | 1 | 1 | 1 | 1 | 1 | 1 |
| | AB-009815 | | 1 | 2 | 1 | 1 | 2 | 2 | 2 | 1 | 1 | 2 | 1 | 1 | 1 |
| | AB-009816 | | 1 | 2 | 1 | 1 | 2 | 2 | 2 | 1 | 1 | 2 | 1 | 1 | 1 |
| EphA2 antibodies derived from clinical candidates | AB-010018 | | 2 | 2 | 1 | 1 | 3 | 2 | 2 | 2 | 2 | 2 | 1 | 1 | 1 |
| | AB-010016 | | 1 | 1 | 1 | 1 | 1.5 | 1 | 1 | 1 | 1 | 1 | 1 | 1 | 1 |
| | AB-010017 | | 1 | 2 | 1 | 1 | 2 | 1 | 1 | 1 | 1 | 1 | 2 | 1 | 1 |
| Commercial anti-EphA2 Abs | Extracellular | MAB3035 (Gln25-Asn534) | 2 | 2 | 1 | 1 | 3 | 2 | 2 | 1 | 1 | 1 | 1 | 2 | 1 |
| | | LS-C36249-100 (extracellular) | 2 | 2 | 1 | 1 | 3 | 2 | 2 | 1 | 1 | 2 | 1 | 1 | 1 |
| | | LS-C1002 55-400 (AA 30-60) | 1 | 1 | 1 | 1 | 2 | 1 | 1 | 1 | 1 | 1 | 1 | 1 | 1 |
| | | LS-B1794-50 (AA 450-500) | 1 | 2 | 1 | 2 | 2 | 1 | 1 | 1 | 1 | 1 | 1 | 1 | 1 |
| | | Ab73254 (extracellular) | 2 | 2 | 1 | 1 | 2 | 1 | 1 | 1 | 1 | 1 | 1 | 1 | 1 |
| | Cytoplasmic | 6997S (around Arg907) | 1 | 1 | 1 | 1 | 2 | 2 | 1 | 1 | 1 | 1 | 1 | 1 | 1 |

TABLE 35-continued

IHC score of AB-008873 and its variants on 21 types of fresh frozen human tumor and TAT

| Ab Info | | | STS | URO | ANC | HNC | GAC | UCEC-endo-metriod | UCEC-clear cell | UCEC-papillary | % overlap of positive cancer types between 8873 and other Abs | % overlap of positive cancer types between DS-8895 and other Abs |
|---|---|---|---|---|---|---|---|---|---|---|---|---|
| 8873 and variants | | AB-008873 | 2 | 1 | 2 | 2 | 2 | 1 | 2 | 2 | | 69% |
| | | AB-009812 | 2 | 1 | 2 | 2 | 2 | 1 | 1 | 2 | 91% | 62% |
| | | AB-009813 | 2 | 1 | 2 | 2 | 2 | 1 | 2 | 2 | 91% | 62% |
| | | AB-009815 | 2 | 1 | 2 | 2 | 2 | 1 | 2 | 2 | 100% | 69% |
| | | AB-009816 | 2 | 1 | 2 | 2 | 2 | 1 | 2 | 2 | 100% | 69% |
| EphA2 antibodies derived from clinical candidates | | AB-010018 | 2 | 1 | 2 | 1 | 1 | 2 | 2 | 2 | 82% | |
| | | AB-010016 | 1 | 1 | 2 | 2 | 1 | 1 | 2 | 2 | 45% | 31% |
| | | AB-010017 | 1 | 1 | 2 | 2 | 1 | 2 | 2 | 3 | 55% | 46% |
| Commercial anti-EphA2 Abs | Extra-cellular | MAB3 035 (Gln25-Asn534) | 1 | 1 | 2 | 2 | 1 | 2 | 2 | 2 | 73% | 69% |
| | | LS-C3624 9-100 (extra-cellular) | 2 | 1 | 2 | 2 | 1 | 2 | 2 | 3 | 91% | 85% |
| | | LS-C1002 55-400 (AA 30-60) | 1 | 1 | 1 | 1 | 1 | 1 | 2 | 2 | 27% | 23% |
| | | LS-B1794-50 (AA 450-500) | 1 | 1 | 1 | 1 | 1 | 1 | 2 | 2 | 36% | 31% |
| | | Ab732 54 (extra-cellular) | 1 | 1 | 1 | 1 | 1 | 1 | 2 | 1 | 27% | 31% |
| | Cyto-plasmic | 6997S (around Arg907) | 1 | 1 | 2 | 1 | 1 | 1 | 2 | 2 | 45% | 38% |

AB-010361 and AB-010363 were assayed as above. Both variants retained similar reactivity as AB-008873 to most of the tested cancer samples. However, there were some notable differences observed for reactivity to melanoma, soft tissue sarcoma, endometrioid uterine cancer, esophageal cancer, triple negative breast cancer, ovarian cancer, and urothelial cancer. AB-010361 and AB-010363 show higher binding affinity than AB-008873 on melanoma, soft tissue sarcoma, endometrioid uterine cancer. AB-010361 shows higher binding affinity than AB-008873 on esophageal cancer and triple negative breast cancer. AB-010363 shows higher binding affinity than AB-008873 on ovarian cancer, and urothelial cancer. Furthermore, AB-010361 shows enhanced reactivity in triple negative breast cancer as compared to AB-010363, but diminished reactivity as compared to AB-010363 in ovarian and urologic cancer. AB-010363 shows enhanced reactivity in urothelial cancer compared to AB-010361, AB-010018, AB-010016, and AB-010017, but diminished tumor-selective binding in esophageal cancer as compared to AB-008873. Table 36 illustrates reactivity of anti-EphA2 antibodies to cancers.

TABLE 36

Reactivity of anti-EphA2 antibodies to cancers

| | AB-008873 | | | | | AB-010361 | | | | | AB-010363 | | | | |
|---|---|---|---|---|---|---|---|---|---|---|---|---|---|---|---|
| Indication | 30 µg/ml | 10 µg/ml | 3 µg/ml | 1 µg/ml | 0.3 µg/ml | 30 µg/ml | 10 µg/ml | 3 µg/ml | 1 µg/ml | 0.3 µg/ml | 30 µg/ml | 10 µg/ml | 3 µg/ml | 1 µg/ml | 0.3 µg/ml |
| MELA | 2 | 2 | 1 | 1 | 1 | 2 | 2 | 2 | 1 | 1 | 2 | 2 | 2 | 1 | 1 |
| STS | 2 | 2 | 2 | 2 | 1 | 2 | 2 | 2 | 2 | 2 | 2 | 2 | 2 | 2 | 2 |

TABLE 36-continued

|  | \<AB-010016\> | | | | | \<AB-010018\> | | | | |
|---|---|---|---|---|---|---|---|---|---|---|
| Indication | 30 µg/ml | 10 µg/ml | 3 µg/ml | 1 µg/ml | 0.3 µg/ml | 30 µg/ml | 10 µg/ml | 3 µg/ml | 1 µg/ml | 0.3 µg/ml |
| UCEC-endometrioid | 2 | 2 | 1 | 1 | 1 | 2 | 2 | 2 | 1 | 1 | 2 | 2 | 2 | 1 | 1 |
| ESO | 2 | 2 | 1 | 1 | 1 | 2 | 2 | 2 | 2 | 1 | 1 | 1 | 1 | 1 | 1 |
| OVA | 2 | 1 | 1 | 1 | 1 | 1 | 1 | 1 | 1 | 1 | 2 | 2 | 2 | 2 | 1 |
| TNBC | 1 | 1 | 1 | 1 | 1 | 2 | 2 | 1 | 1 | 1 | 1 | 1 | 1 | 1 | 1 |
| URO | 1 | 1 | 1 | 1 | 1 | 1 | 1 | 1 | 1 | 1 | 2 | 2 | 2 | 1 | 1 |
| UCEC-clear cell | 2 | 2 | 2 | 2 | 2 | 2 | 2 | 2 | 2 | 2 | 2 | 2 | 2 | 2 | 2 |
| UCEC-papillary | 2 | 2 | 2 | 2 | 1 | 2 | 2 | 2 | 2 | 1 | 2 | 2 | 2 | 2 | 1 |
| NSCLC-SQ | 1 | 1 | 1 | 1 | 1 | 1 | 1 | 1 | 1 | 1 | 1 | 1 | 1 | 1 | 1 |
| NSCLC-Adeno | 1 | 1 | 1 | 1 | 1 | 1 | 1 | 1 | 1 | 1 | 1 | 1 | 1 | 1 | 1 |
| RCC-clear cell | 1 | 1 | 1 | 1 | 1 | 1 | 1 | 1 | 1 | 1 | 1 | 1 | 1 | 1 | 1 |
| RCC-papillary | 1 | 1 | 1 | 1 | 1 | 1 | 1 | 1 | 1 | 1 | 1 | 1 | 1 | 1 | 1 |
| ER+ BRC | 1 | 1 | 1 | 1 | 1 | 1 | 1 | 1 | 1 | 1 | 1 | 1 | 1 | 1 | 1 |
| Her2+ BRC | 1 | 1 | 1 | 1 | 1 | 1 | 1 | 1 | 1 | 1 | 1 | 1 | 1 | 1 | 1 |
| CRC | 1 | 1 | 1 | 1 | 1 | 1 | 1 | 1 | 1 | 1 | 1 | 1 | 1 | 1 | 1 |
| PANC | 1 | 1 | 1 | 1 | 1 | 1 | 1 | 1 | 1 | 1 | 1 | 1 | 1 | 1 | 1 |
| PROC | 1 | 1 | 1 | 1 | 1 | 1 | 1 | 1 | 1 | 1 | 1 | 1 | 1 | 1 | 1 |

| | AB-010016 | | | | | AB-010018 | | | | |
|---|---|---|---|---|---|---|---|---|---|---|
| Indication | 30 µg/ml | 10 µg/ml | 3 µg/ml | 1 µg/ml | 0.3 µg/ml | 30 µg/ml | 10 µg/ml | 3 µg/ml | 1 µg/ml | 0.3 µg/ml |
| MELA | 1 | 1 | 1 | 1 | 1 | 2 | 2 | 2 | 2 | 2 |
| STS | 2 | 1 | 1 | 1 | 1 | 2 | 2 | 2 | 2 | 2 |
| UCEC-endometrioid | 1 | 1 | 1 | 1 | 1 | 2 | 2 | 2 | 2 | 2 |
| ESO | 1 | 1 | 1 | 1 | 1 | 2 | 2 | 2 | 2 | 2 |
| OVA | 1 | 1 | 1 | 1 | 1 | 1 | 1 | 1 | 1 | 1 |
| TNBC | 1 | 1 | 1 | 1 | 1 | 1 | 1 | 1 | 1 | 1 |
| URO | 2 | 1 | 1 | 1 | 1 | 1 | 1 | 1 | 1 | 1 |
| UCEC-clear cell | 2 | 1 | 1 | 1 | 1 | 2 | 2 | 2 | 2 | 2 |
| UCEC-papillary | 1 | 1 | 1 | 1 | 1 | 2 | 2 | 2 | 2 | 2 |
| NSCLC-SQ | 1 | 1 | 1 | 1 | 1 | 1 | 1 | 1 | 1 | 1 |
| NSCLC-Adeno | 1 | 1 | 1 | 1 | 1 | 1 | 1 | 1 | 1 | 1 |
| RCC-clear cell | 1 | 1 | 1 | 1 | 1 | 1 | 1 | 1 | 1 | 1 |
| RCC-papillary | 1 | 1 | 1 | 1 | 1 | 1 | 1 | 1 | 1 | 1 |
| ER+ BRC | 1 | 1 | 1 | 1 | 1 | 1 | 1 | 1 | 1 | 1 |
| Her2+ BRC | 1 | 1 | 1 | 1 | 1 | 1 | 1 | 1 | 1 | 1 |
| CRC | 1 | 1 | 1 | 1 | 1 | 1 | 1 | 1 | 1 | 1 |
| PANC | 1 | 1 | 1 | 1 | 1 | 1 | 1 | 1 | 1 | 1 |
| PROC | 1 | 1 | 1 | 1 | 1 | 1 | 1 | 1 | 1 | 1 |

Score of 1 indicates no signal above TAT or isotype control.

Figure 42:
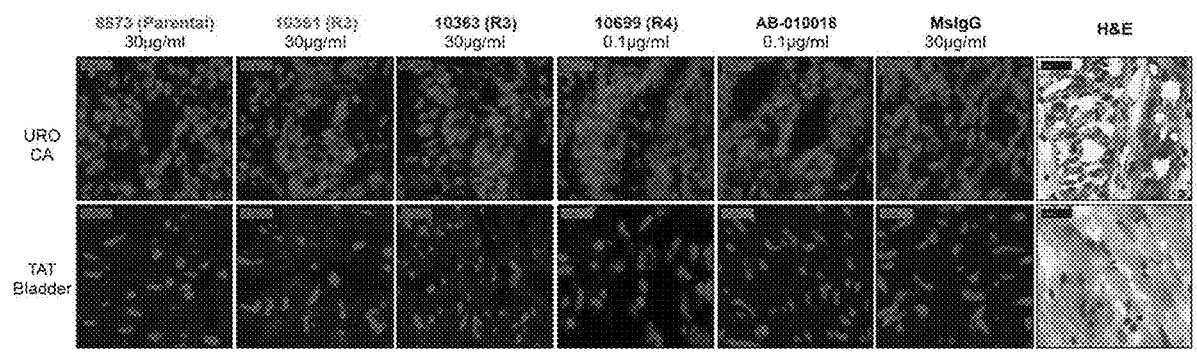
FIG. 42 shows the results of immunofluorescence staining of AB-008873 variants as compared to AB-008873, and AB-010018.

AB-010699 showed increased potency in many tumor types as compared to AB-010018 and AB-00873 and AB-010361. However, AB-010699 is less potent than its parent AB-010361 against soft tissue carcinoma in this assay. FIG. 42; Table 37, 38, and 39.

TABLE 37

Binding to EphA2 epitopes across cancer types by various EphA2 antibodies

| | AB-008873 (µg/ml) | | | | | | AB-010361 (µg/ml) | | | | | | AB-010699 (µg/ml) | | | | | | AB-010018 (µg/ml) | | | | | |
|---|---|---|---|---|---|---|---|---|---|---|---|---|---|---|---|---|---|---|---|---|---|---|---|---|
| Indication | 30 | 10 | 3 | 1 | 0.3 | 0.1 | 30 | 10 | 3 | 1 | 0.3 | 0.1 | 30 | 10 | 3 | 1 | 0.3 | 0.1 | 30 | 10 | 3 | 1 | 0.3 | 0.1 |
| NSCLC-SQ | 2 | 2 | 1 | 1 | 1 | 1 | 2 | 1 | 1 | 1 | 1 | 1 | 2 | 2 | 2 | 2 | 2 | 2 | 2 | 1 | 1 | 1 | 1 | 1 |
| NSCLC-Adeno | 2 | 1 | 1 | 1 | 1 | 1 | 2 | 2 | 1 | 1 | 1 | 1 | 2 | 2 | 1 | 1 | 1 | 1 | 1 | 1 | 1 | 1 | 1 | 1 |
| RCC-papillary | 1 | 1 | 1 | 1 | 1 | 1 | 1 | 1 | 1 | 1 | 1 | 1 | 1 | 1 | 1 | 1 | 1 | 1 | 2 | 2 | 2 | 1 | 1 | 1 |
| MELA | 2 | 2 | 1 | 1 | 1 | 1 | 2 | 2 | 2 | 1 | 1 | 1 | 2 | 2 | 2 | 2 | 2 | 1 | 2 | 2 | 2 | 2 | 2 | 1 |
| ESO | 2 | 1 | 1 | 1 | 1 | 1 | 2 | 1 | 1 | 1 | 1 | 1 | 2 | 2 | 1 | 1 | 1 | 1 | 2 | 1 | 1 | 1 | 1 | 1 |
| PANC | 1 | 1 | 1 | 1 | 1 | 1 | 1 | 1 | 1 | 1 | 1 | 1 | 1 | 1 | 1 | 1 | 1 | 1 | 2 | 2 | 2 | 2 | 2 | 2 |
| STS | 2 | 2 | 2 | 1 | 1 | 1 | 2 | 2 | 2 | 2 | 1 | 1 | 1 | 1 | 1 | 1 | 1 | 1 | 2 | 1 | 1 | 1 | 1 | 1 |
| URO | 1 | 1 | 1 | 1 | 1 | 1 | 1 | 1 | 1 | 1 | 1 | 1 | 2 | 2 | 2 | 2 | 2 | 2 | 2 | 2 | 2 | 2 | 2 | 2 |
| Uterine | 2 | 1 | 1 | 1 | 1 | 1 | 2 | 2 | 1 | 1 | 1 | 1 | 2 | 2 | 2 | 2 | 1 | 1 | 2 | 2 | 2 | 2 | 2 | 1 |

Score of 1 indicates no signal above TAT or isotype control.

TABLE 38

Binding to EphA2 epitopes across cancer types by various EphA2 antibodies

| | AB-008873 (µg/ml) | | | | | | AB-010361 (µg/ml) | | | | | | stage AB-010699 (µg/ml) | | | | | | AB-010018 (µg/ml) | | | | | |
|---|---|---|---|---|---|---|---|---|---|---|---|---|---|---|---|---|---|---|---|---|---|---|---|---|
| Indication | 30 | 10 | 3 | 1 | 0.3 | 0.1 | 30 | 10 | 3 | 1 | 0.3 | 0.1 | 30 | 10 | 3 | 1 | 0.3 | 0.1 | 30 | 10 | 3 | 1 | 0.3 | 0.1 |
| NSCLC-SQ | 2 | 2 | 1 | 1 | 1 | 1 | 2 | 1 | 1 | 1 | 1 | 1 | 2 | 2 | 2 | 2 | 2 | 2 | 2 | 1 | 1 | 1 | 1 | 1 |
| NSCLC-Adeno | 2 | 1 | 1 | 1 | 1 | 1 | 2 | 2 | 1 | 1 | 1 | 1 | 2 | 2 | 1 | 1 | 1 | 1 | 1 | 1 | 1 | 1 | 1 | 1 |
| RCC-papillary | 1 | 1 | 1 | 1 | 1 | 1 | 1 | 1 | 1 | 1 | 1 | 1 | 1 | 1 | 1 | 1 | 1 | 1 | 2 | 2 | 2 | 1 | 1 | 1 |
| MELA | 2 | 2 | 1 | 1 | 1 | 1 | 2 | 2 | 2 | 1 | 1 | 1 | 2 | 2 | 2 | 2 | 2 | 1 | 2 | 2 | 2 | 2 | 2 | 1 |
| ESO | 2 | 1 | 1 | 1 | 1 | 1 | 2 | 1 | 1 | 1 | 1 | 1 | 2 | 2 | 1 | 1 | 1 | 1 | 2 | 1 | 1 | 1 | 1 | 1 |
| PANC | 1 | 1 | 1 | 1 | 1 | 1 | 1 | 1 | 1 | 1 | 1 | 1 | 1 | 1 | 1 | 1 | 1 | 1 | 2 | 2 | 2 | 2 | 2 | 2 |
| STS | 2 | 2 | 2 | 1 | 1 | 1 | 2 | 2 | 2 | 2 | 1 | 1 | 1 | 1 | 1 | 1 | 1 | 1 | 2 | 1 | 1 | 1 | 1 | 1 |
| URO | 1 | 1 | 1 | 1 | 1 | 1 | 1 | 1 | 1 | 1 | 1 | 1 | 2 | 2 | 2 | 2 | 2 | 2 | 2 | 2 | 2 | 2 | 2 | 2 |
| Uterine | 2 | 1 | 1 | 1 | 1 | 1 | 2 | 2 | 1 | 1 | 1 | 1 | 2 | 2 | 2 | 2 | 1 | 1 | 2 | 2 | 2 | 2 | 2 | 1 |

Score of 1 indicates no signal above TAT or isotype control.

TABLE 39

Binding to EphA2 epitopes across cancer types by various EphA2 antibodies

| Cancer Indication | AB-008873 (parental) | | | AB-010361 | | | AB-010699 | | |
|---|---|---|---|---|---|---|---|---|---|
| | Reactive # | Total # | Reactivity % | Reactive # | Total # | Reactivity % | Reactive # | Total # | Reactivity % |
| Esophageal (Squamous) | 0 | 10 | 0% | 3 | 10 | 30% | 8 | 10 | 80% |
| Lung (Squamous) | 5 | 20 | 25% | 8 | 20 | 40% | | | |
| Breast | 2 | 32 | 6% | 10 | 32 | 31% | | | |
| Renal | 1 | 34 | 3% | 10 | 34 | 29% | | | |
| Ovarian | 2 | 36 | 6% | 6 | 36 | 17% | | | |

Figure 22:
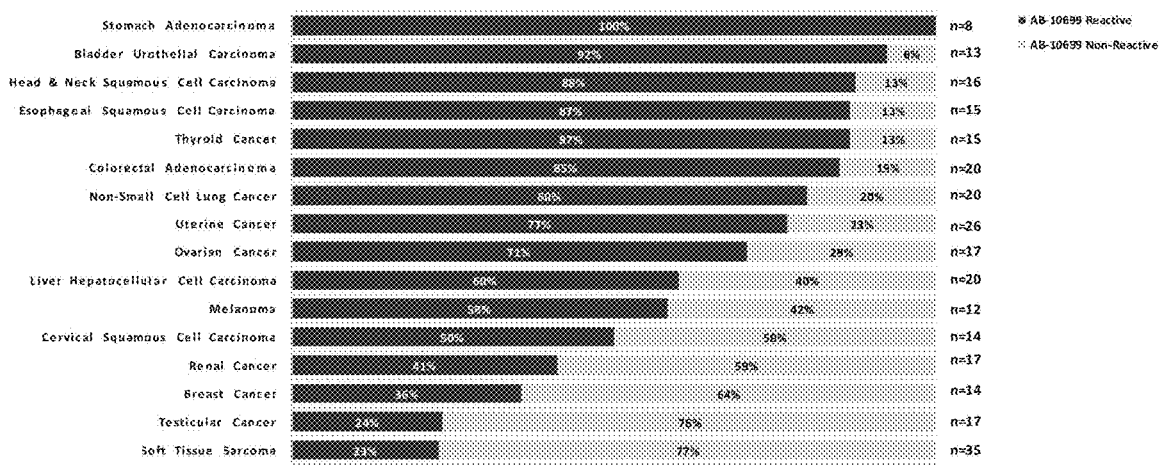
FIG. 22 shows the reactivity of AB-010699 across a panel of human cancer samples.
Figure 24B:
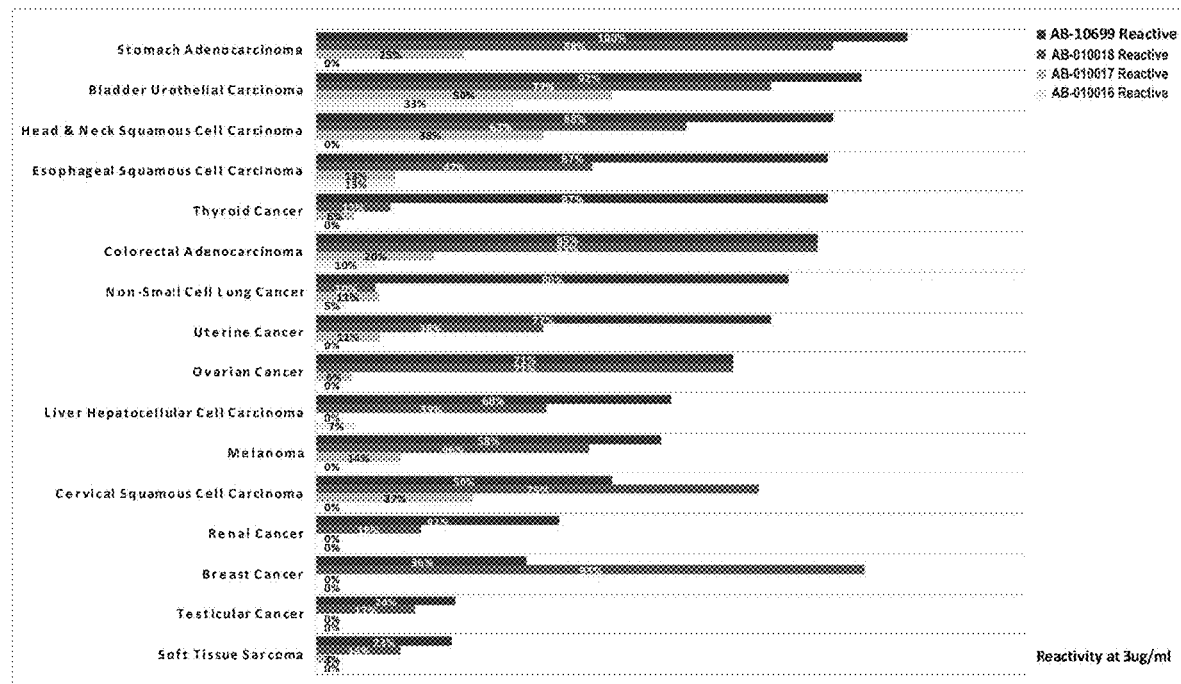
Figure 31:
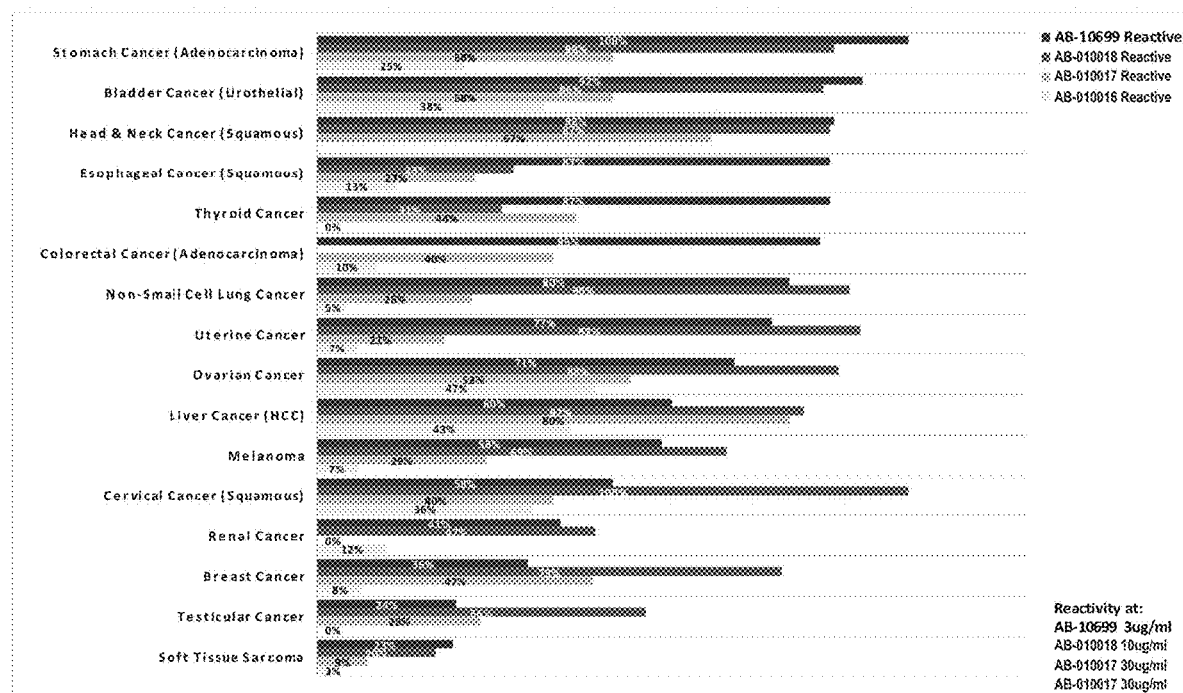
FIG. 31 shows the reactivity of EphA2 antibodies across a panel of additional human cancer samples.

The reactivity of AB-010699 at 3 ug/ml in human cancers was tested across a panel of human cancer samples. As shown in FIG. 22, AB-010699 showed greater than 20% reactivity across all cancers tested, with results ranging from 100% reactivity in stomach adenocarcinoma (number of samples tested=8) to 23% reactivity in soft tissue sarcoma (number of samples tested –35). AB-010016 and AB-010017 (that bind to the ligand binding domain of EphA2) and AB-010018 were tested for reactivity over the same set of tissue samples as AB-010699, all at a concentration of 3 ug/ml. As shown in FIG. 24, the signal of these three comparator antibodies was very low for many of the samples tested. The assay was repeated with increased concentrations, with AB-010016 and AB-010017 being tested at 30 ug/ml and AB-010018 being tested at 10 ug/ml while AB-010699 was maintained at 3 ug/ml. AB-010699 showed a differentiated reactivity over all three comparator antibodies tested. FIG. 31.

Immunohistochemistry staining was performed on fresh frozen TMAs of select normal human tissues (i.e., liver, kidney, stomach, heart, pancreas, lung; n=3 per tissue type) with human uterine cancer as the positive control, following the manufacturer's instructions of Vector Laboratory's standard MOM protocol. In short, the frozen slides were dried at room temperature for 15 minutes and fixed with 4% PFA at room temperature for 15 minutes. After fixation the slides were washed with wash buffer and incubated in MOM blocking reagent. After blocking the slides were incubated with AB-008873, its engineered variants, antibody AB-010018, or mouse IgG2a, the isotype control, at 3 µg/mL, overnight at 4° C. Commercial antibodies were also tested at 10 µg/mL. Next, the slides were washed with Wash Buffer and incubated with a secondary for 40 minutes at room temperature. The slides were washed and then the chromogenic reaction was developed by incubating them in Betazoid DAB for 2 minutes. After the color development the slides were counter stained with Hematoxylin QS for 15 seconds, dehydrated, mounted and then imaged in AxioScan whole slide scanner. Antibodies being tested include AB-008873 and engineered variants include AB-009812, AB-009813, AB-009815, AB-009816, AB-010018, and commercial anti-Eph2A antibody (LC-C100255-400, LS-B174-50).

Figure 33:
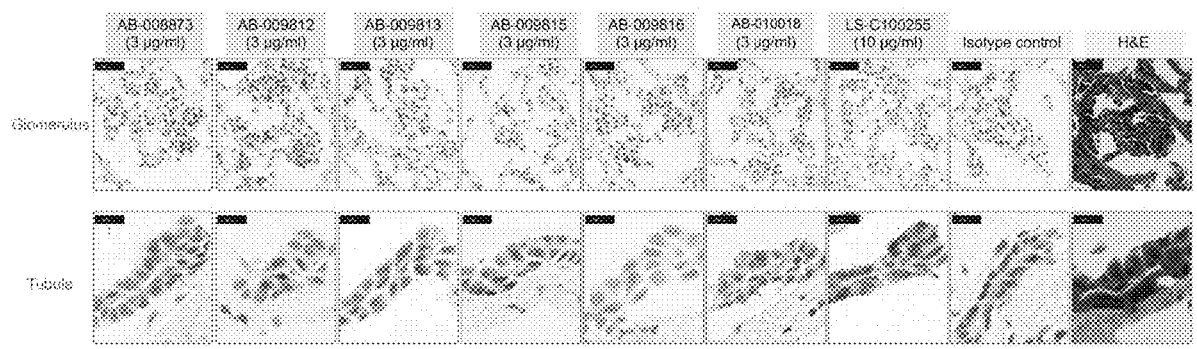
FIG. 33 shows the binding of AB-008873, variants thereof, AB-010018 and commercial anti-EphA2 antibodies to normal kidney.
Figure 34:
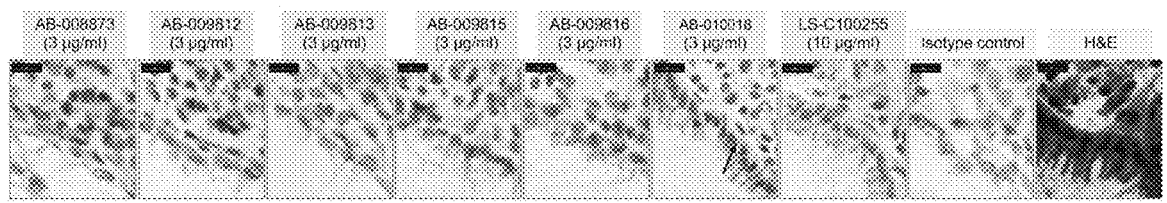
FIG. 34 shows the binding of AB-008873 and its variants, AB-010018 and a commercial anti-EphA2 antibody to normal stomach.

The results show that AB-008873 and its engineered variants demonstrated no detectable to faint cytoplasmic signal in all normal human tissues tested. Table 40. Unlike AB-008873, the antibody AB-010018 revealed enhanced labeling of epithelium in stomach as well as moderate signal with renal tubules. Similar normal tissue staining profiles were noted with the commercial antibodies tested. FIG. 33-34.

TABLE 40

Results of the binding of anti-EphA2 antibodies to normal human tissue

| Ab Info | | Normal Human Tissue IHC Screen | | | | | |
|---|---|---|---|---|---|---|---|
| | | Liver | Kidney | Stomach | Heart | Pancreas | Lung |
| 8873 and variants | AB-008873 | Neg to faint | Faint | Faint | Faint | Faint | Neg to faint |
| | AB-009812 | Neg to faint | Faint | Faint | Faint | Faint | Faint |
| | AB-009813 | Neg to faint | Faint | Faint | Faint | Faint | Neg to faint |
| | AB-009815 | Neg to faint | Faint | Faint | Faint | Faint | Faint |
| | AB-009816 | Neg to faint | Faint | Faint | Faint | Faint | Neg to faint |
| EphA2 Abs derived from clinical candidates | AB-010018 | Neg to faint | Moderate | Faint to mod | Neg to faint | Neg to faint | Neg to faint |
| Commercial EphA2 Ab | LS-C100255-400 | Faint | Moderate | Faint to mod | Faint | Faint | Faint |
| | LS-B1794-50 | Faint | Moderate | Faint to mod | Faint | Faint | Faint |

Note
all antibodies were used at 3 µg/ml, except for LS-C100255-400 and LS-B1794-50, which were used at 10 µg/ml

Example 5. EphA2 Signaling

The effect of AB-008873 and variants AB-010361 and AB-010699 on EphA2 signaling was tested along with antibodies AB-010016 and AB-010018. To assess EphA2 signaling, antibodies specific to described phosphorylation sites in the intracellular domain were used. In brief, MDA-MB-231 cells were seeded in 6 well plates and allowed to attach overnight. Next day, cells were serum-starved for 24 h. Following, antibodies and ephrin-A1 Fc were added at the respective concentrations and allowed to incubate for 15 min at 37° C. and 5% $CO_2$. Cells were immediately lysed and processed for Western Blot analysis. Samples were loaded on a gel and run for 70 min at 200V. After transfer to PVDF membrane, phospho-specific antibodies were used quantify receptor activation. In parallel, total EphA2 and GAPDH were detected and quantified and used for normalization post image analysis. To assess agonistic effects of the antibodies on the ephrinA1-EphA2 signaling axis, MDA-MB-231 cells were incubated with different concentrations of antibody for 15 min followed by ephrinA1-FC at 1 µg/mL. Cells were subsequently processed for Western Blot analysis as described above.

For all phosphorylation sites tested, weak or no agonistic activation and no interference in ephrinA1-EphA2 signaling axis were detected for AB-008873 and AB-010361. AB-010699 exhibited agonistic activity but only at 20% the activation induced by the natural ligand ephrin A1 (in Fc format). FIG. A.

In contrast AB-010016 and AB-010018 significantly interfere with EphA2 signaling, with AB-010016 acting as a strong agonist and AB-010018 acting as an antagonist of the signaling activity. FIGS. 43A and B. AB-010016 activated signaling at comparable levels to the ephrin A1 ligand. FIG. 43A

Example 6. Epitope Binning by Bio-Layer Interferometry

Epitope binning was performed using an Octet Red 96E instrument (Sartorius) using the in-tandem format. In this format, antigen is captured on a biosensor tip, a first antibody (or other binding partner) is bound to saturation, and subsequently the ability of a second antibody (or binding partner) known to recognize the antigen is assessed. If substantial binding by the second species is no longer observed, it is supportive that simultaneous binding is sterically hindered (i.e., the second species is "blocked" by pre-saturation of the $1^{st}$) and that the two may bind overlapping epitopes. If, however, substantial binding of the second species is observed, despite saturation of the first, it is supportive that the two bind non-overlapping epitopes. Groups of antibodies that block one another can be considered to populate the same epitope bin.

In this experiment four antibodies and one natural ligand that recognize EphA2 were tested. The Fv regions for three of the antibodies were derived from therapeutic candidates that entered human clinical trials: AB-010016 derived from MedImmune's MEDI-547, disclosed in Peng et al., J. Mol. Biol. 2011 Oct. 21; 413(2):390-405. doi: 10.1016/j.jmb.2011.08.018; AB-010017 derived from Merrimack's MM-310, disclosed in Geddie et al., MAbs. 2017 January; 9(1): 58-67. Doi: 10.1080/19420862.2016.125904; Kamoun et al., Nat Biomed Eng. 2019 April; 3(4):264-280. doi: 10.1038/s41551-019-0385-4. Epub 2019 Apr. 5; and AB-010018 mouse monoclonal antibody precursor (U.S. Pat. No. 9,150,657, Sequences 35 and 37) of Daiichi-Sankyo's DS-8895a, disclosed in Hasegawa J. et al., Cancer Biol Ther. 2016 November; 17(11):1158-1167. doi: 10.1080/15384047.2016.1235663. Epub 2016 Sep. 21; Shitara K. et al., J Immunother Cancer, 2019 Aug. 14; 7(1):219. doi: 10.1186/s40425-019-0679-9, U.S. Pat. Nos. 844,988; 9,150,657.

Figure 5A:
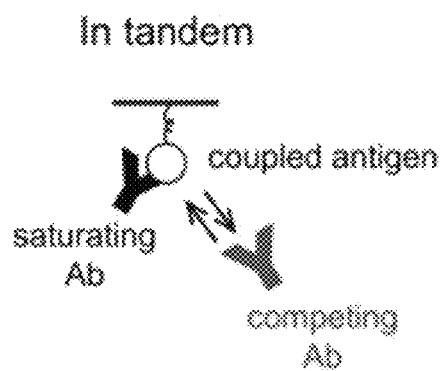
FIG. 5A illustrates a method of octet in tandem binning for epitope mapping.
Figure 5B:
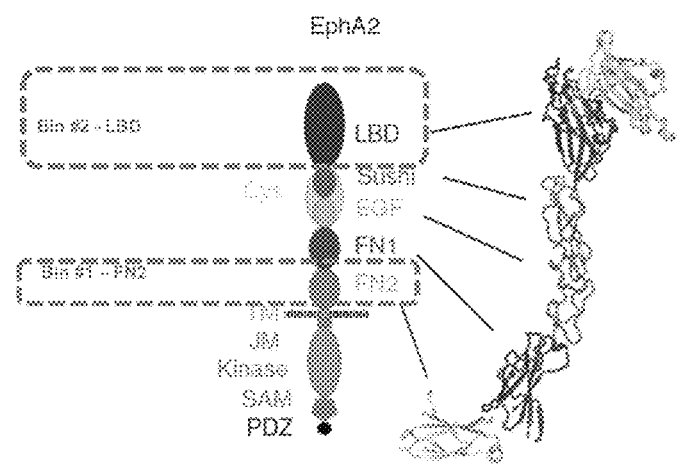
FIG. 5B illustrates the epitopes in the EphA2 domains that are recognized by EphA2 antibodies.

The fourth antibody Fv region (AB-008873) was discovered via Atreca's Immune Repertoire Capture (IRC™). Antibodies were produced with mouse IgG2a constant regions. The natural ligand tested was EphrinA1 fused to Fc (Acro, EF1-H5251). Antigen immobilized on the biosensor was the extracellular domain of human EphA2 (25-534) with a C-terminal HIS tag (R&D Systens, 3035-A2) and captured using Ni-NTA tips (Sartorius, 18-5102). Protein solutions were made in 1× Kinetics buffer (Sartorius, 18-1092) supplemented with 2.5 mM Imidazole to reduce non-specific binding. Each pairwise interaction was assessed in both orders of addition, and controls for binding in the absence of antigen or with antigen but without a first binding species included. Binning indicated the five molecules populated only two Bins. The first bin contains molecules AB-008873 and AB-010018 and was interpreted to represent epitopes on the membrane proximal fibronectin domain of EphA2 based on the reported epitope location of DS-8895a (Hasegawa, J., et al., Novel anti-EPHA2 antibody, DS-8895a for cancer treatment. *Cancer Biology and Therapy*, 17(11), 1158-1167 (2016)). The second bin contains molecules AB-010017, AB-010016, and EphrinA1-Fc and was interpreted to represent epitopes on the ligand binding domain (Peng, L. et al., Structural and functional characterization of an agonistic anti-human EphA2 monoclonal antibody. *Journal of Molecular Biology*, 413(2), 390-405 (2011); Geddie, M. L., et al., Improving the developability of an anti-EphA2 single-chain variable fragment for nanoparticle targeting. *MAbs*, 9(1), 58-67 (2017)). FIG. 5, Tables 41-42. Referring to FIG. 5, the FN2 location in the first bin is inferred from domain deletion data reported in Hasegawa et al., 2016, FIG. 1, noting that the reported MMP cleavage sites are (385/395/432/435).

TABLE 41

Results of Octet in tandem binning for epitope mapping

| Analyte 1 | Analyte 2 | Notes/Scoring | TIP | Ligand |
|---|---|---|---|---|
| 8873-02 | 8873-02 | Blocks (self) despite faster dissoc. | NiNTA | R&D ECD-06 |
| 10016-01 | 8873-02 | Binding observed (curve behind light green) | NiNTA | R&D ECD-06 |
| 10017-01 | 8873-02 | Binding observed | NiNTA | R&D ECD-06 |
| 10018-01 | 8873-02 | Blocks | NiNTA | R&D ECD-06 |
| Ephrin-A1 | 8873-02 | Binding observed | NiNTA | R&D ECD-06 |
| Buffer | 8873-02 | Positive control OK-EphA2 + competitor | NiNTA | R&D ECD-06 |
| Buffer | 8873-02 | Background control OK-competitor alone | NiNTA | Buffer |

TABLE 42

Epitope recognized by AB-008873 overlaps with that of AB-010018

| | Bin #1-FN2 | | Bin #2-LBD | | |
|---|---|---|---|---|---|
| | 8873-2 | 10018-01 | 10017-01 | 10016-01 | Ephrin-A1 |
| 8873-2 | blocked | blocked | binds | binds | binds |
| 100018-01 | blocked | blocked | binds | binds | binds |
| 10017-01 | binds | binds | blocked | blocked | blocked |
| 10016-01 | binds | binds | blocked | blocked | blocked |
| Ephrin-A1 | binds | binds | blocked | blocked | blocked |

Epitope Domain Investigation by Yeast Surface Display

To further validate AB-008873 epitope domain mapping, subdomains of human EphA2 and chimeras of human EphA2 and human EphA4 were displayed on the surface of yeast. AB-008873 had shown binding to EphA2 but not homologous receptor EphA4 in other assays (screening at Integral Molecular). 5 constructs (shown in Table 43) were selected for display on the surface of yeast and staining via AB-008873:

TABLE 43

| EphA2 subdomains | | |
|---|---|---|
| EphA2 (aa 25-534) | Full ECD | QGKEVVLLDFAAAGGELGWL THPYGKGWDLMQNIMNDMPI YMYSVCNVMSGDQDNWLRTN WVYRGEAERIFIELKFTVRD CNSFPGGASSCKETFNLYYA ESDLDYGTNFQKRLFTKIDT IAPDEITVSSDFEARHVKLN VEERSVGPLTRKGFYLAFQD IGACVALLSVRVYYKKCPEL LQGLAHFPETIAGSDAPSLA TVAGTCVDHAVVPPGGEEPR MHCAVDGEWLVPIGQCLCQA GYEKVEDACQACSPGFFKFE ASESPCLECPEHTLPSPEGA TSCECEEGFFRAPQDPASMP CTRPPSAPHYLTAVGMGAKV ELRWTPPQDSGGREDIVYSV TCEQCWPESGECGPCEASVR YSEPPHGLTRTSVTVSDLEP HMNYTFTVEARNGVSGLVTS RSFRTASVSINQTEPPKVRL EGRSTTSLSVSWSIPPPQQS RVWKYEVTYRKKGDSNSYNV RRTEGFSVTLDDLAPDTTYL VQVQALTQEGQGAGSKVHEF QTLSPEGSGN (SEQ ID NO: 101) |
| EphA2 (aa 437-534) | FN2 only | TEPPKVRLEGRSTTSLSVSW SIPPPQQSRVWKYEVTYRKK GDSNSYNVRRTEGFSVTLDD LAPDTTYLVQVQALTQEGQG AGSKVHEFQTLSPEGSGN (SEQ ID NO: 95) |
| EphA4_ECD (aa 23-546) | Full ECD | SRVYPANEVTLLDSRSVQGE LGWIASPLEGGWEEVSIMDE KNTPIRTYQVCNVMEPSQNN WLRTDWITREGAQRVYIEIK FTLRDCNSLPGVMGTCKETF NLYYYESDNDKERFIRENQF VKIDTIAADESFTQVDIGDR IMKLNTEIRDVGPLSKKGFY LAFQDVGACIALVSVRVFYK KCPLTVRNLAQFPDTITGAD TSSLVEVRGSCVNNSEEKDV PKMYCGADGEWLVPIGNCLC NAGHEERSGECQACKIGYYK ALSTDATCAKCPPHSYSVWE GATSCTCDRGFFRADNDAAS MPCTRPPSAPLNLISNVNET SVNLEWSSPQNTGGRQDISY NWCKKCGAGDPSKCRPCGSG VHYTPQQNGLKTTKVSITDL LAHTNYTFEIWAVNGVSKYN PNPDQSVSVTVTTNQAAPSS IALVQAKEVTRYSVALAWLE PDRPNGVILEYEVKYYEKDQ NERSYRIVRTAARNTDIKGL NPLTSYVFHVRARTAAGYGD FSEPLEVTTNTVPSRIIGDG ANS (SEQ ID NO: 102) |
| EphA2_A4in_FN1 | EphA2 with EphA4 FN1 domain | QGKEVVLLDFAAAGGELGWL THPYGKGWDLMQNIMNDMPI YMYSVCNVMSGDQDNWLRTN WVYRGEAERIFIELKFTVRD CNSFPGGASSCKETFNLYYA ESDLDYGTNFQKRLFTKIDT IAPDEITVSSDFEARHVKLN VEERSVGPLTRKGFYLAFQD IGACVALLSVRVYYKKCPEL LQGLAHFPETIAGSDAPSLA TVAGTCVDHAVVPPGGEEPR MHCAVDGEWLVPIGQCLCQA GYEKVEDACQACSPGFFKFE ASESPCLECPEHTLPSPEGA TSCECEEGFFRAPQDPASMP CTRPPSAPLNLISNVNETSV NLEWSSPQNTGGRQDISYNW CKKCGAGDPSKCRPCGSGVH |

TABLE 43-continued

EphA2 subdomains

| | | |
|---|---|---|
| | | YTPQQNGLKTTKVSITDLLA<br>HTNYTFEIWAVNGVSKYNPN<br>PDQSVSVTVTTNQTEPPKVR<br>LEGRSTTSLSVSWSIPPPQQ<br>SRVWKYEVTYRKKGDSNSYN<br>VRRTEGFSVTLDDLAPDTTY<br>LVQVQALTQEGQGAGSKVUE<br>FQTLSPEGSGN<br>(SEQ ID NO: 103) |
| EphA2_<br>A4in_FN2 | EphA2 with<br>EphA4 FN2<br>domain | QGKEVVLLDFAAAGGELGWL<br>THPYGKGWDLMQNIMNDMPI<br>YMYSVCNVMSGDQDNWLRTN<br>WVYRGEAERIFIELKFTVRD<br>CNSFPGGASSCKETFNLYYA<br>ESDLDYGTNFQKRLFTKIDT<br>IAPDEITVSSDFEARHVKLN<br>VEERSVGPLTRKGFYLAFQD<br>IGACVALLSVRVYYKKCPEL<br>LQGLAHFPETIAGSDAPSLA<br>TVAGTCVDHAVVPPGGEEPR<br>MHCAVDGEWLVPIGQCLCQA<br>GYEKVEDACQACSPGFFKFE<br>ASESPCLECPEHTLPSPEGA<br>TSCECEEGFFRAPQDPASMP<br>CTRPPSAPHYLTAVGMGAKV<br>ELRWTPPQDSGGREDIVYSV<br>TCEQCWPESGECGPCEASVR<br>YSEPPHGLTRTSVTVSDLEP<br>HMNYTFTVEARNGVSGLVTS<br>RSFRTASVSINQAAPSSIAL<br>VQAKEVTRYSVALAWLEPDR<br>PNGVILEYEVKYYEKDQNER<br>SYRIVRTAARNTDIKGLNPL<br>TSYVFHVRARTAAGYGDFSE<br>PLEVTTNTVPSRIIGDGANS<br>(SEQ ID NO: 104) |

Figure 6:
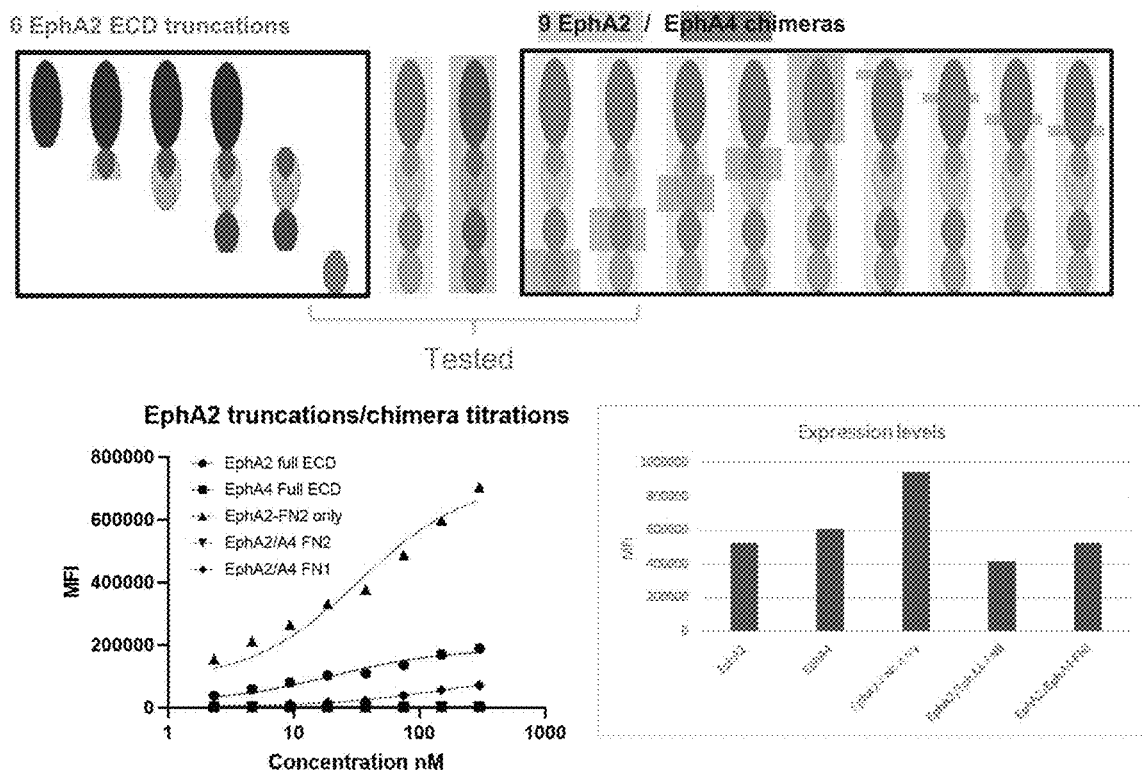
FIG. 6 shows the results from a yeast display that demonstrates the binding of AB-008873 to FN2 of EphA2.

Constructs were expressed as Aga2 fusions with an internal HA tag between Aga2 and the displayed protein as well as a C-terminal Myc tag (Boder, E. T., & Wittrup, K. D., Yeast surface display for screening combinatorial polypeptide libraries. Nature Biotechnology, 15(6), 553-557 (1997)). Yeast cells were cultured in SDCAA (Teknova, S0543) and induced with SGCAA (Teknova, S0542). Cells were stained with pairs of primary and secondary antibodies. AB-008873 Lot 2 (Atum, mIgG2a) and Donkey anti-Mouse IgG AF647 (JacksonImmunoResearch 715-605-150) were used for 10-point titrations to assess 8873 binding. Chicken IgY anti-cMyc (Life technologies A21281) and Goat anti Chicken Ig Y FITC (Life technologies A11039) were used to assess expression levels. The analysis was run on the iQue3 flow cytometer. Staining demonstrates binding of AB-008873 to the full extracellular domains EphA2, but not EphA4. The FN2 domain of EphA2 alone is sufficient to mediate binding and expresses at high levels. When the FN2 domain of EphA4 is swapped into EphA2, the binding to AB-008873 was lost. When the FN1 domain of EphA4 was swapped into in EphA2, the binding to AB-008873 was still observed. FIG. 6. As shown in FIG. 6, EphA4 chimeras offer stability advantages and can inform the finer mapping at the domain-level by expressing EphA2 trucations. Referring to FIG. 6 lower panel, FN2 domain (EphA2-FN2) alone shows strong binding signal (triangle). FN2 domain alone also has high relative expression. EphA2 full ECD shows a binding signal (circle) relatively lower than the binding signal driven by the FN2 domain alone. EphA4 full ECD shows no binding signal (square). Swapping the FN1 domain from EphA4 into EphA2 enables binding of the epitope (diamond). Binding is lost when the FN2 domain from EphA4 is swapped into EphA2. These results indicate that the epitope of AB-008873 is located at the membrane-proximal FN2 domain of EphA2.

Finer, residue-level resolution for AB-008873's epitope was determined by generating a library of FN2 mutants and testing their binding to AB-008873 via yeast display. The results of the testing indicated that AB-008873 binds a conformational epitope, spanning four stretches of primary sequence of EphA2, comprising the following residues: Pro439, Lys441, Arg443, Leu444, Arg447, Lys476, Gly477, Leu504, Gln506, Ser519, Lys520, Val521, His522, Glu523, Phe524, and Gln525. FIG. 44. The residues contained in the epitope are not conserved within the EphA2 family. FIG. 45. However, the epitope residues are conserved across species commonly used in toxicology studies. FIG. 46. The epitope of AB-008873 is located on the opposite side of the FN2 domain from the reported LBD-FN2 site. See Nikolov, D. B, et. al. (2014) Cell Adh Migr 8, 360-365.

Figure 47:
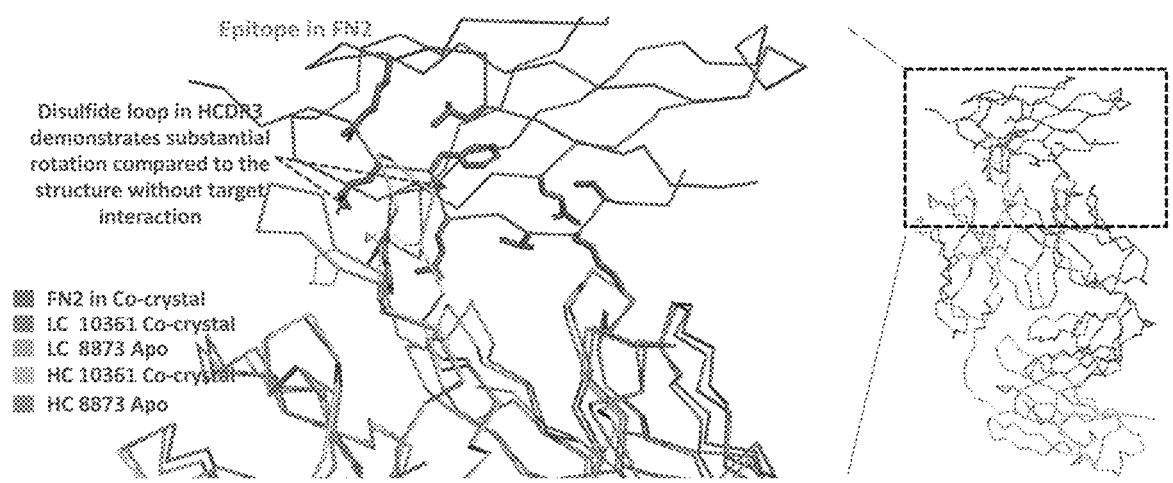
FIG. 47 illustrates the co-crystallization configuration of the EphA2 protein and the AB-008873 antibody. It indicates that the HCDRs changes conformation upon binding to the EphA2 protein: the disulfide loop in HCDR3 shows substantial rotation as compared to the structure that is not in contact with EphA2.

Co-crystallization studies showed that the disulfide loop in the HCDR3 of AB-008873 demonstrated substantial rotation as compared to the structure without target interaction. FIG. 47. Furthermore, the co-crystal and yeast display data aligned and provided additional details on the epitope. Combining these data indicated epitope residues that are not in direct contact with the CDRs of AB-008873 (as defined by a 4 Angstron distance constraint) but can substantially reduce or abrogate binding when mutated in yeast display: Pro439, Lys441, Arg443, Gly477, Leu504, and His522.

Additional yeast display assays indicated that the epitopes of AB-008873 and AB-010018 overlap but are distinct. The epitope of AB-010018 is a protrusion on an adjacent face of FN2 relative to the AB-008873 epitope, with two residues shared between epitopes. AB-010018 was shown to bind to Thr472, Arg474, Asp478, Ser479, Asn480, Gly477, and Leu504 in this assay.

Example 7. Binding Affinity

Steady State KD

Binding of antibodies to the FN2 domain of hEphA2 was measured using the Biacore® T200 SPR system at 25° C. using HBS-EP+ buffer (0.01 M HEPES pH 7.4, 0.15 M NaCl, 3 mM EDTA, 0.005% v/v Surfactant P20). Antibodies in mIgG2a format were captured at levels between 475-715 RU via an anti-mouse Fc antibody immobilized to a CM5 chip. Binding was assessed using a titration of C-terminally His-tagged hEphA2-FN2 (Thr437-Asn534+His tag) associated for 30 s or 75 s at 30 uL/min. Data was double-reference subtracted using both a surface without captured antibody and from injections of HBS-EP+ buffer. The equilibrium response was measured at 4 seconds before the end of association with a window of 5 seconds and fit using the Biacore T200 Evaluation Software 3.1 with the Steady State Affinity Model. The results are shown in Table 44.

TABLE 44

The binding kinetics of the EphA2 antibodies to the FN2 domain of hEphA2

| Antibody | Steady-State Monovalent KD (M) | Standard Error of KD | Chi2 (RU2) | n |
|---|---|---|---|---|
| AB-008873 | 2.26E−06 | 5.9E−08 | 0.134 | 2 |
| AB-010361 | 1.11E−06 | 5.5E−08 | 0.363 | 3 |

TABLE 44-continued

The binding kinetics of the EphA2 antibodies to
the FN2 domain of hEphA2

| Antibody | Steady-State Monovalent KD (M) | Standard Error of KD | Chi2 (RU2) | n |
|---|---|---|---|---|
| AB-010363 | 1.31E−06 | 2.6E−08 | 0.068 | 3 |
| AB-010699 | 1.89E−08 | 2.9E−10 | 0.286 | 3 |

Monovalent affinity to hEphA2-FN2 increased from ~2 uM from parental antibody AB-008873 to ~20 nM for the engineered variant AB-010699.

Binding of EphA2 Antibodies to the FN2 Domain of hEphA2

Binding of EphA2 antibodies to the FN2 domain of hEphA2 was measured using the Biacore® T200 SPR system. Biacore® assays were conducted at 25° C. using HBS-EP+ buffer (0.01 M HEPES pH 7.4, 0.15 M NaCl, 3 mM EDTA, 0.005% v/v Surfactant P20) using the FN2 domain as the analyte with the antibodies in mIgG2a format as the immobilized ligand. Data was analyzed using 1:1 Langmuir binding model and steady-state model in Biacore Evaluation software.

C-terminally His-tagged human EphA2 FN2 domain (Thr437-Asn534+His tag) was used as the analyte. The analyte was associated for 120 seconds and dissociated for 100 seconds or 300 seconds at 30 uL/min. Titration of 0, 11.1 nM, 33.3 nM, 100 nM, 300 nM, and 900 nM run for AB-010699 and AB-010018 as mIgG2a. The results are shown in Table 45.

TABLE 45

Measurement results of binding of EphA2 antibodies
to the FN2 domain of hEphA2

| Antibody | ka (1/Ms) | kd (1/s) | KD (M) | Rmax (RU) |
|---|---|---|---|---|
| AB-010699 | 3.9E+6 | 0.075 | 1.9E−08 | 110.2 |
| AB-010018 | 4.9E+6 | 0.0021 | 4.3E−09 | 74.9 |

Binding of EphA2 Antibodies to the FN2 Domain, and Fragments of the FN1-FN2 Domains of the EphA2

Additional Biacore® assays were conducted to determine binding of AB-010699 human Fab fragment and AB-010018 human Fab fragment to the ECD, FN1-FN2 domains, FN2 domain, and fragments of the FN1-FN2 domains of the EphA2 protein. These assays were conducted using the EphA2 proteins fused to the N-terminal side of a human Fc (hEphA2-Fc fusion) as the immobilized ligand and AB-010699 and AB-010018 in Fab format as the analyte. The hEphA2-Fc fusions were captured with an anti-human Fc immobilized to a CM5 chip.

Biacore® assays were conducted at 25° C. using HBS-EP+ buffer (0.01 M HEPES pH 7.4, 0.15 M NaCl, 3 mM EDTA, 0.005% v/v Surfactant P20). Data was double-reference subtracted and data was analyzed using 1:1 Langmuir binding model and steady-state model in Biacore Evaluation software.

The analyte was associated for 120 seconds and dissociated for 100 seconds for AB-010699 or 300 seconds for AB-010018 at 30 uL/min. Binding to hEphA2-ECD-Fc tested using 100, 300, and 900 nM analyte. Binding to all other ligands tested using 33.3, 100, and 300 nM analyte. The results are shown in Tables 46-47.

TABLE 46

Binding kinetics of AB-010699

| Ligand | ka (1/Ms) | kd (1/s) | KD (M) | Rmax (RU) |
|---|---|---|---|---|
| hEphA2-FN12-(327-534)-Fc | 5.0E+6 | 4.3E−2 | 8.6E−9 | 149.9 |
| hEphA2-FN2-(437-534)-Fc | 1.0E+7 | 8.5E−2 | 8.6E−9 | 59.2 |
| hEphA2-clv385-534-Fc | 6.05E+6 | 7.2E−2 | 1.2E−8 | 136.4 |
| hEphA2-clv395-534-Fc | 5.72E+6 | 7.0E−2 | 1.2E−8 | 155.5 |
| hEphA2-clv432-534-Fc | 7.78E+6 | 7.5E−2 | 9.6E−9 | 145.9 |
| hEphA2-clv435-534-Fc | 8.42E+6 | 7.8E−2 | 9.3E−9 | 150.1 |

TABLE 47

Binding kinetics of for AB-010018

| Ligand | ka (1/Ms) | kd (1/s) | KD (M) | Rmax (RU) |
|---|---|---|---|---|
| hEphA2-ECD(25-534) | 3.2E+5 | 2.0E−3 | 6.3E−9 | 120.2 |
| hEphA2-FN12-(327-534)-Fc | 1.8E+5 | 1.9E−3 | 1.1E−8 | 115.7 |
| hEphA2-FN2-(437-534)-Fc | 4.3E+5 | 2.7E−3 | 6.1E−9 | 52.4 |
| hEphA2-clv385-534-Fc | 2.6E+5 | 2.7E−3 | 1.0E−8 | 111.9 |
| hEphA2-clv395-534-Fc | 2.6E+5 | 2.6E−3 | 1.0E−8 | 138.4 |
| hEphA2-clv432-534-Fc | 4.0E+5 | 3.0E−3 | 7.5E−9 | 112.3 |
| hEphA2-clv435-534-Fc | 4.3E+5 | 3.1E−3 | 7.3E−9 | 114.5 |

The calculated monovalent KD of AB-010699 is similar across all hEphA2 variants (ranging from 9 to 12 nM) and there appears to be no differentiated binding to different hEphA2 recombinant fragment representing cleavage forms (ranging from 9 to 12 nM).

The calculated monovalent KD of AB-010018 is also similar across all hEphA2 variants (ranging from 6 to 11 nM) and there also appears to be no differentiated binding to different hEphA2 cleavage forms (ranging from 7 to 10 nM).

Binding of EphA2 Antibodies as SCFV

Single-chain variable fragments (SCFVs) of 10699 were expressed with C-terminal His-tags in mammalian cells and purified by Nickel Sepharose affinity chromatography. SCFVs were assayed in triplicate for thermostability using an Unchained Labs UNcle instrument. The concentration of purified antibodies was adjusted to 0.5 mg/ml in PBS immediately prior to analysis. To determine melting temperature (Tm) intrinsic protein fluorescence was measured at 473 nm every 1.1° C. as temperature was increased linearly from 25° C. to 95° C. at a rate of 0.3° C./min. The UNcle Analysis software (version 4.01) was used to find the Tm as the first derivative of the barycentric mean (BCM). Binding of the SCFVs to the FN2 domain of hEphA2 was measured in triplicate using the Biacore T200 SPR system at 25° C. using HBS-EP+ buffer (0.01 M HEPES pH 7.4, 0.15 M NaCl, 3 mM EDTA, 0.005% v/v Surfactant P20). SCFVs were captured at levels between 200-300 RU via an anti-His antibody immobilized to a CM5 chip. Binding was assessed using a titration of FLAG-tagged hEphA2-FN2 (300 nM, 100 nM, 33 nM, 11 nM, 3.7 nM) associated for 120 s and dissociated for 30 s at 30 uL/min. Data was double-reference subtracted using both a surface without captured SCFV and from injections of HBS-EP+ buffer. The 1:1 Langmuir binding model was used to fit each titration and the average of three replicates is reported. Table 48 shows amino acide sequences in SCFV constructs, and the results are shown in Table 49.

TABLE 48

SCFV Constructs

| Construct | Orientation | Linker | Sequence |
|---|---|---|---|
| SCFV-010699-01 | VH-VL | (G4S)4 (SEQ ID NO: 782) | QVQLQQWGAGLLKPSETLSLTCAVYGGSFSGYYWSWIRQPPGKGLEWIGEINHRGSINYNNYNPSLKSRVTISVDTSKNQFSLKLSSVTAADTAVYYCAKPLRPHCINGVCYSGDAFDIWGQGTMVTVASGGGGSGGGGSGGGGSGGGGSSYVLTQPPSVSVAPGQTARITCGGNNIGYKNVHWYQQKPGQAPVLVVYDDSDRPSGIPERFSGSNSGNTATLTISRVEAGDEADYYCQVWDHSSDHVVFGGGTKLTVLGGGHHHHHH (SEQ ID NO: 765) |
| SCFV-010699-02 | VL-VH | (G4S)4 (SEQ ID NO: 782) | SYVLTQPPSVSVAPGQTARITCGGNNIGYKNVHWYQQKPGQAPVLVVYDDSDRPSGIPERFSGSNSGNTATLTISRVEAGDEADYYCQVWDHSSDHVVFGGGTKLTVLGGGGSGGGGSGGGGSGGGGSQVQLQQWGAGLLKPSETLSLTCAVYGGSFSGYYWSWIRQPPGKGLEWIGEINHRGSINYNNYNPSLKSRVTISVDTSKNQFSLKLSSVTAADTAVYYCAKPLRPHCINGVCYSGDAFDIWGQGTMVTVASGGHHHHHH (SEQ ID NO: 766) |
| SCFV-010699-05 | VH-VL | (G4S)3 (SEQ ID NO: 91) | QVQLQQWGAGLLKPSETLSLTCAVYGGSFSGYYWSWIRQPPGKGLEWIGEINHRGSINYNNYNPSLKSRVTISVDTSKNQFSLKLSSVTAADTAVYYCAKPLRPHCINGVCYSGDAFDIWGQGTMVTVASGGGGSGGGGSGGGGSSYVLTQPPSVSVAPGQTARITCGGNNIGYKNVHWYQQKPGQAPVLVVYDDSDRPSGIPERFSGSNSGNTATLTISRVEAGDEADYYCQVWDHSSDHVVFGGGTKLTVLGGGHHHHHH (SEQ ID NO: 767) |
| SCFV-010699-06 | VL-VH | (G4S)3 (SEQ ID NO: 91) | SYVLTQPPSVSVAPGQTARITCGGNNIGYKNVHWYQQKPGQAPVLVVYDDSDRPSGIPERFSGSNSGNTATLTISRVEAGDEADYYCQVWDHSSDHVVFGGGTKLTVLGGGGSGGGGSGGSQVQLQQWGAGLLKPSETLSLTCAVYGGSFSGYYWSWIRQPPGKGLEWIGEINHRGSINYNNYNPSLKSRVTISVDTSKNQFSLKLSSVTAADTAVYYCAKPLRPHCINGVCYSGDAFDIWGQGTMVTVASGGGHHHHHH (SEQ ID NO: 768) |

TABLE 49

| Binding kinetics of EphA2 scFvs SCFV construct | mg/L yield | Average Tm (° C.) [Standard Deviation] | Average KD (M) to FN2_FLAG [% CV] | Average ka (1/Ms) [% CV] | Average kd (1/s) [% CV] |
|---|---|---|---|---|---|
| SCFV-010699-01 | 160 | 66.3 [0.6] | 2.4E−08 [0.6%] | 4.2E+06 [1.4%] | 0.10 [1.0%] |
| SCFV-010699-02 | 82 | 65.0 [0.3] | 3.0E−08 [0.9%] | 5.2E+06 [0.7%] | 0.16 [1.6%] |
| SCFV-010699-05 | 97 | 65.0 [0.6] | 2.7E−08 [1.1%] | 3.9E+06 [3.2%] | 0.11 [2.4%] |
| SCFV-010699-06 | 179 | 63.7 [0.7] | 3.1E−08 [1.2%] | 4.4E+06 [1.4%] | 0.13 [0.7%] |

All of the SCFV constructs exhibited an average KD (24-31 nM) that is comparable to that of the native AB-010669 monovalent KD.

Example 8. Multivalent Formats

Figure 32:
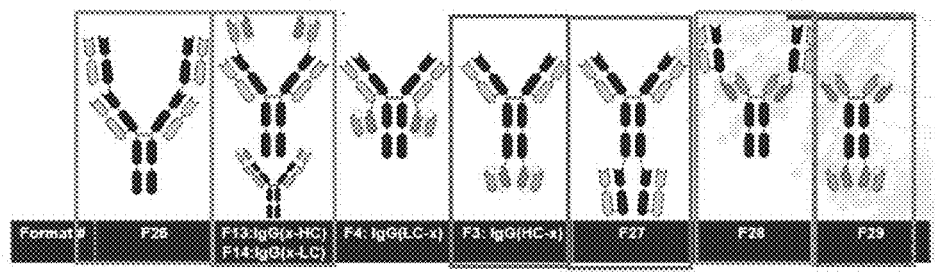
FIG. 32 shows schematics of the formats of multivalent antibodies, including the format of the Fc regions.

AB-008873 was used to construct tetravalent molecules that had four EphA2 binding arms per molecule. FIG. 32 shows schematics of the formats, including the format of the Fc regions. The constructs were tested for ADCC and cell binding activity as described above. Certain of the tetravalent constructs tested exhibited improved ADCC and cell binding over the bivalent format. FIG. 32 (RR) and Table 50. Those constructs that included components fused to the C-terminus of Fc exhibited substantial reduction of ADCC activity.

TABLE 50

Tetravalent constructs

| Molecule | ADCC-EC50 M | Fold rel AB-8873 IgG | ADCC-dAct % | Fold rel AB-8873 IgG | Flow Binding-EC50 M | Fold rel AB-8873 IgG | Flow Binding-dAct MedFl | Fold rel AB-8873 IgG |
|---|---|---|---|---|---|---|---|---|
| AB-008873-hIgG1 | 1.6E−08 | 1.0 | 30.0 | 1.0 | 6.1E−09 | 1.0 | 609705 | 1.0 |
| SCFV-8873-01_hFc1_F2 | 1.8E−08 | 0.9 | 28.3 | 0.9 | 1.4E−08 | 0.4 | 223880 | 0.4 |
| Fab8873-(GGSGG)3-HC-AB-008873-h1-4p0_F26 | 1.5E−09 | 10.5 | 32.8 | 1.1 | 1.3E−09 | 4.6 | 2230775 | 3.7 |

TABLE 50-continued

Tetravalent constructs

| Molecule | ADCC-EC50 M | Fold rel AB-8873 IgG | ADCC-dAct % | Fold rel AB-8873 IgG | Flow Binding-EC50 | | Flow Binding-dAct | |
|---|---|---|---|---|---|---|---|---|
| | | | | | M | Fold rel AB-8873 IgG | MedFl | Fold rel AB-8873 IgG |
| Fab8873-(GGSPG)3-HC-AB-008873-h1-4p0_F26 | 1.2E−09 | 13.3 | 31.0 | 1.0 | 4.8E−10 | 17.6 | 1556556 | 3.4 |
| SCFV8873-01-(GGSGG)3-HC-AB-008873-h1-2p2_F13 | 1.9E−09 | 8.3 | 27.6 | 0.9 | 4.4E−10 | 13.5 | 1835412 | 3.1 |
| SCFV8873-01-(GGSPG)3-HC-AB-008873-h1-2p2_F13 | 1.4E−09 | 11.9 | 34.4 | 1.1 | 1.8E−09 | 3.8 | 2658851 | 4.5 |
| SCFV8873-01-(GGSGG)3-LC-AB-008873-h1-2p2_F14 | 1.1E−09 | 15.0 | 29.8 | 1.0 | 2.1E−09 | 3.0 | 2558140 | 4.4 |
| SCFV8873-01-(GGSPG)3-LC-AB-008873-h1-2p2_F14 | 3.1E−10 | 52.3 | 36.9 | 1.2 | 4.4E−10 | 13.6 | 2873733 | 5.0 |
| AB-8873-h1-2p2-LC-SCFV-008873-01_F4 | 1.2E−08 | 1.3 | 30.9 | 1.0 | 7.5E−10 | 7.8 | 1307497 | 2.2 |
| Ab8873-h1-2p2-HC-(GGSGG)3-SCFV8873-01_F3 | 1.0E−07 | 0.2 | 3.3 | 0.1 | 6.7E−10 | 10.2 | 737080 | 1.2 |
| Ab8873-h1-2p2-HC-(GGSPG)3-SCFV8873-01_F3 | 1.0E−07 | 0.2 | 3.6 | 0.1 | 3.0E−09 | 1.9 | 913380 | 1.6 |
| Ab8873-h1-4p0-HC-(GGSGG)3-Fab8873_F27 | 1.0E−07 | 0.2 | 1.6 | 0.1 | 1.3E−09 | 4.5 | 1042829 | 1.8 |
| Ab8873-h1-4p0-HC-(GGSPG)3-Fab8873_F27 | 1.0E−07 | 0.2 | 8.9 | 0.3 | 1.7E−09 | 5.0 | 615030 | 1.3 |
| Fab8873-SCFV8873-01 h1-2p2_F28 | 2.9E−09 | 5.5 | 33.8 | 1.1 | 9.9E−10 | 5.9 | 1442867 | 2.4 |
| SCFV8873-01-h1-2p2-HC-(GGSGG)3-SCFV8873-01_F29 | 1.0E−07 | 0.2 | 3.5 | 0.1 | 1.3E−09 | 4.6 | 1109331 | 2.0 |
| SCFV8873-01-h1-2p2-HC-(GGSPG)3-SCFV8873-01_F29 | 1.7E−09 | 9.7 | 7.6 | 0.3 | 3.4E−09 | 2.2 | 1393777 | 2.3 |

Example 9. AB-008873-IL15 Fusions

Receptor-linked interleukin-15 (RLI) is made by covalently joining the IL-15 receptor alpha sushi domain to IL-15 via a glycine-serine linker. RLI enables trans presentation of II-15 to the IL-15 receptor complex (IL-15 receptor beta and IL-15 common gamma chain) on T and NK immune cells, and this trans presentation encourages immune responses such as proliferation and survival of naïve CD8+ T cells, development of memory CD8+ T cells, improved survival and upregulation of lytic molecules and CD16a on NK cells, etc.

Bispecific antibodies, referred to as IL-15 MultiMabs, that couple RLI to the anti-tumor antibody AB-008873 were developed. In one example of an IL-15 MultiMab, a 2-plus-2 molecule (2p2) that links an RLI domain to the C-terminus of each light chain of an IgG molecule via a glycine-serine linker was created. These RLI domains can be either wild-type ("wt/RLI") or a mutated variant expected to have lower affinity for the IL-15 receptor complex ("low/RLI"). The two molecules described are shown here as FIG. 36, and sequences of the component parts are provided in Table 15 above.

Figure 37:
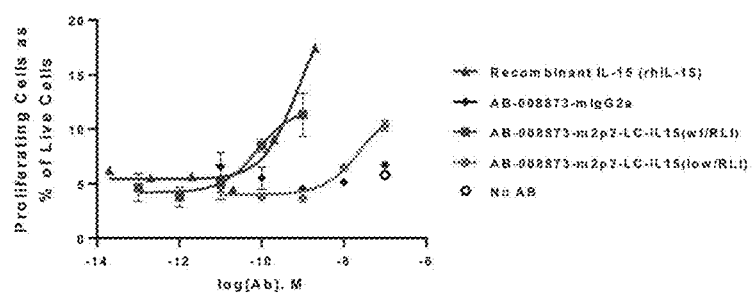
FIG. 37 shows the results that demonstrate AB-008873-IL15 multiMabs treatment resulted in dose-dependent increases in human NK cell proliferation.

These IL-15 MultiMabs have been assessed for their ability to induce proliferation of primary NK cells. Primary human NK cells were labeled with CellTrace CFSE cell proliferation dye (Invitrogen Cat. C4554) and mixed with AB-008873 IL-15 MultiMabs. After 3 days of treatment, cells were analyzed with a flow cytometer and gated for cells that lost signal from proliferation dye relative to untreated cells. See FIG. 37.

The AB-008873 IL-15 MultiMabs showed dose-dependent increases in human NK cell proliferation. Antibodies fused with wild-type RLI ("wt/RLI") were more potent than those fused with low affinity RLI ("low/RLI") and unmodified antibodies ("AB-008873-mIgG2a") did not show a measurable response up to 100 nM.

Figure 38:
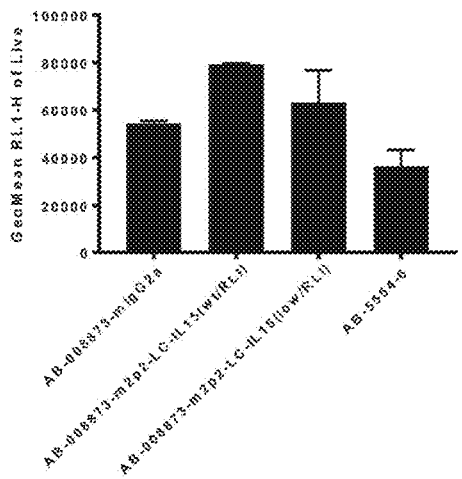
FIG. 38 shows the flow cytometry analysis of binding of the AB-008873-IL15 multiMabs to tumor cells using flow cytometry.

AB-008873 IL15 MultiMabs were assessed for their ability to bind to target tumor cells using flow cytometry. Parental antibody or IL-15 MultiMabs were added to CT26 ex vivo cells at 100 nM and incubated on ice, followed by washing. Secondary Alexa Fluor 647-conjugated anti-mouse antibody and cell membrane integrity dye was added and incubated on ice, followed by washing. Stained cells were analyzed by flow cytometry, gated for viable cells, and quantified for Alexa Fluor 647 detection. The data is shown in FIG. 38. The results indicate that addition of the RLI domain to AB-008873 did not negatively impact binding of the antibody to tumor target cells.

Figure 48:
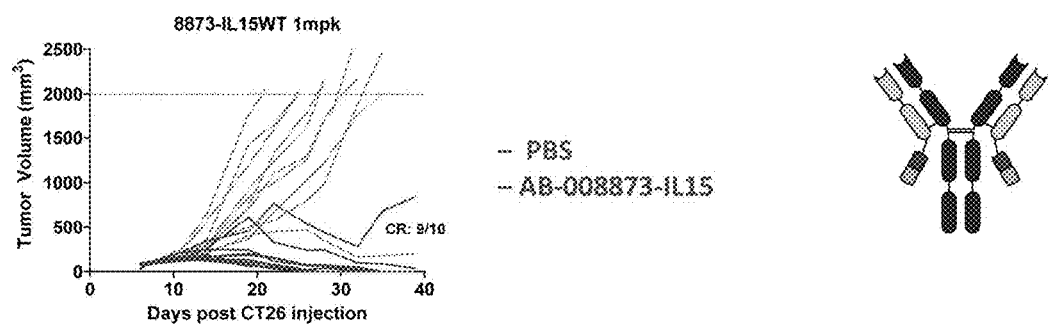
FIG. 48 shows measurements of tumor growth in mice inoculated with CT26 cells upon treatment of the AB-008873-IL15.

As shown in FIG. 48, AB-008873-m2p2-LC-IL15 (wt/RLI) was active in tumor growth inhibition and regression (TGI/R) studies in syngeneic mouse models using CT26 tumor cells.

Example 10. 4-1BB and 4-1BBL Constructs 4-1BB fusion proteins were tested for their tumor targeting activities. These fusion proteins comprise (i) at least the antigen binding domains of the EphA2 antibodies and 4-1BB ligand domains (Table 13) or (ii) at least the antigen binding domains of the EphA2 antibodies and the ScFv portions of the anti-4-1BB antibodies (Table 10).

Bispecific antibodies that comprise two scFv fragments of anti-4-1BB antibody linked to the HC of the EphA2 antibodies AB-008873 or AB-010361 (EphA2-4-1BB bispecific antibodies) were constructed. Anti-hen egg lysozyme targeting anti-4-1BB antibody (5554-41BB) was also constructed and used as a negative control.

After confirming that they retained the ability to bind to PC3 cells, the EphA2-4-1BB bispecific antibodies were assayed for their ability to activate human 4-1BB using an inducible reporter cell system (Promega cat JA2351). 4-1BB reporter cells were either cultured alone with the EphA2-4-1BB bispecific antibodies or co-cultured with A549 tumor cells that had been treated with the EphA2-4-1BB bispecific antibodies. The 4-1BB antibody Urelumab (AB-009811) was included as a non-tumor targeting control. After 5 hours of culture, 4-1BB activation was determined from the reporter cells by measuring bioluminescence output.

Results from this assay indicated that the EphA2-4-1BB bispecific antibodies only exhibited 4-1BB activation in the presence of tumor cells while the Urelumab control activated 4-1BB with our without the presence of tumor cells.

The activation assay was repeated using MDA-MB-231, CT26, or PC3 tumor cells. The EphA2-4-1BB bispecific antibodies showed activation of 4-1BB on all tumor cell lines tested. FIG. 19A-D.

The bispecific antibody that comprises two scFv fragments of anti-4-1BB antibody linked to the HC of the EphA2 antibody AB-010361 was tested in BALB/c mice that developed tumors after they have been inoculated with CT26 cells. Mice were dosed intraperitoneally with test article once a week for four weeks (7, 14, 21, and 28 days post CT26 implantation) at a dose level of 10 mg/kg. Vehicle control, PBS, was dosed at 10 mL/kg. As compared to the group that were treated with PBS and the group of mice that were treated with an anti-hen egg lysozyme targeting anti-4-1BB antibody ("5554-41BB"), mice treated with the EphA2-4-1BB bispecific antibody showed reduced tumor growth during the treatment period. FIG. 49.

The mice treated with the EphA2-4-1BB bispecific antibodies as above were assayed for the presence of liver toxicity, a known side effect of certain 4-1BB agonist based therapeutics, including anti-4-1BB antibody Urelumab. Liver toxicity was determined by measuring ALT (alanine aminotransferase) and AST (aspartate aminotransferase) which are released into the bloodstream when liver damage occurs. The ALT was measured using the MAK052 assay kit (Sigma-Aldrich) which measures the amount of pyruvate generated and AST was measured using the MAK055 assay kits (Sigma-Aldrich) which measures the amount of glutamate generated.

Results of these assays showed that mice treated with the AB-01361-4-1BB bispecific antibody and the AB-5554-41BB negative control do not show increase over vehicle of ALT & AST levels while the antibody 3H3 at 10 mpk (mouse surrogate for Urelumab) shows increased serum ALT & AST levels (ALT~8-fold increase, p<0.0001).

Furthermore, livers from mice treated with the AB-01361-4-1BB bispecific antibody showed no visible signs of liver inflammation as determined by tissue staining using hematoxylin and eosin.

Portal vein infiltration and expansion to parenchyma was detected with 10 mpk 3H3 but not AB-010361-41BB.

Figure 19A:
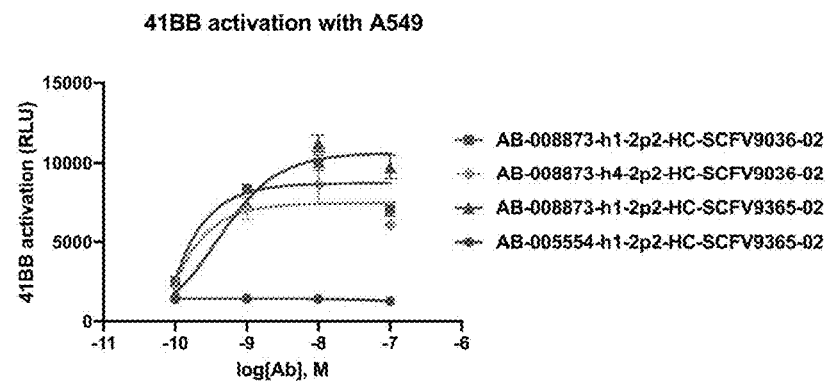
FIGS. 19A, 19B, 19C, 19D, and 19E show results of activation of 4-1BB by EphA2-4-1BB bispecific antibodies in tumor cell lines.
Figure 19B:
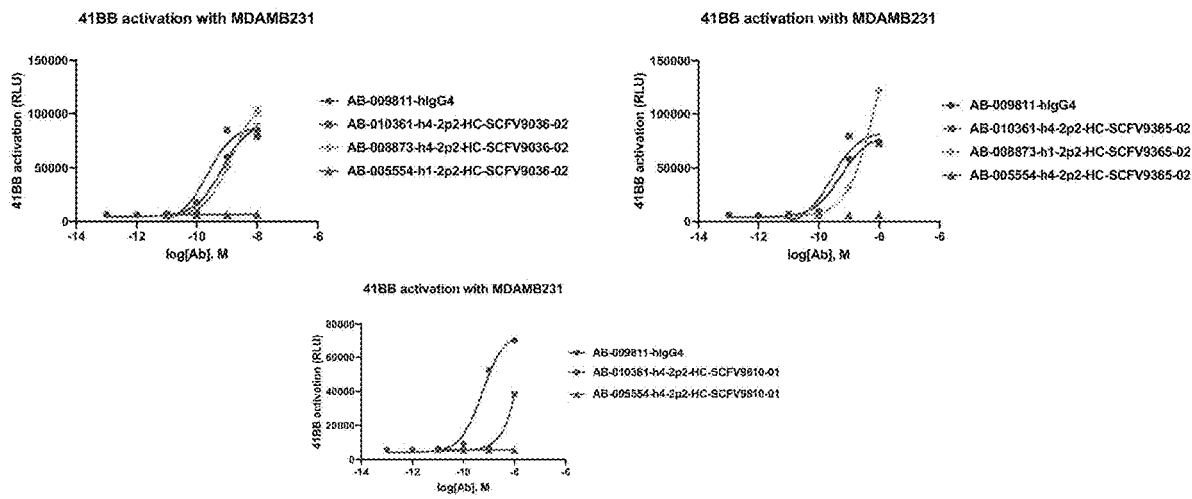
Figure 19C:
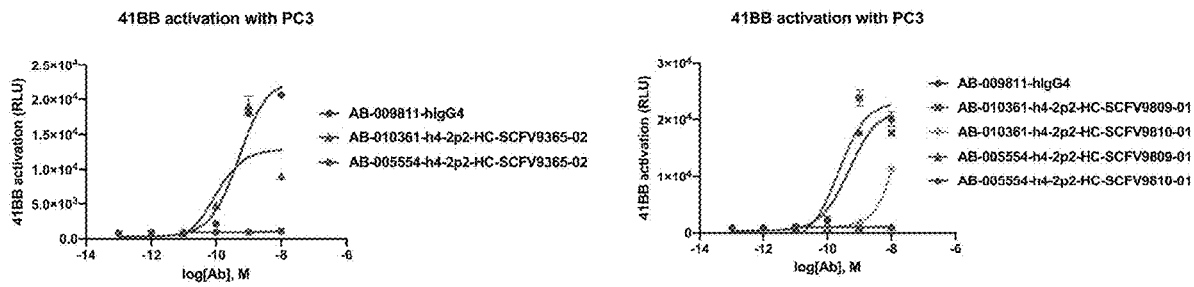
Figure 19D:
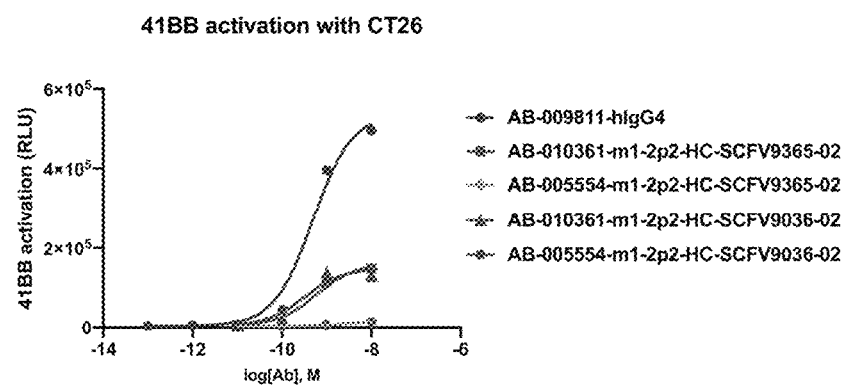
Figure 19E:
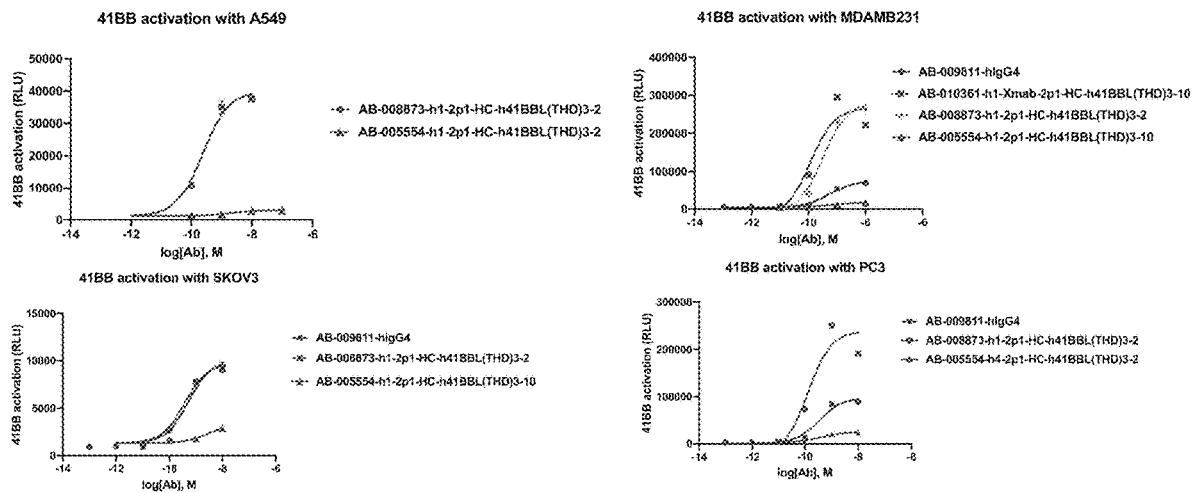

Constructs that comprise AB-008873 fused with h41BBL (THD) 3-2 were generated and assayed for the ability to activate 4-1BB for tumor cell lines A549, MDA-MB231, SKOV3, and PC3, as described above for the EphA2-4-1BB bispecific antibodies. AB-009811 was included as a positive control and 5554-41BBL (THD) 3-10 or 5554-41BBL (THD) 3-2 was used as a negative control. The AB-008873-h41BBL construct activated 4-1BB in all cell lines tested. FIG. 19E.

Example 11. CD3 Bispecific Constructs

This example describes CD3 bispecific antibodies comprising the anti-tumor antibodies described herein. Table 9 provides specific examples of anti-CD3 binding arms that can be combined with any of the anti-EphA2 antibodies described herein. FIG. 53 provides examples of anti-EphA2/anti-CD3 bispecific constructs that can be generated.

Bispecific constructs generated using a 1+1 format with the CD3 arm comprising the VH/VL sequence of AB-008707 were assayed for in vivo activity in a mouse model as follows. NSG-DKO mice were inoculated subcutaneously in the flank with 5e6 PC3 tumor cells in 50% matrigel on Day 0. Human PBMCs from three individual donors were engrafted via IV tail vein injection on day 1 following inoculation (10e6 cells/mouse). Mice were randomized into 5 mice per group per donor based on tumor volume and treated with either vehicle, 5 mg/kg anti-hen egg lysozyme non-targeting control 5554/CD3, 5 mg/kg AB-010361/CD3, or 1 mg/kg cetuximab/CD3 positive control intraperitoneally 1×/week for 3 weeks (indicated by the dotted vertical lines). Tumor volumes were measured twice per week until mice were euthanized. The results show that treatment with AB-010361/CD3 ("AB-010361/CD3") and cetuximab/CD3 positive control ("Positive CD3 control"), but not AB-05554/CD3 negative control ("Non-targeting CD3 control"), led to a decrease in tumor burden, effectively eliminating tumors. FIG. 54. Averaging across the 3 hPBMC donors, comparing 10361-CD3 vs 5554-CD3 is significant with p=3e-7 for NAAC. Positive control 129-CD3 is significant vs 5554-CD3 with p=2e-7 for NAAC.

INCORPORATION BY REFERENCE

Each and every publication and patent document referred to in this disclosure is incorporated herein by reference in its entirety for all purposes to the same extent as if each such publication or document was specifically and individually indicated to be incorporated herein by reference.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

What is claimed is:

1. An antibody that binds to ephrin receptor A2 (EphA2), wherein the antibody comprises:
   a variable heavy chain (VH) region comprising amino acid sequence SEQ ID NO: 607 and a variable light chain (VL) region comprising amino acid sequence SEQ ID NO: 672;
   a VH region comprising amino acid sequence SEQ ID NO: 652 and a VL region comprising amino acid sequence SEQ ID NO: 717;
   a VH region comprising amino acid sequence SEQ ID NO: 67 and a VL region comprising amino acid sequence SEQ ID NO: 78;
   a VH region comprising amino acid sequence SEQ ID NO: 68 and a VL region comprising amino acid sequence SEQ ID NO: 79;
   a VH region comprising amino acid sequence SEQ ID NO: 69 and a VL region comprising amino acid sequence SEQ ID NO: 80;
   a VH region comprising amino acid sequence SEQ ID NO: 70 and a VL region comprising amino acid sequence SEQ ID NO: 81;
   a VH region comprising amino acid sequence SEQ ID NO: 71 and a VL region comprising amino acid sequence SEQ ID NO: 82;
   a VH region comprising amino acid sequence SEQ ID NO: 72 and a VL region comprising amino acid sequence SEQ ID NO: 83;
   a VH region comprising amino acid sequence SEQ ID NO: 73 and a VL region comprising amino acid sequence SEQ ID NO: 84;
   a VH region comprising amino acid sequence SEQ ID NO: 74 and a VL region comprising amino acid sequence SEQ ID NO: 85;
   a VH region comprising amino acid sequence SEQ ID NO: 75 and a VL region comprising amino acid sequence SEQ ID NO: 86;
   a VH region comprising amino acid sequence SEQ ID NO: 76 and a VL region comprising amino acid sequence SEQ ID NO: 87; or
   a VH region comprising amino acid sequence SEQ ID NO: 77 and a VL region comprising amino acid sequence SEQ ID NO: 88.

2. An antibody that binds to EphA2, wherein the antibody comprises a heavy chain complementarity determining region (HCDR)1, HCDR2, HCDR3, light chain complementarity determining region (LCDR)1, LCDR2, and LCDR3 of an antibody designated as AB-010361, AB-010699, AB-008873, AB-009805, AB-009806, AB-009807, AB-009808, AB-009812, AB-009813, AB-009814, AB-009815, AB-009816, AB-009817, AB-010141, AB-010142, AB-010143, AB-010144, AB-010145, AB-010146, AB-010147, AB-010148, AB-010149, AB-010150, AB-010151, AB-010152, AB-010357, AB-010358, AB-010359, AB-010360, AB-010362, AB-010363, AB-010364, AB-010365, AB-010366, AB-010367, AB-010661, AB-010662, AB-010663, AB-010664, AB-010665, AB-010666, AB-010667, AB-010668, AB-010669, AB-010670, AB-010671, AB-010672, AB-010673, AB-010674, AB-010675, AB-010676, AB-010677, AB-010678, AB-010679, AB-010680, AB-010681, AB-010682, AB-010683, AB-010684, AB-010685, AB-010686, AB-010687, AB-010688, AB-010689, AB-010690, AB-010691, AB-010692, AB-010693, AB-010694, AB-010695, AB-010696, AB-010697, AB-010698, AB-010700, AB-010701, or AB-010702.

3. The antibody of claim 2, wherein the antibody is a bispecific antibody comprising a first antigen-binding fragment and a second antigen-binding fragment, wherein the first antigen-binding fragment binds to EphA2, and the second antigen-binding fragment binds to a second antigen.

4. The antibody of claim 3, wherein the second antigen is TNF Receptor Superfamily Member 9 or CD3.

5. A pharmaceutical composition comprising an antibody of claim 2 and a pharmaceutically acceptable carrier.

* * * * *

SEQUENCE LISTING

<160> NUMBER OF SEQ ID NOS: 841

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Ser Phe Ser Asp Tyr Tyr Trp Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ser Leu Ser Asp Tyr His Trp Ser
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Phe Ser Asp Tyr Tyr Trp Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Phe Asn Asp Tyr Tyr Trp Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Ser Phe Ser Asp Tyr Tyr Trp Ser
1               5                   10

<210> SEQ ID NO 6
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 6

Gly Gly Ser Phe Ser Asp Tyr Tyr Trp Ser
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Ser Phe Ser Asp Tyr Tyr Trp Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Ser Phe Ser Asp Tyr Tyr Trp Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Ser Phe Ser Asp Tyr Tyr Trp Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Phe Ser Asp Tyr Tyr Trp Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Ser Phe Ser Asp Tyr Tyr Trp Ser
1               5                   10

```
<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Val Asn His Arg Gly Ser Ile Asn Tyr Asn Asn Tyr Asn Pro Ser
1               5                   10                  15

Leu Lys Ser

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Ile Asn His Ser Gly Ser Thr Asn Tyr Asn Pro Ser Leu Lys Ser
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ile Asn His Ser Gly Ser Thr Asn Tyr Asn Pro Ser Leu Lys Ser
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Val Asn His Ser Gly Ser Thr Ser Tyr Asn Pro Ser Leu Lys Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Ile Asn His Ser Gly Ser Thr Asn Tyr Asn Pro Ser Leu Lys Ser
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 17

Glu Val Asn His Ser Gly Ser Ile Asn Tyr Asn Asn Tyr Asn Pro Ser
1               5                   10                  15

Leu Lys Ser

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Val Asn His Ala Gly Ser Ile Asn Tyr Asn Asn Tyr Asn Pro Ser
1               5                   10                  15

Leu Lys Ser

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Val Asn His Arg Gly Ser Ile Asn Tyr Asn Pro Ser Leu Lys Ser
1               5                   10                  15

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Val Asn His Arg Gly Ser Ile Asn Tyr Asn Asn Tyr Asn Pro Ser
1               5                   10                  15

Leu Lys Ser

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Val Asn His Arg Gly Ser Ile Asn Tyr Asn Asn Tyr Asn Pro Ser
1               5                   10                  15

Leu Lys Ser

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 22

Glu Val Asn His Arg Gly Ser Ile Asn Tyr Asn Asn Tyr Asn Pro Ser
1               5                   10                  15

Leu Lys Ser

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Lys Pro Leu Arg Pro His Cys Thr Asn Gly Val Cys Tyr Ser Gly
1               5                   10                  15

Asp Ala Phe Asp Ile
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Lys Pro Phe Arg Pro His Cys Thr Asn Gly Val Cys His Ser Gly
1               5                   10                  15

Asp Ala Phe Asp Ile
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Lys Pro Phe Arg Pro His Cys Thr Asn Gly Val Cys Tyr Ser Gly
1               5                   10                  15

Asp Ala Phe Asp Ile
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Lys Pro Phe Arg Pro His Cys Thr Asn Gly Val Cys Tyr Ser Gly
1               5                   10                  15

Asp Ala Phe Asp Ile
            20

<210> SEQ ID NO 27
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 27

Ala Lys Pro Phe Arg Pro His Cys Thr Asn Gly Val Cys Tyr Ser Gly
1               5                   10                  15

Asp Ala Phe Asp Ile
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Lys Pro Leu Arg Pro His Cys Thr Asn Gly Val Cys Tyr Ser Gly
1               5                   10                  15

Asp Ala Phe Asp Ile
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Lys Pro Leu Arg Pro His Cys Thr Asn Gly Val Cys Tyr Ser Gly
1               5                   10                  15

Asp Ala Phe Asp Ile
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Lys Pro Leu Arg Pro His Cys Thr Asn Gly Val Cys Tyr Ser Gly
1               5                   10                  15

Asp Ala Phe Asp Ile
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 31

Ala Lys Pro Leu Arg Pro His Cys Thr Asn Gly Val Cys Tyr Ser Gly
1               5                   10                  15

Asp Ala Phe Asp Ile
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Lys Pro Leu Arg Pro His Cys Thr Asn Gly Val Cys Tyr Ser Gly
1               5                   10                  15

Asp Ala Phe Asp Ile
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Lys Pro Leu Arg Pro His Cys Thr Asn Ala Val Cys Tyr Ser Gly
1               5                   10                  15

Asp Ala Phe Asp Ile
            20

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Asn Asn Ile Gly Ser Lys Asn Val His
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Asn Asn Ile Gly Ser Lys Asn Val His
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 36

Gly Gly Asn Asn Ile Gly Thr Lys Asn Val His
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Asn Asn Ile Gly Ser Lys Asn Val His
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Asn Asn Ile Gly Ser Lys Asn Val His
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Asn Asn Ile Gly Ser Lys Asn Val His
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Asn Asn Ile Gly Ser Lys Asn Val His
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Asn Asn Ile Gly Ser Lys Asn Val His
1               5                   10

<210> SEQ ID NO 42
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Asn Asn Ile Gly Ser Lys Asn Val His
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Asn Asn Ile Gly Ser Lys Asn Val His
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Asn Asn Ile Gly Ser Lys Asn Val His
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Ser Asp Arg Pro Ser
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Asp Ser Asp Arg Pro Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Asp Asp Ser Asp Arg Pro Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Asp Ser Asp Arg Pro Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Asp Ser Asp Arg Pro Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Asp Ser Asp Arg Pro Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asp Ser Asp Arg Pro Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Asp Ser Asp Arg Pro Ser
1               5

<210> SEQ ID NO 53
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Asp Ser Asp Arg Pro Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Asp Ser Asp Arg Pro Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Asp Ser Asp Arg Pro Ser
1               5

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Val Trp Asp Ser Ser Ser Asp His Leu Val
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Val Trp Asp Ser Ser Ser Asp His Leu Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 58

Gln Val Trp Asp Ser Ser Ser Asp His Leu Val
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Val Trp Asp Ser Ser Ser Asp His Leu Val
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Val Trp Asp Ser Ser Ser Asp His Leu Val
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Val Trp Asp Ser Ser Ser Asp His Leu Val
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Val Trp Asp Ser Ser Ser Asp His Leu Val
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Val Trp Asp Ser Ser Ser Asp His Leu Val
1               5                   10

<210> SEQ ID NO 64
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Val Trp Asp Ser Ser Ser Asp His Leu Val
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Val Trp Asp Ser Ser Ser Asp His Leu Val
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Val Trp Asp Ser Ser Ser Asp His Leu Val
1               5                   10

<210> SEQ ID NO 67
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Val Asn His Arg Gly Ser Ile Asn Tyr Asn Asn Tyr Asn Pro
    50                  55                  60

Ser Leu Lys Ser Arg Val Thr Ile Ser Val Asp Pro Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 68
```

<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Asp Tyr
            20                  25                  30

His Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Ser Ala Ala Asp Thr Ala Val Tyr Tyr Cys Ala
                85                  90                  95

Lys Pro Phe Arg Pro His Cys Thr Asn Gly Val Cys His Ser Gly Asp
            100                 105                 110

Ala Phe Asp Ile Trp Gly Gln Gly Thr Met Ala Thr Val Ser Ser
        115                 120                 125

<210> SEQ ID NO 69
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Pro Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Lys Pro Phe Arg Pro His Cys Thr Asn Gly Val Cys Tyr Ser Gly Asp
            100                 105                 110

Ala Phe Asp Ile Trp Gly Gln Gly Thr Met Val Thr Val Ser Ser
        115                 120                 125

<210> SEQ ID NO 70
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Asn Asp Tyr
            20                  25                  30

Tyr Trp Ser Trp Ile Arg Gln Pro Pro Gly Lys Gly Leu Glu Trp Ile
        35                  40                  45

Gly Glu Val Asn His Ser Gly Ser Thr Ser Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Pro Phe Arg Pro His Cys Thr Asn Gly Val Cys Tyr Ser Gly Asp
            100                 105                 110

Ala Phe Asp Ile Trp Gly Gln Gly Thr Met Val Thr Val Ser Ser
        115                 120                 125

<210> SEQ ID NO 71
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Pro Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Lys Pro Phe Arg Pro His Cys Thr Asn Gly Val Cys Tyr Ser Gly Asp
            100                 105                 110

Ala Phe Asp Ile Trp Gly Gln Gly Thr Met Val Thr Val Ser Ser
        115                 120                 125

<210> SEQ ID NO 72
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
            35                  40                  45

Gly Glu Val Asn His Ser Gly Ser Ile Asn Tyr Asn Asn Tyr Asn Pro
    50                  55                  60

Ser Leu Lys Ser Arg Val Thr Ile Ser Val Asp Pro Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
                100                 105                 110

Ser Gly Asp Ala Phe Asp Ile Trp Gly Gln Gly Thr Met Val Thr Val
            115                 120                 125

Ala Ser
    130

<210> SEQ ID NO 73
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
            35                  40                  45

Gly Glu Val Asn His Ala Gly Ser Ile Asn Tyr Asn Asn Tyr Asn Pro
    50                  55                  60

Ser Leu Lys Ser Arg Val Thr Ile Ser Val Asp Pro Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
                100                 105                 110

Ser Gly Asp Ala Phe Asp Ile Trp Gly Gln Gly Thr Met Val Thr Val
            115                 120                 125

Ala Ser
    130

<210> SEQ ID NO 74
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
            35                  40                  45

```
Gly Glu Val Asn His Arg Gly Ser Ile Asn Tyr Asn Pro Ser Leu Lys
        50                  55                  60

Ser Arg Val Thr Ile Ser Val Asp Pro Ser Lys Asn Gln Phe Ser Leu
 65                  70                  75                  80

Lys Leu Thr Ser Val Thr Ala Ala Asp Thr Ala Val Tyr Tyr Cys Ala
                 85                  90                  95

Lys Pro Leu Arg Pro His Cys Thr Asn Gly Val Cys Tyr Ser Gly Asp
                100                 105                 110

Ala Phe Asp Ile Trp Gly Gln Gly Thr Met Val Thr Val Ala Ser
                115                 120                 125
```

<210> SEQ ID NO 75
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
                 20                  25                  30

Tyr Trp Ser Trp Ile Arg Gln Pro Pro Gly Lys Gly Leu Glu Trp Ile
             35                  40                  45

Gly Glu Val Asn His Arg Gly Ser Ile Asn Tyr Asn Asn Tyr Asn Pro
        50                  55                  60

Ser Leu Lys Ser Arg Val Thr Ile Ser Val Asp Thr Ser Lys Asn Gln
 65                  70                  75                  80

Phe Ser Leu Lys Leu Thr Ser Val Thr Ala Ala Asp Thr Ala Val Tyr
                 85                  90                  95

Tyr Cys Ala Lys Pro Leu Arg Pro His Cys Thr Asn Gly Val Cys Tyr
                100                 105                 110

Ser Gly Asp Ala Phe Asp Ile Trp Gly Gln Gly Thr Met Val Thr Val
            115                 120                 125

Ala Ser
    130
```

<210> SEQ ID NO 76
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
                 20                  25                  30

Tyr Trp Ser Trp Ile Arg Gln Pro Pro Gly Lys Gly Leu Glu Trp Ile
             35                  40                  45

Gly Glu Val Asn His Arg Gly Ser Ile Asn Tyr Asn Asn Tyr Asn Pro
        50                  55                  60

Ser Leu Lys Ser Arg Val Thr Ile Ser Val Asp Ala Ser Lys Asn Gln
 65                  70                  75                  80
```

```
Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 77
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Val Asn His Arg Gly Ser Ile Asn Tyr Asn Tyr Asn Pro
    50                  55                  60

Ser Leu Lys Ser Arg Val Thr Ile Ser Val Asp Pro Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Ala Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 78
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

Leu Val Phe Gly Gly Gly Thr Lys Leu Thr Val Leu
            100                 105

<210> SEQ ID NO 79
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 80
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Thr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Ala Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Leu Val Phe Gly Gly Gly Thr Lys Leu Thr Val Leu
            100                 105

<210> SEQ ID NO 84
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ser Tyr Val Leu Thr Gln Pro Pro Ser Val Ser Val Ala Pro Gly Gln
 1               5                   10                  15

Thr Ala Arg Ile Thr Cys Gly Gly Asn Asn Ile Gly Ser Lys Asn Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Gln Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Leu Val Phe Gly Gly Gly Thr Lys Leu Thr Val Leu
            100                 105

<210> SEQ ID NO 85
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ser Tyr Val Leu Thr Gln Pro Pro Ser Val Ser Val Ala Pro Gly Gln
 1               5                   10                  15

Thr Ala Arg Ile Thr Cys Gly Gly Asn Asn Ile Gly Ser Lys Asn Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Gln Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Leu Val Phe Gly Gly Gly Thr Lys Leu Thr Val Leu
            100                 105

<210> SEQ ID NO 86
<211> LENGTH: 108
<212> TYPE: PRT
<213> ORGANISM: Artificial Sequence
<220> FEATURE:
```

-continued

<223> OTHER INFORMATION: Description of Artificial Sequence: Synthetic
     polypeptide

<400> SEQUENCE: 86

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 87
<211> LENGTH: 108
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 87

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 88
<211> LENGTH: 108
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 88

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

```
Asp Asp Ser Asp Arg Pro Ser Gly Ile Pro Glu Gln Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                85                  90                  95

Leu Val Phe Gly Gly Gly Thr Lys Leu Thr Val Leu
            100                 105
```

<210> SEQ ID NO 89
<211> LENGTH: 459
<212> TYPE: PRT
<213> ORGANISM: Artificial Sequence
<220> FEATURE:
<223> OTHER INFORMATION: Description of Artificial Sequence: Synthetic
        polypeptide

<400> SEQUENCE: 89

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
                20                  25                  30

Tyr Trp Ser Trp Ile Arg Gln Pro Pro Gly Lys Gly Leu Glu Trp Ile
            35                  40                  45

Gly Glu Val Asn His Arg Gly Ser Ile Asn Tyr Asn Asn Tyr Asn Pro
 50                  55                  60

Ser Leu Lys Ser Arg Val Thr Ile Ser Val Asp Pro Ser Lys Asn Gln
 65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
            115                 120                 125

Ala Ser Ala Lys Thr Thr Ala Pro Ser Val Tyr Pro Leu Ala Pro Val
130                 135                 140

Cys Gly Asp Thr Thr Gly Ser Ser Val Thr Leu Gly Cys Leu Val Lys
145                 150                 155                 160

Gly Tyr Phe Pro Glu Pro Val Thr Leu Thr Trp Asn Ser Gly Ser Leu
                165                 170                 175

Ser Ser Gly Val His Thr Phe Pro Ala Val Leu Gln Ser Asp Leu Tyr
            180                 185                 190

Thr Leu Ser Ser Ser Val Thr Val Thr Ser Ser Thr Trp Pro Ser Gln
        195                 200                 205

Ser Ile Thr Cys Asn Val Ala His Pro Ala Ser Ser Thr Lys Val Asp
    210                 215                 220

Lys Lys Ile Glu Pro Arg Gly Pro Thr Ile Lys Pro Cys Pro Pro Cys
225                 230                 235                 240

Lys Cys Pro Ala Pro Asn Leu Leu Gly Gly Pro Ser Val Phe Ile Phe
                245                 250                 255

Pro Pro Lys Ile Lys Asp Val Leu Met Ile Ser Leu Ser Pro Ile Val
            260                 265                 270

Thr Cys Val Val Val Asp Val Ser Glu Asp Asp Pro Asp Val Gln Ile
        275                 280                 285
```

```
Ser Trp Phe Val Asn Asn Val Glu Val His Thr Ala Gln Thr Gln Thr
    290                 295                 300

His Arg Glu Asp Tyr Asn Ser Thr Leu Arg Val Val Ser Ala Leu Pro
305                 310                 315                 320

Ile Gln His Gln Asp Trp Met Ser Gly Lys Glu Phe Lys Cys Lys Val
                    325                 330                 335

Asn Asn Lys Asp Leu Pro Ala Pro Ile Glu Arg Thr Ile Ser Lys Pro
                340                 345                 350

Lys Gly Ser Val Arg Ala Pro Gln Val Tyr Val Leu Pro Pro Pro Glu
                355                 360                 365

Glu Glu Met Thr Lys Lys Gln Val Thr Leu Thr Cys Met Val Thr Asp
370                 375                 380

Phe Met Pro Glu Asp Ile Tyr Val Glu Trp Thr Asn Asn Gly Lys Thr
385                 390                 395                 400

Glu Leu Asn Tyr Lys Asn Thr Glu Pro Val Leu Asp Ser Asp Gly Ser
                405                 410                 415

Tyr Phe Met Tyr Ser Lys Leu Arg Val Glu Lys Lys Asn Trp Val Glu
                420                 425                 430

Arg Asn Ser Tyr Ser Cys Ser Val Val His Glu Gly Leu His Asn His
                435                 440                 445

His Thr Thr Lys Ser Phe Ser Arg Thr Pro Gly
                450                 455

<210> SEQ ID NO 90
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu Gly Gln Pro Lys
            100                 105                 110

Ser Ser Pro Ser Val Thr Leu Phe Pro Pro Ser Ser Glu Glu Leu Glu
        115                 120                 125

Thr Asn Lys Ala Thr Leu Val Cys Thr Ile Thr Asp Phe Tyr Pro Gly
    130                 135                 140

Val Val Thr Val Asp Trp Lys Val Asp Gly Thr Pro Val Thr Gln Gly
145                 150                 155                 160

Met Glu Thr Thr Gln Pro Ser Lys Gln Ser Asn Asn Lys Tyr Met Ala
                165                 170                 175
```

```
Ser Ser Tyr Leu Thr Leu Thr Ala Arg Ala Trp Glu Arg His Ser Ser
            180                 185                 190

Tyr Ser Cys Gln Val Thr His Glu Gly His Thr Val Glu Lys Ser Leu
        195                 200                 205

Ser Arg Ala Asp Cys Ser
    210

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Gly Gly Ser Gly Gly Gly Ser Gly Gly Gly Gly Ser
1               5                  10                  15

<210> SEQ ID NO 92
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Gly Gly Gly
65                  70                  75                  80

Gly Ser Gly Gly Gly Gly Ser Gly Gly Gly Ser Gly Gly Gly Gly Ser
                85                  90                  95

Leu Gln Asn Trp Val Asn Val Ile Ser Asp Leu Lys Lys Ile Glu Asp
            100                 105                 110

Leu Ile Gln Ser Met His Ile Asp Ala Thr Leu Tyr Thr Glu Ser Asp
        115                 120                 125

Val His Pro Ser Cys Lys Val Thr Ala Met Lys Cys Phe Leu Leu Glu
    130                 135                 140

Leu Gln Val Ile Ser Leu Glu Ser Gly Asp Ala Ser Ile His Asp Thr
145                 150                 155                 160

Val Glu Asn Leu Ile Ile Leu Ala Asn Asn Ser Leu Ser Ser Asn Gly
                165                 170                 175

Asn Val Thr Glu Ser Gly Cys Lys Glu Cys Glu Glu Leu Glu Glu Lys
            180                 185                 190

Asn Ile Lys Glu Phe Leu Gln Ser Phe Val His Ile Val Gln Met Phe
        195                 200                 205

Ile Asn Thr Ser
    210

<210> SEQ ID NO 93
```

<211> LENGTH: 212
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Ile Thr Cys Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg Asp Pro Ala Leu Val His Gln Arg Pro Ala Pro Pro Gly Gly Gly
65                  70                  75                  80
Gly Ser Gly Gly Gly Ser Gly Gly Gly Ser Gly Gly Gly Gly Ser
                85                  90                  95
Leu Gln Asn Trp Val Asn Val Ile Ser Asp Leu Lys Lys Ile Glu Asp
            100                 105                 110
Leu Ile Gln Ser Met His Ile Asp Ala Thr Leu Tyr Thr Glu Ser Asn
        115                 120                 125
Val His Pro Ser Cys Lys Val Thr Ala Met Lys Cys Phe Leu Leu Glu
    130                 135                 140
Leu Gln Val Ile Ser Leu Glu Ser Gly Asp Ala Ser Ile His Asp Thr
145                 150                 155                 160
Val Gln Asp Leu Ile Ile Leu Ala Asn Asn Ser Leu Ser Ser Asn Gly
                165                 170                 175
Asn Val Thr Glu Ser Gly Cys Lys Glu Cys Glu Glu Leu Glu Glu Lys
            180                 185                 190
Asn Ile Lys Glu Phe Leu Gln Ser Phe Val His Ile Val Gln Met Phe
        195                 200                 205
Ile Asn Thr Ser
    210

<210> SEQ ID NO 94
<211> LENGTH: 976
<212> TYPE: PRT
<213> ORGANISM: Homo sapiens

<400> SEQUENCE: 94

Met Glu Leu Gln Ala Ala Arg Ala Cys Phe Ala Leu Leu Trp Gly Cys
1               5                   10                  15
Ala Leu Ala Ala Ala Ala Ala Gln Gly Lys Glu Val Val Leu Leu
            20                  25                  30
Asp Phe Ala Ala Ala Gly Gly Glu Leu Gly Trp Leu Thr His Pro Tyr
        35                  40                  45
Gly Lys Gly Trp Asp Leu Met Gln Asn Ile Met Asn Asp Met Pro Ile
    50                  55                  60
Tyr Met Tyr Ser Val Cys Asn Val Met Ser Gly Asp Gln Asp Asn Trp
65                  70                  75                  80
Leu Arg Thr Asn Trp Val Tyr Arg Gly Glu Ala Glu Arg Ile Phe Ile
                85                  90                  95
Glu Leu Lys Phe Thr Val Arg Asp Cys Asn Ser Phe Pro Gly Gly Ala
            100                 105                 110

```
Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
            165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
    450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525
```

-continued

```
Pro Glu Gly Ser Gly Asn Leu Ala Val Ile Gly Gly Val Ala Val Gly
            530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
                595                 600                 605

His Pro Ser Cys Val Thr Arg Gln Lys Val Ile Gly Ala Gly Glu Phe
610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
                660                 665                 670

His Asn Ile Ile Arg Leu Glu Gly Val Ile Ser Lys Tyr Lys Pro Met
            675                 680                 685

Met Ile Ile Thr Glu Tyr Met Glu Asn Gly Ala Leu Asp Lys Phe Leu
690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
            740                 745                 750

Cys Lys Val Ser Asp Phe Gly Leu Ser Arg Val Leu Glu Asp Asp Pro
            755                 760                 765

Glu Ala Thr Tyr Thr Thr Ser Gly Gly Lys Ile Pro Ile Arg Trp Thr
770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
            835                 840                 845

Leu Met Met Gln Cys Trp Gln Gln Glu Arg Ala Arg Arg Pro Lys Phe
            850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
                915                 920                 925

Gly Tyr Thr Ala Ile Glu Lys Val Val Gln Met Thr Asn Asp Asp Ile
930                 935                 940
```

```
Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
            965                 970                 975
```

<210> SEQ ID NO 95
<211> LENGTH: 98
<212> TYPE: PRT
<213> ORGANISM: Homo sapiens

<400> SEQUENCE: 95

```
Thr Glu Pro Pro Lys Val Arg Leu Glu Gly Arg Ser Thr Thr Ser Leu
1               5                   10                  15

Ser Val Ser Trp Ser Ile Pro Pro Gln Gln Ser Arg Val Trp Lys
                20                  25                  30

Tyr Glu Val Thr Tyr Arg Lys Lys Gly Asp Ser Asn Ser Tyr Asn Val
                35                  40                  45

Arg Arg Thr Glu Gly Phe Ser Val Thr Leu Asp Asp Leu Ala Pro Asp
        50                  55                  60

Thr Thr Tyr Leu Val Gln Val Gln Ala Leu Thr Gln Glu Gly Gln Gly
65                  70                  75                  80

Ala Gly Ser Lys Val His Glu Phe Gln Thr Leu Ser Pro Glu Gly Ser
                85                  90                  95

Gly Asn
```

<210> SEQ ID NO 96
<211> LENGTH: 24
<212> TYPE: PRT
<213> ORGANISM: Homo sapiens

<400> SEQUENCE: 96

```
Met Glu Leu Gln Ala Ala Arg Ala Cys Phe Ala Leu Leu Trp Gly Cys
1               5                   10                  15

Ala Leu Ala Ala Ala Ala Ala Ala
                20
```

<210> SEQ ID NO 97
<211> LENGTH: 175
<212> TYPE: PRT
<213> ORGANISM: Homo sapiens

<400> SEQUENCE: 97

```
Gln Gly Lys Glu Val Val Leu Leu Asp Phe Ala Ala Ala Gly Gly Glu
1               5                   10                  15

Leu Gly Trp Leu Thr His Pro Tyr Gly Lys Gly Trp Asp Leu Met Gln
                20                  25                  30

Asn Ile Met Asn Asp Met Pro Ile Tyr Met Tyr Ser Val Cys Asn Val
                35                  40                  45

Met Ser Gly Asp Gln Asp Asn Trp Leu Arg Thr Asn Trp Val Tyr Arg
        50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
                100                 105                 110
```

```
Arg Leu Phe Thr Lys Ile Asp Thr Ile Ala Pro Asp Glu Ile Thr Val
        115                 120                 125

Ser Ser Asp Phe Glu Ala Arg His Val Lys Leu Asn Val Glu Glu Arg
    130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys
                165                 170                 175

<210> SEQ ID NO 98
<211> LENGTH: 62
<212> TYPE: PRT
<213> ORGANISM: Homo sapiens

<400> SEQUENCE: 98

Lys Cys Pro Glu Leu Leu Gln Gly Leu Ala His Phe Pro Glu Thr Ile
1               5                   10                  15

Ala Gly Ser Asp Ala Pro Ser Leu Ala Thr Val Ala Gly Thr Cys Val
            20                  25                  30

Asp His Ala Val Val Pro Pro Gly Gly Glu Glu Pro Arg Met His Cys
        35                  40                  45

Ala Val Asp Gly Glu Trp Leu Val Pro Ile Gly Gln Cys Leu
    50                  55                  60

<210> SEQ ID NO 99
<211> LENGTH: 65
<212> TYPE: PRT
<213> ORGANISM: Homo sapiens

<400> SEQUENCE: 99

Cys Gln Ala Gly Tyr Glu Lys Val Glu Asp Ala Cys Gln Ala Cys Ser
1               5                   10                  15

Pro Gly Phe Phe Lys Phe Glu Ala Ser Glu Ser Pro Cys Leu Glu Cys
            20                  25                  30

Pro Glu His Thr Leu Pro Ser Pro Glu Gly Ala Thr Ser Cys Glu Cys
        35                  40                  45

Glu Glu Gly Phe Phe Arg Ala Pro Gln Asp Pro Ala Ser Met Pro Cys
    50                  55                  60

Thr
65

<210> SEQ ID NO 100
<211> LENGTH: 110
<212> TYPE: PRT
<213> ORGANISM: Homo sapiens

<400> SEQUENCE: 100

Arg Pro Pro Ser Ala Pro His Tyr Leu Thr Ala Val Gly Met Gly Ala
1               5                   10                  15

Lys Val Glu Leu Arg Trp Thr Pro Pro Gln Asp Ser Gly Gly Arg Glu
            20                  25                  30

Asp Ile Val Tyr Ser Val Thr Cys Glu Gln Cys Trp Pro Glu Ser Gly
        35                  40                  45

Glu Cys Gly Pro Cys Glu Ala Ser Val Arg Tyr Ser Glu Pro Pro His
    50                  55                  60

Gly Leu Thr Arg Thr Ser Val Thr Val Ser Asp Leu Glu Pro His Met
65                  70                  75                  80
```

```
Asn Tyr Thr Phe Thr Val Glu Ala Arg Asn Gly Val Ser Gly Leu Val
                85                  90                  95

Thr Ser Arg Ser Phe Arg Thr Ala Ser Val Ser Ile Asn Gln
            100                 105                 110

<210> SEQ ID NO 101
<211> LENGTH: 510
<212> TYPE: PRT
<213> ORGANISM: Homo sapiens

<400> SEQUENCE: 101

Gln Gly Lys Glu Val Val Leu Leu Asp Phe Ala Ala Gly Gly Glu
1               5                   10                  15

Leu Gly Trp Leu Thr His Pro Tyr Gly Lys Gly Trp Asp Leu Met Gln
                20                  25                  30

Asn Ile Met Asn Asp Met Pro Ile Tyr Met Tyr Ser Val Cys Asn Val
                35                  40                  45

Met Ser Gly Asp Gln Asp Asn Trp Leu Arg Thr Asn Trp Val Tyr Arg
    50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
                100                 105                 110

Arg Leu Phe Thr Lys Ile Asp Thr Ile Ala Pro Asp Glu Ile Thr Val
                115                 120                 125

Ser Ser Asp Phe Glu Ala Arg His Val Lys Leu Asn Val Glu Glu Arg
    130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys Lys
                165                 170                 175

Cys Pro Glu Leu Leu Gln Gly Leu Ala His Phe Pro Glu Thr Ile Ala
                180                 185                 190

Gly Ser Asp Ala Pro Ser Leu Ala Thr Val Ala Gly Thr Cys Val Asp
                195                 200                 205

His Ala Val Val Pro Pro Gly Gly Glu Pro Arg Met His Cys Ala
                210                 215                 220

Val Asp Gly Glu Trp Leu Val Pro Ile Gly Gln Cys Leu Cys Gln Ala
225                 230                 235                 240

Gly Tyr Glu Lys Val Glu Asp Ala Cys Gln Ala Cys Ser Pro Gly Phe
                245                 250                 255

Phe Lys Phe Glu Ala Ser Glu Ser Pro Cys Leu Glu Cys Pro Glu His
                260                 265                 270

Thr Leu Pro Ser Pro Glu Gly Ala Thr Ser Cys Glu Cys Glu Glu Gly
                275                 280                 285

Phe Phe Arg Ala Pro Gln Asp Pro Ala Ser Met Pro Cys Thr Arg Pro
                290                 295                 300

Pro Ser Ala Pro His Tyr Leu Thr Ala Val Gly Met Gly Ala Lys Val
305                 310                 315                 320

Glu Leu Arg Trp Thr Pro Pro Gln Asp Ser Gly Gly Arg Glu Asp Ile
                325                 330                 335

Val Tyr Ser Val Thr Cys Glu Gln Cys Trp Pro Glu Ser Gly Glu Cys
                340                 345                 350
```

```
Gly Pro Cys Glu Ala Ser Val Arg Tyr Ser Glu Pro His Gly Leu
            355                 360                 365

Thr Arg Thr Ser Val Thr Val Ser Asp Leu Glu Pro His Met Asn Tyr
    370                 375                 380

Thr Phe Thr Val Glu Ala Arg Asn Gly Val Ser Gly Leu Val Thr Ser
385                 390                 395                 400

Arg Ser Phe Arg Thr Ala Ser Val Ser Ile Asn Gln Thr Glu Pro Pro
                405                 410                 415

Lys Val Arg Leu Glu Gly Arg Ser Thr Thr Ser Leu Ser Val Ser Trp
                420                 425                 430

Ser Ile Pro Pro Gln Gln Ser Arg Val Trp Lys Tyr Glu Val Thr
                435                 440                 445

Tyr Arg Lys Lys Gly Asp Ser Asn Ser Tyr Asn Val Arg Arg Thr Glu
    450                 455                 460

Gly Phe Ser Val Thr Leu Asp Asp Leu Ala Pro Asp Thr Thr Tyr Leu
465                 470                 475                 480

Val Gln Val Gln Ala Leu Thr Gln Glu Gly Gln Ala Gly Ser Lys
                485                 490                 495

Val His Glu Phe Gln Thr Leu Ser Pro Glu Gly Ser Gly Asn
                500                 505                 510

<210> SEQ ID NO 102
<211> LENGTH: 524
<212> TYPE: PRT
<213> ORGANISM: Homo sapiens

<400> SEQUENCE: 102

Ser Arg Val Tyr Pro Ala Asn Glu Val Thr Leu Leu Asp Ser Arg Ser
1               5                   10                  15

Val Gln Gly Glu Leu Gly Trp Ile Ala Ser Pro Leu Glu Gly Gly Trp
                20                  25                  30

Glu Glu Val Ser Ile Met Asp Glu Lys Asn Thr Pro Ile Arg Thr Tyr
            35                  40                  45

Gln Val Cys Asn Val Met Glu Pro Ser Gln Asn Asn Trp Leu Arg Thr
    50                  55                  60

Asp Trp Ile Thr Arg Glu Gly Ala Gln Arg Val Tyr Ile Glu Ile Lys
65              70                  75                  80

Phe Thr Leu Arg Asp Cys Asn Ser Leu Pro Gly Val Met Gly Thr Cys
                85                  90                  95

Lys Glu Thr Phe Asn Leu Tyr Tyr Tyr Glu Ser Asp Asn Asp Lys Glu
                100                 105                 110

Arg Phe Ile Arg Glu Asn Gln Phe Val Lys Ile Asp Thr Ile Ala Ala
                115                 120                 125

Asp Glu Ser Phe Thr Gln Val Asp Ile Gly Asp Arg Ile Met Lys Leu
                130                 135                 140

Asn Thr Glu Ile Arg Asp Val Gly Pro Leu Ser Lys Lys Gly Phe Tyr
145                 150                 155                 160

Leu Ala Phe Gln Asp Val Gly Ala Cys Ile Ala Leu Val Ser Val Arg
                165                 170                 175

Val Phe Tyr Lys Lys Cys Pro Leu Thr Val Arg Asn Leu Ala Gln Phe
                180                 185                 190

Pro Asp Thr Ile Thr Gly Ala Asp Thr Ser Ser Leu Val Glu Val Arg
                195                 200                 205
```

Gly Ser Cys Val Asn Asn Ser Glu Glu Lys Asp Val Pro Lys Met Tyr
    210                 215                 220

Cys Gly Ala Asp Gly Glu Trp Leu Val Pro Ile Gly Asn Cys Leu Cys
225                 230                 235                 240

Asn Ala Gly His Glu Glu Arg Ser Gly Glu Cys Gln Ala Cys Lys Ile
            245                 250                 255

Gly Tyr Tyr Lys Ala Leu Ser Thr Asp Ala Thr Cys Ala Lys Cys Pro
        260                 265                 270

Pro His Ser Tyr Ser Val Trp Glu Gly Ala Thr Ser Cys Thr Cys Asp
    275                 280                 285

Arg Gly Phe Phe Arg Ala Asp Asn Asp Ala Ala Ser Met Pro Cys Thr
290                 295                 300

Arg Pro Pro Ser Ala Pro Leu Asn Leu Ile Ser Asn Val Asn Glu Thr
305                 310                 315                 320

Ser Val Asn Leu Glu Trp Ser Ser Pro Gln Asn Thr Gly Gly Arg Gln
                325                 330                 335

Asp Ile Ser Tyr Asn Val Val Cys Lys Lys Cys Gly Ala Gly Asp Pro
            340                 345                 350

Ser Lys Cys Arg Pro Cys Gly Ser Gly Val His Tyr Thr Pro Gln Gln
        355                 360                 365

Asn Gly Leu Lys Thr Thr Lys Val Ser Ile Thr Asp Leu Leu Ala His
    370                 375                 380

Thr Asn Tyr Thr Phe Glu Ile Trp Ala Val Asn Gly Val Ser Lys Tyr
385                 390                 395                 400

Asn Pro Asn Pro Asp Gln Ser Val Ser Val Thr Val Thr Thr Asn Gln
                405                 410                 415

Ala Ala Pro Ser Ser Ile Ala Leu Val Gln Ala Lys Glu Val Thr Arg
            420                 425                 430

Tyr Ser Val Ala Leu Ala Trp Leu Glu Pro Asp Arg Pro Asn Gly Val
        435                 440                 445

Ile Leu Glu Tyr Glu Val Lys Tyr Tyr Glu Lys Asp Gln Asn Glu Arg
450                 455                 460

Ser Tyr Arg Ile Val Arg Thr Ala Ala Arg Asn Thr Asp Ile Lys Gly
465                 470                 475                 480

Leu Asn Pro Leu Thr Ser Tyr Val Phe His Val Arg Ala Arg Thr Ala
                485                 490                 495

Ala Gly Tyr Gly Asp Phe Ser Glu Pro Leu Glu Val Thr Thr Asn Thr
            500                 505                 510

Val Pro Ser Arg Ile Ile Gly Asp Gly Ala Asn Ser
        515                 520

<210> SEQ ID NO 103
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Gly Lys Glu Val Val Leu Leu Asp Phe Ala Ala Ala Gly Gly Glu
1               5                   10                  15

Leu Gly Trp Leu Thr His Pro Tyr Gly Lys Gly Trp Asp Leu Met Gln
                20                  25                  30

```
Asn Ile Met Asn Asp Met Pro Ile Tyr Met Tyr Ser Val Cys Asn Val
            35                  40                  45

Met Ser Gly Asp Gln Asp Asn Trp Leu Arg Thr Asn Trp Val Tyr Arg
    50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
                100                 105                 110

Arg Leu Phe Thr Lys Ile Asp Thr Ile Ala Pro Asp Glu Ile Thr Val
        115                 120                 125

Ser Ser Asp Phe Glu Ala Arg His Val Lys Leu Asn Val Glu Glu Arg
    130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys Lys
                165                 170                 175

Cys Pro Glu Leu Leu Gln Gly Leu Ala His Phe Pro Glu Thr Ile Ala
                180                 185                 190

Gly Ser Asp Ala Pro Ser Leu Ala Thr Val Ala Gly Thr Cys Val Asp
        195                 200                 205

His Ala Val Val Pro Pro Gly Gly Glu Glu Pro Arg Met His Cys Ala
    210                 215                 220

Val Asp Gly Glu Trp Leu Val Pro Ile Gly Gln Cys Leu Cys Gln Ala
225                 230                 235                 240

Gly Tyr Glu Lys Val Glu Asp Ala Cys Gln Ala Cys Ser Pro Gly Phe
                245                 250                 255

Phe Lys Phe Glu Ala Ser Glu Ser Pro Cys Leu Glu Cys Pro Glu His
                260                 265                 270

Thr Leu Pro Ser Pro Glu Gly Ala Thr Ser Cys Glu Cys Glu Glu Gly
        275                 280                 285

Phe Phe Arg Ala Pro Gln Asp Pro Ala Ser Met Pro Cys Thr Arg Pro
    290                 295                 300

Pro Ser Ala Pro Leu Asn Leu Ile Ser Asn Val Asn Glu Thr Ser Val
305                 310                 315                 320

Asn Leu Glu Trp Ser Ser Pro Gln Asn Thr Gly Gly Arg Gln Asp Ile
                325                 330                 335

Ser Tyr Asn Val Val Cys Lys Lys Cys Gly Ala Gly Asp Pro Ser Lys
                340                 345                 350

Cys Arg Pro Cys Gly Ser Gly Val His Tyr Thr Pro Gln Gln Asn Gly
        355                 360                 365

Leu Lys Thr Thr Lys Val Ser Ile Thr Asp Leu Leu Ala His Thr Asn
    370                 375                 380

Tyr Thr Phe Glu Ile Trp Ala Val Asn Gly Val Ser Lys Tyr Asn Pro
385                 390                 395                 400

Asn Pro Asp Gln Ser Val Ser Val Thr Val Thr Thr Asn Gln Thr Glu
                405                 410                 415

Pro Pro Lys Val Arg Leu Glu Gly Arg Ser Thr Thr Ser Leu Ser Val
                420                 425                 430

Ser Trp Ser Ile Pro Pro Pro Gln Gln Ser Arg Val Trp Lys Tyr Glu
        435                 440                 445
```

```
Val Thr Tyr Arg Lys Lys Gly Asp Ser Asn Ser Tyr Asn Val Arg Arg
    450                 455                 460

Thr Glu Gly Phe Ser Val Thr Leu Asp Asp Leu Ala Pro Asp Thr Thr
465                 470                 475                 480

Tyr Leu Val Gln Val Gln Ala Leu Thr Gln Glu Gly Gln Gly Ala Gly
                485                 490                 495

Ser Lys Val His Glu Phe Gln Thr Leu Ser Pro Glu Gly Ser Gly Asn
                500                 505                 510

<210> SEQ ID NO 104
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Gly Lys Glu Val Val Leu Leu Asp Phe Ala Ala Ala Gly Gly Glu
1               5                   10                  15

Leu Gly Trp Leu Thr His Pro Tyr Gly Lys Gly Trp Asp Leu Met Gln
                20                  25                  30

Asn Ile Met Asn Asp Met Pro Ile Tyr Met Tyr Ser Val Cys Asn Val
            35                  40                  45

Met Ser Gly Asp Gln Asp Asn Trp Leu Arg Thr Asn Trp Val Tyr Arg
50                  55                  60

Gly Glu Ala Glu Arg Ile Phe Ile Glu Leu Lys Phe Thr Val Arg Asp
65                  70                  75                  80

Cys Asn Ser Phe Pro Gly Gly Ala Ser Ser Cys Lys Glu Thr Phe Asn
                85                  90                  95

Leu Tyr Tyr Ala Glu Ser Asp Leu Asp Tyr Gly Thr Asn Phe Gln Lys
            100                 105                 110

Arg Leu Phe Thr Lys Ile Asp Thr Ile Ala Pro Asp Glu Ile Thr Val
        115                 120                 125

Ser Ser Asp Phe Glu Ala Arg His Val Lys Leu Asn Val Glu Glu Arg
130                 135                 140

Ser Val Gly Pro Leu Thr Arg Lys Gly Phe Tyr Leu Ala Phe Gln Asp
145                 150                 155                 160

Ile Gly Ala Cys Val Ala Leu Leu Ser Val Arg Val Tyr Tyr Lys Lys
                165                 170                 175

Cys Pro Glu Leu Leu Gln Gly Leu Ala His Phe Pro Glu Thr Ile Ala
            180                 185                 190

Gly Ser Asp Ala Pro Ser Leu Ala Thr Val Ala Gly Thr Cys Val Asp
        195                 200                 205

His Ala Val Val Pro Pro Gly Gly Glu Glu Pro Arg Met His Cys Ala
        210                 215                 220

Val Asp Gly Glu Trp Leu Val Pro Ile Gly Gln Cys Leu Cys Gln Ala
225                 230                 235                 240

Gly Tyr Glu Lys Val Glu Asp Ala Cys Gln Ala Cys Ser Pro Gly Phe
                245                 250                 255

Phe Lys Phe Glu Ala Ser Glu Ser Pro Cys Leu Glu Cys Pro Glu His
            260                 265                 270

Thr Leu Pro Ser Pro Glu Gly Ala Thr Ser Cys Glu Cys Glu Glu Gly
        275                 280                 285

Phe Phe Arg Ala Pro Gln Asp Pro Ala Ser Met Pro Cys Thr Arg Pro
        290                 295                 300
```

Pro Ser Ala Pro His Tyr Leu Thr Ala Val Gly Met Gly Ala Lys Val
305                 310                 315                 320

Glu Leu Arg Trp Thr Pro Pro Gln Asp Ser Gly Gly Arg Glu Asp Ile
                325                 330                 335

Val Tyr Ser Val Thr Cys Glu Gln Cys Trp Pro Glu Ser Gly Glu Cys
                340                 345                 350

Gly Pro Cys Glu Ala Ser Val Arg Tyr Ser Glu Pro His Gly Leu
            355                 360                 365

Thr Arg Thr Ser Val Thr Val Ser Asp Leu Glu Pro His Met Asn Tyr
370                 375                 380

Thr Phe Thr Val Glu Ala Arg Asn Gly Val Ser Gly Leu Val Thr Ser
385                 390                 395                 400

Arg Ser Phe Arg Thr Ala Ser Val Ser Ile Asn Gln Ala Ala Pro Ser
                405                 410                 415

Ser Ile Ala Leu Val Gln Ala Lys Glu Val Thr Arg Tyr Ser Val Ala
            420                 425                 430

Leu Ala Trp Leu Glu Pro Asp Arg Pro Asn Gly Val Ile Leu Glu Tyr
            435                 440                 445

Glu Val Lys Tyr Glu Lys Asp Gln Asn Glu Arg Ser Tyr Arg Ile
    450                 455                 460

Val Arg Thr Ala Ala Arg Asn Thr Asp Ile Lys Gly Leu Asn Pro Leu
465                 470                 475                 480

Thr Ser Tyr Val Phe His Val Arg Ala Arg Thr Ala Ala Gly Tyr Gly
                485                 490                 495

Asp Phe Ser Glu Pro Leu Glu Val Thr Thr Asn Thr Val Pro Ser Arg
                500                 505                 510

Ile Ile Gly Asp Gly Ala Asn Ser
            515                 520

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Ser Gly Gly Gly Gly Ser Gly Gly Gly Gly Ser Gly Gly Gly Gly
1               5                   10                  15

Ser

<210> SEQ ID NO 106
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
                20                  25                  30

Thr Gly Gly Leu Ser Tyr Lys Glu Asp Thr Lys Glu Leu Val Val Ala
            35                  40                  45

```
Lys Ala Gly Val Tyr Tyr Val Phe Phe Gln Leu Glu Leu Arg Arg Val
            50                  55                  60

Val Ala Gly Glu Gly Ser Gly Ser Val Ser Leu Ala Leu His Leu Gln
 65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
                    100                 105                 110

Gly Arg Leu Leu His Leu Ser Ala Gly Gln Arg Leu Gly Val His Leu
                115                 120                 125

His Thr Glu Ala Arg Ala Arg His Ala Trp Gln Leu Thr Gln Gly Ala
    130                 135                 140

Thr Val Leu Gly Leu Phe Arg Val Thr Pro
145                 150

<210> SEQ ID NO 107
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Gly Met Phe Ala Gln Leu Val Ala Gln Asn Val Leu Leu Ile Asp
  1               5                  10                  15

Gly Pro Leu Ser Trp Tyr Ser Asp Pro Gly Leu Ala Gly Val Ser Leu
                 20                  25                  30

Thr Gly Gly Leu Ser Tyr Lys Glu Asp Thr Lys Glu Leu Val Val Ala
             35                  40                  45

Lys Ala Gly Val Tyr Tyr Val Phe Phe Gln Leu Glu Leu Arg Arg Val
            50                  55                  60

Val Ala Gly Glu Gly Ser Gly Ser Val Ser Leu Ala Leu His Leu Gln
 65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
                    100                 105                 110

Gly Arg Leu Leu His Leu Ser Ala Gly Gln Arg Leu Gly Val His Leu
                115                 120                 125

His Thr Glu Ala Arg Ala Arg His Ala Trp Gln Leu Thr Gln Gly Ala
    130                 135                 140

Thr Val Leu Gly Leu Phe Arg Val Thr Pro Gly Gly Ser Gly Gly
145                 150                 155                 160

Gly Ser Gly Gly Gln Gly Met Phe Ala Gln Leu Val Ala Gln Asn Val
                165                 170                 175

Leu Leu Ile Asp Gly Pro Leu Ser Trp Tyr Ser Asp Pro Gly Leu Ala
                180                 185                 190

Gly Val Ser Leu Thr Gly Gly Leu Ser Tyr Lys Glu Asp Thr Lys Glu
            195                 200                 205

Leu Val Val Ala Lys Ala Gly Val Tyr Tyr Val Phe Phe Gln Leu Glu
        210                 215                 220

Leu Arg Arg Val Val Ala Gly Glu Gly Ser Gly Ser Val Ser Leu Ala
225                 230                 235                 240

Leu His Leu Gln Pro Leu Arg Ser Ala Ala Gly Ala Ala Ala Leu Ala
                245                 250                 255
```

```
Leu Thr Val Asp Leu Pro Pro Ala Ser Ser Glu Ala Arg Asn Ser Ala
                260                 265                 270

Phe Gly Phe Gln Gly Arg Leu Leu His Leu Ser Ala Gly Gln Arg Leu
            275                 280                 285

Gly Val His Leu His Thr Glu Ala Arg Ala Arg His Ala Trp Gln Leu
        290                 295                 300

Thr Gln Gly Ala Thr Val Leu Gly Leu Phe Arg Val Thr Pro Gly Gly
305                 310                 315                 320

Ser Gly Gly Gly Ser Gly Gly Gln Gly Met Phe Ala Gln Leu Val
                325                 330                 335

Ala Gln Asn Val Leu Leu Ile Asp Gly Pro Leu Ser Trp Tyr Ser Asp
                340                 345                 350

Pro Gly Leu Ala Gly Val Ser Leu Thr Gly Gly Leu Ser Tyr Lys Glu
            355                 360                 365

Asp Thr Lys Glu Leu Val Val Ala Lys Ala Gly Val Tyr Tyr Val Phe
        370                 375                 380

Phe Gln Leu Glu Leu Arg Arg Val Val Ala Gly Glu Gly Ser Gly Ser
385                 390                 395                 400

Val Ser Leu Ala Leu His Leu Gln Pro Leu Arg Ser Ala Ala Gly Ala
                405                 410                 415

Ala Ala Leu Ala Leu Thr Val Asp Leu Pro Pro Ala Ser Ser Glu Ala
            420                 425                 430

Arg Asn Ser Ala Phe Gly Phe Gln Gly Arg Leu Leu His Leu Ser Ala
        435                 440                 445

Gly Gln Arg Leu Gly Val His Leu His Thr Glu Ala Arg Ala Arg His
    450                 455                 460

Ala Trp Gln Leu Thr Gln Gly Ala Thr Val Leu Gly Leu Phe Arg Val
465                 470                 475                 480

Thr Pro

<210> SEQ ID NO 108
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Gly Met Phe Ala Gln Leu Val Ala Gln Asn Val Leu Leu Ile Asp
1               5                   10                  15

Gly Pro Leu Ser Trp Tyr Ser Asp Pro Gly Leu Ala Gly Val Ser Leu
            20                  25                  30

Thr Gly Gly Leu Ser Tyr Lys Glu Asp Thr Lys Glu Leu Val Val Ala
        35                  40                  45

Lys Ala Gly Val Tyr Tyr Val Phe Phe Gln Leu Glu Leu Arg Arg Val
    50                  55                  60

Val Ala Gly Glu Gly Ser Gly Ser Val Ser Leu Ala Leu His Leu Gln
65                  70                  75                  80

Pro Leu Arg Ser Ala Ala Gly Ala Ala Ala Leu Ala Leu Thr Val Asp
                85                  90                  95

Leu Pro Pro Ala Ser Ser Glu Ala Arg Asn Ser Ala Phe Gly Phe Gln
            100                 105                 110

Gly Arg Leu Leu His Leu Ser Ala Gly Gln Arg Leu Gly Val His Leu
        115                 120                 125
```

His Thr Glu Ala Arg Ala Arg His Ala Trp Gln Leu Thr Gln Gly Ala
130                 135                 140

Thr Val Leu Gly Leu Phe Arg Val Thr Pro Gly Gly Gln Gly Met Phe
145                 150                 155                 160

Ala Gln Leu Val Ala Gln Asn Val Leu Leu Ile Asp Gly Pro Leu Ser
            165                 170                 175

Trp Tyr Ser Asp Pro Gly Leu Ala Gly Val Ser Leu Thr Gly Gly Leu
            180                 185                 190

Ser Tyr Lys Glu Asp Thr Lys Glu Leu Val Val Ala Lys Ala Gly Val
            195                 200                 205

Tyr Tyr Val Phe Phe Gln Leu Glu Leu Arg Arg Val Val Ala Gly Glu
210                 215                 220

Gly Ser Gly Ser Val Ser Leu Ala Leu His Leu Gln Pro Leu Arg Ser
225                 230                 235                 240

Ala Ala Gly Ala Ala Ala Leu Ala Leu Thr Val Asp Leu Pro Pro Ala
            245                 250                 255

Ser Ser Glu Ala Arg Asn Ser Ala Phe Gly Phe Gln Gly Arg Leu Leu
            260                 265                 270

His Leu Ser Ala Gly Gln Arg Leu Gly Val His Leu His Thr Glu Ala
            275                 280                 285

Arg Ala Arg His Ala Trp Gln Leu Thr Gln Gly Ala Thr Val Leu Gly
            290                 295                 300

Leu Phe Arg Val Thr Pro Gly Gly Gln Gly Met Phe Ala Gln Leu Val
305                 310                 315                 320

Ala Gln Asn Val Leu Leu Ile Asp Gly Pro Leu Ser Trp Tyr Ser Asp
            325                 330                 335

Pro Gly Leu Ala Gly Val Ser Leu Thr Gly Gly Leu Ser Tyr Lys Glu
            340                 345                 350

Asp Thr Lys Glu Leu Val Val Ala Lys Ala Gly Val Tyr Tyr Val Phe
            355                 360                 365

Phe Gln Leu Glu Leu Arg Arg Val Val Ala Gly Glu Gly Ser Gly Ser
            370                 375                 380

Val Ser Leu Ala Leu His Leu Gln Pro Leu Arg Ser Ala Ala Gly Ala
385                 390                 395                 400

Ala Ala Leu Ala Leu Thr Val Asp Leu Pro Pro Ala Ser Ser Glu Ala
            405                 410                 415

Arg Asn Ser Ala Phe Gly Phe Gln Gly Arg Leu Leu His Leu Ser Ala
            420                 425                 430

Gly Gln Arg Leu Gly Val His Leu His Thr Glu Ala Arg Ala Arg His
            435                 440                 445

Ala Trp Gln Leu Thr Gln Gly Ala Thr Val Leu Gly Leu Phe Arg Val
            450                 455                 460

Thr Pro
465

<210> SEQ ID NO 109
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu
```

<210> SEQ ID NO 110
<211> LENGTH: 554
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Leu Ala Leu Thr
            100                 105                 110

Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160
```

```
Gly Ala Thr Val Leu Gly Leu Phe Arg Val Thr Pro Glu Ile Pro Ala
            165                 170                 175

Gly Leu Gly Gly Ser Gly Gly Gly Ser Gly Gly Arg Glu Gly Pro
        180                 185                 190

Glu Leu Ser Pro Asp Asp Pro Ala Gly Leu Leu Asp Leu Arg Gln Gly
            195                 200                 205

Met Phe Ala Gln Leu Val Ala Gln Asn Val Leu Leu Ile Asp Gly Pro
    210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
            260                 265                 270

Gly Glu Gly Ser Gly Ser Val Ser Leu Ala Leu His Leu Gln Pro Leu
        275                 280                 285

Arg Ser Ala Ala Gly Ala Ala Ala Leu Ala Leu Thr Val Asp Leu Pro
    290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
            340                 345                 350

Leu Gly Leu Phe Arg Val Thr Pro Glu Ile Pro Ala Gly Leu Gly Gly
        355                 360                 365

Ser Gly Gly Gly Ser Gly Gly Arg Glu Gly Pro Glu Leu Ser Pro
    370                 375                 380

Asp Asp Pro Ala Gly Leu Leu Asp Leu Arg Gln Gly Met Phe Ala Gln
385                 390                 395                 400

Leu Val Ala Gln Asn Val Leu Leu Ile Asp Gly Pro Leu Ser Trp Tyr
                405                 410                 415

Ser Asp Pro Gly Leu Ala Gly Val Ser Leu Thr Gly Gly Leu Ser Tyr
            420                 425                 430

Lys Glu Asp Thr Lys Glu Leu Val Val Ala Lys Ala Gly Val Tyr Tyr
        435                 440                 445

Val Phe Phe Gln Leu Glu Leu Arg Arg Val Val Ala Gly Glu Gly Ser
    450                 455                 460

Gly Ser Val Ser Leu Ala Leu His Leu Gln Pro Leu Arg Ser Ala Ala
465                 470                 475                 480

Gly Ala Ala Ala Leu Ala Leu Thr Val Asp Leu Pro Pro Ala Ser Ser
                485                 490                 495

Glu Ala Arg Asn Ser Ala Phe Gly Phe Gln Gly Arg Leu Leu His Leu
            500                 505                 510

Ser Ala Gly Gln Arg Leu Gly Val His Leu His Thr Glu Ala Arg Ala
        515                 520                 525

Arg His Ala Trp Gln Leu Thr Gln Gly Ala Thr Val Leu Gly Leu Phe
    530                 535                 540

Arg Val Thr Pro Glu Ile Pro Ala Gly Leu
545                 550

<210> SEQ ID NO 111
<211> LENGTH: 252
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Gln Gln Ser Gly Ala Glu Leu Ala Lys Pro Gly Thr
1               5                   10                  15

Ser Val Lys Leu Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Ile
        35                  40                  45

Gly Asn Ile Trp Pro Gly Asn Gly Gly Thr Phe Tyr Gly Glu Lys Phe
    50                  55                  60

Met Gly Lys Ala Thr Phe Thr Ala Asp Thr Ser Ser Thr Ala Tyr
65                  70                  75                  80

Met Leu Leu Gly Ser Leu Thr Pro Glu Asp Ser Ala Tyr Tyr Phe Cys
                85                  90                  95

Ala Arg Arg Pro Asp Tyr Ser Gly Asp Tyr Phe Asp Tyr Trp Gly
                100                 105                 110

Gln Gly Val Leu Val Thr Val Ser Ser Gly Gly Gly Ser Gly Gly
                115                 120                 125

Gly Gly Ser Gly Gly Gly Ser Gly Gly Gly Ser Gln Val Val
            130                 135                 140

Leu Thr Gln Pro Lys Ser Val Ser Thr Ser Leu Lys Ser Thr Val Lys
145                 150                 155                 160

Leu Ser Cys Lys Leu Asn Ser Gly Asn Ile Gly Ser Tyr Tyr Val His
                165                 170                 175

Trp Tyr Gln Gln His Ala Gly Arg Ser Pro Thr Thr Met Ile Tyr Arg
                180                 185                 190

Asp Asp Lys Arg Pro Asp Gly Val Pro Asp Arg Phe Ser Gly Ser Ile
                195                 200                 205

Asp Ser Ser Ser Asn Ser Ala Phe Leu Thr Ile Asn Asn Val Gln Thr
                210                 215                 220

Glu Asp Asp Ala Ile Tyr Phe Cys His Ser Tyr Asp Ser Thr Ile Thr
225                 230                 235                 240

Pro Val Phe Gly Gly Gly Thr Lys Leu Thr Val Leu
                245                 250

<210> SEQ ID NO 112
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Val Leu Thr Gln Pro Lys Ser Val Ser Thr Ser Leu Lys Ser
1               5                   10                  15

Thr Val Lys Leu Ser Cys Lys Leu Asn Ser Gly Asn Ile Gly Ser Tyr
            20                  25                  30

Tyr Val His Trp Tyr Gln Gln His Ala Gly Arg Ser Pro Thr Thr Met
        35                  40                  45

Ile Tyr Arg Asp Asp Lys Arg Pro Asp Gly Val Pro Asp Arg Phe Ser
    50                  55                  60

Gly Ser Ile Asp Ser Ser Asn Ser Ala Phe Leu Thr Ile Asn Asn
65                  70                  75                  80

Val Gln Thr Glu Asp Asp Ala Ile Tyr Phe Cys His Ser Tyr Asp Ser
            85                  90                  95

Thr Ile Thr Pro Val Phe Gly Gly Gly Thr Lys Leu Thr Val Leu Gly
            100                 105                 110

Gly Gly Gly Ser Gly Gly Gly Ser Gly Gly Gly Ser Gly Gly
        115                 120                 125

Gly Gly Ser Gln Val Gln Leu Gln Gln Ser Gly Ala Glu Leu Ala Lys
        130                 135                 140

Pro Gly Thr Ser Val Lys Leu Ser Cys Lys Ala Ser Gly Tyr Thr Phe
145                 150                 155                 160

Thr Ser Tyr Tyr Ile Tyr Trp Val Lys Gln Arg Pro Gly Gln Gly Leu
                165                 170                 175

Glu Trp Ile Gly Asn Ile Trp Pro Gly Asn Gly Gly Thr Phe Tyr Gly
            180                 185                 190

Glu Lys Phe Met Gly Lys Ala Thr Phe Thr Ala Asp Thr Ser Ser Ser
        195                 200                 205

Thr Ala Tyr Met Leu Leu Gly Ser Leu Thr Pro Glu Asp Ser Ala Tyr
    210                 215                 220

Tyr Phe Cys Ala Arg Arg Pro Asp Tyr Ser Gly Asp Asp Tyr Phe Asp
225                 230                 235                 240

Tyr Trp Gly Gln Gly Val Leu Val Thr Val Ser Ser
                245                 250

<210> SEQ ID NO 113
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Val Ser Ala Ser
145                 150                 155                 160

```
Val Gly Asp Arg Val Thr Ile Thr Cys Arg Ala Ser Gln Gly Ile Ser
            165                 170                 175

Ser Trp Leu Ala Trp Tyr Gln Gln Lys Pro Gly Lys Ala Pro Lys Leu
        180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
        210                 215                 220

Gln Pro Glu Asp Phe Ala Thr Tyr Tyr Cys Gln Gln Gly His Leu Phe
225                 230                 235                 240

Pro Ile Thr Phe Gly Gly Gly Thr Lys Val Glu Ile Lys
                245                 250

<210> SEQ ID NO 114
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Leu Phe Pro Ile
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Leu Glu Ser Gly Gly Gly Leu Val Gln Pro Gly Gly Ser
    130                 135                 140

Leu Arg Leu Ser Cys Ala Ala Ser Gly Phe Thr Phe Ser Ser Tyr Ala
145                 150                 155                 160

Met Ser Trp Val Arg Gln Ala Pro Gly Lys Gly Leu Glu Trp Val Ser
                165                 170                 175

Ala Ile Ser Gly Ser Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Lys Asp Ser Pro Phe Leu Leu Asp Asp Tyr Tyr Tyr Tyr Tyr Met
225                 230                 235                 240

Asp Val Trp Gly Lys Gly Thr Thr Val Thr Val Ser Ser
                245                 250
```

```
<210> SEQ ID NO 115
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr Tyr
            100                 105                 110

Met Asp Val Trp Gly Lys Gly Thr Thr Val Thr Val Ser Ser Gly Gly
        115                 120                 125

Gly Gly Ser Gly Gly Gly Ser Gly Gly Gly Ser Gly Gly Gly
    130                 135                 140

Gly Ser Asp Ile Gln Met Thr Gln Ser Pro Ser Ser Val Ser Ala Ser
145                 150                 155                 160

Val Gly Asp Arg Val Thr Ile Thr Cys Arg Ala Ser Gln Gly Ile Ser
                165                 170                 175

Ser Trp Leu Ala Trp Tyr Gln Gln Lys Pro Gly Lys Ala Pro Lys Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Gly His Leu Phe
225                 230                 235                 240

Pro Ile Thr Phe Gly Gly Gly Thr Lys Val Glu Ile Lys
                245                 250

<210> SEQ ID NO 116
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Leu Phe Pro Ile
                 85                  90                  95

Thr Phe Gly Gly Gly Thr Lys Val Glu Ile Lys Gly Gly Gly Gly Ser
                100                 105                 110

Gly Gly Gly Gly Ser Gly Gly Gly Ser Gly Gly Gly Gly Ser Glu
             115                 120                 125

Val Gln Leu Leu Glu Ser Gly Gly Leu Val Gln Pro Gly Gly Ser
        130                 135                 140

Leu Arg Leu Ser Cys Ala Ala Ser Gly Phe Thr Phe Arg Asn Tyr Ala
145                 150                 155                 160

Met Ser Trp Val Arg Gln Ala Pro Gly Lys Gly Leu Glu Trp Val Ser
                165                 170                 175

Ala Ile Ser Gly Ser Gly Asp Thr Thr Tyr Tyr Ala Asp Ser Val Lys
                180                 185                 190

Gly Arg Phe Thr Ile Ser Arg Asp Asn Ser Lys Asn Thr Leu Tyr Leu
                195                 200                 205

Gln Met Asn Ser Leu Arg Ala Glu Asp Thr Ala Val Tyr Tyr Cys Ala
        210                 215                 220

Lys Asp Ser Pro Phe Leu Leu Asp Tyr Tyr Tyr Tyr Tyr Tyr Met
225                 230                 235                 240

Asp Val Trp Gly Lys Gly Thr Thr Val Thr Val Ser Ser
                245                 250

<210> SEQ ID NO 117
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Lys Leu Val Gln Ser Gly Ala Ala Leu Val Lys Pro Gly Ala
 1               5                  10                  15

Ser Val Lys Met Ser Cys Lys Ala Ser Asp Tyr Thr Phe Asn Asp Tyr
                20                  25                  30

Trp Val Ser Trp Val Lys Gln Arg His Gly Glu Ser Leu Glu Trp Ile
            35                  40                  45

Gly Glu Ile Tyr Pro Asn Ser Gly Ala Thr Asn Phe Asn Gly Lys Phe
         50                  55                  60

Arg Gly Lys Ala Thr Leu Thr Val Asp Asn Pro Thr Ser Thr Ala Tyr
 65                  70                  75                  80

Met Glu Leu Ser Arg Leu Thr Ser Glu Asp Ser Ala Ile Tyr Tyr Cys
                 85                  90                  95

Thr Arg Glu Tyr Thr Arg Asp Trp Phe Ala Tyr Trp Gly Gln Gly Thr
                100                 105                 110

Leu Val Thr Val Ser Ser Gly Gly Gly Ser Gly Gly Gly Gly Ser
            115                 120                 125

Gly Gly Gly Gly Ser Gly Gly Gly Gly Ser Asp Val Val Leu Thr Gln
        130                 135                 140
```

```
Thr Pro Ser Ile Leu Ser Ala Thr Ile Gly Gln Ser Val Ser Ile Ser
145                 150                 155                 160

Cys Arg Ser Ser Gln Ser Leu Leu Asp Ser Asp Gly Asn Thr Tyr Leu
                165                 170                 175

Tyr Trp Phe Leu Gln Arg Pro Gly Gln Ser Pro Gln Arg Leu Ile Tyr
            180                 185                 190

Leu Val Ser Asn Leu Gly Ser Gly Val Pro Asn Arg Phe Ser Gly Ser
                195                 200                 205

Gly Ser Gly Thr Asp Phe Thr Leu Lys Ile Ser Gly Val Glu Ala Glu
        210                 215                 220

Asp Leu Gly Ile Tyr Tyr Cys Met Gln Pro Thr His Ala Pro Tyr Thr
225                 230                 235                 240

Phe Gly Ala Gly Thr Lys Leu Glu Leu Lys
                245                 250

<210> SEQ ID NO 118
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Val Val Leu Thr Gln Thr Pro Ser Ile Leu Ser Ala Thr Ile Gly
1               5                   10                  15

Gln Ser Val Ser Ile Ser Cys Arg Ser Ser Gln Ser Leu Leu Asp Ser
            20                  25                  30

Asp Gly Asn Thr Tyr Leu Tyr Trp Phe Leu Gln Arg Pro Gly Gln Ser
        35                  40                  45

Pro Gln Arg Leu Ile Tyr Leu Val Ser Asn Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Ile Tyr Tyr Cys Met Gln Pro
                85                  90                  95

Thr His Ala Pro Tyr Thr Phe Gly Ala Gly Thr Lys Leu Glu Leu Lys
            100                 105                 110

Gly Gly Gly Gly Ser Gly Gly Gly Ser Gly Gly Gly Gly Ser Gly
        115                 120                 125

Gly Gly Gly Ser Gln Val Lys Leu Val Gln Ser Gly Ala Ala Leu Val
130                 135                 140

Lys Pro Gly Ala Ser Val Lys Met Ser Cys Lys Ala Ser Asp Tyr Thr
145                 150                 155                 160

Phe Asn Asp Tyr Trp Val Ser Trp Val Lys Gln Arg His Gly Glu Ser
                165                 170                 175

Leu Glu Trp Ile Gly Glu Ile Tyr Pro Asn Ser Gly Ala Thr Asn Phe
            180                 185                 190

Asn Gly Lys Phe Arg Gly Lys Ala Thr Leu Thr Val Asp Asn Pro Thr
        195                 200                 205

Ser Thr Ala Tyr Met Glu Leu Ser Arg Leu Thr Ser Glu Asp Ser Ala
    210                 215                 220

Ile Tyr Tyr Cys Thr Arg Glu Val Thr Arg Asp Trp Phe Ala Tyr Trp
225                 230                 235                 240
```

```
Gly Gln Gly Thr Leu Val Thr Val Ser Ser
                245                 250

<210> SEQ ID NO 119
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Ala Phe Leu Ser Val Thr Pro Gly Glu Lys Val Thr Ile
145                 150                 155                 160

Thr Cys Arg Ala Ser Gln Thr Ile Ser Asp Tyr Leu His Trp Tyr Gln
                165                 170                 175

Gln Lys Pro Asp Gln Ala Pro Lys Leu Leu Ile Lys Tyr Ala Ser Gln
            180                 185                 190

Ser Ile Ser Gly Ile Pro Ser Arg Phe Ser Gly Ser Gly Ser Gly Thr
        195                 200                 205

Asp Phe Thr Phe Thr Ile Ser Ser Leu Glu Ala Glu Asp Ala Ala Thr
    210                 215                 220

Tyr Tyr Cys Gln Asp Gly His Ser Phe Pro Pro Thr Phe Gly Gln Gly
225                 230                 235                 240

Thr Lys Leu Glu Ile Lys
                245

<210> SEQ ID NO 120
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30
```

Leu His Trp Tyr Gln Gln Lys Pro Asp Gln Ala Pro Lys Leu Leu Ile
                35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Asp Gly His Ser Phe Pro Pro
                 85                  90                  95

Thr Phe Gly Gln Gly Thr Lys Leu Glu Ile Lys Gly Gly Gly Gly Ser
                100                 105                 110

Gly Gly Gly Gly Ser Gly Gly Gly Ser Gly Gly Gly Gly Ser Gln
                115                 120                 125

Val Gln Leu Gln Gln Ser Gly Ala Glu Val Ile Lys Pro Gly Ala Ser
130                 135                 140

Val Lys Leu Ser Cys Lys Ala Ser Gly Tyr Thr Phe Ser Ser Tyr Trp
145                 150                 155                 160

Met His Trp Val Arg Gln Ala Pro Gly Gln Gly Leu Glu Trp Ile Gly
                165                 170                 175

Glu Ile Asn Pro Gly Asn Gly His Thr Asn Tyr Asn Glu Lys Phe Lys
                180                 185                 190

Ser Arg Ala Thr Leu Thr Gly Asp Thr Ser Thr Ser Thr Val Tyr Met
                195                 200                 205

Glu Leu Ser Ser Leu Arg Ser Glu Asp Thr Ala Val Tyr Tyr Cys Ala
                210                 215                 220

Arg Ser Phe Thr Thr Ala Arg Ala Phe Ala Tyr Trp Gly Gln Gly Thr
225                 230                 235                 240

Leu Val Thr Val Ser Ser
                245

<210> SEQ ID NO 121
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asp Tyr
                20                  25                  30

Trp Met Ser Trp Val Arg Gln Ala Pro Gly Lys Gly Leu Glu Trp Val
                35                  40                  45

Ala Asp Ile Lys Asn Asp Gly Ser Tyr Thr Asn Tyr Ala Pro Ser Leu
 50                  55                  60

Thr Asn Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Thr Gly Thr Trp Gly Gln Gly Thr Met Val Thr Val
                100                 105                 110

Ser Ser Gly Gly Gly Gly Ser Gly Gly Gly Gly Ser Gly Gly Gly Gly
                115                 120                 125

```
Ser Gly Gly Gly Gly Ser Asp Ile Val Met Thr Gln Ser Pro Asp Ser
            130                 135                 140

Leu Ala Val Ser Leu Gly Glu Arg Ala Thr Ile Asn Cys Lys Ser Ser
145                 150                 155                 160

Gln Ser Leu Leu Ser Ser Gly Asn Gln Lys Asn Tyr Leu Ala Trp Tyr
                165                 170                 175

Gln Gln Lys Pro Gly Gln Pro Pro Lys Leu Leu Ile Tyr Tyr Ala Ser
            180                 185                 190

Thr Arg Gln Ser Gly Val Pro Asp Arg Phe Ser Gly Ser Gly Ser Gly
        195                 200                 205

Thr Asp Phe Thr Leu Thr Ile Ser Ser Leu Gln Ala Glu Asp Val Ala
    210                 215                 220

Val Tyr Tyr Cys Leu Gln Tyr Asp Arg Tyr Pro Phe Thr Phe Gly Gln
225                 230                 235                 240

Gly Thr Lys Leu Glu Ile Lys
                245

<210> SEQ ID NO 122
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Tyr Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Leu Gln
                85                  90                  95

Tyr Asp Arg Tyr Pro Phe Thr Phe Gly Gln Gly Thr Lys Leu Glu Ile
            100                 105                 110

Lys Gly Gly Gly Gly Ser Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Phe
145                 150                 155                 160

Thr Phe Ser Asp Tyr Trp Met Ser Trp Val Arg Gln Ala Pro Gly Lys
                165                 170                 175

Gly Leu Glu Trp Val Ala Asp Ile Lys Asn Asp Gly Ser Tyr Thr Asn
            180                 185                 190

Tyr Ala Pro Ser Leu Thr Asn Arg Phe Thr Ile Ser Arg Asp Asn Ala
        195                 200                 205

Lys Asn Ser Leu Tyr Leu Gln Met Asn Ser Leu Arg Ala Glu Asp Thr
    210                 215                 220
```

```
Ala Val Tyr Tyr Cys Ala Arg Glu Leu Thr Gly Thr Trp Gly Gln Gly
225                 230                 235                 240

Thr Met Val Thr Val Ser Ser
                245
```

<210> SEQ ID NO 123
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320
```

Lys Ser Leu Ser Leu Ser Pro Gly
                325

<210> SEQ ID NO 124
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Pro Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly
            325

<210> SEQ ID NO 125
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Gly Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325
```

<210> SEQ ID NO 126
<211> LENGTH: 322
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 126

```
Lys Thr Thr Pro Pro Ser Val Tyr Pro Leu Ala Pro Gly Ser Ala Ala
1               5                   10                  15

Gln Thr Asn Ser Met Val Thr Leu Gly Cys Leu Val Lys Gly Tyr Phe
            20                  25                  30

Pro Glu Pro Val Thr Val Thr Trp Asn Ser Gly Ser Leu Ser Ser Gly
        35                  40                  45

Val His Thr Phe Pro Ala Val Leu Gln Ser Asp Leu Tyr Thr Leu Ser
50                  55                  60

Ser Ser Val Thr Val Pro Ser Ser Thr Trp Pro Ser Glu Thr Val Thr
65                  70                  75                  80

Cys Asn Val Ala His Pro Ala Ser Ser Thr Lys Val Asp Lys Lys Ile
                85                  90                  95

Val Pro Arg Asp Cys Gly Cys Lys Pro Cys Ile Cys Thr Val Pro Glu
            100                 105                 110

Val Ser Ser Val Phe Ile Phe Pro Pro Lys Pro Lys Asp Val Leu Thr
        115                 120                 125

Ile Thr Leu Thr Pro Lys Val Thr Cys Val Val Val Asp Ile Ser Lys
130                 135                 140

Asp Asp Pro Glu Val Gln Phe Ser Trp Phe Val Asp Asp Val Glu Val
145                 150                 155                 160

His Thr Ala Gln Thr Gln Pro Arg Glu Glu Gln Phe Asn Ser Thr Phe
                165                 170                 175

Arg Ser Val Ser Glu Leu Pro Ile Met His Gln Asp Trp Leu Asn Gly
            180                 185                 190

Lys Glu Phe Lys Cys Arg Val Asn Ser Ala Ala Phe Pro Ala Pro Ile
        195                 200                 205

Glu Lys Thr Ile Ser Lys Thr Lys Gly Arg Pro Lys Ala Pro Gln Val
    210                 215                 220

Tyr Thr Ile Pro Pro Pro Lys Glu Gln Met Ala Lys Asp Lys Val Ser
225                 230                 235                 240

Leu Thr Cys Met Ile Thr Asp Phe Phe Pro Glu Asp Ile Thr Val Glu
                245                 250                 255

Trp Gln Trp Asn Gly Gln Pro Ala Glu Asn Tyr Lys Asn Thr Gln Pro
            260                 265                 270

Ile Met Asp Thr Asp Gly Ser Tyr Phe Val Tyr Ser Lys Leu Asn Val
        275                 280                 285

Gln Lys Ser Asn Trp Glu Ala Gly Asn Thr Phe Thr Cys Ser Val Leu
    290                 295                 300

His Glu Gly Leu His Asn His His Thr Glu Lys Ser Leu Ser His Ser
305                 310                 315                 320

Pro Gly
```

<210> SEQ ID NO 127
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Ser Cys Ala Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Val Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325
```

<210> SEQ ID NO 128
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Ser Thr Lys Gly Pro Ser Val Phe Pro Leu Ala Pro Ser Ser Lys Ser
1               5                   10                  15
```

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Trp Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 129
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

```
Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Pro Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Ser Cys Ala Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Val Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly
                325

<210> SEQ ID NO 130
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45
```

Val His Thr Phe Pro Ala Val Leu Gln Ser Ser Gly Leu Tyr Ser Leu
            50                  55                  60

Ser Ser Val Val Thr Val Pro Ser Ser Leu Gly Thr Lys Thr Tyr
 65                  70                  75                  80

Thr Cys Asn Val Asp His Lys Pro Ser Asn Thr Lys Val Asp Lys Arg
                    85                  90                  95

Val Glu Ser Lys Tyr Gly Pro Pro Cys Pro Pro Cys Pro Ala Pro Glu
                100                 105                 110

Phe Leu Gly Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
                180                 185                 190

Leu Asn Gly Lys Glu Tyr Lys Cys Lys Val Ser Asn Lys Gly Leu Pro
                195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Trp Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly
                325

<210> SEQ ID NO 131
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
            50                  55                  60

Ser Ser Val Val Thr Val Pro Ser Ser Leu Gly Thr Gln Thr Tyr
65                  70                  75                  80

Ile Cys Asn Val Asn His Lys Pro Ser Asp Thr Lys Val Asp Lys Lys
                85                  90                  95

Val Glu Pro Lys Ser Cys Asp Lys Thr His Thr Cys Pro Pro Cys Pro
            100                 105                 110

Ala Pro Pro Val Ala Gly Pro Ser Val Phe Leu Phe Pro Pro Lys Pro
            115                 120                 125

Lys Asp Thr Leu Met Ile Ser Arg Thr Pro Glu Val Thr Cys Val Val
130                 135                 140

Val Asp Val Lys His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
            195                 200                 205

Leu Pro Ala Pro Ile Glu Lys Thr Ile Ser Lys Ala Lys Gly Gln Pro
210                 215                 220

Arg Glu Pro Gln Val Tyr Thr Leu Pro Pro Ser Arg Glu Gln Met Thr
225                 230                 235                 240

Lys Asn Gln Val Lys Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
            275                 280                 285

Ser Lys Leu Thr Val Asp Lys Ser Arg Trp Gln Gln Gly Asn Val Phe
290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 132
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Leu Gly Thr Gln Thr Tyr
65                  70                  75                  80

```
Ile Cys Asn Val Asn His Lys Pro Ser Asp Thr Lys Val Asp Lys Lys
                85                  90                  95

Val Glu Pro Lys Ser Cys Asp Lys Thr His Thr Cys Pro Pro Cys Pro
            100                 105                 110

Ala Pro Pro Val Ala Gly Pro Ser Val Phe Leu Phe Pro Pro Lys Pro
            115                 120                 125

Lys Asp Thr Leu Met Ile Ser Arg Thr Pro Glu Val Thr Cys Val Val
130                 135                 140

Val Asp Val Lys His Glu Asp Pro Glu Val Lys Phe Asn Trp Tyr Val
145                 150                 155                 160

Asp Gly Val Glu Val His Asn Ala Lys Thr Lys Pro Arg Glu Glu Glu
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
            195                 200                 205

Leu Pro Ala Pro Ile Glu Lys Thr Ile Ser Lys Ala Lys Gly Gln Pro
            210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Asp Val Ser Gly Phe Tyr Pro Ser
                245                 250                 255

Asp Ile Ala Val Glu Trp Glu Ser Asp Gly Gln Pro Glu Asn Asn Tyr
            260                 265                 270

Lys Thr Thr Pro Pro Val Leu Asp Ser Asp Gly Ser Phe Phe Leu Tyr
            275                 280                 285

Ser Lys Leu Thr Val Asp Lys Ser Arg Trp Glu Gln Gly Asp Val Phe
            290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 133
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95
```

```
Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ala
        115                 120                 125

<210> SEQ ID NO 134
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105

<210> SEQ ID NO 135
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser
        115                 120                 125

<210> SEQ ID NO 136
<211> LENGTH: 109
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 136

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Lys Pro Gly Gln Ala Pro Arg Gly
        35                  40                  45

Leu Ile Gly Gly Thr Lys Phe Leu Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105

<210> SEQ ID NO 137
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 138
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu
            100                 105

<210> SEQ ID NO 139
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ala Met Asn Trp Val Arg Gln Ala Pro Gly Lys Gly Leu Glu Trp Val
         35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 140
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Ala Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
             20                  25                  30

Asn Tyr Ala Asn Trp Val Gln Gln Lys Pro Gly Gln Ala Pro Arg Gly
         35                  40                  45

Leu Ile Gly Gly Thr Asn Lys Arg Ala Pro Trp Thr Pro Ala Arg Phe
 50                  55                  60

Ser Gly Ser Leu Leu Gly Gly Lys Ala Ala Leu Thr Ile Thr Gly Ala
 65                  70                  75                  80

Gln Ala Glu Asp Glu Ala Asp Tyr Tyr Cys Ala Leu Trp Tyr Ser Asn
                 85                  90                  95

Leu Trp Val Phe Gly Gly Gly Thr Lys Leu Thr Val Leu
            100                 105

<210> SEQ ID NO 141
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 142
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 143
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 144
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 145
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45
```

```
Gly Arg Ile Arg Ser Lys Ala Asn Asn Tyr Thr Tyr Tyr Ala Asp
        50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser
                115                 120                 125

<210> SEQ ID NO 146
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
                35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
                100                 105

<210> SEQ ID NO 147
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110
```

```
Asp Tyr Trp Gly Gln Gly Thr Leu Val Thr Val Ser Ser
        115                 120                 125
```

<210> SEQ ID NO 148
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105
```

<210> SEQ ID NO 149
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125
```

<210> SEQ ID NO 150
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 150

Glu Ile Val Val Thr Gln Ser Pro Ala Thr Leu Ser Val Ser Pro Gly
1               5                   10                  15

Glu Arg Ala Thr Leu Ser Cys Arg Ser Ser Thr Gly Ala Val Thr Glu
            20                  25                  30

Ser Asn Tyr Ala Asn Trp Val Gln Glu Lys Pro Gly Gln Ala Phe Arg
        35                  40                  45

Gly Leu Ile Gly Gly Ala Asn Lys Arg Ala Pro Gly Val Pro Ala Arg
    50                  55                  60

Phe Ser Gly Ser Leu Ser Gly Asp Glu Ala Thr Leu Thr Ile Ser Ser
65                  70                  75                  80

Leu Gln Ser Glu Asp Phe Ala Val Tyr Tyr Cys Ala Leu Phe Tyr Ser
                85                  90                  95

Asn Thr Trp Val Phe Gly Gln Gly Thr Lys Leu Glu Ile Lys
            100                 105                 110

<210> SEQ ID NO 151
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 152
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

```
Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu
            100                 105
```

<210> SEQ ID NO 153
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Ile His Trp Val Arg Gln Ala Pro Gly Gln Gly Leu Glu Trp Ile
             35                  40                  45

Gly Trp Ile Tyr Pro Gly Asp Gly Asn Thr Lys Tyr Asn Glu Lys Phe
 50                  55                  60

Lys Gly Arg Ala Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Ser Tyr Ser Asn Tyr Phe Asp Tyr Trp Gly Gln Gly
                100                 105                 110

Thr Leu Val Thr Val Ser Ser
        115
```

<210> SEQ ID NO 154
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Arg Thr Arg Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Thr Gln
                 85                  90                  95

Ser Phe Ile Leu Arg Thr Phe Gly Gln Gly Thr Lys Val Glu Ile Lys
                100                 105                 110
```

<210> SEQ ID NO 155
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
    50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 156
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 157
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Glu Asn Asp Asn Thr Lys Tyr Asn Glu Lys Phe
50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
        115

<210> SEQ ID NO 158
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Thr Ser Arg Lys Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 159
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Val Gln Ser Gly Pro Glu Val Lys Lys Pro Gly Ser
1               5                   10                  15

Ser Val Lys Val Ser Cys Lys Ala Ser Gly Tyr Thr Phe Ser Arg Ser
            20                  25                  30

Thr Met His Trp Val Arg Gln Ala Pro Gly Gln Gly Leu Glu Trp Ile
        35                  40                  45

```
Gly Tyr Ile Asn Pro Ser Ser Ala Tyr Thr Asn Tyr Asn Gln Lys Phe
        50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
            115                 120

<210> SEQ ID NO 160
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Gln Met Thr Gln Ser Pro Ser Thr Leu Ser Ala Ser Val Gly
 1               5                  10                  15

Asp Arg Val Thr Met Thr Cys Ser Ala Ser Ser Ser Val Ser Tyr Met
                 20                  25                  30

Asn Trp Tyr Gln Gln Lys Pro Gly Lys Ala Pro Lys Arg Trp Ile Tyr
             35                  40                  45

Asp Ser Ser Lys Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Asp
 65                  70                  75                  80

Asp Phe Ala Thr Tyr Tyr Cys Gln Gln Trp Ser Arg Asn Pro Pro Thr
                 85                  90                  95

Phe Gly Gly Gly Thr Lys Val Glu Ile Lys
            100                 105

<210> SEQ ID NO 161
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                 20                  25                  30

Thr Met His Trp Val Lys Gln Arg Pro Gly Gln Gly Leu Glu Trp Ile
             35                  40                  45

Gly Tyr Ile Asn Pro Ser Arg Gly Tyr Thr Asn Tyr Asn Gln Lys Phe
         50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110
```

```
Thr Thr Leu Thr Val Ser Ser
            115
```

<210> SEQ ID NO 162
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105
```

<210> SEQ ID NO 163
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser
            115
```

<210> SEQ ID NO 164
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 164

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 165
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Cys Leu Glu Trp Ile
        35                  40                  45

Gly Tyr Ile Asn Pro Ser Arg Gly Tyr Thr Asn Tyr Asn Gln Lys Phe
50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 166
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45
```

```
Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Cys Gly Thr Lys Leu Glu Ile Asn
            100                 105

<210> SEQ ID NO 167
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Cys Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Ser Leu Asp Tyr Trp Gly Gln Gly
                100                 105                 110

Thr Thr Leu Thr Val Ser Ser
            115

<210> SEQ ID NO 168
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Cys Gly Thr Lys Leu Glu Ile Asn
            100                 105
```

<210> SEQ ID NO 169
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Ala Val Ser Ser
        115

<210> SEQ ID NO 170
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Ile Val Leu Thr Cys Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ser Gly Thr Lys Leu Glu Ile Asn
            100                 105

<210> SEQ ID NO 171
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Cys Leu Asp Tyr Trp Gly Gln Gly
                100                 105                 110

Thr Thr Leu Thr Val Ser Ser
            115

<210> SEQ ID NO 172
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
            85                  90                  95

Phe Gly Ala Gly Thr Lys Leu Glu Leu Lys
                100                 105

<210> SEQ ID NO 173
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

```
Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                 85                  90                  95

Ala Arg Tyr Tyr Asp Asp His Tyr Cys Leu Asp Tyr Trp Gly Gln Gly
                100                 105                 110

Thr Thr Val Thr Val Ser Ser
            115
```

<210> SEQ ID NO 174
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Tyr Met
                 20                  25                  30

Asn Trp Tyr Gln Gln Lys Pro Gly Lys Ala Pro Lys Arg Trp Ile Tyr
             35                  40                  45

Asp Thr Ser Lys Val Ala Ser Gly Val Pro Ala Arg Phe Ser Gly Ser
         50                  55                  60

Gly Ser Gly Thr Asp Tyr Ser Leu Thr Ile Asn Ser Leu Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

<210> SEQ ID NO 175
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

```
Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                 20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Val
         50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Cys Leu Asp Tyr Trp Gly Gln Gly
                100                 105                 110
```

Thr Pro Val Thr Val Ser Ser
        115

<210> SEQ ID NO 176
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 177
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Tyr Ala Asp Ser Val
    50                  55                  60

Lys Gly Arg Phe Thr Leu Ser Thr Asp Lys Ser Lys Asn Thr Ala Tyr
65                  70                  75                  80

Leu Gln Met Ser Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser
        115

<210> SEQ ID NO 178
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 178

Asp Ile Gln Leu Thr Gln Ser Pro Ser Leu Ser Ala Ser Val Gly
1               5                   10                  15

Asp Arg Val Thr Ile Thr Cys Arg Ala Ser Ser Val Ser Tyr Val
            20                  25                  30

Ala Trp Tyr Gln Gln Lys Pro Gly Lys Ala Pro Lys Arg Trp Ile Tyr
        35                  40                  45

Asp Thr Ser Lys Leu Tyr Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gln Gly Thr Lys Val Glu Ile Lys
            100                 105

<210> SEQ ID NO 179
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115

<210> SEQ ID NO 180
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

```
Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr
            100                 105

<210> SEQ ID NO 181
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
             20                  25                  30

Thr Met His Trp Val Arg Gln Ala Pro Gly Lys Cys Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115

<210> SEQ ID NO 182
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
             20                  25                  30

Asn Trp Tyr Gln Gln Thr Pro Gly Lys Ala Pro Lys Arg Trp Ile Tyr
         35                  40                  45

Asp Thr Ser Lys Leu Ala Ser Gly Val Pro Ser Arg Phe Ser Gly Ser
     50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Cys Gly Thr Lys Leu Gln Ile Thr
            100                 105
```

<210> SEQ ID NO 183
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 184
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Cys Gly Thr Lys Leu Gln Ile Thr
            100                 105

<210> SEQ ID NO 185
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Met
        35                  40                  45

Gly Leu Ile Asn Pro Tyr Lys Gly Val Ser Thr Tyr Asn Gln Lys Phe
    50                  55                  60

Lys Asp Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Thr Leu Thr Val Phe Ser
            115                 120

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Lys Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Ala Gly Gly Thr Lys Leu Glu Ile Lys
            100                 105

<210> SEQ ID NO 187
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
                 50                  55                  60

Lys Asp Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser
                115                 120

<210> SEQ ID NO 188
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Tyr
                 20                  25                  30

Leu Asn Trp Tyr Gln Gln Lys Pro Gly Lys Ala Pro Lys Leu Leu Ile
                 35                  40                  45

Tyr Tyr Thr Ser Arg Leu Glu Ser Gly Val Pro Ser Arg Phe Ser Gly
             50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys
                100                 105

<210> SEQ ID NO 189
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Leu Gln Leu Gln Glu Ser Gly Pro Gly Leu Val Lys Pro Ser Gln
 1               5                  10                  15

Thr Leu Ser Leu Thr Cys Ser Val Ser Gly Gly Ser Ile Arg Ser Gly
                 20                  25                  30

Gly His Tyr Trp Ser Trp Ile Arg Gln His Pro Gly Lys Gly Leu Glu
                 35                  40                  45

Trp Ile Gly Tyr Ile His His Ser Gly Ser Thr Tyr Tyr Asn Pro Ser
             50                  55                  60

Leu Lys Ser Arg Val Ile Ile Ser Val Asp Thr Ser Lys Asn Gln Phe
 65                  70                  75                  80

Ser Leu Lys Leu Arg Ser Val Thr Ala Ala Asp Thr Ala Ile Tyr Tyr
                 85                  90                  95

Cys Ala Arg Trp Arg His Asp Ile Phe Thr Thr Tyr Pro Tyr Tyr Tyr
                100                 105                 110

```
Tyr Gly Met Asp Val Trp Gly Gln Gly Thr Leu Val Thr Val Ser Ser
            115                 120                 125
```

<210> SEQ ID NO 190
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105
```

<210> SEQ ID NO 191
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

```
Gln Leu Gln Leu Gln Glu Ser Gly Pro Gly Leu Val Lys Pro Ser Gln
1               5                   10                  15

Thr Leu Ser Leu Thr Cys Ser Val Ser Gly Ser Ile Arg Ser Gly
            20                  25                  30

Gly His Tyr Trp Ser Trp Ile Arg Gln His Pro Gly Lys Gly Leu Glu
        35                  40                  45

Trp Ile Gly Tyr Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Arg His Asp Ile Leu Thr Ala Tyr Pro Tyr Tyr Tyr
            100                 105                 110

Tyr Gly Met Asp Val Trp Gly Gln Gly Thr Leu Val Thr Val Ser Ser
            115                 120                 125
```

<210> SEQ ID NO 192
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 192

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 193
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45
```

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Trp
                 85                  90                  95

Thr Phe Gly Gln Gly Thr Lys Val Glu Ile Lys
            100                 105

<210> SEQ ID NO 195
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asn Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
             85                  90                  95

Ala Lys Asp Ser Arg Gly Tyr Gly Asp Tyr Ser Arg Gly Gly Ala Tyr
            100                 105                 110

Trp Gly Gln Gly Thr Leu Val Thr Val Ser Ser
            115                 120

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Trp
             85                  90                  95

Thr Phe Gly Gln Gly Thr Lys Val Glu Ile Lys
            100                 105

<210> SEQ ID NO 197
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 197

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120

<210> SEQ ID NO 198
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 199
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

```
<400> SEQUENCE: 199

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Ser Gly Tyr Gly Lys Phe Tyr Tyr Tyr Gly Met Asp
            100                 105                 110

Val Trp Gly Gln Gly Thr Thr Val Thr Val Ser Ser
        115                 120

<210> SEQ ID NO 200
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Ser Phe Ser Gly Tyr Tyr Trp Ser
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 202

Gly Gly Ser Phe Ser Asp Tyr Tyr Trp Ser
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Ser Phe Ser Asp Tyr Tyr Trp Ser
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Gly Ser Phe Ser Asp Tyr Tyr Trp Ser
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Gly Ser Phe Ser Asp Tyr Tyr Trp Ser
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Gly Ser Phe Ser Asp Tyr Tyr Trp Ser
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Gly Ser Phe Ser Asp Tyr Tyr Trp Ser
1               5                   10

<210> SEQ ID NO 208
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 208

Gly Gly Ser Phe Ser Asp Tyr Tyr Trp Ser
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Ser Phe Ser Asp Tyr Tyr Trp Ser
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Ser Phe Ser Asp Tyr Tyr Trp Ser
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Ser Phe Ser Asp Tyr Tyr Trp Ser
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Gly Ser Phe Ser Asp Tyr Tyr Trp Ser
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Gly Ser Phe Ser Asp Tyr Tyr Trp Ser
1               5                   10
```

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Ser Phe Ser Asp Tyr Tyr Trp Ser
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Gly Ser Phe Ser Asp Tyr Tyr Trp Ser
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Gly Ser Phe Ser Gly Tyr Tyr Trp Ser
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Gly Ser Phe Ser Gly Tyr Tyr Trp Ser
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Gly Ser Phe Ser Gly Tyr Tyr Trp Ser
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Gly Ser Phe Ser Gly Tyr Tyr Trp Ser
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Gly Ser Phe Ser Gly Tyr Tyr Trp Ser
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Ser Phe Ser Gly Tyr Tyr Trp Ser
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly Ser Phe Ser Gly Tyr Tyr Trp Ser
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Ser Phe Ser Gly Tyr Tyr Trp Ser
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Gly Ser Phe Ser Asp Tyr Tyr Trp Ser
1               5                   10

<210> SEQ ID NO 225
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Gly Ser Phe Ser Asp Tyr Tyr Trp Ser
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Ser Phe Ser Asp Tyr Tyr Trp Ser
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Gly Ser Phe Ser Asp Tyr Tyr Trp Ser
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Gly Ser Phe Ser Asp Tyr Tyr Trp Ser
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Gly Ser Phe Ser Asp Tyr Tyr Trp Ser
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 230

Gly Gly Ser Phe Ser Asp Tyr Tyr Trp Ser
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gly Gly Ser Phe Ser Asp Tyr Tyr Trp Ser
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Gly Ser Phe Ser Asp Tyr Tyr Trp Ser
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Gly Ser Phe Ser Asp Tyr Tyr Trp Ser
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Gly Ser Phe Ser Asp Tyr Tyr Trp Ser
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Gly Ser Phe Ser Asp Tyr Tyr Trp Ser
1               5                   10

<210> SEQ ID NO 236
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Gly Ser Phe Ser Asp Tyr Tyr Trp Ser
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gly Ser Phe Ser Asp Tyr Tyr Trp Ser
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Gly Ser Phe Ser Gly Tyr Tyr Trp Ser
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Gly Ser Phe Ser Gly Tyr Tyr Trp Ser
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Ser Phe Ser Gly Tyr Tyr Trp Ser
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 241

Gly Gly Ser Phe Ser Gly Tyr Tyr Trp Ser
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Gly Ser Phe Ser Gly Tyr Tyr Trp Ser
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Gly Ser Phe Ser Gly Tyr Tyr Trp Ser
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Gly Ser Phe Ser Gly Tyr Tyr Trp Ser
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Gly Ser Phe Ser Gly Tyr Tyr Trp Ser
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Ser Phe Ser Gly Tyr Tyr Trp Ser
1               5                   10

<210> SEQ ID NO 247
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gly Ser Phe Ser Gly Tyr Tyr Trp Ser
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Gly Ser Phe Ser Gly Tyr Tyr Trp Ser
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Gly Ser Phe Ser Gly Tyr Tyr Trp Ser
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Gly Ser Phe Ser Gly Tyr Tyr Trp Ser
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gly Gly Ser Phe Ser Gly Tyr Tyr Trp Ser
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 252

Gly Gly Ser Phe Ser Gly Tyr Tyr Trp Ser
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Gly Ser Phe Ser Gly Tyr Tyr Trp Ser
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Gly Ser Phe Ser Gly Tyr Tyr Trp Ser
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Gly Ser Phe Ser Gly Tyr Tyr Trp Ser
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Gly Ser Phe Ser Gly Tyr Tyr Trp Ser
1               5                   10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Gly Ser Phe Ser Gly Tyr Tyr Trp Ser
1               5                   10

<210> SEQ ID NO 258
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Gly Ser Phe Ser Gly Tyr Tyr Trp Ser
1               5                   10

<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Gly Ser Phe Ser Gly Tyr Tyr Trp Ser
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Gly Ser Phe Ser Gly Tyr Tyr Trp Ser
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Gly Ser Phe Ser Gly Tyr Tyr Trp Ser
1               5                   10

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Gly Ser Phe Ser Gly Tyr Tyr Trp Ser
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 263

Gly Gly Ser Phe Ser Gly Tyr Tyr Trp Ser
1               5                   10

<210> SEQ ID NO 264
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Gly Ser Phe Ser Gly Tyr Tyr Trp Ser
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Gly Ser Phe Ser Gly Tyr Tyr Trp Ser
1               5                   10

<210> SEQ ID NO 266
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Glu Val Asn His Arg Gly Ser Ile Asn Tyr Asn Asn Tyr Asn Pro Ser
1               5                   10                  15

Leu Lys Ser

<210> SEQ ID NO 267
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Glu Val Asn His Arg Gly Ser Ile Asn Tyr Asn Asn Tyr Asn Pro Ser
1               5                   10                  15

Leu Lys Ser

<210> SEQ ID NO 268
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Glu Val Asn His Arg Gly Ser Ile Asn Tyr Asn Asn Tyr Asn Pro Ser
1               5                   10                  15

Leu Lys Ser

<210> SEQ ID NO 269
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Glu Ile Asn His Arg Gly Ser Ile Asn Tyr Asn Asn Tyr Asn Pro Ser
1               5                   10                  15

Leu Lys Ser

<210> SEQ ID NO 270
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Glu Val Asn His Arg Gly Ser Ile Asn Tyr Asn Asn Tyr Asn Pro Ser
1               5                   10                  15

Leu Lys Ser

<210> SEQ ID NO 271
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Glu Val Asn His Arg Gly Ser Ile Asn Tyr Asn Asn Tyr Asn Pro Ser
1               5                   10                  15

Leu Lys Ser

<210> SEQ ID NO 272
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Glu Val Asn His Arg Gly Ser Ile Asn Tyr Asn Asn Tyr Asn Pro Ser
1               5                   10                  15

Leu Lys Ser

<210> SEQ ID NO 273
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 273

Glu Ile Asn His Arg Gly Ser Ile Asn Tyr Asn Asn Tyr Asn Pro Ser
1               5                   10                  15

Leu Lys Ser

<210> SEQ ID NO 274
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Glu Ile Asn His Arg Gly Ser Ile Asn Tyr Asn Asn Tyr Asn Pro Ser
1               5                   10                  15

Leu Lys Ser

<210> SEQ ID NO 275
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Glu Val Asn His Arg Gly Ser Ile Asn Tyr Asn Asn Tyr Asn Pro Ser
1               5                   10                  15

Leu Lys Ser

<210> SEQ ID NO 276
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Glu Ile Asn His Arg Gly Ser Ile Asn Tyr Asn Asn Tyr Asn Pro Ser
1               5                   10                  15

Leu Lys Ser

<210> SEQ ID NO 277
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Glu Ile Asn His Arg Gly Ser Ile Asn Tyr Asn Asn Tyr Asn Pro Ser
1               5                   10                  15

Leu Lys Ser

<210> SEQ ID NO 278
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 278

Glu Ile Asn His Arg Gly Ser Ile Asn Tyr Asn Asn Tyr Asn Pro Ser
1               5                   10                  15

Leu Lys Ser

<210> SEQ ID NO 279
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Glu Ile Asn His Arg Gly Ser Ile Asn Tyr Asn Asn Tyr Asn Pro Ser
1               5                   10                  15

Leu Lys Ser

<210> SEQ ID NO 280
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Glu Ile Asn His Arg Gly Ser Ile Asn Tyr Asn Asn Tyr Asn Pro Ser
1               5                   10                  15

Leu Lys Ser

<210> SEQ ID NO 281
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Glu Ile Asn His Arg Gly Ser Ile Asn Tyr Asn Asn Tyr Asn Pro Ser
1               5                   10                  15

Leu Lys Ser

<210> SEQ ID NO 282
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Glu Ile Asn His Arg Gly Ser Ile Asn Tyr Asn Asn Tyr Asn Pro Ser
1               5                   10                  15

Leu Lys Ser

<210> SEQ ID NO 283
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 283

Glu Ile Asn His Arg Gly Ser Ile Asn Tyr Asn Asn Tyr Asn Pro Ser
1               5                   10                  15

Leu Lys Ser

<210> SEQ ID NO 284
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Glu Ile Asn His Arg Gly Ser Ile Asn Tyr Asn Asn Tyr Asn Pro Ser
1               5                   10                  15

Leu Lys Ser

<210> SEQ ID NO 285
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Glu Ile Asn His Ala Gly Ser Ile Asn Tyr Asn Asn Tyr Asn Pro Ser
1               5                   10                  15

Leu Lys Ser

<210> SEQ ID NO 286
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Glu Ile Asn His Ala Gly Ser Ile Asn Tyr Asn Asn Tyr Asn Pro Ser
1               5                   10                  15

Leu Lys Ser

<210> SEQ ID NO 287
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Glu Ile Asn His Gln Gly Ser Ile Asn Tyr Asn Asn Tyr Asn Pro Ser
1               5                   10                  15

Leu Lys Ser

<210> SEQ ID NO 288
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Glu Ile Asn His Gln Gly Ser Ile Asn Tyr Asn Tyr Asn Pro Ser
1               5                   10                  15

Leu Lys Ser

<210> SEQ ID NO 289
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Glu Ile Asn His Arg Gly Ser Ile Asn Tyr Asn Tyr Asn Pro Ser
1               5                   10                  15

Leu Lys Ser

<210> SEQ ID NO 290
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Glu Ile Asn His Arg Gly Ser Ile Asn Tyr Asn Tyr Asn Pro Ser
1               5                   10                  15

Leu Lys Ser

<210> SEQ ID NO 291
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Glu Ile Asn His Arg Gly Ser Ile Asn Tyr Asn Tyr Asn Pro Ser
1               5                   10                  15

Leu Lys Ser

<210> SEQ ID NO 292
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Glu Ile Asn His Arg Gly Ser Ile Asn Tyr Asn Tyr Asn Pro Ser
1               5                   10                  15

Leu Lys Ser

<210> SEQ ID NO 293
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Glu Ile Asn His Arg Gly Ser Ile Asn Tyr Asn Asn Tyr Asn Pro Ser
1               5                   10                  15

Leu Lys Ser

<210> SEQ ID NO 294
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Glu Ile Asn His Arg Gly Ser Ile Asn Tyr Asn Asn Tyr Asn Pro Ser
1               5                   10                  15

Leu Lys Ser

<210> SEQ ID NO 295
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Glu Ile Asn His Arg Gly Ser Ile Asn Tyr Asn Asn Tyr Asn Pro Ser
1               5                   10                  15

Leu Lys Ser

<210> SEQ ID NO 296
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Glu Ile Asn His Arg Gly Ser Ile Asn Tyr Asn Asn Tyr Asn Pro Ser
1               5                   10                  15

Leu Lys Ser

<210> SEQ ID NO 297
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Glu Ile Asn His Arg Gly Ser Ile Asn Tyr Asn Asn Tyr Asn Pro Ser
1               5                   10                  15

Leu Lys Ser
```

```
<210> SEQ ID NO 298
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Glu Ile Asn His Arg Gly Ser Ile Asn Tyr Asn Asn Tyr Asn Pro Ser
1               5                   10                  15

Leu Lys Ser

<210> SEQ ID NO 299
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Glu Ile Asn His Arg Gly Ser Ile Asn Tyr Asn Asn Tyr Asn Pro Ser
1               5                   10                  15

Leu Lys Ser

<210> SEQ ID NO 300
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Glu Ile Asn His Arg Gly Ser Ile Asn Tyr Asn Asn Tyr Asn Pro Ser
1               5                   10                  15

Leu Lys Ser

<210> SEQ ID NO 301
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Ile Asn His Arg Gly Ser Ile Asn Tyr Asn Asn Tyr Asn Pro Ser
1               5                   10                  15

Leu Lys Ser

<210> SEQ ID NO 302
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Glu Ile Asn His Arg Gly Ser Ile Asn Tyr Asn Asn Tyr Asn Pro Ser
1               5                   10                  15

Leu Lys Ser
```

```
<210> SEQ ID NO 303
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Glu Ile Asn His Arg Gly Ser Ile Asn Tyr Asn Asn Tyr Asn Pro Ser
1               5                   10                  15

Leu Lys Ser

<210> SEQ ID NO 304
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Glu Ile Asn His Arg Gly Ser Ile Asn Tyr Asn Asn Tyr Asn Pro Ser
1               5                   10                  15

Leu Lys Ser

<210> SEQ ID NO 305
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Glu Ile Asn His Arg Gly Ser Ile Asn Tyr Asn Asn Tyr Asn Pro Ser
1               5                   10                  15

Leu Lys Ser

<210> SEQ ID NO 306
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Glu Ile Asn His Arg Gly Ser Ile Asn Tyr Asn Asn Tyr Asn Pro Ser
1               5                   10                  15

Leu Lys Ser

<210> SEQ ID NO 307
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Glu Ile Asn His Arg Gly Ser Ile Asn Tyr Asn Asn Tyr Asn Pro Ser
1               5                   10                  15

Leu Lys Ser
```

<210> SEQ ID NO 308
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Glu Ile Asn His Arg Gly Ser Ile Asn Tyr Asn Asn Tyr Asn Pro Ser
1               5                   10                  15

Leu Lys Ser

<210> SEQ ID NO 309
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Glu Ile Asn His Arg Gly Ser Ile Asn Tyr Asn Asn Tyr Asn Pro Ser
1               5                   10                  15

Leu Lys Ser

<210> SEQ ID NO 310
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Glu Ile Asn His Arg Gly Ser Ile Asn Tyr Asn Asn Tyr Asn Pro Ser
1               5                   10                  15

Leu Lys Ser

<210> SEQ ID NO 311
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Glu Ile Asn His Arg Gly Ser Ile Asn Tyr Asn Asn Tyr Asn Pro Ser
1               5                   10                  15

Leu Lys Ser

<210> SEQ ID NO 312
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Glu Ile Asn His Arg Gly Ser Ile Asn Tyr Asn Asn Tyr Asn Pro Ser
1               5                   10                  15

Leu Lys Ser

<210> SEQ ID NO 313
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Glu Ile Asn His Arg Gly Ser Ile Asn Tyr Asn Asn Tyr Asn Pro Ser
1               5                   10                  15

Leu Lys Ser

<210> SEQ ID NO 314
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Glu Ile Asn His Arg Gly Ser Ile Asn Tyr Asn Asn Tyr Asn Pro Ser
1               5                   10                  15

Leu Lys Ser

<210> SEQ ID NO 315
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Glu Ile Asn His Arg Gly Ser Ile Asn Tyr Asn Asn Tyr Asn Pro Ser
1               5                   10                  15

Leu Lys Ser

<210> SEQ ID NO 316
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Glu Ile Asn His Arg Gly Ser Ile Asn Tyr Asn Asn Tyr Asn Pro Ser
1               5                   10                  15

Leu Lys Ser

<210> SEQ ID NO 317
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 317

Glu Ile Asn His Arg Gly Ser Ile Asn Tyr Asn Asn Tyr Asn Pro Ser
1               5                   10                  15

Leu Lys Ser

<210> SEQ ID NO 318
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Ile Asn His Arg Gly Ser Ile Asn Tyr Asn Asn Tyr Asn Pro Ser
1               5                   10                  15

Leu Lys Ser

<210> SEQ ID NO 319
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Glu Ile Asn His Arg Gly Ser Ile Asn Tyr Asn Asn Tyr Asn Pro Ser
1               5                   10                  15

Leu Lys Ser

<210> SEQ ID NO 320
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Glu Ile Asn His Arg Gly Ser Ile Asn Tyr Asn Asn Tyr Asn Pro Ser
1               5                   10                  15

Leu Lys Ser

<210> SEQ ID NO 321
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Glu Ile Asn His Arg Gly Ser Ile Asn Tyr Asn Asn Tyr Asn Pro Ser
1               5                   10                  15

Leu Lys Ser

<210> SEQ ID NO 322
<211> LENGTH: 19
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 322

Glu Ile Asn His Arg Gly Ser Ile Asn Tyr Asn Asn Tyr Asn Pro Ser
1               5                   10                  15

Leu Lys Ser

<210> SEQ ID NO 323
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Ile Asn His Arg Gly Ser Ile Asn Tyr Asn Asn Tyr Asn Pro Ser
1               5                   10                  15

Leu Lys Ser

<210> SEQ ID NO 324
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Glu Ile Asn His Arg Gly Ser Ile Asn Tyr Asn Asn Tyr Asn Pro Ser
1               5                   10                  15

Leu Lys Ser

<210> SEQ ID NO 325
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Glu Ile Asn His Arg Gly Ser Ile Asn Tyr Asn Asn Tyr Asn Pro Ser
1               5                   10                  15

Leu Lys Ser

<210> SEQ ID NO 326
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Glu Ile Asn His Arg Gly Ser Ile Asn Tyr Asn Asn Tyr Asn Pro Ser
1               5                   10                  15

Leu Lys Ser

<210> SEQ ID NO 327
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Glu Ile Asn His Arg Gly Ser Ile Asn Tyr Asn Tyr Asn Pro Ser
1               5                   10                  15

Leu Lys Ser

<210> SEQ ID NO 328
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Glu Ile Asn His Arg Gly Ser Ile Asn Tyr Asn Tyr Asn Pro Ser
1               5                   10                  15

Leu Lys Ser

<210> SEQ ID NO 329
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Glu Ile Asn His Arg Gly Ser Ile Asn Tyr Asn Tyr Asn Pro Ser
1               5                   10                  15

Leu Lys Ser

<210> SEQ ID NO 330
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Glu Ile Asn His Arg Gly Ser Ile Asn Tyr Asn Tyr Asn Pro Ser
1               5                   10                  15

Leu Lys Ser

<210> SEQ ID NO 331
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Lys Pro Leu Arg Pro His Cys Thr Asn Gly Val Cys Tyr Ser Gly
1               5                   10                  15

Asp Ala Phe Asp Ile
            20
```

```
<210> SEQ ID NO 332
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Lys Pro Leu Arg Pro His Cys Thr Asn Gly Val Cys Tyr Ser Gly
1               5                   10                  15

Asp Ala Phe Asp Ile
            20

<210> SEQ ID NO 333
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ala Lys Pro Leu Arg Pro His Cys Thr Asn Gly Val Cys Tyr Ser Gly
1               5                   10                  15

Asp Ala Phe Asp Ile
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ala Lys Pro Leu Arg Pro His Cys Thr Asn Gly Val Cys Tyr Ser Gly
1               5                   10                  15

Asp Ala Phe Asp Ile
            20

<210> SEQ ID NO 335
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ala Lys Pro Leu Arg Pro His Cys Thr Asn Gly Val Cys Tyr Ser Gly
1               5                   10                  15

Asp Ala Phe Asp Ile
            20

<210> SEQ ID NO 336
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 336

Ala Lys Pro Leu Arg Pro His Cys Thr Asn Gly Val Cys Tyr Ser Gly
1               5                   10                  15

Asp Ala Phe Asp Ile
            20

<210> SEQ ID NO 337
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ala Lys Pro Leu Arg Pro His Cys Thr Asn Gly Val Cys Tyr Ser Gly
1               5                   10                  15

Asp Ala Phe Asp Ile
            20

<210> SEQ ID NO 338
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ala Lys Pro Leu Arg Pro His Cys Thr Asn Gly Val Cys Tyr Ser Gly
1               5                   10                  15

Asp Ala Phe Asp Ile
            20

<210> SEQ ID NO 339
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ala Lys Pro Leu Arg Pro His Cys Thr Asn Gly Val Cys Tyr Ser Gly
1               5                   10                  15

Asp Ala Phe Asp Ile
            20

<210> SEQ ID NO 340
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Ala Lys Pro Leu Arg Pro His Cys Thr Asn Gly Val Cys Tyr Ser Gly
1               5                   10                  15

Asp Ala Phe Asp Ile
            20

<210> SEQ ID NO 341

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ala Lys Pro Leu Arg Pro His Cys Thr Asn Gly Val Cys Tyr Ser Gly
1               5                   10                  15

Asp Ala Phe Asp Ile
            20

<210> SEQ ID NO 342
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ala Lys Pro Leu Arg Pro His Cys Thr Asn Gly Val Cys Tyr Ser Gly
1               5                   10                  15

Asp Ala Phe Asp Ile
            20

<210> SEQ ID NO 343
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ala Lys Pro Leu Arg Pro His Cys Thr Asn Gly Val Cys Tyr Ser Gly
1               5                   10                  15

Asp Ala Phe Asp Ile
            20

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ala Lys Pro Leu Arg Pro His Cys Thr Asn Gly Val Cys Tyr Ser Gly
1               5                   10                  15

Asp Ala Phe Asp Ile
            20

<210> SEQ ID NO 345
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ala Lys Pro Leu Arg Pro His Cys Thr Asn Gly Val Cys Tyr Ser Gly
1               5                   10                  15
```

Asp Ala Phe Asp Ile
            20

<210> SEQ ID NO 346
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ala Lys Pro Leu Arg Pro His Cys Thr Asn Gly Val Cys Tyr Ser Gly
1               5                   10                  15

Asp Ala Phe Asp Ile
            20

<210> SEQ ID NO 347
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ala Lys Pro Leu Arg Pro His Cys Thr Asn Gly Val Cys Tyr Ser Gly
1               5                   10                  15

Asp Ala Phe Asp Ile
            20

<210> SEQ ID NO 348
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ala Lys Pro Leu Arg Pro His Cys Thr Asn Gly Val Cys Tyr Ser Gly
1               5                   10                  15

Asp Ala Phe Asp Ile
            20

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ala Lys Pro Leu Arg Pro His Cys Thr Asn Gly Val Cys Tyr Ser Gly
1               5                   10                  15

Asp Ala Phe Asp Ile
            20

<210> SEQ ID NO 350
<211> LENGTH: 21
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 350

Ala Lys Pro Leu Arg Pro His Cys Thr Asn Gly Val Cys Tyr Ser Gly
1               5                   10                  15

Asp Ala Phe Asp Ile
            20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ala Lys Pro Leu Arg Pro His Cys Thr Asn Gly Val Cys Tyr Ser Gly
1               5                   10                  15

Asp Ala Phe Asp Ile
            20

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ala Lys Pro Leu Arg Pro His Cys Thr Asn Gly Val Cys Tyr Ser Gly
1               5                   10                  15

Asp Ala Phe Asp Ile
            20

<210> SEQ ID NO 353
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ala Lys Pro Leu Arg Pro His Cys Thr Asn Gly Val Cys Tyr Ser Gly
1               5                   10                  15

Asp Ala Phe Asp Ile
            20

<210> SEQ ID NO 354
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ala Lys Pro Leu Arg Pro His Cys Ile Asn Gly Val Cys Tyr Ser Gly
1               5                   10                  15

Asp Ala Phe Asp Ile
            20
```

```
<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ala Lys Pro Leu Arg Pro His Cys Thr Asn Gly Val Cys Tyr Ser Gly
1               5                   10                  15

Asp Ala Phe Asp Ile
            20

<210> SEQ ID NO 356
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Lys Pro Leu Arg Pro His Cys Thr Asn Gly Val Cys Tyr Ser Gly
1               5                   10                  15

Asp Ala Phe Asp Ile
            20

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ala Lys Pro Leu Arg Pro His Cys Thr Asn Gly Val Cys Tyr Ser Gly
1               5                   10                  15

Asp Ala Phe Asp Ile
            20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ala Lys Pro Leu Arg Pro His Cys Ile Asn Gly Val Cys Tyr Ser Gly
1               5                   10                  15

Asp Ala Phe Asp Ile
            20

<210> SEQ ID NO 359
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 359

Ala Lys Pro Leu Arg Pro His Cys Thr Asn Gly Val Cys Tyr Ser Gly
1               5                   10                  15

Asp Ala Phe Asp Ile
            20

<210> SEQ ID NO 360
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ala Lys Pro Leu Arg Pro His Cys Thr Asn Gly Val Cys Tyr Ser Gly
1               5                   10                  15

Asp Ala Phe Asp Ile
            20

<210> SEQ ID NO 361
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ala Lys Pro Leu Arg Pro His Cys Ile Asn Gly Val Cys Tyr Ser Gly
1               5                   10                  15

Asp Ala Phe Asp Ile
            20

<210> SEQ ID NO 362
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ala Lys Pro Leu Arg Pro His Cys Thr Asn Gly Val Cys Tyr Ser Gly
1               5                   10                  15

Asp Ala Phe Asp Ile
            20

<210> SEQ ID NO 363
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Lys Pro Leu Arg Pro His Cys Ile Asn Gly Val Cys Tyr Ser Gly
1               5                   10                  15

Asp Ala Phe Asp Ile
            20

<210> SEQ ID NO 364

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ala Lys Pro Leu Arg Pro His Cys Ile Asn Gly Val Cys Tyr Ser Gly
1               5                   10                  15

Asp Ala Phe Asp Ile
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala Lys Pro Leu Arg Pro His Cys Thr Asn Gly Val Cys Tyr Ser Gly
1               5                   10                  15

Asp Ala Phe Asp Ile
            20

<210> SEQ ID NO 366
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Lys Pro Leu Arg Pro His Cys Thr Asn Gly Val Cys Tyr Ser Gly
1               5                   10                  15

Asp Ala Phe Asp Ile
            20

<210> SEQ ID NO 367
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Lys Pro Leu Arg Pro His Cys Thr Asn Gly Val Cys Tyr Ser Gly
1               5                   10                  15

Asp Ala Phe Asp Ile
            20

<210> SEQ ID NO 368
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Lys Pro Leu Arg Pro His Cys Ile Asn Gly Val Cys Tyr Ser Gly
1               5                   10                  15
```

Asp Ala Phe Asp Ile
            20

<210> SEQ ID NO 369
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Lys Pro Leu Arg Pro His Cys Thr Asn Gly Val Cys Tyr Ser Gly
1               5                   10                  15

Asp Ala Phe Asp Ile
            20

<210> SEQ ID NO 370
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Ala Lys Pro Leu Arg Pro His Cys Thr Asn Gly Val Cys Tyr Ser Gly
1               5                   10                  15

Asp Ala Phe Asp Ile
            20

<210> SEQ ID NO 371
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ala Lys Pro Leu Arg Pro His Cys Thr Asn Gly Val Cys Tyr Ser Gly
1               5                   10                  15

Asp Ala Phe Asp Ile
            20

<210> SEQ ID NO 372
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Lys Pro Leu Arg Pro His Cys Ile Asn Gly Val Cys Tyr Ser Gly
1               5                   10                  15

Asp Ala Phe Asp Ile
            20

<210> SEQ ID NO 373
<211> LENGTH: 21
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 373

Ala Lys Pro Leu Arg Pro His Cys Thr Asn Gly Val Cys Tyr Ser Gly
1               5                   10                  15

Asp Ala Phe Asp Ile
            20

<210> SEQ ID NO 374
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ala Lys Pro Leu Arg Pro His Cys Thr Asn Gly Val Cys Tyr Ser Gly
1               5                   10                  15

Asp Ala Phe Asp Ile
            20

<210> SEQ ID NO 375
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ala Lys Pro Leu Arg Pro His Cys Ile Asn Gly Val Cys Tyr Ser Gly
1               5                   10                  15

Asp Ala Phe Asp Ile
            20

<210> SEQ ID NO 376
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ala Lys Pro Leu Arg Pro His Cys Thr Asn Gly Val Cys Tyr Ser Gly
1               5                   10                  15

Asp Ala Phe Asp Ile
            20

<210> SEQ ID NO 377
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Ala Lys Pro Leu Arg Pro His Cys Ile Asn Gly Val Cys Tyr Ser Gly
1               5                   10                  15

Asp Ala Phe Asp Ile
            20

<210> SEQ ID NO 378
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Lys Pro Leu Arg Pro His Cys Ile Asn Gly Val Cys Tyr Ser Gly
1               5                   10                  15

Asp Ala Phe Asp Ile
            20

<210> SEQ ID NO 379
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ala Lys Pro Leu Arg Pro His Cys Thr Asn Gly Val Cys Tyr Ser Gly
1               5                   10                  15

Asp Ala Phe Asp Ile
            20

<210> SEQ ID NO 380
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ala Lys Pro Leu Arg Pro His Cys Thr Asn Gly Val Cys Tyr Ser Gly
1               5                   10                  15

Asp Ala Phe Asp Ile
            20

<210> SEQ ID NO 381
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ala Lys Pro Leu Arg Pro His Cys Thr Asn Gly Val Cys Tyr Ser Gly
1               5                   10                  15

Asp Ala Phe Asp Ile
            20

<210> SEQ ID NO 382
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ala Lys Pro Leu Arg Pro His Cys Ile Asn Gly Val Cys Tyr Ser Gly
1               5                   10                  15

Asp Ala Phe Asp Ile
            20

<210> SEQ ID NO 383
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Lys Pro Leu Arg Pro His Cys Thr Asn Gly Val Cys Tyr Ser Gly
1               5                   10                  15

Asp Ala Phe Asp Ile
            20

<210> SEQ ID NO 384
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ala Lys Pro Leu Arg Pro His Cys Thr Asn Gly Val Cys Tyr Ser Gly
1               5                   10                  15

Asp Ala Phe Asp Ile
            20

<210> SEQ ID NO 385
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ala Lys Pro Leu Arg Pro His Cys Thr Asn Gly Val Cys Tyr Ser Gly
1               5                   10                  15

Asp Ala Phe Asp Ile
            20

<210> SEQ ID NO 386
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Lys Pro Leu Arg Pro His Cys Ile Asn Gly Val Cys Tyr Ser Gly
1               5                   10                  15

Asp Ala Phe Asp Ile
            20

<210> SEQ ID NO 387

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ala Lys Pro Leu Arg Pro His Cys Thr Asn Gly Val Cys Tyr Ser Gly
1               5                   10                  15

Asp Ala Phe Asp Ile
            20

<210> SEQ ID NO 388
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ala Lys Pro Leu Arg Pro His Cys Thr Asn Gly Val Cys Tyr Ser Gly
1               5                   10                  15

Asp Ala Phe Asp Ile
            20

<210> SEQ ID NO 389
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Ala Lys Pro Leu Arg Pro His Cys Ile Asn Gly Val Cys Tyr Ser Gly
1               5                   10                  15

Asp Ala Phe Asp Ile
            20

<210> SEQ ID NO 390
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Ala Lys Pro Leu Arg Pro His Cys Thr Asn Gly Val Cys Tyr Ser Gly
1               5                   10                  15

Asp Ala Phe Asp Ile
            20

<210> SEQ ID NO 391
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ala Lys Pro Leu Arg Pro His Cys Ile Asn Gly Val Cys Tyr Ser Gly
1               5                   10                  15
```

-continued

Asp Ala Phe Asp Ile
            20

<210> SEQ ID NO 392
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Lys Pro Leu Arg Pro His Cys Ile Asn Gly Val Cys Tyr Ser Gly
1               5                   10                  15

Asp Ala Phe Asp Ile
            20

<210> SEQ ID NO 393
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Lys Pro Leu Arg Pro His Cys Thr Asn Gly Val Cys Tyr Ser Gly
1               5                   10                  15

Asp Ala Phe Asp Ile
            20

<210> SEQ ID NO 394
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Lys Pro Leu Arg Pro His Cys Thr Asn Gly Val Cys Tyr Ser Gly
1               5                   10                  15

Asp Ala Phe Asp Ile
            20

<210> SEQ ID NO 395
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Ala Lys Pro Leu Arg Pro His Cys Thr Asn Gly Val Cys Tyr Ser Gly
1               5                   10                  15

Asp Ala Phe Asp Ile
            20

<210> SEQ ID NO 396
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 396

Gly Gly Asn Asn Ile Gly Ser Lys Asn Val His
1               5                   10

<210> SEQ ID NO 397
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Gly Asn Asn Ile Gly Ser Lys Ser Val His
1               5                   10

<210> SEQ ID NO 398
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Gly Asn Asn Ile Gly Ser Lys Asn Val His
1               5                   10

<210> SEQ ID NO 399
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Gly Asn Asn Ile Gly Ser Lys Asn Val His
1               5                   10

<210> SEQ ID NO 400
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gly Gly Asn Asn Ile Gly Ser Lys Asn Val His
1               5                   10

<210> SEQ ID NO 401
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Gly Asn Asn Ile Gly Ser Lys Asn Val His
1               5                   10

<210> SEQ ID NO 402
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Gly Gly Asn Asn Ile Gly Ser Lys Asn Val His
1               5                   10

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly Gly Asn Asn Ile Gly Ser Lys Asn Val His
1               5                   10

<210> SEQ ID NO 404
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Gly Gly Asn Asn Ile Gly Ser Lys Asn Val His
1               5                   10

<210> SEQ ID NO 405
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Gly Asn Asn Ile Gly Ser Lys Asn Val His
1               5                   10

<210> SEQ ID NO 406
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gly Gly Asn Asn Ile Gly Ser Lys Asn Val His
1               5                   10

<210> SEQ ID NO 407
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gly Gly Asn Asn Ile Gly Ser Lys Asn Val His
1               5                   10

<210> SEQ ID NO 408
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gly Gly Asn Asn Ile Gly Ser Lys Asn Val His
1               5                   10

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gly Gly Asn Asn Ile Gly Ser Lys Asn Val His
1               5                   10

<210> SEQ ID NO 410
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Gly Gly Asn Asn Ile Gly Ser Lys Asn Val His
1               5                   10

<210> SEQ ID NO 411
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Gly Asn Asn Ile Gly Ser Lys Asn Val His
1               5                   10

<210> SEQ ID NO 412
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Gly Asn Asn Ile Gly Ser Lys Asn Val His
1               5                   10

<210> SEQ ID NO 413
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Gly Gly Asn Asn Ile Gly Ser Lys Asn Val His
1               5                   10

<210> SEQ ID NO 414
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Gly Asn Asn Ile Gly Ser Lys Asn Val His
1               5                   10

<210> SEQ ID NO 415
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gly Gly Asn Asn Ile Gly Ser Lys Asn Val His
1               5                   10

<210> SEQ ID NO 416
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Gly Asn Asn Ile Gly Ser Lys Asn Val His
1               5                   10

<210> SEQ ID NO 417
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gly Gly Asn Asn Ile Gly Ser Lys Asn Val His
1               5                   10

<210> SEQ ID NO 418
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 418

Gly Gly Asn Asn Ile Gly Ser Lys Asn Val His
1               5                   10

<210> SEQ ID NO 419
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Arg Gly Asn Asn Ile Gly Ser Lys Asn Val His
1               5                   10

<210> SEQ ID NO 420
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Arg Gly Asn Asn Ile Gly Tyr Lys Asn Val His
1               5                   10

<210> SEQ ID NO 421
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Arg Gly Asn Asn Ile Gly Ser Met Asn Val His
1               5                   10

<210> SEQ ID NO 422
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Arg Gly Asn Asn Ile Gly Ser Lys Asn Val His
1               5                   10

<210> SEQ ID NO 423
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gly Gly Asn Asn Ile Gly Tyr Lys Asn Val His
1               5                   10

<210> SEQ ID NO 424
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gly Gly Asn Asn Ile Gly Tyr Met Asn Val His
1               5                   10

<210> SEQ ID NO 425
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Gly Gly Asn Asn Ile Gly Tyr Lys Asn Val His
1               5                   10

<210> SEQ ID NO 426
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Gly Gly Asn Asn Ile Gly Ser Met Asn Val His
1               5                   10

<210> SEQ ID NO 427
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Gly Gly Asn Asn Ile Gly Ser Met Asn Val His
1               5                   10

<210> SEQ ID NO 428
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Gly Gly Asn Asn Ile Gly Ser Lys Asn Val His
1               5                   10

<210> SEQ ID NO 429
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 429

Gly Gly Asn Asn Ile Gly Tyr Lys Asn Val His
1               5                   10

<210> SEQ ID NO 430
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly Gly Asn Asn Ile Gly Ser Lys Asn Val His
1               5                   10

<210> SEQ ID NO 431
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Gly Gly Asn Asn Ile Gly Ser Lys Asn Val His
1               5                   10

<210> SEQ ID NO 432
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Gly Gly Asn Asn Ile Gly Tyr Lys Asn Val His
1               5                   10

<210> SEQ ID NO 433
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Arg Gly Asn Asn Ile Gly Ser Lys Asn Val His
1               5                   10

<210> SEQ ID NO 434
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Arg Gly Asn Asn Ile Gly Tyr Lys Asn Val His
1               5                   10

<210> SEQ ID NO 435
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Arg Gly Asn Asn Ile Gly Ser Met Asn Val His
1               5                   10

<210> SEQ ID NO 436
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Arg Gly Asn Asn Ile Gly Ser Lys Asn Val His
1               5                   10

<210> SEQ ID NO 437
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Gly Asn Asn Ile Gly Tyr Lys Asn Val His
1               5                   10

<210> SEQ ID NO 438
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gly Gly Asn Asn Ile Gly Tyr Met Asn Val His
1               5                   10

<210> SEQ ID NO 439
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Gly Gly Asn Asn Ile Gly Tyr Lys Asn Val His
1               5                   10

<210> SEQ ID NO 440
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 440

Gly Gly Asn Asn Ile Gly Ser Met Asn Val His
1               5                   10

<210> SEQ ID NO 441
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gly Gly Asn Asn Ile Gly Ser Met Asn Val His
1               5                   10

<210> SEQ ID NO 442
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Gly Gly Asn Asn Ile Gly Ser Lys Asn Val His
1               5                   10

<210> SEQ ID NO 443
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Gly Gly Asn Asn Ile Gly Tyr Lys Asn Val His
1               5                   10

<210> SEQ ID NO 444
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Gly Gly Asn Asn Ile Gly Ser Lys Asn Val His
1               5                   10

<210> SEQ ID NO 445
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Gly Gly Asn Asn Ile Gly Ser Lys Asn Val His
1               5                   10

<210> SEQ ID NO 446
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Gly Gly Asn Asn Ile Gly Tyr Lys Asn Val His
1               5                   10

<210> SEQ ID NO 447
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Arg Gly Asn Asn Ile Gly Ser Lys Asn Val His
1               5                   10

<210> SEQ ID NO 448
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Arg Gly Asn Asn Ile Gly Tyr Lys Asn Val His
1               5                   10

<210> SEQ ID NO 449
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Arg Gly Asn Asn Ile Gly Ser Met Asn Val His
1               5                   10

<210> SEQ ID NO 450
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Arg Gly Asn Asn Ile Gly Ser Lys Asn Val His
1               5                   10

<210> SEQ ID NO 451
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Gly Gly Asn Asn Ile Gly Tyr Lys Asn Val His
1               5                   10

<210> SEQ ID NO 452
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Gly Gly Asn Asn Ile Gly Tyr Met Asn Val His
1               5                   10

<210> SEQ ID NO 453
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Gly Gly Asn Asn Ile Gly Tyr Lys Asn Val His
1               5                   10

<210> SEQ ID NO 454
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Gly Gly Asn Asn Ile Gly Ser Met Asn Val His
1               5                   10

<210> SEQ ID NO 455
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Gly Gly Asn Asn Ile Gly Ser Met Asn Val His
1               5                   10

<210> SEQ ID NO 456
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gly Gly Asn Asn Ile Gly Ser Lys Asn Val His
1               5                   10

<210> SEQ ID NO 457
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Gly Gly Asn Asn Ile Gly Tyr Lys Asn Val His
1               5                   10

<210> SEQ ID NO 458
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Gly Gly Asn Asn Ile Gly Ser Lys Asn Val His
1               5                   10

<210> SEQ ID NO 459
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Gly Gly Asn Asn Ile Gly Ser Lys Asn Val His
1               5                   10

<210> SEQ ID NO 460
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Gly Gly Asn Asn Ile Gly Tyr Lys Asn Val His
1               5                   10

<210> SEQ ID NO 461
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Asp Asp Ser Asp Arg Pro Ser
1               5

<210> SEQ ID NO 462
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 462

Asp Asp Ser Asp Arg Pro Ser
1               5

<210> SEQ ID NO 463
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Asp Asp Ser Asp Arg Pro Ser
1               5

<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Asp Asp Ser Asp Arg Pro Ser
1               5

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Asp Asp Ser Asp Arg Pro Ser
1               5

<210> SEQ ID NO 466
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Asp Asp Ser Asp Arg Pro Ser
1               5

<210> SEQ ID NO 467
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Asp Asp Ser Asp Arg Pro Ser
1               5

<210> SEQ ID NO 468
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Asp Asp Ser Asp Arg Pro Ser
1               5

<210> SEQ ID NO 469
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Asp Asp Ser Asp Arg Pro Ser
1               5

<210> SEQ ID NO 470
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Asp Asp Ser Asp Arg Pro Ser
1               5

<210> SEQ ID NO 471
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Asp Asp Ser Asp Arg Pro Ser
1               5

<210> SEQ ID NO 472
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Asp Asp Ser Asp Arg Pro Ser
1               5

<210> SEQ ID NO 473
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 473

Asp Asp Ser Asp Arg Pro Ser
1               5

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Asp Asp Ser Asp Arg Pro Ser
1               5

<210> SEQ ID NO 475
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Asp Asp Ser Asp Arg Pro Ser
1               5

<210> SEQ ID NO 476
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Asp Asp Ser Asp Arg Pro Ser
1               5

<210> SEQ ID NO 477
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Asp Asp Ser Asp Arg Pro Ser
1               5

<210> SEQ ID NO 478
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Asp Asp Ser Asp Arg Pro Ser
1               5

<210> SEQ ID NO 479
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Asp Asp Ser Asp Arg Pro Ser
1               5

<210> SEQ ID NO 480
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Asp Asp Ser Asp Arg Pro Ser
1               5

<210> SEQ ID NO 481
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Asp Asp Ser Asp Arg Pro Ser
1               5

<210> SEQ ID NO 482
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Asp Asp Ser Asp Arg Pro Ser
1               5

<210> SEQ ID NO 483
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Asp Asp Ser Asp Arg Pro Ser
1               5

<210> SEQ ID NO 484
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 484

Asp Asp Ser Asp Arg Pro Ser
1               5

<210> SEQ ID NO 485
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Asp Asp Ser Asp Arg Pro Ser
1               5

<210> SEQ ID NO 486
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Asp Asp Ser Asp Arg Pro Ser
1               5

<210> SEQ ID NO 487
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Asp Asp Ser Asp Arg Pro Ser
1               5

<210> SEQ ID NO 488
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Asp Asp Ser Asp Arg Pro Ser
1               5

<210> SEQ ID NO 489
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Asp Asp Ser Asp Arg Pro Ser
1               5

<210> SEQ ID NO 490
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Asp Asp Ser Asp Arg Pro Ser
1               5

<210> SEQ ID NO 491
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Asp Asp Ser Asp Arg Pro Ser
1               5

<210> SEQ ID NO 492
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Asp Asp Ser Asp Arg Pro Ser
1               5

<210> SEQ ID NO 493
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Asp Asp Ser Asp Arg Pro Ser
1               5

<210> SEQ ID NO 494
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Asp Asp Ser Asp Arg Pro Ser
1               5

<210> SEQ ID NO 495
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 495

Asp Asp Ser Asp Arg Pro Ser
1               5

<210> SEQ ID NO 496
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Asp Asp Ser Asp Arg Pro Ser
1               5

<210> SEQ ID NO 497
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Asp Asp Ser Asp Arg Pro Ser
1               5

<210> SEQ ID NO 498
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Asp Asp Ser Asp Arg Pro Ser
1               5

<210> SEQ ID NO 499
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Asp Asp Ser Asp Arg Pro Ser
1               5

<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Asp Asp Ser Asp Arg Pro Ser
1               5

<210> SEQ ID NO 501
<211> LENGTH: 7
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Asp Asp Ser Asp Arg Pro Ser
1               5

<210> SEQ ID NO 502
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Asp Asp Ser Asp Arg Pro Ser
1               5

<210> SEQ ID NO 503
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Asp Asp Ser Asp Arg Pro Ser
1               5

<210> SEQ ID NO 504
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Asp Asp Ser Asp Arg Pro Ser
1               5

<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Asp Asp Ser Asp Arg Pro Ser
1               5

<210> SEQ ID NO 506
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 506

Asp Asp Ser Asp Arg Pro Ser
1               5

<210> SEQ ID NO 507
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Asp Asp Ser Asp Arg Pro Ser
1               5

<210> SEQ ID NO 508
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Asp Asp Ser Asp Arg Pro Ser
1               5

<210> SEQ ID NO 509
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Asp Asp Ser Asp Arg Pro Ser
1               5

<210> SEQ ID NO 510
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Asp Asp Ser Asp Arg Pro Ser
1               5

<210> SEQ ID NO 511
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Asp Asp Ser Asp Arg Pro Ser
1               5

<210> SEQ ID NO 512
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Asp Asp Ser Asp Arg Pro Ser
1               5

<210> SEQ ID NO 513
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Asp Asp Ser Asp Arg Pro Ser
1               5

<210> SEQ ID NO 514
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Asp Asp Ser Asp Arg Pro Ser
1               5

<210> SEQ ID NO 515
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Asp Asp Ser Asp Arg Pro Ser
1               5

<210> SEQ ID NO 516
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Asp Asp Ser Asp Arg Pro Ser
1               5

<210> SEQ ID NO 517
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 517

Asp Asp Ser Asp Arg Pro Ser
1               5

<210> SEQ ID NO 518
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Asp Asp Ser Asp Arg Pro Ser
1               5

<210> SEQ ID NO 519
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Asp Asp Ser Asp Arg Pro Ser
1               5

<210> SEQ ID NO 520
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Asp Asp Ser Asp Arg Pro Ser
1               5

<210> SEQ ID NO 521
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Asp Asp Ser Asp Arg Pro Ser
1               5

<210> SEQ ID NO 522
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Asp Asp Ser Asp Arg Pro Ser
1               5

<210> SEQ ID NO 523
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Asp Asp Ser Asp Arg Pro Ser
1               5

<210> SEQ ID NO 524
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Asp Asp Ser Asp Arg Pro Ser
1               5

<210> SEQ ID NO 525
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Asp Asp Ser Asp Arg Pro Ser
1               5

<210> SEQ ID NO 526
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Gln Val Trp Asp Ser Ser Ser Asp His Leu Val
1               5                   10

<210> SEQ ID NO 527
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Gln Val Trp Asp Ser Ser Ser Asp His Leu Val
1               5                   10

<210> SEQ ID NO 528
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 528

Gln Val Trp Asp Ser Ser Ser Asp His Val Val
1               5                   10

<210> SEQ ID NO 529
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gln Val Trp Asp Ser Ser Ser Asp His Leu Val
1               5                   10

<210> SEQ ID NO 530
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Gln Val Trp Asp Ser Ser Ser Asp His Leu Val
1               5                   10

<210> SEQ ID NO 531
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gln Val Trp Asp Ser Ser Ser Asp His Leu Val
1               5                   10

<210> SEQ ID NO 532
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Gln Val Trp Asp Ser Ser Ser Asp His Leu Val
1               5                   10

<210> SEQ ID NO 533
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gln Val Trp Asp Ser Ser Ser Asp His Leu Val
1               5                   10

<210> SEQ ID NO 534
<211> LENGTH: 11

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Gln Val Trp Asp Ser Ser Ser Asp His Leu Val
1               5                   10

<210> SEQ ID NO 535
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Gln Val Trp Asp Ser Ser Ser Asp His Leu Val
1               5                   10

<210> SEQ ID NO 536
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Gln Val Trp Asp Ser Ser Ser Asp His Leu Val
1               5                   10

<210> SEQ ID NO 537
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Gln Val Trp Asp Ser Ser Ser Asp His Leu Val
1               5                   10

<210> SEQ ID NO 538
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Gln Val Trp Asp Ser Ser Ser Asp His Val Val
1               5                   10

<210> SEQ ID NO 539
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 539

Gln Val Trp Asp Ser Ser Ser Asp His Leu Val
1               5                   10

<210> SEQ ID NO 540
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gln Val Trp Asp Ser Ser Ser Asp His Val Val
1               5                   10

<210> SEQ ID NO 541
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Gln Val Trp Asp Ser Ser Ser Asp His Leu Val
1               5                   10

<210> SEQ ID NO 542
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Gln Val Trp Asp Ser Ser Ser Asp His Val Val
1               5                   10

<210> SEQ ID NO 543
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Gln Val Trp Asp Ser Ser Ser Asp His Leu Val
1               5                   10

<210> SEQ ID NO 544
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Gln Val Trp Asp Ser Ser Ser Asp His Val Val
1               5                   10

<210> SEQ ID NO 545
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Gln Val Trp Asp Ser Ser Ser Asp His Val Val
1               5                   10

<210> SEQ ID NO 546
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Gln Val Trp Asp Ser Ser Ser Asp His Val Val
1               5                   10

<210> SEQ ID NO 547
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Gln Val Trp Asp Ser Ser Ser Asp His Val Val
1               5                   10

<210> SEQ ID NO 548
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gln Val Trp Asp Ser Ser Ser Asp His Val Val
1               5                   10

<210> SEQ ID NO 549
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gln Val Trp Asp Ser Ser Ser Asp His Val Val
1               5                   10

<210> SEQ ID NO 550
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 550

Gln Val Trp Asp Ser Ser Ser Asp His Val Val
1               5                   10

<210> SEQ ID NO 551
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Gln Val Trp Asp Ser Ser Ser Asp His Val Val
1               5                   10

<210> SEQ ID NO 552
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Gln Val Trp Asp His Ser Ser Asp His Val Val
1               5                   10

<210> SEQ ID NO 553
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Gln Val Trp Asp Ser Ser Ser Asp His Val Val
1               5                   10

<210> SEQ ID NO 554
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Gln Val Trp Asp Ser Ser Ser Asp His Val Val
1               5                   10

<210> SEQ ID NO 555
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Gln Val Trp Asp His Ser Ser Asp His Val Val
1               5                   10

<210> SEQ ID NO 556
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gln Val Trp Asp Ser Ser Ser Asp His Val Val
1               5                   10

<210> SEQ ID NO 557
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Gln Val Trp Asp His Ser Ser Asp His Val Val
1               5                   10

<210> SEQ ID NO 558
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gln Val Trp Asp His Ser Ser Asp His Val Val
1               5                   10

<210> SEQ ID NO 559
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Gln Val Trp Asp His Ser Ser Asp His Val Val
1               5                   10

<210> SEQ ID NO 560
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gln Val Trp Asp Ser Arg Ser Asp His Val Val
1               5                   10

<210> SEQ ID NO 561
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 561

Gln Val Trp Asp Ser Glu Ser Asp His Val Val
1               5                   10

<210> SEQ ID NO 562
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Gln Val Trp Asp Ser Glu Ser Asp His Val Val
1               5                   10

<210> SEQ ID NO 563
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Gln Val Trp Asp Ser Ser Ser Asp His Val Val
1               5                   10

<210> SEQ ID NO 564
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gln Val Trp Asp Ser Ser Ser Asp His Val Val
1               5                   10

<210> SEQ ID NO 565
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Gln Val Trp Asp Ser Ser Ser Asp His Val Val
1               5                   10

<210> SEQ ID NO 566
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Gln Val Trp Asp His Ser Ser Asp His Val Val
1               5                   10

<210> SEQ ID NO 567
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gln Val Trp Asp Ser Ser Ser Asp His Val Val
1               5                   10

<210> SEQ ID NO 568
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gln Val Trp Asp Ser Ser Ser Asp His Val Val
1               5                   10

<210> SEQ ID NO 569
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Gln Val Trp Asp His Ser Ser Asp His Val Val
1               5                   10

<210> SEQ ID NO 570
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gln Val Trp Asp Ser Ser Ser Asp His Val Val
1               5                   10

<210> SEQ ID NO 571
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gln Val Trp Asp His Ser Ser Asp His Val Val
1               5                   10

<210> SEQ ID NO 572
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 572

Gln Val Trp Asp His Ser Ser Asp His Val Val
1               5                   10

<210> SEQ ID NO 573
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Gln Val Trp Asp His Ser Ser Asp His Val Val
1               5                   10

<210> SEQ ID NO 574
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gln Val Trp Asp Ser Arg Ser Asp His Val Val
1               5                   10

<210> SEQ ID NO 575
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Gln Val Trp Asp Ser Glu Ser Asp His Val Val
1               5                   10

<210> SEQ ID NO 576
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Gln Val Trp Asp Ser Glu Ser Asp His Val Val
1               5                   10

<210> SEQ ID NO 577
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Gln Val Trp Asp Ser Ser Ser Asp His Val Val
1               5                   10

<210> SEQ ID NO 578
<211> LENGTH: 11
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gln Val Trp Asp Ser Ser Ser Asp His Val Val
1               5                   10

<210> SEQ ID NO 579
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Gln Val Trp Asp Ser Ser Ser Asp His Val Val
1               5                   10

<210> SEQ ID NO 580
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Gln Val Trp Asp His Ser Ser Asp His Val Val
1               5                   10

<210> SEQ ID NO 581
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Gln Val Trp Asp Ser Ser Ser Asp His Val Val
1               5                   10

<210> SEQ ID NO 582
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Gln Val Trp Asp Ser Ser Ser Asp His Val Val
1               5                   10

<210> SEQ ID NO 583
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gln Val Trp Asp His Ser Ser Asp His Val Val
1               5                   10

<210> SEQ ID NO 584
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gln Val Trp Asp Ser Ser Ser Asp His Val Val
1               5                   10

<210> SEQ ID NO 585
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gln Val Trp Asp His Ser Ser Asp His Val Val
1               5                   10

<210> SEQ ID NO 586
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Gln Val Trp Asp His Ser Ser Asp His Val Val
1               5                   10

<210> SEQ ID NO 587
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Gln Val Trp Asp His Ser Ser Asp His Val Val
1               5                   10

<210> SEQ ID NO 588
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Gln Val Trp Asp Ser Arg Ser Asp His Val Val
1               5                   10

<210> SEQ ID NO 589
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Gln Val Trp Asp Ser Glu Ser Asp His Val Val
1               5                   10

<210> SEQ ID NO 590
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Gln Val Trp Asp Ser Glu Ser Asp His Val Val
1               5                   10

<210> SEQ ID NO 591
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 591

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Val Asn His Arg Gly Ser Ile Asn Tyr Asn Asn Tyr Asn Pro
        50                  55                  60

Ser Leu Lys Ser Arg Val Thr Ile Ser Val Asp Thr Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 592
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 592

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30
```

```
Tyr Trp Ser Trp Ile Arg Gln Pro Pro Gly Lys Gly Leu Glu Trp Ile
        35                  40                  45

Gly Glu Val Asn His Arg Gly Ser Ile Asn Tyr Asn Asn Tyr Asn Pro
 50                  55                  60

Ser Leu Lys Ser Arg Val Thr Ile Ser Val Asp Thr Ser Lys Asn Gln
 65                  70                  75                  80

Phe Ser Leu Lys Leu Thr Ser Val Thr Ala Ala Asp Thr Ala Val Tyr
                 85                  90                  95

Tyr Cys Ala Lys Pro Leu Arg Pro His Cys Thr Asn Gly Val Cys Tyr
                100                 105                 110

Ser Gly Asp Ala Phe Asp Ile Trp Gly Gln Gly Thr Met Val Thr Val
        115                 120                 125

Ala Ser
    130

<210> SEQ ID NO 593
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 593

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Asp Tyr
                 20                  25                  30

Tyr Trp Ser Trp Ile Arg Gln Pro Pro Gly Lys Gly Leu Glu Trp Ile
        35                  40                  45

Gly Glu Val Asn His Arg Gly Ser Ile Asn Tyr Asn Asn Tyr Asn Pro
 50                  55                  60

Ser Leu Lys Ser Arg Val Thr Ile Ser Val Asp Thr Ser Lys Asn Gln
 65                  70                  75                  80

Phe Ser Leu Lys Leu Thr Ser Val Thr Ala Ala Asp Thr Ala Val Tyr
                 85                  90                  95

Tyr Cys Ala Lys Pro Leu Arg Pro His Cys Thr Asn Gly Val Cys Tyr
                100                 105                 110

Ser Gly Asp Ala Phe Asp Ile Trp Gly Gln Gly Thr Met Val Thr Val
        115                 120                 125

Ala Ser
    130

<210> SEQ ID NO 594
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 594

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Asp Tyr
                 20                  25                  30

Tyr Trp Ser Trp Ile Arg Gln Pro Pro Gly Lys Gly Leu Glu Trp Ile
        35                  40                  45
```

-continued

Gly Glu Ile Asn His Arg Gly Ser Ile Asn Tyr Asn Tyr Asn Pro
    50                  55                  60

Ser Leu Lys Ser Arg Val Thr Ile Ser Val Asp Thr Ser Lys Asn Gln
 65                  70                  75                  80

Phe Ser Leu Lys Leu Thr Ser Val Thr Ala Ala Asp Thr Ala Val Tyr
                 85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 595
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30

Tyr Trp Ser Trp Ile Arg Gln Pro Pro Gly Lys Gly Leu Glu Trp Ile
            35                  40                  45

Gly Glu Val Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
 65                  70                  75                  80

Phe Ser Leu Lys Leu Ser Ser Val Thr Ala Ala Asp Thr Ala Val Tyr
                 85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 596
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 596

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30

Tyr Trp Ser Trp Ile Arg Gln Pro Pro Gly Lys Gly Leu Glu Trp Ile
            35                  40                  45

Gly Glu Val Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ser Ser
    130

<210> SEQ ID NO 597
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 597

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Val Asn His Arg Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 598
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 598

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

```
Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 599
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 599

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Thr Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ser Ser
    130

<210> SEQ ID NO 600
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 600

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Val Asn His Arg Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95
```

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ser Ser
    130

<210> SEQ ID NO 601
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 601

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ser Ser
    130

<210> SEQ ID NO 602
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 602

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
         115                 120                 125

Ser Ser
    130

<210> SEQ ID NO 603
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 603

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
         115                 120                 125

Ala Ser
    130

<210> SEQ ID NO 604
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 604

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
         115                 120                 125

Ala Ser
    130

<210> SEQ ID NO 605
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 606
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 606

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 607
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 607

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 608
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 608

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 609

```
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 609

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Tyr Asn Pro
50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 610
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 610

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Ile Asn Tyr Asn Asn Tyr Asn Pro
50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 611
<211> LENGTH: 130
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 611

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 612
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 612

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Gln Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 613
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 613

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Gln Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
            115                 120                 125

Ala Ser
    130

<210> SEQ ID NO 614
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 614

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
            115                 120                 125

Ala Ser
    130

<210> SEQ ID NO 615
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 615

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 616
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 616

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 617
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 617

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
130

<210> SEQ ID NO 618
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 618

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
130

<210> SEQ ID NO 619
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 619

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 620
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 620

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 621
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 621

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 622
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 622

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 623
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
            115                 120                 125

Ala Ser
    130

<210> SEQ ID NO 624
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 624

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
            115                 120                 125

Ala Ser
    130

<210> SEQ ID NO 625
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 625

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 626
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 626

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 627
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 628
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 628

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 629
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 629

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 630
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 630

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 631
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 631

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 632
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 632

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 633
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 633

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 634
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 634

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 635
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 635

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Arg Gly Ser Ile Asn Tyr Asn Asn Tyr Asn Pro
    50                  55                  60
Ser Leu Lys Ser Arg Val Thr Ile Ser Val Asp Thr Ser Lys Asn Gln
65                  70                  75                  80
Phe Ser Leu Lys Leu Ser Ser Val Thr Ala Ala Asp Thr Ala Val Tyr
                85                  90                  95
Tyr Cys Ala Lys Pro Leu Arg Pro His Cys Ile Asn Gly Val Cys Tyr
            100                 105                 110
Ser Gly Asp Ala Phe Asp Ile Trp Gly Gln Gly Thr Met Val Thr Val
        115                 120                 125
Ala Ser
    130
```

<210> SEQ ID NO 636
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 636

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Arg Gly Ser Ile Asn Tyr Asn Asn Tyr Asn Pro
    50                  55                  60
Ser Leu Lys Ser Arg Val Thr Ile Ser Val Asp Thr Ser Lys Asn Gln
65                  70                  75                  80
Phe Ser Leu Lys Leu Ser Ser Val Thr Ala Ala Asp Thr Ala Val Tyr
                85                  90                  95
Tyr Cys Ala Lys Pro Leu Arg Pro His Cys Thr Asn Gly Val Cys Tyr
            100                 105                 110
Ser Gly Asp Ala Phe Asp Ile Trp Gly Gln Gly Thr Met Val Thr Val
        115                 120                 125
Ala Ser
    130
```

<210> SEQ ID NO 637
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 637

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 638
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 638

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 639
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 639

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 640
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 640

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 641
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 641

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 642
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 642

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 643
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 643

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 644
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 644

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 645
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 645

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 646
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 647
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 647

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 648
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 649
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 649

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 650
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 650

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 651
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 651

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 652
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 652

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 653
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 653

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 654
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 655
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 655

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Thr Asn Gly Val Cys Tyr
            100                 105                 110

Ser Gly Asp Ala Phe Asp Ile Trp Gly Gln Gly Thr Met Val Thr Val
        115                 120                 125

Ala Ser
    130

<210> SEQ ID NO 656
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 656

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 657
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 657

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 658
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 658

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 659
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 659

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 660
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 660

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 661
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 661

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 662
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 662

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 663
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 663

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 664
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 664

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

```
Leu Val Phe Gly Gly Gly Thr Lys Leu Thr Val Leu
            100                 105

<210> SEQ ID NO 665
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 665

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 666
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 666

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 667
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 667

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 668
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 669
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 669

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

-continued

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 670
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 670

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 671
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 671

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 672
<211> LENGTH: 108
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 672

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 673
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 673

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Val Phe Gly Gly Gly Thr Lys Leu Thr Val Leu
            100                 105

<210> SEQ ID NO 674
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 674

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

```
Asp Asp Ser Asp Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
            100                 105

<210> SEQ ID NO 675
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Asn Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Gln Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
            100                 105

<210> SEQ ID NO 676
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Asn Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
            100                 105

<210> SEQ ID NO 677
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 677

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 678
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 678

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 679
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 679

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Lys Asn Val
            20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 680
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 680

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Tyr Lys Asn Val
                20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 681
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 681

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Met Asn Val
                20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 682
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 682

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 683
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 684
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 684

Ser Tyr Val Leu Thr Gln Pro Pro Ser Val Ser Val Ala Pro Gly Gln
1               5                   10                  15

```
Thr Ala Arg Ile Thr Cys Gly Gly Asn Asn Ile Gly Tyr Met Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
50                      55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 685
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 685

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
50                      55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 686
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 686

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Met Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
50                      55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

```
Val Val Phe Gly Gly Gly Thr Lys Leu Thr Val Leu
            100                 105

<210> SEQ ID NO 687
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 687

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Met Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 688
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 689
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 689

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 690
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 690

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp His
                85                  90                  95

Val Val Phe Gly Gly Gly Thr Lys Leu Thr Val Leu
            100                 105

<210> SEQ ID NO 691
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 691

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Glu Ser Asp His
                 85                  90                  95

Val Val Phe Gly Gly Gly Thr Lys Leu Thr Val Leu
            100                 105

<210> SEQ ID NO 692
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 692

Ser Tyr Val Leu Thr Gln Pro Pro Ser Val Ser Val Ala Pro Gly Gln
  1               5                  10                  15

Thr Ala Arg Ile Thr Cys Gly Gly Asn Asn Ile Gly Tyr Lys Asn Val
                 20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Glu Ser Asp His
                 85                  90                  95

Val Val Phe Gly Gly Gly Thr Lys Leu Thr Val Leu
            100                 105

<210> SEQ ID NO 693
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 693

Ser Tyr Val Leu Thr Gln Pro Pro Ser Val Ser Val Ala Pro Gly Gln
  1               5                  10                  15

Thr Ala Arg Ile Thr Cys Arg Gly Asn Asn Ile Gly Ser Lys Asn Val
                 20                  25                  30

His Trp Tyr Gln Gln Lys Pro Gly Gln Ala Pro Val Leu Val Val Tyr
             35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
            100                 105

<210> SEQ ID NO 694
<211> LENGTH: 108
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 694

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 695
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 695

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Met Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 696
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 696

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

```
Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 697
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 697

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 698
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Met Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 699
```

```
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 700
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Met Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 701
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Met Asn Val
            20                  25                  30
```

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp His Ser Ser Asp His
                 85                  90                  95

Val Val Phe Gly Gly Gly Thr Lys Leu Thr Val Leu
            100                 105

<210> SEQ ID NO 702
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp His Ser Ser Asp His
                 85                  90                  95

Val Val Phe Gly Gly Gly Thr Lys Leu Thr Val Leu
            100                 105

<210> SEQ ID NO 703
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp His Ser Ser Asp His
                 85                  90                  95

Val Val Phe Gly Gly Gly Thr Lys Leu Thr Val Leu
            100                 105

<210> SEQ ID NO 704
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Arg Ser Asp His
                85                  90                  95

Val Val Phe Gly Gly Gly Thr Lys Leu Thr Val Leu
            100                 105

<210> SEQ ID NO 705
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 705

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Gln Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Glu Ser Asp His
                85                  90                  95

Val Val Phe Gly Gly Gly Thr Lys Leu Thr Val Leu
            100                 105

<210> SEQ ID NO 706
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

Ser Tyr Val Leu Thr Gln Pro Pro Ser Val Ser Val Ala Pro Gly Gln
1               5                   10                  15

```
Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Gln Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Glu Ser Asp His
                 85                  90                  95

Val Val Phe Gly Gly Gly Thr Lys Leu Thr Val Leu
            100                 105

<210> SEQ ID NO 707
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
            100                 105

<210> SEQ ID NO 708
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Tyr Lys Asn Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95
```

Val Val Phe Gly Gly Gly Thr Lys Leu Thr Val Leu
            100                 105

<210> SEQ ID NO 709
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 709

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Met Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 710
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 710

Ser Tyr Val Leu Thr Gln Pro Pro Ser Val Ser Val Ala Pro Gly Gln
1               5                   10                  15

Thr Ala Arg Ile Thr Cys Arg Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 711
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 711

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 712
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 712

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Met Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 713
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 713

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60
```

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 714
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Met Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 715
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Met Asn Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 716
<211> LENGTH: 108
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 716

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 717
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 717

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu
            100                 105

<210> SEQ ID NO 718
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 718

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
        35                  40                  45

```
Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Arg Ser Asp His
                 85                  90                  95

Val Val Phe Gly Gly Gly Thr Lys Leu Thr Val Leu
            100                 105

<210> SEQ ID NO 719
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 719

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Glu Ser Asp His
                 85                  90                  95

Val Val Phe Gly Gly Gly Thr Lys Leu Thr Val Leu
            100                 105

<210> SEQ ID NO 720
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 720

Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Glu Ser Asp His
                 85                  90                  95

Val Val Phe Gly Gly Gly Thr Lys Leu Thr Val Leu
            100                 105

<210> SEQ ID NO 721
```

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 721

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Tyr Ile Tyr Trp Val Arg Gln Ala Pro Gly Gln Gly Leu Glu Trp Ile
        35                  40                  45

Gly Asn Ile Trp Pro Gly Asn Gly Gly Thr Phe Tyr Gly Glu Lys Phe
    50                  55                  60

Met Gly Arg Ala Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Asp Tyr Ser Gly Asp Asp Tyr Phe Asp Tyr Trp Gly
            100                 105                 110

Gln Gly Thr Leu Val Thr Val Ser Ser
        115                 120

<210> SEQ ID NO 722
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 722

Gln Val Gln Leu Gln Gln Ser Gly Ala Glu Leu Ala Lys Pro Gly Thr
1               5                   10                  15

Ser Val Lys Leu Ser Cys Lys Ala Ser Gly Tyr Thr Phe Thr Ser Tyr
            20                  25                  30

Tyr Ile Tyr Trp Val Lys Gln Arg Pro Gly Gln Gly Leu Glu Trp Ile
        35                  40                  45

Gly Asn Ile Trp Pro Gly Asn Gly Gly Thr Phe Tyr Gly Glu Lys Phe
    50                  55                  60

Met Gly Lys Ala Thr Phe Thr Ala Asp Thr Ser Ser Ser Thr Ala Tyr
65                  70                  75                  80

Met Leu Leu Gly Ser Leu Thr Pro Glu Asp Ser Ala Tyr Tyr Phe Cys
                85                  90                  95

Ala Arg Arg Pro Asp Tyr Ser Gly Asp Asp Tyr Phe Asp Tyr Trp Gly
            100                 105                 110

Gln Gly Val Leu Val Thr Val Ser Ser
        115                 120

<210> SEQ ID NO 723
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 723

Gln Val Lys Leu Val Gln Ser Gly Ala Ala Leu Val Lys Pro Gly Ala
1               5                   10                  15

Ser Val Lys Met Ser Cys Lys Ala Ser Asp Tyr Thr Phe Asn Asp Tyr
            20                  25                  30

Trp Val Ser Val Lys Gln Arg His Gly Glu Ser Leu Glu Trp Ile
        35                  40                  45

Gly Glu Ile Tyr Pro Asn Ser Gly Ala Thr Asn Phe Asn Gly Lys Phe
50                  55                  60

Arg Gly Lys Ala Thr Leu Thr Val Asp Asn Pro Thr Ser Thr Ala Tyr
65                  70                  75                  80

Met Glu Leu Ser Arg Leu Thr Ser Glu Asp Ser Ala Ile Tyr Tyr Cys
                85                  90                  95

Thr Arg Glu Tyr Thr Arg Asp Trp Phe Ala Tyr Trp Gly Gln Gly Thr
            100                 105                 110

Leu Val Thr Val Ser Ser
        115

<210> SEQ ID NO 724
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 724

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
            100                 105                 110

Thr Leu Val Thr Val Ser Ser
        115

<210> SEQ ID NO 725
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 725

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

```
Trp Met Ser Trp Val Arg Gln Ala Pro Gly Lys Gly Leu Glu Trp Val
            35                  40                  45

Ala Asp Ile Lys Asn Asp Gly Ser Tyr Thr Asn Tyr Ala Pro Ser Leu
 50                  55                  60

Thr Asn Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Thr Gly Thr Trp Gly Gln Gly Thr Met Val Thr Val
            100                 105                 110

Ser Ser

<210> SEQ ID NO 726
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 726

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
            35                  40                  45

Gly Glu Ile Asn His Gly Gly Tyr Val Thr Tyr Asn Pro Ser Leu Glu
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
            115                 120

<210> SEQ ID NO 727
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 727

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80
```

-continued

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr
            100                 105                 110

Met Asp Val Trp Gly Lys Gly Thr Thr Val Thr Val Ser Ser
        115                 120                 125

<210> SEQ ID NO 728
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 728

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Pro Phe Leu Leu Asp Asp Tyr Tyr Tyr Tyr Tyr
            100                 105                 110

Met Asp Val Trp Gly Lys Gly Thr Thr Val Thr Val Ser Ser
        115                 120                 125

<210> SEQ ID NO 729
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Gly Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Asn Glu Glu Asp Gly Gly Phe Asp His Trp Gly Gln Gly
            100                 105                 110

Thr Leu Val Thr Val Ser Ser
        115

<210> SEQ ID NO 730
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 730

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Val Arg Gln Ala Pro Gly Lys Gly Leu Glu Trp Val
        35                  40                  45

Ser Val Ile Ser Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ala Gln Phe Glu Gly Asp Phe Trp Gly Gln Gly Thr
            100                 105                 110

Leu Val Thr Val Ser Ser
        115

<210> SEQ ID NO 731
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 731

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 732
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 732

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 733
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 733

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115

<210> SEQ ID NO 734
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 734

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

```
Trp Ile Ser Trp Val Arg Gln Met Pro Gly Lys Gly Leu Glu Trp Met
            35                  40                  45

Gly Lys Ile Tyr Pro Gly Asp Ser Tyr Thr Asn Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
                100                 105                 110

Thr Val Ser Ser
        115
```

<210> SEQ ID NO 735
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 735

```
Gln Val Gln Leu Val Gln Ser Gly Ala Glu Val Lys Lys Pro Gly Ala
 1                5                  10                  15

Ser Val Lys Leu Ser Cys Lys Ala Ser Gly Tyr Thr Phe Ser Ser Tyr
                 20                  25                  30

Trp Met His Trp Val Arg Gln Ala Pro Gly Gln Gly Leu Glu Trp Ile
            35                  40                  45

Gly Glu Ile Asn Pro Gly Asn Gly His Thr Asn Tyr Asn Glu Lys Phe
 50                  55                  60

Lys Ser Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Phe Lys Thr Ala Arg Ala Phe Ala Tyr Trp Gly Gln Gly
                100                 105                 110

Thr Leu Val Thr Val Ser Ser
        115
```

<210> SEQ ID NO 736
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 736

```
Glu Val Gln Leu Val Glu Ser Gly Gly Gly Leu Val Lys Pro Gly Gly
 1                5                  10                  15

Ser Leu Arg Leu Ser Cys Ala Ala Ser Gly Phe Thr Phe Ser Thr Phe
                 20                  25                  30

Thr Met Asn Trp Val Arg Gln Ala Pro Gly Lys Gly Leu Glu Trp Val
            35                  40                  45

Ser Ser Ile Ser Ser Lys Ser Thr Tyr Ile Glu Tyr Ala Asp Ser Phe
 50                  55                  60

Lys Val Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                85                  90                  95

Ala Arg Tyr Gly Ala Lys Asn Phe Leu Asn Trp Val Phe Asp Tyr Trp
            100                 105                 110

Gly Gln Gly Thr Leu Val Thr Val Ser Ser
        115                 120

<210> SEQ ID NO 737
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 737

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Gly Phe
            20                  25                  30

Glu Met His Trp Val Arg Gln Ala Pro Gly Gln Gly Leu Glu Trp Met
        35                  40                  45

Gly Ala Ile Asp Pro Lys Thr Gly Gly Thr Asp Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Gly Tyr Phe Asp Val Trp Gly Gln Gly Thr Leu Val
            100                 105                 110

Thr Val Ser Ser
        115

<210> SEQ ID NO 738
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid

<400> SEQUENCE: 738

Xaa Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Gly Tyr Tyr Gly Ser Gly Leu Asp Tyr Trp Gly Gln
            100                 105                 110
```

Gly Thr Leu Val Thr Val Ser Ser
        115                 120

<210> SEQ ID NO 739
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 739

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Gly
            20                  25                  30

Gly Val Gly Val Gly Trp Ile Arg Gln Ala Pro Gly Lys Gly Leu Glu
        35                  40                  45

Trp Leu Ala Leu Ile Asp Trp Ala Asp Asp Lys Tyr Tyr Ser Pro Ser
    50                  55                  60

Leu Lys Ser Arg Leu Thr Ile Ser Arg Asp Asn Ser Lys Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Gly Gly Ser Asp Thr Val Ile Gly Asp Trp Phe Ala Tyr
            100                 105                 110

Trp Gly Gln Gly Thr Leu Val Thr Val Ser Ser
        115                 120

<210> SEQ ID NO 740
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 740

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Gly Tyr Ser
            20                  25                  30

Tyr Met Ser Trp Val Arg Gln Ala Pro Gly Lys Gly Leu Glu Trp Val
        35                  40                  45

Ser Ser Ile Gly Ser Thr Ser Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Ser Ser Pro Gly Ile Asp Tyr Trp Gly Gln Gly Thr
            100                 105                 110

Leu Val Thr Val Ser Ser
        115

<210> SEQ ID NO 741
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 741

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Lys Gln Ala Pro Gly Gln Val Leu Glu Trp Ile
            35                  40                  45

Gly Glu Ile Asn Pro Gly Asn Gly His Thr Asn Tyr Asn Glu Lys Phe
50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
                100                 105                 110

Thr Leu Val Thr Val Ser Ser
            115

<210> SEQ ID NO 742
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 742

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
                20                  25                  30

Trp Met His Trp Val Arg Gln Ala Pro Gly Gln Arg Leu Glu Trp Met
            35                  40                  45

Gly Glu Ile Asn Pro Gly Asn Gly His Thr Asn Tyr Ser Gln Lys Phe
50                  55                  60

Gln Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
                100                 105                 110

Thr Leu Val Thr Val Ser Ser
            115

<210> SEQ ID NO 743
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 743

Asn Val Met Leu Thr Gln Pro His Ser Val Ser Glu Ser Pro Gly Lys
1               5                   10                  15
```

-continued

Thr Val Thr Ile Ser Cys Lys Leu Asn Ser Gly Asn Ile Gly Ser Tyr
            20                  25                  30

Tyr Val His Trp Tyr Gln Gln Arg Pro Gly Ser Pro Thr Thr Met
        35                  40                  45

Ile Tyr Arg Asp Asp Lys Arg Pro Asp Gly Val Pro Asp Arg Phe Ser
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys His Ser Tyr Asp Ser
                85                  90                  95

Thr Ile Thr Pro Val Phe Gly Gly Gly Thr Lys Leu Thr Val Leu
            100                 105                 110

<210> SEQ ID NO 744
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 744

Gln Val Val Leu Thr Gln Pro Lys Ser Val Ser Thr Ser Leu Lys Ser
1               5                   10                  15

Thr Val Lys Leu Ser Cys Lys Leu Asn Ser Gly Asn Ile Gly Ser Tyr
            20                  25                  30

Tyr Val His Trp Tyr Gln Gln His Ala Gly Arg Ser Pro Thr Thr Met
        35                  40                  45

Ile Tyr Arg Asp Asp Lys Arg Pro Asp Gly Val Pro Asp Arg Phe Ser
50                  55                  60

Gly Ser Ile Asp Ser Ser Asn Ser Ala Phe Leu Thr Ile Asn Asn
65                  70                  75                  80

Val Gln Thr Glu Asp Asp Ala Ile Tyr Phe Cys His Ser Tyr Asp Ser
                85                  90                  95

Thr Ile Thr Pro Val Phe Gly Gly Gly Thr Lys Leu Thr Val Leu
            100                 105                 110

<210> SEQ ID NO 745
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 745

Asp Val Val Leu Thr Gln Thr Pro Ser Ile Leu Ser Ala Thr Ile Gly
1               5                   10                  15

Gln Ser Val Ser Ile Ser Cys Arg Ser Ser Gln Ser Leu Leu Asp Ser
            20                  25                  30

Asp Gly Asn Thr Tyr Leu Tyr Trp Phe Leu Gln Arg Pro Gly Gln Ser
        35                  40                  45

Pro Gln Arg Leu Ile Tyr Leu Val Ser Asn Leu Gly Ser Gly Val Pro
50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Ile Tyr Tyr Cys Met Gln Pro
                85                  90                  95

Thr His Ala Pro Tyr Thr Phe Gly Ala Gly Thr Lys Leu Glu Leu Lys
            100                 105                 110

<210> SEQ ID NO 746
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 746

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95

Thr Phe Gly Gln Gly Thr Lys Leu Glu Ile Lys
            100                 105

<210> SEQ ID NO 747
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 747

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Tyr Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Leu Gln
                85                  90                  95

Tyr Asp Arg Tyr Pro Phe Thr Phe Gly Gln Gly Thr Lys Leu Glu Ile
            100                 105                 110

Lys

<210> SEQ ID NO 748
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 748

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105
```

<210> SEQ ID NO 749
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 749

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Leu Phe Pro Ile
                85                  90                  95

Thr Phe Gly Gly Gly Thr Lys Val Glu Ile Lys
            100                 105
```

<210> SEQ ID NO 750
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 750

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Leu Phe Pro Ile
                85                  90                  95

Thr Phe Gly Gly Gly Thr Lys Val Glu Ile Lys
            100                 105

<210> SEQ ID NO 751
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 751

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Asp Tyr Tyr Ala
            20                  25                  30

Ser Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Trp Asp Gly Thr Leu His Phe
                85                  90                  95

Val Phe Gly Gly Gly Thr Lys Leu Thr Val Leu
            100                 105

<210> SEQ ID NO 752
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 752

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Lys Tyr Val
            20                  25                  30

Ser Trp Tyr Gln Gln Lys Pro Gly Gln Ala Pro Val Leu Val Ile Tyr
        35                  40                  45

Ser Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Gly Ser Ile Ser Arg
                85                  90                  95

Val Phe Gly Gly Gly Thr Lys Leu Thr Val Leu
            100                 105

<210> SEQ ID NO 753
<211> LENGTH: 108
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 753

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 754
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 754

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105

<210> SEQ ID NO 755
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 755

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asp Gln Tyr Ala
            20                  25                  30

His Trp Tyr Gln Gln Lys Pro Gly Gln Ala Pro Val Val Val Ile Tyr
        35                  40                  45

Gln Asp Lys Asn Arg Pro Ser Gly Ile Pro Glu Arg Phe Ser Gly Ser
                50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Thr Tyr Thr Phe Val Gly Phe Thr
                 85                  90                  95

Thr Val Phe Gly Gly Gly Thr Lys Leu Thr Val Leu
            100                 105

<210> SEQ ID NO 756
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 756

Ser Tyr Glu Leu Thr Gln Pro Pro Ser Val Ser Val Ser Pro Gly Gln
  1               5                  10                  15

Thr Ala Ser Ile Thr Cys Ser Gly Asp Asn Ile Gly Asp Gln Tyr Ala
                 20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Ala Thr Tyr Thr Gly Phe Gly Ser Leu
                 85                  90                  95

Ala Val Phe Gly Gly Gly Thr Lys Leu Thr Val Leu
            100                 105

<210> SEQ ID NO 757
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 757

Asp Ile Val Met Thr Gln Ser Pro Ala Phe Leu Ser Val Thr Pro Gly
  1               5                  10                  15

Glu Lys Val Thr Ile Thr Cys Arg Ala Ser Gln Thr Ile Ser Asp Tyr
                 20                  25                  30

Leu His Trp Tyr Gln Gln Lys Pro Asp Gln Ala Pro Lys Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gln Asp Gly His Ser Trp Pro Pro
                 85                  90                  95

Thr Phe Gly Gln Gly Thr Lys Leu Glu Ile Lys
            100                 105

<210> SEQ ID NO 758

<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 758

Gln Ser Ala Leu Thr Gln Pro Pro Ser Ala Ser Gly Ser Pro Gly Gln
1               5                   10                  15

Thr Val Thr Ile Ser Cys Thr Gly Thr Arg Tyr Asp Val Gly Tyr Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu
            100                 105                 110

<210> SEQ ID NO 759
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 759

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Asn
            20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Glu Lys Leu Pro Arg
                85                  90                  95

Thr Phe Gly Gly Gly Thr Lys Val Glu Ile Arg
            100                 105

<210> SEQ ID NO 760
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 760

Ser Tyr Val Leu Thr Gln Pro Pro Ser Val Ser Val Ala Pro Gly Glu
1               5                   10                  15

Thr Ala Arg Ile Thr Cys Gly Gly Asp Asp Ile Gly Asp Lys Arg Val
            20                  25                  30

-continued

His Trp Tyr Gln Lys Lys Pro Asp Gln Ala Pro Val Leu Val Val Tyr
                35                  40                  45

Glu Asp Arg Tyr Arg Pro Ser Gly Ile Pro Glu Arg Ile Ser Gly Ser
 50                  55                  60

Asn Ser Gly Asn Thr Ala Thr Leu Thr Leu Ser Arg Val Glu Ala Gly
 65                  70                  75                  80

Asp Glu Ala Asp Tyr Tyr Cys Gln Val Trp Asp Ser Ser Asp His
                 85                  90                  95

Pro Gly Val Phe Gly Gly Gly Thr Gln Leu Ile Ile Leu
            100                 105

<210> SEQ ID NO 761
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 761

Asp Ile Gln Leu Thr Gln Ser Pro Ser Ser Leu Ser Ala Ser Val Gly
 1               5                   10                  15

Asp Arg Val Thr Ile Thr Cys Arg Ala Ser Gln Ser Ile Gly Ser Tyr
                20                  25                  30

Leu Ala Trp Tyr Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Tyr Leu Trp Thr
                 85                  90                  95

Phe Gly Gln Gly Thr Lys Val Glu Ile Lys
            100                 105

<210> SEQ ID NO 762
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 762

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Gly Ser Thr
                20                  25                  30

Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Thr Trp Val Pro
                 85                  90                  95

Phe Thr Phe Gly Gln Gly Thr Lys Leu Glu Ile Lys
            100                 105

<210> SEQ ID NO 763
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 763

Asp Ile Val Met Thr Gln Ser Pro Ala Thr Gln Ser Val Ser Pro Gly
1               5                   10                  15

Glu Arg Val Thr Leu Ser Cys Arg Ala Ser Gln Thr Ile Ser Asp Tyr
            20                  25                  30

Leu His Trp Tyr Gln Gln Lys Pro Gly Gln Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Thr Ile Ser Ser Val Glu Pro
65                  70                  75                  80

Glu Asp Phe Gly Val Tyr Tyr Cys Gln Asp Gly His Ser Phe Pro Pro
                85                  90                  95

Thr Phe Gly Gly Gly Thr Lys Leu Glu Ile Lys
            100                 105

<210> SEQ ID NO 764
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 764

Asp Ile Val Met Thr Gln Ser Pro Pro Thr Leu Ser Leu Ser Pro Gly
1               5                   10                  15

Glu Arg Val Thr Leu Ser Cys Arg Ala Ser Gln Ser Ile Ser Asp Tyr
            20                  25                  30

Leu His Trp Tyr Gln Gln Lys Pro Gly Gln Ser Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asp Gly His Ser Phe Pro Pro
                85                  90                  95

Thr Phe Gly Gly Gly Thr Lys Val Glu Ile Lys
            100                 105

<210> SEQ ID NO 765
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 765

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser Gly Gly Gly Gly Ser Gly Gly Gly Gly Ser Gly Gly Gly Gly
    130                 135                 140

Ser Gly Gly Gly Gly Ser Ser Tyr Val Leu Thr Gln Pro Pro Ser Val
145                 150                 155                 160

Ser Val Ala Pro Gly Gln Thr Ala Arg Ile Thr Cys Gly Gly Asn Asn
                165                 170                 175

Ile Gly Tyr Lys Asn Val His Trp Tyr Gln Gln Lys Pro Gly Gln Ala
            180                 185                 190

Pro Val Leu Val Val Tyr Asp Asp Ser Asp Arg Pro Ser Gly Ile Pro
        195                 200                 205

Glu Arg Phe Ser Gly Ser Asn Ser Gly Asn Thr Ala Thr Leu Thr Ile
    210                 215                 220

Ser Arg Val Glu Ala Gly Asp Glu Ala Asp Tyr Tyr Cys Gln Val Trp
225                 230                 235                 240

Asp His Ser Ser Asp His Val Val Phe Gly Gly Gly Thr Lys Leu Thr
                245                 250                 255

Val Leu Gly Gly Gly His His His His His His
            260                 265

<210> SEQ ID NO 766
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 766

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu Gly Gly Gly
                100                 105                 110

Ser Gly Gly Gly Gly Ser Gly Gly Gly Ser Gly Gly Gly Gly Ser
            115                 120                 125

Gln Val Gln Leu Gln Gln Trp Gly Ala Gly Leu Leu Lys Pro Ser Glu
130                 135                 140

Thr Leu Ser Leu Thr Cys Ala Val Tyr Gly Gly Ser Phe Ser Gly Tyr
145                 150                 155                 160

Tyr Trp Ser Trp Ile Arg Gln Pro Pro Gly Lys Gly Leu Glu Trp Ile
                165                 170                 175

Gly Glu Ile Asn His Arg Gly Ser Ile Asn Tyr Asn Asn Tyr Asn Pro
            180                 185                 190

Ser Leu Lys Ser Arg Val Thr Ile Ser Val Asp Thr Ser Lys Asn Gln
        195                 200                 205

Phe Ser Leu Lys Leu Ser Ser Val Thr Ala Ala Asp Thr Ala Val Tyr
    210                 215                 220

Tyr Cys Ala Lys Pro Leu Arg Pro His Cys Ile Asn Gly Val Cys Tyr
225                 230                 235                 240

Ser Gly Asp Ala Phe Asp Ile Trp Gly Gln Gly Thr Met Val Thr Val
                245                 250                 255

Ala Ser Gly Gly Gly His His His His His His
            260                 265

<210> SEQ ID NO 767
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 767

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Ser Ile Asn Tyr Asn Asn Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Lys Pro Leu Arg Pro His Cys Ile Asn Gly Val Cys Tyr
            100                 105                 110

Ser Gly Asp Ala Phe Asp Ile Trp Gly Gln Gly Thr Met Val Thr Val
        115                 120                 125

Ala Ser Gly Gly Gly Gly Ser Gly Gly Gly Gly Ser Gly Gly Gly Gly
    130                 135                 140

Ser Ser Tyr Val Leu Thr Gln Pro Pro Ser Val Ser Val Ala Pro Gly
145                 150                 155                 160

Gln Thr Ala Arg Ile Thr Cys Gly Gly Asn Asn Ile Gly Tyr Lys Asn
                165                 170                 175

```
Val His Trp Tyr Gln Gln Lys Pro Gly Gln Ala Pro Val Leu Val Val
            180                 185                 190

Tyr Asp Asp Ser Asp Arg Pro Ser Gly Ile Pro Glu Arg Phe Ser Gly
            195                 200                 205

Ser Asn Ser Gly Asn Thr Ala Thr Leu Thr Ile Ser Arg Val Glu Ala
210                 215                 220

Gly Asp Glu Ala Asp Tyr Tyr Cys Gln Val Trp Asp His Ser Ser Asp
225                 230                 235                 240

His Val Val Phe Gly Gly Gly Thr Lys Leu Thr Val Leu Gly Gly Gly
            245                 250                 255

His His His His His His
            260

<210> SEQ ID NO 768
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 768

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Tyr Lys Asn Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp His Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gln Val Gln Leu Gln
        115                 120                 125

Gln Trp Gly Ala Gly Leu Leu Lys Pro Ser Glu Thr Leu Ser Leu Thr
    130                 135                 140

Cys Ala Val Tyr Gly Gly Ser Phe Ser Gly Tyr Tyr Trp Ser Trp Ile
145                 150                 155                 160

Arg Gln Pro Pro Gly Lys Gly Leu Glu Trp Ile Gly Glu Ile Asn His
                165                 170                 175

Arg Gly Ser Ile Asn Tyr Asn Asn Tyr Asn Pro Ser Leu Lys Ser Arg
            180                 185                 190

Val Thr Ile Ser Val Asp Thr Ser Lys Asn Gln Phe Ser Leu Lys Leu
        195                 200                 205

Ser Ser Val Thr Ala Ala Asp Thr Ala Val Tyr Tyr Cys Ala Lys Pro
    210                 215                 220

Leu Arg Pro His Cys Ile Asn Gly Val Cys Tyr Ser Gly Asp Ala Phe
225                 230                 235                 240

Asp Ile Trp Gly Gln Gly Thr Met Val Thr Val Ala Ser Gly Gly Gly
                245                 250                 255
```

His His His His His His
        260

<210> SEQ ID NO 769
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: F or L
<220> FEATURE:
<221> NAME/KEY: MOD_RES
<222> LOCATION: (5)..(5)
<223> OTHER INFORMATION: S or N
<220> FEATURE:
<221> NAME/KEY: MOD_RES
<222> LOCATION: (6)..(6)
<223> OTHER INFORMATION: D or G
<220> FEATURE:
<221> NAME/KEY: MOD_RES
<222> LOCATION: (8)..(8)
<223> OTHER INFORMATION: Y or H

<400> SEQUENCE: 769

Gly Gly Ser Xaa Xaa Xaa Tyr Xaa Trp Ser
1               5                   10

<210> SEQ ID NO 770
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I or V
<220> FEATURE:
<221> NAME/KEY: MOD_RES
<222> LOCATION: (5)..(5)
<223> OTHER INFORMATION: A, Q, R or S
<220> FEATURE:
<221> NAME/KEY: MOD_RES
<222> LOCATION: (8)..(8)
<223> OTHER INFORMATION: I or T
<220> FEATURE:
<221> NAME/KEY: MOD_RES
<222> LOCATION: (9)..(9)
<223> OTHER INFORMATION: N or S

<400> SEQUENCE: 770

Glu Xaa Asn His Xaa Gly Ser Xaa Xaa Tyr Asn Asn Tyr Asn Pro Ser
1               5                   10                  15

Leu Lys Ser

<210> SEQ ID NO 771
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: L or F
<220> FEATURE:

```
<221> NAME/KEY: MOD_RES
<222> LOCATION: (9)..(9)
<223> OTHER INFORMATION: I or T
<220> FEATURE:
<221> NAME/KEY: MOD_RES
<222> LOCATION: (14)..(14)
<223> OTHER INFORMATION: Y or S

<400> SEQUENCE: 771

Ala Lys Pro Xaa Arg Pro His Cys Xaa Asn Gly Val Cys Xaa Ser Gly
1               5                   10                  15

Asp Ala Phe Asp Ile
            20

<210> SEQ ID NO 772
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or R
<220> FEATURE:
<221> NAME/KEY: MOD_RES
<222> LOCATION: (7)..(7)
<223> OTHER INFORMATION: S, T, or Y
<220> FEATURE:
<221> NAME/KEY: MOD_RES
<222> LOCATION: (8)..(8)
<223> OTHER INFORMATION: K or M
<220> FEATURE:
<221> NAME/KEY: MOD_RES
<222> LOCATION: (9)..(9)
<223> OTHER INFORMATION: N or S

<400> SEQUENCE: 772

Xaa Gly Asn Asn Ile Gly Xaa Xaa Xaa Val His
1               5                   10

<210> SEQ ID NO 773
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: H or S
<220> FEATURE:
<221> NAME/KEY: MOD_RES
<222> LOCATION: (6)..(6)
<223> OTHER INFORMATION: E, R, or S
<220> FEATURE:
<221> NAME/KEY: MOD_RES
<222> LOCATION: (10)..(10)
<223> OTHER INFORMATION: L or V

<400> SEQUENCE: 773

Gln Val Trp Asp Xaa Xaa Ser Asp His Xaa Val
1               5                   10

<210> SEQ ID NO 774
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I or V
<220> FEATURE:
<221> NAME/KEY: MOD_RES
<222> LOCATION: (5)..(5)
<223> OTHER INFORMATION: A, Q, R or S
<220> FEATURE:
<221> NAME/KEY: MOD_RES
<222> LOCATION: (8)..(8)
<223> OTHER INFORMATION: I or T
<220> FEATURE:
<221> NAME/KEY: MOD_RES
<222> LOCATION: (9)..(9)
<223> OTHER INFORMATION: N or S

<400> SEQUENCE: 774

Glu Xaa Asn His Xaa Gly Ser Xaa Xaa Tyr Asn Pro Ser Leu Lys Ser
1               5                   10                  15

<210> SEQ ID NO 775
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: F or L
<220> FEATURE:
<221> NAME/KEY: MOD_RES
<222> LOCATION: (5)..(5)
<223> OTHER INFORMATION: S or N
<220> FEATURE:
<221> NAME/KEY: MOD_RES
<222> LOCATION: (8)..(8)
<223> OTHER INFORMATION: Y or H

<400> SEQUENCE: 775

Gly Gly Ser Xaa Xaa Asp Tyr Xaa Trp Ser
1               5                   10

<210> SEQ ID NO 776
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I or V
<220> FEATURE:
<221> NAME/KEY: MOD_RES
<222> LOCATION: (5)..(5)
<223> OTHER INFORMATION: R or S
<220> FEATURE:
<221> NAME/KEY: MOD_RES
<222> LOCATION: (8)..(8)
<223> OTHER INFORMATION: I or T
<220> FEATURE:
<221> NAME/KEY: MOD_RES
<222> LOCATION: (9)..(9)
<223> OTHER INFORMATION: N or S

<400> SEQUENCE: 776

Glu Xaa Asn His Xaa Gly Ser Xaa Xaa Tyr Asn Pro Ser Leu Lys Ser
1               5                   10                  15
```

```
<210> SEQ ID NO 777
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: I or V
<220> FEATURE:
<221> NAME/KEY: MOD_RES
<222> LOCATION: (5)..(5)
<223> OTHER INFORMATION: R or S
<220> FEATURE:
<221> NAME/KEY: MOD_RES
<222> LOCATION: (8)..(8)
<223> OTHER INFORMATION: I or T
<220> FEATURE:
<221> NAME/KEY: MOD_RES
<222> LOCATION: (9)..(9)
<223> OTHER INFORMATION: N or S

<400> SEQUENCE: 777

Glu Xaa Asn His Xaa Gly Ser Xaa Xaa Tyr Asn Asn Tyr Asn Pro Ser
1               5                   10                  15

Leu Lys Ser

<210> SEQ ID NO 778
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: L or F
<220> FEATURE:
<221> NAME/KEY: MOD_RES
<222> LOCATION: (14)..(14)
<223> OTHER INFORMATION: Y or S

<400> SEQUENCE: 778

Ala Lys Pro Xaa Arg Pro His Cys Thr Asn Gly Val Cys Xaa Ser Gly
1               5                   10                  15

Asp Ala Phe Asp Ile
            20

<210> SEQ ID NO 779
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: S or T

<400> SEQUENCE: 779

Gly Gly Asn Asn Ile Gly Xaa Lys Asn Val His
1               5                   10

<210> SEQ ID NO 780
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: G or R
<220> FEATURE:
<221> NAME/KEY: MOD_RES
<222> LOCATION: (7)..(7)
<223> OTHER INFORMATION: S, T, or Y
<220> FEATURE:
<221> NAME/KEY: MOD_RES
<222> LOCATION: (8)..(8)
<223> OTHER INFORMATION: K or M
<220> FEATURE:
<221> NAME/KEY: MOD_RES
<222> LOCATION: (9)..(9)
<223> OTHER INFORMATION: N or I

<400> SEQUENCE: 780

Xaa Gly Asn Asn Ile Gly Xaa Xaa Xaa Val His
1               5                   10

<210> SEQ ID NO 781
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 781

Gly Gly Ser Gly Gly Gly Gly Ser Gly Gly
1               5                   10

<210> SEQ ID NO 782
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Gly Gly Gly Gly Ser Gly Gly Gly Ser Gly Gly Gly Gly Ser Gly
1               5                   10                  15

Gly Gly Gly Ser
            20

<210> SEQ ID NO 783
<211> LENGTH: 13
<212> TYPE: PRT
<213> ORGANISM: Unknown
<220> FEATURE:
<223> OTHER INFORMATION: Description of Unknown:
      EphA2 sequence

<400> SEQUENCE: 783

Thr Glu Pro Pro Lys Val Arg Leu Glu Gly Arg Ser Thr
1               5                   10

<210> SEQ ID NO 784
<211> LENGTH: 5
<212> TYPE: PRT
<213> ORGANISM: Unknown
<220> FEATURE:
```

-continued

<223> OTHER INFORMATION: Description of Unknown:
      EphA2 sequence

<400> SEQUENCE: 784

Lys Lys Gly Asp Ser
1               5

<210> SEQ ID NO 785
<211> LENGTH: 7
<212> TYPE: PRT
<213> ORGANISM: Unknown
<220> FEATURE:
<223> OTHER INFORMATION: Description of Unknown:
      EphA2 sequence

<400> SEQUENCE: 785

Thr Tyr Leu Val Gln Val Gln
1               5

<210> SEQ ID NO 786
<211> LENGTH: 11
<212> TYPE: PRT
<213> ORGANISM: Unknown
<220> FEATURE:
<223> OTHER INFORMATION: Description of Unknown:
      EphA2 sequence

<400> SEQUENCE: 786

Ala Gly Ser Lys Val His Glu Phe Gln Thr Leu
1               5                   10

<210> SEQ ID NO 787
<211> LENGTH: 16
<212> TYPE: PRT
<213> ORGANISM: Unknown
<220> FEATURE:
<223> OTHER INFORMATION: Description of Unknown:
      EphA1 sequence

<400> SEQUENCE: 787

Ala Glu Ser Leu Ser Gly Leu Ser Leu Arg Leu Val Lys Lys Glu Pro
1               5                   10                  15

<210> SEQ ID NO 788
<211> LENGTH: 5
<212> TYPE: PRT
<213> ORGANISM: Unknown
<220> FEATURE:
<223> OTHER INFORMATION: Description of Unknown:
      EphA1 sequence

<400> SEQUENCE: 788

Leu Asn Gln Asp Glu
1               5

<210> SEQ ID NO 789
<211> LENGTH: 7
<212> TYPE: PRT
<213> ORGANISM: Unknown
<220> FEATURE:
<223> OTHER INFORMATION: Description of Unknown:
      EphA1 sequence

<400> SEQUENCE: 789

Thr Tyr Ile Val Arg Val Arg
1               5

```
<210> SEQ ID NO 790
<211> LENGTH: 11
<212> TYPE: PRT
<213> ORGANISM: Unknown
<220> FEATURE:
<223> OTHER INFORMATION: Description of Unknown:
      EphA1 sequence

<400> SEQUENCE: 790

Pro Phe Ser Pro Asp His Glu Phe Arg Thr Ser
1               5                   10

<210> SEQ ID NO 791
<211> LENGTH: 16
<212> TYPE: PRT
<213> ORGANISM: Unknown
<220> FEATURE:
<223> OTHER INFORMATION: Description of Unknown:
      EphA3 sequence

<400> SEQUENCE: 791

Ala Ala Pro Ser Pro Val Leu Thr Ile Lys Lys Asp Arg Thr Ser Arg
1               5                   10                  15

<210> SEQ ID NO 792
<211> LENGTH: 5
<212> TYPE: PRT
<213> ORGANISM: Unknown
<220> FEATURE:
<223> OTHER INFORMATION: Description of Unknown:
      EphA3 sequence

<400> SEQUENCE: 792

Lys Gln Glu Gln Glu
1               5

<210> SEQ ID NO 793
<211> LENGTH: 7
<212> TYPE: PRT
<213> ORGANISM: Unknown
<220> FEATURE:
<223> OTHER INFORMATION: Description of Unknown:
      EphA3 sequence

<400> SEQUENCE: 793

Ile Tyr Val Phe Gln Ile Arg
1               5

<210> SEQ ID NO 794
<211> LENGTH: 11
<212> TYPE: PRT
<213> ORGANISM: Unknown
<220> FEATURE:
<223> OTHER INFORMATION: Description of Unknown:
      EphA3 sequence

<400> SEQUENCE: 794

Thr Asn Ser Arg Lys Phe Glu Phe Glu Thr Ser
1               5                   10

<210> SEQ ID NO 795
<211> LENGTH: 16
<212> TYPE: PRT
<213> ORGANISM: Unknown
<220> FEATURE:
<223> OTHER INFORMATION: Description of Unknown:
      EphA4 sequence
```

-continued

```
<400> SEQUENCE: 795

Ala Ala Pro Ser Ser Ile Ala Leu Val Gln Ala Lys Glu Val Thr Arg
1               5                   10                  15

<210> SEQ ID NO 796
<211> LENGTH: 5
<212> TYPE: PRT
<213> ORGANISM: Unknown
<220> FEATURE:
<223> OTHER INFORMATION: Description of Unknown:
      EphA4 sequence

<400> SEQUENCE: 796

Lys Asp Gln Asn Glu
1               5

<210> SEQ ID NO 797
<211> LENGTH: 7
<212> TYPE: PRT
<213> ORGANISM: Unknown
<220> FEATURE:
<223> OTHER INFORMATION: Description of Unknown:
      EphA4 sequence

<400> SEQUENCE: 797

Ser Tyr Val Phe His Val Arg
1               5

<210> SEQ ID NO 798
<211> LENGTH: 11
<212> TYPE: PRT
<213> ORGANISM: Unknown
<220> FEATURE:
<223> OTHER INFORMATION: Description of Unknown:
      EphA4 sequence

<400> SEQUENCE: 798

Asp Phe Ser Glu Pro Leu Glu Val Thr Thr Asn
1               5                   10

<210> SEQ ID NO 799
<211> LENGTH: 16
<212> TYPE: PRT
<213> ORGANISM: Unknown
<220> FEATURE:
<223> OTHER INFORMATION: Description of Unknown:
      EphA5 sequence

<400> SEQUENCE: 799

Ala Ala Pro Ser Pro Val Thr Asn Val Lys Lys Gly Lys Ile Ala Lys
1               5                   10                  15

<210> SEQ ID NO 800
<211> LENGTH: 4
<212> TYPE: PRT
<213> ORGANISM: Unknown
<220> FEATURE:
<223> OTHER INFORMATION: Description of Unknown:
      EphA5 sequence

<400> SEQUENCE: 800

Lys Asp Gln Glu
1

<210> SEQ ID NO 801
<211> LENGTH: 7
```

```
<212> TYPE: PRT
<213> ORGANISM: Unknown
<220> FEATURE:
<223> OTHER INFORMATION: Description of Unknown:
      EphA5 sequence

<400> SEQUENCE: 801

Val Tyr Val Phe Gln Ile Arg
1               5

<210> SEQ ID NO 802
<211> LENGTH: 11
<212> TYPE: PRT
<213> ORGANISM: Unknown
<220> FEATURE:
<223> OTHER INFORMATION: Description of Unknown:
      EphA5 sequence

<400> SEQUENCE: 802

Val Phe Ser Arg Arg Phe Glu Phe Glu Thr Thr
1               5                   10

<210> SEQ ID NO 803
<211> LENGTH: 16
<212> TYPE: PRT
<213> ORGANISM: Unknown
<220> FEATURE:
<223> OTHER INFORMATION: Description of Unknown:
      EphA6 sequence

<400> SEQUENCE: 803

Asp Ala Pro Ser Leu Ile Gly Met Met Arg Lys Asp Trp Ala Ser Gln
1               5                   10                  15

<210> SEQ ID NO 804
<211> LENGTH: 5
<212> TYPE: PRT
<213> ORGANISM: Unknown
<220> FEATURE:
<223> OTHER INFORMATION: Description of Unknown:
      EphA6 sequence

<400> SEQUENCE: 804

Lys Glu His Glu Gln
1               5

<210> SEQ ID NO 805
<211> LENGTH: 7
<212> TYPE: PRT
<213> ORGANISM: Unknown
<220> FEATURE:
<223> OTHER INFORMATION: Description of Unknown:
      EphA6 sequence

<400> SEQUENCE: 805

Lys Tyr Val Phe His Ile Arg
1               5

<210> SEQ ID NO 806
<211> LENGTH: 11
<212> TYPE: PRT
<213> ORGANISM: Unknown
<220> FEATURE:
<223> OTHER INFORMATION: Description of Unknown:
      EphA6 sequence
```

```
<400> SEQUENCE: 806

Gly Tyr Ser Gln Lys Phe Glu Phe Glu Thr Gly
1               5                   10

<210> SEQ ID NO 807
<211> LENGTH: 16
<212> TYPE: PRT
<213> ORGANISM: Unknown
<220> FEATURE:
<223> OTHER INFORMATION: Description of Unknown:
      EphA7 sequence

<400> SEQUENCE: 807

Ala Ala Pro Ser Gln Val Ser Gly Val Met Lys Glu Arg Val Leu Gln
1               5                   10                  15

<210> SEQ ID NO 808
<211> LENGTH: 5
<212> TYPE: PRT
<213> ORGANISM: Unknown
<220> FEATURE:
<223> OTHER INFORMATION: Description of Unknown:
      EphA7 sequence

<400> SEQUENCE: 808

Lys Asp Gln Arg Glu
1               5

<210> SEQ ID NO 809
<211> LENGTH: 7
<212> TYPE: PRT
<213> ORGANISM: Unknown
<220> FEATURE:
<223> OTHER INFORMATION: Description of Unknown:
      EphA7 sequence

<400> SEQUENCE: 809

Val Tyr Val Phe Gln Ile Arg
1               5

<210> SEQ ID NO 810
<211> LENGTH: 11
<212> TYPE: PRT
<213> ORGANISM: Unknown
<220> FEATURE:
<223> OTHER INFORMATION: Description of Unknown:
      EphA7 sequence

<400> SEQUENCE: 810

Asn Tyr Ser Pro Arg Leu Asp Val Ala Thr Leu
1               5                   10

<210> SEQ ID NO 811
<211> LENGTH: 16
<212> TYPE: PRT
<213> ORGANISM: Unknown
<220> FEATURE:
<223> OTHER INFORMATION: Description of Unknown:
      EphA8 sequence

<400> SEQUENCE: 811

Ala Ala Pro Ser Gln Val Val Val Ile Arg Gln Glu Arg Ala Gly Gln
1               5                   10                  15

<210> SEQ ID NO 812
<211> LENGTH: 5
```

-continued

```
<212> TYPE: PRT
<213> ORGANISM: Unknown
<220> FEATURE:
<223> OTHER INFORMATION: Description of Unknown:
      EphA8 sequence

<400> SEQUENCE: 812

Lys Asp Lys Glu Met
1               5

<210> SEQ ID NO 813
<211> LENGTH: 7
<212> TYPE: PRT
<213> ORGANISM: Unknown
<220> FEATURE:
<223> OTHER INFORMATION: Description of Unknown:
      EphA8 sequence

<400> SEQUENCE: 813

Arg Tyr Val Phe Gln Val Arg
1               5

<210> SEQ ID NO 814
<211> LENGTH: 11
<212> TYPE: PRT
<213> ORGANISM: Unknown
<220> FEATURE:
<223> OTHER INFORMATION: Description of Unknown:
      EphA8 sequence

<400> SEQUENCE: 814

Arg Phe Ser Gln Ala Met Glu Val Glu Thr Gly
1               5                   10

<210> SEQ ID NO 815
<211> LENGTH: 16
<212> TYPE: PRT
<213> ORGANISM: Unknown
<220> FEATURE:
<223> OTHER INFORMATION: Description of Unknown:
      EphA10 sequence

<400> SEQUENCE: 815

Gly Ala Pro Trp Glu Glu Gly Glu Ile Arg Arg Asp Arg Val Glu Pro
1               5                   10                  15

<210> SEQ ID NO 816
<211> LENGTH: 5
<212> TYPE: PRT
<213> ORGANISM: Unknown
<220> FEATURE:
<223> OTHER INFORMATION: Description of Unknown:
      EphA10 sequence

<400> SEQUENCE: 816

Lys Gly Gln Ser Glu
1               5

<210> SEQ ID NO 817
<211> LENGTH: 7
<212> TYPE: PRT
<213> ORGANISM: Unknown
<220> FEATURE:
<223> OTHER INFORMATION: Description of Unknown:
      EphA10 sequence
```

```
<400> SEQUENCE: 817

Arg Tyr Val Phe Gln Ile Arg
1               5

<210> SEQ ID NO 818
<211> LENGTH: 11
<212> TYPE: PRT
<213> ORGANISM: Unknown
<220> FEATURE:
<223> OTHER INFORMATION: Description of Unknown:
      EphA10 sequence

<400> SEQUENCE: 818

Ser Phe Asn Pro Ser Ile Glu Val Gln Thr Leu
1               5                   10

<210> SEQ ID NO 819
<211> LENGTH: 16
<212> TYPE: PRT
<213> ORGANISM: Unknown
<220> FEATURE:
<223> OTHER INFORMATION: Description of Unknown:
      EphB1 sequence

<400> SEQUENCE: 819

Ala Ala Pro Ser Thr Val Pro Ile Met His Gln Val Ser Ala Thr Met
1               5                   10                  15

<210> SEQ ID NO 820
<211> LENGTH: 5
<212> TYPE: PRT
<213> ORGANISM: Unknown
<220> FEATURE:
<223> OTHER INFORMATION: Description of Unknown:
      EphB1 sequence

<400> SEQUENCE: 820

Lys Glu His Asn Glu
1               5

<210> SEQ ID NO 821
<211> LENGTH: 7
<212> TYPE: PRT
<213> ORGANISM: Unknown
<220> FEATURE:
<223> OTHER INFORMATION: Description of Unknown:
      EphB1 sequence

<400> SEQUENCE: 821

Val Tyr Val Val Gln Val Arg
1               5

<210> SEQ ID NO 822
<211> LENGTH: 11
<212> TYPE: PRT
<213> ORGANISM: Unknown
<220> FEATURE:
<223> OTHER INFORMATION: Description of Unknown:
      EphB1 sequence

<400> SEQUENCE: 822

Lys Phe Ser Gly Lys Met Cys Phe Gln Thr Leu
1               5                   10

<210> SEQ ID NO 823
<211> LENGTH: 16
```

```
<212> TYPE: PRT
<213> ORGANISM: Unknown
<220> FEATURE:
<223> OTHER INFORMATION: Description of Unknown:
      EphB2 sequence

<400> SEQUENCE: 823

Ala Ala Pro Ser Ala Val Ser Ile Met His Gln Val Ser Arg Thr Val
1               5                   10                  15

<210> SEQ ID NO 824
<211> LENGTH: 5
<212> TYPE: PRT
<213> ORGANISM: Unknown
<220> FEATURE:
<223> OTHER INFORMATION: Description of Unknown:
      EphB2 sequence

<400> SEQUENCE: 824

Lys Glu Leu Ser Glu
1               5

<210> SEQ ID NO 825
<211> LENGTH: 7
<212> TYPE: PRT
<213> ORGANISM: Unknown
<220> FEATURE:
<223> OTHER INFORMATION: Description of Unknown:
      EphB2 sequence

<400> SEQUENCE: 825

Ile Tyr Val Phe Gln Val Arg
1               5

<210> SEQ ID NO 826
<211> LENGTH: 11
<212> TYPE: PRT
<213> ORGANISM: Unknown
<220> FEATURE:
<223> OTHER INFORMATION: Description of Unknown:
      EphB2 sequence

<400> SEQUENCE: 826

Arg Tyr Ser Gly Lys Met Tyr Phe Gln Thr Met
1               5                   10

<210> SEQ ID NO 827
<211> LENGTH: 16
<212> TYPE: PRT
<213> ORGANISM: Unknown
<220> FEATURE:
<223> OTHER INFORMATION: Description of Unknown:
      EphB3 sequence

<400> SEQUENCE: 827

Ala Ala Pro Ser Glu Val Pro Thr Leu Arg Leu His Ser Ser Ser Gly
1               5                   10                  15

<210> SEQ ID NO 828
<211> LENGTH: 7
<212> TYPE: PRT
<213> ORGANISM: Rattus sp.

<400> SEQUENCE: 828

Ser Lys Val His Glu Phe Gln
1               5
```

```
<210> SEQ ID NO 829
<211> LENGTH: 7
<212> TYPE: PRT
<213> ORGANISM: Unknown
<220> FEATURE:
<223> OTHER INFORMATION: Description of Unknown:
      EphB3 sequence

<400> SEQUENCE: 829

Arg Tyr Val Val Gln Val Arg
1               5

<210> SEQ ID NO 830
<211> LENGTH: 11
<212> TYPE: PRT
<213> ORGANISM: Unknown
<220> FEATURE:
<223> OTHER INFORMATION: Description of Unknown:
      EphB3 sequence

<400> SEQUENCE: 830

Gln Tyr Ser Arg Pro Ala Glu Phe Glu Thr Thr
1               5                   10

<210> SEQ ID NO 831
<211> LENGTH: 16
<212> TYPE: PRT
<213> ORGANISM: Unknown
<220> FEATURE:
<223> OTHER INFORMATION: Description of Unknown:
      EphB4 sequence

<400> SEQUENCE: 831

Glu Val Pro Pro Ala Val Ser Asp Ile Arg Val Thr Arg Ser Ser Pro
1               5                   10                  15

<210> SEQ ID NO 832
<211> LENGTH: 5
<212> TYPE: PRT
<213> ORGANISM: Unknown
<220> FEATURE:
<223> OTHER INFORMATION: Description of Unknown:
      EphB4 sequence

<400> SEQUENCE: 832

Lys Gly Ala Glu Gly
1               5

<210> SEQ ID NO 833
<211> LENGTH: 7
<212> TYPE: PRT
<213> ORGANISM: Unknown
<220> FEATURE:
<223> OTHER INFORMATION: Description of Unknown:
      EphB4 sequence

<400> SEQUENCE: 833

Ser Tyr Leu Val Gln Val Arg
1               5

<210> SEQ ID NO 834
<211> LENGTH: 11
<212> TYPE: PRT
<213> ORGANISM: Unknown
<220> FEATURE:
<223> OTHER INFORMATION: Description of Unknown:
      EphB4 sequence
```

```
<400> SEQUENCE: 834

Pro Phe Gly Gln Glu His His Ser Gln Thr Gln
1               5                   10

<210> SEQ ID NO 835
<211> LENGTH: 16
<212> TYPE: PRT
<213> ORGANISM: Unknown
<220> FEATURE:
<223> OTHER INFORMATION: Description of Unknown:
      EphB6 sequence

<400> SEQUENCE: 835

Glu Val Pro Ser Ala Val Pro Val Val His Gln Val Ser Arg Ala Ser
1               5                   10                  15

<210> SEQ ID NO 836
<211> LENGTH: 5
<212> TYPE: PRT
<213> ORGANISM: Unknown
<220> FEATURE:
<223> OTHER INFORMATION: Description of Unknown:
      EphB6 sequence

<400> SEQUENCE: 836

Gln Ala Glu Asp Glu
1               5

<210> SEQ ID NO 837
<211> LENGTH: 7
<212> TYPE: PRT
<213> ORGANISM: Unknown
<220> FEATURE:
<223> OTHER INFORMATION: Description of Unknown:
      EphB6 sequence

<400> SEQUENCE: 837

Ile Tyr Gly Phe Gln Val Arg
1               5

<210> SEQ ID NO 838
<211> LENGTH: 11
<212> TYPE: PRT
<213> ORGANISM: Unknown
<220> FEATURE:
<223> OTHER INFORMATION: Description of Unknown:
      EphB6 sequence

<400> SEQUENCE: 838

Pro Tyr Gly Gly Lys Val Tyr Phe Gln Thr Leu
1               5                   10

<210> SEQ ID NO 839
<211> LENGTH: 7
<212> TYPE: PRT
<213> ORGANISM: Homo sapiens

<400> SEQUENCE: 839

Ser Lys Val His Glu Phe Gln
1               5

<210> SEQ ID NO 840
<211> LENGTH: 7
<212> TYPE: PRT
<213> ORGANISM: Mus sp.
```

```
<400> SEQUENCE: 840

Ser Lys Val His Glu Phe Gln
1               5

<210> SEQ ID NO 841
<211> LENGTH: 7
<212> TYPE: PRT
<213> ORGANISM: Macaca sp.

<400> SEQUENCE: 841

Ser Lys Val His Glu Phe Gln
1               5
```